United States Patent
Worley et al.

(10) Patent No.: US 6,699,660 B2
(45) Date of Patent: Mar. 2, 2004

(54) IMMEDIATE EARLY GENES AND METHODS OF USE THEREFOR

(75) Inventors: Paul F. Worley, Baltimore, MD (US); Anthony Lanahan, Baltimore, MD (US); Bernhard Goetz, Heidelberg (DE); Holger Hiemisch, Heidelberg (DE); Rohini Kuner, Heidelberg (DE); Sigrid Scheek, Dossenheim (DE); Karoly Nikolich, Redwood City, CA (US); Eugene Zhukovsky, San Francisco, CA (US)

(73) Assignee: The Johns Hopkins University School of Medicine, Baltimore, MD (US)

( * ) Notice: Subject to any disclaimer, the term of this patent is extended or adjusted under 35 U.S.C. 154(b) by 164 days.

(21) Appl. No.: 09/244,805

(22) Filed: Feb. 5, 1999

(65) Prior Publication Data

US 2003/0203840 A1 Oct. 30, 2003

Related U.S. Application Data

(60) Provisional application No. 60/074,518, filed on Feb. 12, 1998, and provisional application No. 60/074,135, filed on Feb. 9, 1998.

(51) Int. Cl.⁷ .............. C12N 15/63; C12N 15/00; C07H 21/04; C12Q 1/68
(52) U.S. Cl. .............. 435/6; 435/320.1; 435/325; 536/23.5
(58) Field of Search ................ 435/6, 320.1, 325; 536/23.5

(56) References Cited

PUBLICATIONS

Marra, M. vj90d06.s1 Knowles Solter mouse 2 cell Mus musculus cDNA clone IMAGE:944363 5' mRNA sequence. EST. Accession No. AA545549. Aug. 4, 1997.*

Fujiwara, T. HUM084F06B Clontech human fetal brain polyA+ mRNA (#6535) Homo sapiens cDNA clone GEN–084F06 5' mRNA sequence. EST. Accession No. D60079. Aug. 28, 1995.*

Molven, A. R. Chromosomal assignment of the human gene encoding the FOS–related antigen–2 (FRA2) to chromosome 2p22–p23. Genomics vol. 38(1) p. 72–75, 1997.*

Hillier, L. y176a03.r1 Soares Infant brain 1NIB Homo sapiens cDNA clone IMAGE:43682 5' similar to SP:CRAL_HUMNAN P12271 Cellular Retinaldehyde–Binding Protein; mRNA sequence, EST. Accession No. H05988. Jun. 21, 1995.*

Hillier et al. EST AA458676. Jun. 9, 1997.*

Mikayama T. Molecular cloning and functional expression of a cDNA encoding glycosylation–inhibiting factor. Proc. Natl. Acad. Sci. USA vol. 90, pp. 10056–10060, 1993.*

Voet et al. Biochemistry. 1990. John Wiley & Sons, Inc.. pp. 126–128 and 228–234.*

Cole, A.J. et al., "Rapid Rise in Transcription Factor Messenger mRNAs in Rat Brain After Electroshock–Induced Seizures", *Journal of Neurochemistry*, vol. 55, No. 6, 1920–1927, 1990.

Mohn, Kenneth L. et al., "The Immediate–Early Growth Response I Regenerating Liver and Insulin–Stimulated H–35 Cells: Comparision with Serum–Stimulated 3T3 Cells and Identification of 41 Novel Immediate–Early Genes" *Molecular and Cellular Biology* vol. 11, No. 1, 381–390, 1991.

Scearce, L. Marie, et al., "RNR–1, a Nuclear Receptor in the NGFI–B/Nurr77 Family That Is Rapidly Induced in Regenerating Liver" *Journal of Biological Chemsitry*, vol. 268, No. 12, 8855–8861, 1993.

Bonaldo, Fatima de M., et al., "Normalization and Subtraction: Two Approaches to Facilitate Gene Discovery", *Genome Research*, vol. 6, No. 9, 1996.

Xing, G., et al., Rat nurr1 is prominently expressed in perirhinal cortex, and differentially induced in the hippocampal dentate gyrus by electroconvulsive vs. kindled seizures, *Molecular Brain Research*, vol. 47, 251–261, 1997.

Lloyd, C., "Human DNA sequence", Database accession No. Z84493; XP–002217259, Jan. 1997.

Lloyd, C., Caenorhabditis eleganas cosmid C44DE1, Database accession No. Z9277;, XP00217258, Mar. 1997.

Clark, M., a03d10.s1 Zebrafish ICRFzfls Danio rerio CDNA clone 4H2r 3', mRNA sequence, database accession No. AA459466; XP002217260, Jul. 1997.

Sulston, J.E., "Homo sapiens BAC clone CTA–252P22", database accession No. AC005079; XP002217257, Jun. 1998.

National Cancer Institute, Cancer Genome Anatomy Project: "qa01h09.x1 Soares_parathyroid_tumor_NbHPA Homo sapiens cDNA clone IMAGE: 1683617.3'", database accession No. AI123514; XP002217256, Sep. 1998.

Smith, D.R., "b240g16, complete sequence", database accession No. AC005886; XP002217255, Oct. 1998.

(List continued on next page.)

*Primary Examiner*—Yvonne Eyler
*Assistant Examiner*—Joseph F. Murphy
(74) *Attorney, Agent, or Firm*—Gray Cary Ware & Freidenrich, LLP; Lisa A. Haile; Kelly K. Reynolds

(57) ABSTRACT

The present invention provides methods and materials related to immediate early genes. Specifically, the invention provides isolated immediate early gene nucleic acid, cells that contain isolated immediate early gene nucleic acid, substantially pure polypeptides encoded by immediate early gene nucleic acid, and antibodies having specific binding affinity for a polypeptide encoded by immediate early gene nucleic acid. In addition, the invention provides cDNA libraries enriched for immediate early genes cDNAs, isolated nucleic acid derived from such cDNA libraries, and methods for treating conditions related to a deficiency in a neuron's immediate early gene responsiveness to a stimulus.

13 Claims, No Drawings

OTHER PUBLICATIONS

Adams, Mark D., et al., "Sequence identification of 2,375 human brain genes", *Nature, Macmillan Journals, Ltd., London GB*, vol. 355, No. 6361, pp. 632–634, 1992.

Adams, Mark D., et al., "EST01263 Subtracted hippocampus, Stratagene (cat. #936205) Homo sapiens cDNA clone HHCPL60, mRNA sequence", *DATABASE EMBL* Online!, Accession No. M79115, 1992.

Marra M., et al., "mh88h02.r1 Soares mouse placeta 4NbMP13.5 14.5 Mus musculus cDNA IMAGE: 458067 5', MRNA sequence", *DATABASE EMBL* Online!, Accession No. AAS030668 XP002230624, 1996.

Adams, M.D., et al., "EST182124 Jurkat T–cells V Homo sapiens cDNA5"end", *DATABASE EBI* Online!, Accession No. AA311360 XP00223623, Mar. 1997.

* cited by examiner

US 6,699,660 B2

IMMEDIATE EARLY GENES AND METHODS OF USE THEREFOR

RELATED APPLICATIONS

This application claims priority to U.S. provisional application No. 60/074,518, filed Feb. 12, 1998 and No. 60/074,135, filed Feb. 9, 1998, both of which are incorporated herein by reference.

STATEMENT AS TO FEDERALLY SPONSORED RESEARCH

Funding for the work described herein was provided by the federal government, which may have certain rights in the invention.

BACKGROUND

1. Technical Field

The present invention generally relates to gene expression and more specifically to immediate early genes in the brain and polypeptides encoded by such immediate early genes.

2. Background Information

An immediate early gene (IEG) is a gene whose expression is rapidly increased immediately following a stimulus. For example, genes expressed by neurons that exhibit a rapid increase in expression immediately following neuronal stimulation are neuronal IEGs. Such neuronal IEGs have been found to encode a wide variety of polypeptides including transcription factors, cytoskeletal polypeptides, growth factors, and metabolic enzymes as well as polypeptides involved in signal transduction. The identification of neuronal IEGs and the polypeptides they encode provides important information about the function of neurons in, for example, learning, memory, synaptic transmission, tolerance, and neuronal plasticity.

SUMMARY

The present invention involves methods and materials related to IEGs. Specifically, the invention provides isolated IEG nucleic acid sequences, cells that contain isolated IEG nucleic acid, substantially pure polypeptides encoded by IEG nucleic acid, and antibodies having specific binding affinity for a polypeptide encoded by IEG nucleic acid. In addition, the invention provides cDNA libraries enriched for IEG cDNAs, isolated nucleic acid derived from such cDNA libraries, and methods for treating conditions related to a deficiency in a neuron's IEG responsiveness to a stimulus.

In one aspect, the invention features an isolated nucleic acid having at least one adenine base, at least one guanine base, at least one cytosine base, and at least one thymine or uracil base. The isolated nucleic acid is at least 12 bases in length, and hybridizes to the sense or antisense strand of a second nucleic acid under hybridization conditions. The second nucleic acid has a sequence as set forth in SEQ ID NO:1, 2, 3, 4, 5, 6, 7, 8, 9, 10, 12, 13, 14, 15, 16, 17, 18, 19, 20, 22, 23, 24, 25, 26, 28, 29, 31, 33, 34, 35, 37, 39, 40, 41, 42, 43, 44, 45, 46, 47, 49, 50, 51, 52, 53, 54, 55, 56, 57, 58, 59, or 60. The hybridization conditions can be moderately or highly stringent hybridization conditions.

In another embodiment, the invention features an isolated nucleic acid having a nucleic acid sequence that encodes an amino acid sequence at least five amino acids in length. The amino acid sequence contains at least three different amino acid residues, and is identical to a contiguous portion of sequence set forth in SEQ ID NO:11, 21, 27, 30, 32, 36, 38, 48, 61, or 62.

Another embodiment of the invention features an isolated nucleic acid having a nucleic acid sequence at least 60 percent identical to the sequence set forth in SEQ ID NO:1, 2, 3, 4, 5, 6, 7, 8, 9, 10, 12, 13, 14, 15, 16, 17, 18, 19, 20, 22, 23, 24, 25, 26, 28, 29, 31, 33, 34, 35, 37, 39, 40, 41, 42, 43, 44, 45, 46, 47, 49, 50, 51, 52, 53, 54, 55, 56, 57, 58, 59, or 60.

Another embodiment of the invention features an isolated nucleic acid having a nucleic acid sequence that encodes an amino acid sequence at least 60 percent identical to the sequence set forth in SEQ ID NO:11, 21, 27, 30, 32, 36, 38, 48, 61, or 62.

Another embodiment of the invention features an isolated nucleic acid having a nucleic acid sequence as set forth in SEQ ID NO:1, 2, 3, 4, 5, 6, 7, 8, 9, 10, 12, 13, 14, 15, 16, 17, 18, 19, 20, 22, 23, 24, 25, 26, 28, 29, 31, 33, 34, 35, 37, 39, 40, 41, 42, 43, 44, 45, 46, 47, 49, 50, 51, 52, 53, 54, 55, 56, 57, 58, 59, or 60.

In another aspect, the invention features a substantially pure polypeptide having an amino acid sequence encoded by a nucleic acid having at least one adenine base, at least one guanine base, at least one cytosine base, and at least one thymine or uracil base. The nucleic acid is at least 12 bases in length, and hybridizes to the sense or antisense strand of a second nucleic acid under hybridization conditions. The second nucleic acid has a sequence as set forth in SEQ ID NO:1, 2, 3, 4, 5, 6, 7, 8, 9, 10, 12, 13, 14, 15, 16, 17, 18, 19, 20, 22, 23, 24, 25, 26, 28, 29, 31, 33, 34, 35, 37, 39, 40, 41, 42, 43, 44, 45, 46, 47, 49, 50, 51, 52, 53, 54, 55, 56, 57, 58, 59, or 60.

In another embodiment, the invention features a substantially pure polypeptide having an amino acid sequence as set forth in SEQ ID NO:11, 21, 27, 30, 32, 36, 38, 48, 61, or 62.

Another embodiment of the invention features a substantially pure polypeptide having an amino acid sequence at least 60 percent identical to the sequence set forth in SEQ ID NO:11, 21, 27, 30, 32, 36, 38, 48, 61, or 62.

Another embodiment of the invention features a substantially pure polypeptide having an amino acid sequence at least five amino acids in length. The amino acid sequence contains at least three different amino acid residues, and is identical to a contiguous stretch of sequence set forth in SEQ ID NO:11, 21, 27, 30, 32, 36, 38, 48, 61, or 62.

Another aspect of the invention features a host cell (e.g., a eukaryotic or prokaryotic cell) containing an isolated nucleic acid having at least one adenine base, at least one guanine base, at least one cytosine base, and at least one thymine or uracil base. The isolated nucleic acid is at least 12 bases in length, and hybridizes to the sense or antisense strand of a second nucleic acid under hybridization conditions. The second nucleic acid has a sequence as set forth in SEQ ID NO:1, 2, 3, 4, 5, 6, 7, 8, 9, 10, 12, 13, 14, 15, 16, 17, 18, 19, 20, 22, 23, 24, 25, 26, 28, 29, 31, 33, 34, 35, 37, 39, 40, 41, 42, 43, 44, 45, 46, 47, 49, 50, 51, 52, 53, 54, 55, 56, 57, 58, 59, or 60.

Another aspect of the invention features an antibody (e.g., a monoclonal or polyclonal antibody) having specific binding affinity for an amino acid sequence encoded by a nucleic acid having at least one adenine base, at least one guanine base, at least one cytosine base, and at least one thymine or uracil base. The nucleic acid is at least 12 bases in length, and hybridizes to the sense or antisense strand of a second nucleic acid under hybridization conditions. The second nucleic acid has a sequence as set forth in SEQ ID NO:1, 2, 3, 4, 5, 6, 7, 8, 9, 10, 12, 13, 14, 15, 16, 17, 18, 19, 20, 22, 23, 24, 25, 26, 28, 29, 31, 33, 34, 35, 37, 39, 40, 41, 42, 43, 44, 45, 46, 47, 49, 50, 51, 52, 53, 54, 55, 56, 57, 58, 59, or 60.

Another aspect of the invention features a cDNA library having a plurality of clones with each clone having a cDNA insert. In addition, at least about 15 percent (e.g., at least about 20 or 25 percent) of the clones have cDNA derived from immediate early genes (e.g., immediate early genes responsive to a maximal electroconvulsive seizure). The cDNA library can be a subtracted cDNA library. For example, the subtracted cDNA library can be the IEG-Reg or IEG-Lg cDNA library.

Another aspect of the invention features an isolated nucleic acid derived from a cDNA library. The cDNA library has a plurality of clones with each clone having a cDNA insert. In addition, at least about 15 percent of the clones have cDNA derived from immediate early genes. The isolated nucleic acid can have a nucleic acid sequence of an immediate early gene.

Another aspect of the invention features a method of obtaining immediate early gene nucleic acid. The method includes providing a cDNA library having a plurality of clones with each clone having a cDNA insert. In addition, at least about 15 percent of the clones have cDNA derived from immediate early genes. The method also includes contacting at least a portion of the cDNA library with a probe containing at least one nucleic acid having a nucleic acid sequence derived from an immediate early gene, and selecting a member of the plurality of clones based on the hybridization of the at least one nucleic acid to the member under hybridization conditions.

Another aspect of the invention features a method of treating an animal (e.g., human) having a deficiency in a neuron's immediate early gene responsiveness to a stimulus. The method includes administering a nucleic acid to the animal such that the effect of the deficiency is minimized. The nucleic acid has at least one adenine base, at least one guanine base, at least one cytosine base, and at least one thymine or uracil base. In addition, the nucleic acid is at least 12 bases in length, and hybridizes to the sense or antisense strand of a second nucleic acid under hybridization conditions. The second nucleic acid has a sequence as set forth in SEQ ID NO:1, 2, 3, 4, 5, 6, 7, 8, 9, 10, 12, 13, 14, 15, 16, 17, 18, 19, 20, 22, 23, 24, 25, 26, 28, 29, 31, 33, 34, 35, 37, 39, 40, 41, 42, 43, 44, 45, 46, 47, 49, 50, 51, 52, 53, 54, 55, 56, 57, 58, 59, or 60. The deficiency can include a reduced level of expression of an immediate early gene. In addition, the stimulus can influence learning or memory. For example, the stimulus can include a maximal electroconvulsive seizure.

In another embodiment, the invention features a method of treating an animal (e.g., human) having a deficiency in a neuron's immediate early gene responsiveness to a stimulus. The method includes administering a therapeutically effective amount of a substantially pure polypeptide to the animal such that the effect of the deficiency is minimized. The polypeptide contains an amino acid sequence encoded by a nucleic acid having at least one adenine base, at least one guanine base, at least one cytosine base, and at least one thymine or uracil base. The nucleic acid is at least 12 bases in length, and hybridizes to the sense or antisense strand of a second nucleic acid under hybridization conditions. The second nucleic acid has a sequence as set forth in SEQ ID NO:1, 2, 3, 4, 5, 6, 7, 8, 9, 10, 12, 13, 14, 15, 16, 17, 18, 19, 20, 22, 23, 24, 25, 26, 28, 29, 31, 33, 34, 35, 37, 39, 40, 41, 42, 43, 44, 45, 46, 47, 49, 50, 51, 52, 53, 54, 55, 56, 57, 58, 59, or 60.

Another embodiment of the invention features a method of treating an animal (e.g., human) having a deficiency in a neuron's immediate early gene responsiveness to a stimulus. The method includes administering an effective amount of cells to the animal such that the effect of the deficiency is minimized. The cells contain a nucleic acid having at least one adenine base, at least one guanine base, at least one cytosine base, and at least one thymine or uracil base. In addition, the nucleic acid is at least 12 bases in length, and hybridizes to the sense or antisense strand of a second nucleic acid under hybridization conditions. The second nucleic acid has a sequence as set forth in SEQ ID NO:1, 2, 3, 4, 5, 6, 7, 8, 9, 10, 12, 13, 14, 15, 16, 17, 18, 19, 20, 22, 23, 24, 25, 26, 28, 29, 31, 33, 34, 35, 37, 39, 40, 41, 42, 43, 44, 45, 46, 47, 49, 50, 51, 52, 53, 54, 55, 56, 57, 58, 59, or 60.

Another embodiment of the invention features a method of treating an animal (e.g., human) having a deficiency in a neuron's immediate early gene responsiveness to a stimulus. The method includes administering a therapeutically effective of antibodies to the animal such that the effect of the deficiency is minimized. The antibodies have specific binding affinity for an amino acid sequence encoded by a nucleic acid having at least one adenine base, at least one guanine base, at least one cytosine base, and at least one thymine or uracil base. The nucleic acid is at least 12 bases in length, and hybridizes to the sense or antisense strand of a second nucleic acid under hybridization conditions. The second nucleic acid has a sequence as set forth in SEQ ID NO:1, 2, 3, 4, 5, 6, 7, 8, 9, 10, 12, 13, 14, 15, 16, 17, 18, 19, 20, 22, 23, 24, 25, 26, 28, 29, 31, 33, 34, 35, 37, 39, 40, 41, 42, 43, 44, 45, 46, 47, 49, 50, 51, 52, 53, 54, 55, 56, 57, 58, 59, or 60. The deficiency can include an elevated level of expression of an immediate early gene.

Another aspect of the invention features a method of identifying a compound that modulates immediate early gene expression. The method includes contacting a test compound with an immediate early gene nucleic acid, and determining whether the test compound effects the expression of the immediate early gene nucleic acid. The presence of an effect indicates that the test compound is a compound that modulates immediate early gene expression. The immediate early gene nucleic acid can contain a nucleic acid sequence as set forth in SEQ ID NO:1, 2, 3, 4, 5, 6, 7, 8, 9, 10, 12, 13, 14, 15, 16, 17, 18, 19, 20, 22, 23, 24, 25, 26, 28, 29, 31, 33, 34, 35, 37, 39, 40, 41, 42, 43, 44, 45, 46, 47, 49, 50, 51, 52, 53, 54, 55, 56, 57, 58, 59, or 60. The effect can be a reduction or increase in the expression of the immediate early gene nucleic acid.

In another embodiment, the invention features a method of identifying a compound that modulates immediate early gene polypeptide activity. The method includes contacting a test compound with an immediate early gene polypeptide, and determining whether the test compound effects the activity of the immediate early gene polypeptide. The presence of an effect indicates that the test compound is a compound that modulates immediate early gene polypeptide activity. The immediate early gene polypeptide can contain an amino acid sequence encoded by a nucleic acid having at least one adenine base, at least one guanine base, at least one cytosine base, and at least one thymine or uracil base. The nucleic acid is at least 12 bases in length, and hybridizes to the sense or antisense strand of a second nucleic acid under hybridization conditions. The second nucleic acid has a sequence as set forth in SEQ ID NO:1, 2, 3, 4, 5, 6, 7, 8, 9, 10, 12, 13, 14, 15, 16, 17, 18, 19, 20, 22, 23, 24, 25, 26, 28, 29, 31, 33, 34, 35, 37, 39, 40, 41, 42, 43, 44, 45, 46, 47, 49, 50, 51, 52, 53, 54, 55, 56, 57, 58, 59, or 60. Alternatively, the immediate early gene polypeptide can contain an amino acid sequence as set forth in SEQ ID NO:11, 21, 27, 30, 32, 36, 38, 48, 61, or 62. The effect can be a reduction or increase in the activity of the immediate early gene polypeptide.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

The present invention provides methods and materials related to IEGs. Specifically, the invention provides isolated IEG nucleic acid, cells that contain isolated IEG nucleic acid, substantially pure polypeptides encoded by IEG nucleic acid, and antibodies having specific binding affinity for a polypeptide encoded by IEG nucleic acid. In addition, the invention provides cDNA libraries enriched for IEG cDNAs, isolated nucleic acid derived from such cDNA libraries, and methods for treating conditions related to a deficiency in a neuron's IEG responsiveness to a stimulus.

The present invention is based on the discovery of nucleic acid clones for many different neuronal IEGs. Specifically, nucleic acid clones for different neuronal IEGs were isolated and identified based on the ability of each IEG to rapidly increase expression upon seizure induction by a maximal electroconvulsive seizure (MECS) method (Cole et al., *J. Neurochem.* 55:1920–1927 (1990)). It is important to note that MECS induction can be considered a model to study long-term plasticity relevant to learning and memory since it is known that a single MBCS can produce extremely robust and long lived potentiation of synaptic contacts in the hippocampus and block spatial learning (Barnes et al., *J. Neurosci.* 14:5793–5806 (1994)). Thus, MECS-responsive IEGs can influence neuronal activities involved in brain functions such as learning and memory. Moreover, the isolation and identification of IEG nucleic acid not only provides research scientists with information about neuronal activity and gene regulation but also provides methods and materials that can be used to manipulate brain function.

Each isolated IEG nucleic acid described herein can be used to produce a polypeptide. In addition, each IEG nucleic acid can be used to identify cells that are responsive to MECS induction. For example, an IEG nucleic acid can be labeled and used as a probe for in situ hybridization analysis. Clearly, having the ability to identify MECS-responsive cells provides one with the ability to isolate or monitor specific brain regions that are involved in learning. Further, any of the isolated partial IEG nucleic acid sequences can be used to obtain a full-length clone that encodes an IEG polypeptide. For example, a fragment from an isolated IEG nucleic acid can be radioactively labeled and used to screen a library such that a full-length clone is obtained.

Cells containing isolated IEG nucleic acid can be used to maintain or propagate the isolated IEG nucleic acid. In addition, such cells can be used to produce large quantities of polypeptides that are encoded by isolated IEG nucleic acid. Further, cells containing isolated IEG nucleic acid can be used to generate virus particles containing the isolated IEG nucleic acid. Such virus particles can be used in vitro or in vivo to provide other cells with the isolated IEG nucleic acid. The polypeptides encoded by IEG nucleic acid can be used as immunogens to produce antibodies. Such antibodies can be used to identify MECS-responsive cells, monitor the level of polypeptide expression following MECS induction, and isolate polypeptides directly from animal tissue.

cDNA libraries enriched for IEG cDNAs can be used to isolate novel IEG cDNA. Clearly, the isolation of novel IEG cDNAs is important to further the understanding of brain function. In addition, isolated nucleic acid derived from such cDNA libraries can be used to produce polypeptides as well as identify cells that are responsive to a stimulus such as MECS induction.

It is important to note that isolated IEG nucleic acid, cells containing isolated IEG nucleic acid, substantially pure IEG polypeptides, and anti-IEG polypeptide antibodies can be used to treat conditions associated with a deficiency in a neuron's ability to express IEGs in response to a stimulus such as MECS. A condition associated with a deficiency in a neuron's IEG responsiveness to a stimulus is any physiological condition characterized as having a lack of a normal level of responsiveness. For example, when a deficiency in a neuron's responsiveness to MECS is characterized as a non- or under-expression of a particular IEG polypeptide by that neuron, the organism having the condition can be treated with isolated IEG nucleic acid, cells containing isolated IEG nucleic acid, or substantially pure IEG polypeptides such that the effect of the deficiency is minimized. Alternatively, when a deficiency in a neuron's responsiveness to MECS is characterized as an over-expression of a particular IEG polypeptide by that neuron, the organism having the condition can be treated with anti-IEG polypeptide antibodies or the anti-sense strand of an isolated IEG nucleic acid such that the effect of the deficiency is minimized.

In addition, isolated IEG nucleic acid, cells containing isolated IEG nucleic acid, substantially pure IEG polypeptides, and anti-IEG polypeptide antibodies can be used to identify pharmaceutical compounds that can be used to treat diseases such as epilepsy, age-dependent memory decline, stroke, and drug addiction. For example, a compound that modulates IEG nucleic acid expression or IEG polypeptide activity can be identified by contacting a test compound with either the IEG nucleic acid or polypeptide, and determining whether the test compound effects expression or activity.

The term "nucleic acid" as used herein encompasses both RNA and DNA, including cDNA, genomic DNA, and synthetic (e.g., chemically synthesized) DNA. The nucleic acid can be double-stranded or single-stranded. Where single-stranded, the nucleic acid can be the sense strand or the antisense strand. In addition, nucleic acid can be circular or linear.

The term "isolated" as used herein with reference to nucleic acid refers to a naturally-occurring nucleic acid that is not immediately contiguous with both of the sequences with which it is immediately contiguous (one on the 5' end and one on the 3' end) in the naturally-occurring genome of the organism from which it is derived. For example, an isolated nucleic acid can be, without limitation, a recombinant DNA molecule of any length, provided one of the nucleic acid sequences normally found immediately flanking that recombinant DNA molecule in a naturally-occurring genome is removed or absent. Thus, an isolated nucleic acid includes, without limitation, a recombinant DNA that exists as a separate molecule (e.g., a cDNA or a genomic DNA fragment produced by PCR or restriction endonuclease treatment) independent of other sequences as well as recombinant DNA that is incorporated into a vector, an autonomously replicating plasmid, a virus (e.g., a retrovirus, adenovirus, or herpes virus), or into the genomic DNA of a prokaryote or eukaryote. In addition, an isolated nucleic acid can include a recombinant DNA molecule that is part of a hybrid or fusion nucleic acid sequence.

The term "isolated" also includes any non-naturally-occurring nucleic acid since non-naturally-occurring nucleic acid sequences are not found in nature and do not have immediately contiguous sequences in a naturally-occurring genome. For example, non-naturally-occurring nucleic acid such as an engineered nucleic acid is considered to be isolated nucleic acid. Engineered nucleic acid can be made using common molecular cloning or chemical nucleic acid synthesis techniques. Isolated non-naturally-occurring nucleic acid can be independent of other sequences, or incorporated into a vector, an autonomously replicating plasmid, a virus (e.g., a retrovirus, adenovirus, or herpes virus), or the genomic DNA of a prokaryote or eukaryote. In addition, a non-naturally-occurring nucleic acid can include, a nucleic acid molecule that is part of a hybrid or fusion nucleic acid sequence.

It will be apparent to those of skill in the art that a nucleic acid existing among hundreds to millions of other nucleic acid molecules within, for example, cDNA or genomic libraries, or gel slices containing a genomic DNA restriction digest is not to be considered an isolated nucleic acid.

Any isolated nucleic acid having a nucleic acid sequence as set forth in SEQ ID NO:1, 2, 3, 4, 5, 6, 7, 8, 9, 10, 12, 13, 14, 15, 16, 17, 18, 19, 20, 22, 23, 24, 25, 26, 28, 29, 31, 33, 34, 35, 37, 39, 40, 41, 42, 43, 44, 45, 46, 47, 49, 50, 51, 52, 53, 54, 55, 56, 57, 58, 59, or 60 is within the scope of the invention. For convenience, these nucleic acid sequences will be referred to collectively as the IEG nucleic acid group. In addition, any isolated nucleic acid having a nucleic acid sequence at least about 60 percent identical (e.g., at least about 65, 70, 75, 80, 85, 90, 95, or 99 percent identical) to a sequence set forth in the IEG nucleic acid group is within the scope of the invention. For the purpose of this invention, the percent identity between a sequence set forth in the IEG nucleic acid group (designated a template sequence) and any other nucleic acid sequence is calculated as follows. First, the two nucleic acid sequences are aligned using the MEGA-LIGN® (DNASTAR, Madison, Wis., 1997) sequence alignment software following the Jotun Heim algorithm with the default settings. Second, the number of matched positions between the two aligned nucleic acid sequences is determined. A matched position refers to a position in which identical bases occur at the same position as aligned by the MEGALIGN® sequence alignment software. Third, the number of matched positions is divided by the total number of bases in the template sequence, and the resulting value multiplied by 100 to obtain the percent identity. If the obtained percent identity is greater than or equal to about 60 percent for a particular nucleic acid sequence, then that particular nucleic acid sequence is a nucleic acid sequence at least about 60 percent identical to a sequence set forth in the IEG nucleic acid group.

Any isolated nucleic acid having a nucleic acid sequence that encodes an amino acid sequence at least about 60 percent identical (e.g., at least about 65, 70, 75, 80, 85, 90, 95, or 99 percent identical) to the sequence set forth in SEQ ID NO:11, 21, 27, 30, 32, 36, 38, 48, 61, or 62 is within the scope of the invention. For convenience, the amino acid sequences set forth in SEQ ID NO:11, 21, 27, 30, 32, 36, 38, 48, 61, and 62 will be referred to collectively as the IEG amino acid group. For the purpose of this invention, the percent identity between a sequence set forth in the IEG amino acid group (designated a template sequence) and any other amino acid sequence is calculated as follows. First, the two amino acid sequences are aligned using the MEGA-LIGN® (DNASTAR, Madison, Wis., 1997) sequence alignment software following the Jotun Heim algorithm with the default settings. Second, the number of matched positions between the two aligned amino acid sequences is determined. A matched position refers to a position in which identical residues occur at the same position as aligned by the MEGALIGN® sequence alignment software. Third, the number of matched positions is divided by the total number of amino acid residues in the template sequence, and the resulting value multiplied by 100 to obtain the percent identity. If the obtained percent identity is greater than or equal to about 60 percent for a particular amino acid sequence, then that particular amino acid sequence is an amino acid sequence at least about 60 percent identical to a sequence set forth in the IEG amino acid group.

Any isolated nucleic acid having a nucleic acid sequence that encodes an amino acid sequence at least five amino acids in length also is within the scope of the invention provided the encoded amino acid sequence has at least three different amino acid residues, and is identical to a contiguous portion of sequence set forth in a sequence within the IEG amino acid group.

Further, any isolated nucleic acid having at least one adenine base, at least one guanine base, at least one cytosine base, and at least one thymine or uracil base is within the scope of the invention provided the isolated nucleic acid is at least about 12 bases in length (e.g., at least about 14, 15, 16, 17, 18, 19, 20, 25, 30, 40, 50, or 60 bases in length), and hybridizes, under hybridization conditions, to the sense or antisense strand of a nucleic acid having a sequence as set forth in the IEG nucleic acid group. The hybridization conditions can be moderately or highly stringent hybridization conditions.

For the purpose of this invention, moderately stringent hybridization conditions mean the hybridization is performed at about 42° C. in a hybridization solution containing 25 mM $KPO_4$ (pH7.4), 5×SSC, 5×Denharts solution, 50 µg/ml denatured, sonicated salmon sperm DNA, 50% formamide, 10% Dextran sulfate, and 1–15 ng/ml probe (>5×$10^7$ cpm/µg), while the washes are performed at about 50° C. with a wash solution containing 2×SSC and 0.1% SDS.

Highly stringent hybridization conditions mean the hybridization is performed at about 42° C. in a hybridization solution containing 25 mM $KPO_4$ (pH7.4), 5×SSC, 5×Denharts solution, 50 µg/ml denatured, sonicated salmon sperm DNA, 50% formamide, 10% Dextran sulfate, and 1–15 ng/ml probe (>5×$10^7$ cpm/µg), while the washes are performed at about 65° C. with a wash solution containing 0.2×SSC and 0.1% SDS.

Nucleic acid within the scope of the invention can be identified and obtained using any method including, without limitation, common molecular cloning and chemical nucleic acid synthesis techniques. For example, PCR can be used to obtain a nucleic acid having a nucleic acid sequence at least about 60 percent identical (e.g., at least about 65, 70, 75, 80, 85, 90, 95, or 99 percent identical) to a sequence set forth in the IEG nucleic acid group. PCR refers to a procedure or technique in which target nucleic acid is amplified in a manner similar to that described in U.S. Pat. No. 4,683,195, and subsequent modifications of the procedure described therein. Generally, sequence information from the ends of the region of interest or beyond are used to design oligonucleotide primers that are identical or similar in sequence to opposite strands of a potential template to be amplified. Using PCR, a nucleic acid sequence can be amplified from RNA or DNA. For example, a nucleic acid sequence can be isolated by PCR amplification from total cellular RNA, total genomic DNA, and cDNA as well as from bacteriophage sequences, plasmid sequences, viral sequences, and the like. When using RNA as a source of template, reverse transcriptase can be used to synthesize complimentary DNA strands.

Nucleic acid within the scope of the invention also can be obtained by mutagenesis. For example, a nucleic acid sequence set forth in the IEG nucleic acid group can be mutated using common molecular cloning techniques (e.g., site-directed mutageneses). Possible mutations include, without limitation, deletions, insertions, and base substitutions, as well as combinations of deletions, insertions, and base substitutions.

In addition, nucleic acid and amino acid databases (e.g., GenBank®) can be used to identify and obtain a nucleic acid within the scope of the invention. For example, any nucleic acid sequence having some homology to a sequence set forth in the IEG nucleic acid group, or any amino acid sequence having some homology to a sequence set forth in the IEG amino acid group can be used as a query to search GenBank®.

Further, nucleic acid hybridization techniques can be used to identify and obtain a nucleic acid within the scope of the invention. Briefly, any nucleic acid having some homology to a sequence set forth in the IEG nucleic acid group, or fragment thereof, can be used as a probe to identify a similar nucleic acid by hybridization under conditions of moderate to high stringency. Such similar nucleic acid then can be isolated, sequenced, and analyzed to determine whether they are within the scope of the invention as described herein.

Hybridization can be done by Southern or Northern analysis to identify a DNA or RNA sequence, respectively, that hybridizes to a probe. The probe can be labeled with a radioisotope such as $^{32}P$, an enzyme, digoxygenin, or by biotinylation. The DNA or RNA to be analyzed can be electrophoretically separated on an agarose or polyacrylamide gel, transferred to nitrocellulose, nylon, or other suitable membrane, and hybridized with the probe using standard techniques well known in the art such as those described in sections 7.39–7.52 of Sambrook et al., (1989) Molecular Cloning, second edition, Cold Spring harbor Laboratory, Plainview, N.Y. Typically, a probe is at least about 20 nucleotides in length. For example, a probe corresponding to a 20 nucleotide sequence set forth in the IEG amino acid group can be used to identify a nucleic acid identical to or similar to a nucleic acid sequence set forth in the IEG nucleic acid group. In addition, probes longer or shorter than 20 nucleotides can be used.

Any cell containing an isolated nucleic acid within the scope of the invention is itself within the scope of the invention. This includes, without limitation, prokaryotic and eukaryotic cells. It is noted that cells containing an isolated nucleic acid of the invention are not required to express the isolated nucleic acid. In addition, the isolated nucleic acid can be integrated into the genome of the cell or maintained in an episomal state. In other words, cells can be stably or transiently transfected with an isolated nucleic acid of the invention.

Any method can be used to introduce an isolated nucleic acid into a cell. In fact, many methods for introducing nucleic acid into a cell, whether in vivo or in vitro, are well known to those skilled in the art. For example, calcium phosphate precipitation, electroporation, heat shock, lipofection, microinjection, and viral-mediated nucleic acid transfer are common methods that can be used to introduce nucleic acid into a cell. In addition, naked DNA can be delivered directly to cells in vivo as describe elsewhere (U.S. Pat. Nos. 5,580,859 and 5,589,466 including continuations thereof). Further, nucleic acid can be introduced into cells by generating transgenic animals.

Transgenic animals can be aquatic animals (such as fish, sharks, dolphin, and the like), farm animals (such as pigs, goats, sheep, cows, horses, rabbits, and the like), rodents (such as rats, guinea pigs, and mice), non-human primates (such as baboon, monkeys, and chimpanzees), and domestic animals (such as dogs and cats). Several techniques known in the art can be used to introduce nucleic acid into animals to produce the founder lines of transgenic animals. Such techniques include, without limitation, pronuclear microinjection (U.S. Pat. No. 4,873,191); retrovirus mediated gene transfer into germ lines (Van der Putten et al., *Proc. Natl. Acad. Sci., USA,* 82:6148–6152 (1985)); gene transfection into embryonic stem cells (Gossler A et al., *Proc Natl Acad Sci USA* 83:9065–9069 (1986)); gene targeting into embryonic stem cells (Thompson et al., *Cell,* 56:313–321 (1989)); nuclear transfer of somatic nuclei (Schnieke AE et al., *Science* 278:2130–2133 (1997)); and electroporation of embryos.

For a review of techniques that can be used to generate and assess transgenic animals, skilled artisans can consult Gordon (*Intl. Rev. Cytol.,* 115:171–229 (1989)), and may obtain additional guidance from, for example: Hogan et al., "Manipulating the Mouse Embryo" Cold Spring Harbor Press, Cold Spring Harbor, N.Y. (1986); Krimpenfort et al., *Bio/Technology,* 9:844–847 (1991); Palmiter et al., *Cell,* 41:343–345 (1985); Kraemer et al., "Genetic Manipulation of the Early Mammalian Embryo" Cold Spring Harbor Press, Cold Spring Harbor, N.Y. (1985); Hammer et al., *Nature,* 315:680–683 (1985); Purscel et al., *Science,* 244:1281–1288 (1986); Wagner et al., U.S. Pat. No. 5,175,385; and Krimpenfort et al., U.S. Pat. No. 5,175,384.

Any method can be used to identify cells that contain an isolated nucleic acid within the scope of the invention. For example, PCR and nucleic acid hybridization techniques such as Northern and Southern analysis can be used. In some cases, immunohistochemistry and biochemical techniques can be used to determine if a cell contains a particular nucleic acid by detecting the expression of a polypeptide encoded by that particular nucleic acid. For example, detection of polypeptide X-immunoreactivity after introduction of an isolated nucleic acid containing a cDNA that encodes polypeptide X into a cell that does not normally express polypeptide X can indicate that that cell not only contains the introduced nucleic acid but also expresses the encoded polypeptide X from that introduced nucleic acid. In this case, the detection of any enzymatic activities of polypeptide X also can indicate that that cell contains the introduced nucleic acid and expresses the encoded polypeptide X from that introduced nucleic acid.

In addition, any method can be used to force a cell to express an encoded amino acid sequence from a nucleic acid. Such methods are well known to those skilled in the art, and include, without limitation, constructing a nucleic acid such that a regulatory element drives the expression of a nucleic acid sequence that encodes a polypeptide. Typically, regulatory elements are DNA sequences that regulate the expression of other DNA sequences at the level of transcription. Such regulatory elements include, without limitation, promoters, enhancers, and the like. Further, any methods can be used to identifying cells that express an amino acid sequence from a nucleic acid. Such methods are well known to those skilled in the art, and include, without limitation, immunocytochemistry, Northern analysis, and RT-PCR.

The term "substantially pure" as used herein with reference to a polypeptide means the polypeptide is substantially free of other polypeptides, lipids, carbohydrates, and nucleic acid with which it is naturally associated. Thus, a substantially pure polypeptide is any polypeptide that is removed from its natural environment and is at least 60 percent free, preferably 75 percent free, and most preferably 90 percent free from other components with which it is naturally associated. Typically, a substantially pure polypeptide will yield a single major band on a non-reducing polyacrylamide gel.

Any substantially pure polypeptide having an amino acid sequence encoded by a nucleic acid within the scope of the invention is itself within the scope of the invention. In addition, any substantially pure polypeptide having an amino acid sequence at least about 60 percent (e.g., at least about 65, 70, 75, 80, 85, 90, 95, or 99 percent) identical to a sequence set forth in the IEG amino acid group is within the scope of the invention. The percent identity between particular amino acid sequences is determined as described herein.

Any method can be used to obtain a substantially pure polypeptide. For example, one skilled in the art can use common polypeptide purification techniques such as affinity chromotography and HPLC as well as polypeptide synthesis techniques. In addition, any material can be used as a source to obtain a substantially pure polypeptide. For example, tissue from wild-type or transgenic animals can be used as a source material. In addition, tissue culture cells engineered to overexpress a particular polypeptide of interest can be used to obtain substantially pure polypeptide. Further, a polypeptide within the scope of the invention can be "engineered" to contain an amino acid sequence that allows the polypeptide to be captured onto an affinity matrix. For example, a tag such as c-myc, hemagglutinin, polyhistidine, or Flag® tag (Kodak) can be used to aid polypeptide purification. Such tags can be inserted anywhere within the polypeptide including at either the carboxyl or amino termini. Other fusions that could be useful include enzymes that aid in the detection of the polypeptide, such as alkaline phosphatase.

The term "antibody" as used herein refers to intact antibodies as well as antibody fragments that retain some ability to selectively bind an epitope. Such fragments include, without limitation, Fab, F(ab')2, and Fv antibody fragments. The term "epitope" refers to an antigenic determinant on an antigen to which the paratope of an antibody binds. Epitopic determinants usually consist of chemically active surface groupings of molecules (e.g., amino acid or sugar residues) and usually have specific three dimensional structural characteristics as well as specific charge characteristics.

Any antibody having specific binding affinity for an amino acid sequence encoded by a nucleic acid within the scope of the invention is itself within the scope of the invention. Thus, any monoclonal or polyclonal antibody having specific binding affinity for an amino acid sequence set forth in the IEG amino acid group is within the scope of the invention. Such antibodies can be used in immunoassays in liquid phase or bound to a solid phase. For example, the antibodies of the invention can be used in competitive and non-competitive immunoassays in either a direct or indirect format. Examples of such immunoassays include the radioimmunoassay (RIA) and the sandwich (immunometric) assay.

Antibodies within the scope of the invention can be prepared using any method. For example, any substantially pure polypeptide provided herein, or fragment thereof, can be used as an immunogen to elicit an immune response in an animal such that specific antibodies are produced. Thus, an intact full-length polypeptide or fragments containing small peptides can be used as an immunizing antigen. In addition, the immunogen used to immunize an animal can be chemically synthesized or derived from translated cDNA. Further, the immunogen can be conjugated to a carrier polypeptide, if desired. Commonly used carriers that are chemically coupled to an immunizing polypeptide include, without limitation, keyhole limpet hemocyanin (KLH), thyroglobulin, bovine serum albumin (BSA), and tetanus toxoid.

The preparation of polyclonal antibodies is well-known to those skilled in the art. See, e.g., Green et al., *Production of Polyclonal Antisera,* in IMMUNOCHEMICAL PROTOCOLS (Manson, ed.), pages 1–5 (Humana Press 1992) and Coligan et al., *Production of Polyclonal Antisera in Rabbits, Rats, Mice and Hamsters,* in CURRENT PROTOCOLS IN IMMUNOLOGY, section 2.4.1 (1992). In addition, those of skill in the art will know of various techniques common in the immunology arts for purification and concentration of polyclonal antibodies, as well as monoclonal antibodies (Coligan, et al., Unit 9, Current Protocols in Immunology, Wiley Interscience, 1994).

The preparation of monoclonal antibodies also is well-known to those skilled in the art. See, e.g., Kohler & Milstein, *Nature* 256:495 (1975); Coligan et al., sections 2.5.1–2.6.7; and Harlow et al., ANTIBODIES: A LABORATORY MANUAL, page 726 (Cold Spring Harbor Pub. 1988). Briefly, monoclonal antibodies can be obtained by injecting mice with a composition comprising an antigen, verifying the presence of antibody production by analyzing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan et al., sections 2.7.1–2.7.12 and sections 2.9.1–2.9.3; Barnes et al., *Purification of Immunoglobulin G* (IgG), in METHODS IN MOLECULAR BIOLOGY, VOL. 10, pages 79–104 (Humana Press 1992).

In addition, methods of in vitro and in vivo multiplication of monoclonal antibodies is well-known to those skilled in the art. Multiplication in vitro can be carried out in suitable culture media such as Dulbecco's Modified Eagle Medium or RPMI 1640 medium, optionally replenished by mammalian serum such as fetal calf serum, or trace elements and growth-sustaining supplements such as normal mouse peritoneal exudate cells, spleen cells, and bone marrow macrophages. Production in vitro provides relatively pure antibody preparations and allows scale-up to yield large amounts of the desired antibodies. Large scale hybridoma cultivation can be carried out by homogenous suspension culture in an airlift reactor, in a continuous stirrer reactor, or in immobilized or entrapped cell culture. Multiplication in vivo may be carried out by injecting cell clones into mammals histocompatible with the parent cells (e.g., osyngeneic mice) to cause growth of antibody-producing tumors. Optionally, the animals are primed with a hydrocarbon, especially oils such as pristane (tetramethylpentadecane) prior to injection. After one to three weeks, the desired monoclonal antibody is recovered from the body fluid of the animal.

The antibodies within the scope of the invention also can be made using non-human primates. General techniques for raising therapeutically useful antibodies in baboons can be found, for example, in Goldenberg et al., International Patent Publication WO 91/11465 (1991) and Losman et al., Int. J. Cancer 46:310 (1990).

Alternatively, the antibodies can be "humanized" monoclonal antibodies. Humanized monoclonal antibodies are produced by transferring mouse complementarity determining regions (CDRs) from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions when treating humans. General techniques for cloning murine immunoglobulin variable domains are described, for example, by Orlandi et al., Proc. Nat'l. Acad. Sci. USA 86:3833 (1989). Techniques for producing humanized monoclonal antibodies are described, for example, by Jones et al., Nature 321:522 (1986); Riechmann et al., Nature 332:323 (1988); Verhoeyen et al., Science 239:1534 (1988); Carter et al., Proc. Nat'l. Acad. Sci. USA 89:4285 (1992); Sandhu, Crit. Rev. Biotech. 12:437 (1992); and Singer et al., J. Immunol. 150:2844 (1993).

Antibodies of the present invention also may be derived from human antibody fragments isolated from a combinatorial immunoglobulin library. See, for example, Barbas et al., METHODS: A COMPANION TO METHODS IN ENZYMOLOGY, VOL. 2, page 119 (1991) and Winter et al., Ann. Rev. Immunol. 12: 433 (1994). Cloning and expression vectors that are useful for producing a human immunoglobulin phage library can be obtained, for example, from STRATAGENE Cloning Systems (La Jolla, Calif.).

In addition, antibodies of the present invention may be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens and can be used to produce human antibody-secreting hybridomas. Methods for obtaining human antibodies from transgenic mice are described by Green et al., Nature Genet. 7:13 (1994); Lonberg et al., Nature 368:856 (1994); and Taylor et al., Int. Immunol. 6:579 (1994).

Antibody fragments of the present invention can be prepared by proteolytic hydrolysis of an intact antibody or by the expression of a nucleic acid encoding the fragment. Antibody fragments can be obtained by pepsin or papain digestion of intact antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg (U.S. Pat. Nos. 4,036,945 and 4,331,647). See also Nisonhoff et al., Arch. Biochem. Biophys. 89:230 (1960); Porter, Biochem. J. 73:119 (1959); Edelman et al., METHODS IN ENZYMOLOGY, VOL. 1, page 422 (Academic Press 1967); and Coligan et al. at sections 2.8.1–2.8.10 and 2.10.1–2.10.4.

Other methods of cleaving antibodies, such as separation of heavy chains to form monovalent light-heavy chain fragments, further cleavage of fragments, or other enzymatic, chemical, or genetic techniques may also be used provided the fragments retain some ability to selectively bind its epitope.

For example, Fv fragments comprise an association of $V_H$ and $V_L$ chains. This association may be noncovalent, as described in Inbar et al., Proc. Nat'l. Acad. Sci. USA 69:2659 (1972). Alternatively, the variable chains can be linked by an intermolecular disulfide bond or cross-linked by chemicals such as glutaraldehyde. See, e.g., Sandhu, supra. Preferably, the Fv fragments comprise $V_H$ and $V_L$ chains connected by a peptide linker. These single-chain antigen binding polypeptides (sFv) are prepared by constructing a nucleic acid construct encoding the $V_H$ and $V_L$ domains connected by an oligonucleotide. This nucleic acid construct is inserted into an expression vector, which is subsequently introduced into a host cell such as E. coli. The recombinant host cells synthesize a single polypeptide chain with a linker peptide bridging the two V domains. Methods for producing sFvs are described, for example, by Whitlow et al., METHODS: A COMPANION TO METHODS IN ENZYMOLOGY, VOL. 2, page 97 (1991); Bird et al., Science 242:423–426 (1988); Ladner et al., U.S. Pat. No. 4,946,778; Pack et al., Bio/Technology 11:1271–77 (1993); and Sandhu, supra.

Another form of an antibody fragment is a peptide coding for a single CDR. CDR peptides ("minimal recognition units") can be obtained by constructing nucleic acid constructs that encode the CDR of an antibody of interest. Such constructs are prepared, for example, by using PCR to synthesize the variable region from RNA of antibody-producing cells. See, e.g., Larrick et al., METHODS: A COMPANION TO METHODS IN ENZYMOLOGY, VOL. 2, page 106 (1991).

It is also possible to use anti-idiotype technology to produce monoclonal antibodies that mimic an epitope. For example, an anti-idiotypic monoclonal antibody made to a first monoclonal antibody will have a binding domain in the hypervariable region that is the "image" of the epitope bound by the first monoclonal antibody. Such anti-idiotypic monoclonal antibodies can be used to inhibit the activity of the polypeptide containing the original epitope.

The invention also provides cDNA libraries enriched for IEGs. As described herein, such cDNA libraries contain an increased frequency of cDNAs derived from IEGs. Specifically, about 15 percent (e.g., about 20 or 25 percent) of the cDNA clones within the cDNA libraries provided herein are derived from IEGs.

A cDNA library within the scope of the invention can be prepared from any tissue containing cells that express an IEG (e.g., hippocampus tissue). Again, an IEG is a gene whose expression is rapidly increased immediately following a stimulus. The stimulus can be electrical or chemical in nature. For example, cells can be treated with electric shock or chemicals such as kainate. Briefly, cDNA libraries are prepared from the hippocampus of control animals (e.g., rats) as well as from animals that receive a stimulus (e.g., multiple MECS) using, for example, a phage vector lambda ZAP II (Stratagene). A subtracted library is then prepared using in vitro mRNA prepared from a control library and subsequent solution phase hybridization with cDNA prepared from a stimulated library. The control in vitro mRNA can be tagged with biotin to permit its removal from solution using avidin beads (Lanahan et al., Mol. Cell. Biol. 12:3919–3929 (1992)). cDNA that remains after removal of mRNA/cDNA hybrids can be recloned into, for example, a lambda ZAPII phage vector. Several rounds of subtraction (e.g., two, three, four, or five rounds) can be used to increase the frequency of IEGs. The subtracted library then can be plated and duplicate phage lifts screened with a radiolabeled cDNA probe. Any probe can be used provided it contains at least one nucleic acid sequence derived from an IEG. For example, a probe can be prepared from mRNA obtained from the hippocampus of a stimulated animal. In addition, the mRNA used to make a probe can be subjected to subtractive hybridization such that IEG sequences are enriched. In general, conventional cDNA libraries contain IEGs at a frequency of <1:30,000 cDNAs. For the cDNA libraries enriched for IEGs, however, about 1 in 5 genes can be induced by a stimulus such as MECS. This represents an about 1000 to 10,000 fold enrichment in brain IEGs.

An animal (e.g., human) having a deficiency in a neuron's IEG responsiveness to a stimulus (e.g., a stimulus that influences learning or memory) can be treated using the methods and materials described herein. A stimulus that influences learning or memory can be a multiple MECS treatment. A deficiency in a neuron's IEG responsiveness to a stimulus means the level of IEG responsiveness is not normal. Such deficiencies can be identified by stimulating a sample of cells and measuring the levels of IEG expression. If the levels are not similar to the levels normally observed in a similar tissue sample, then there is a deficiency. It is noted that increased IEG expression as well as decreased IEG expression can be classified as a deficiency provided the levels are not normal.

A deficiency in a neuron's IEG responsiveness to a stimulus can be treated by administering a nucleic acid of the invention to the animal such that the effect of the deficiency is minimized. The administration can be an in vivo, in vitro, or ex vivo administration as described herein. For example, an in vivo administration can involve administering a viral vector to the hippocampal region of an animal, while an ex vivo administration can involve extracting cells from an animal, transfecting the cells with the nucleic acid in tissue culture, and then introducing the transfected cells back into the same animal.

In addition, a deficiency in a neuron's IEG responsiveness to a stimulus can be treated by administering a therapeutically effective amount cells containing isolated IEG nucleic acid, substantially pure IEG polypeptides, anti-IEG polypeptide antibodies, or combinations thereof. A therapeutically effective amount is any amount that minimizes the effect of the deficiency while not causing significant toxicity to the animal. Such an amount can be determined by assessing the clinical symptoms associated with the deficiency before and after administering a fixed amount of cells, polypeptides, or antibodies. In addition, the effective amount administered to an animal can be adjusted according to the animal's response and desired outcomes. Significant toxicity can vary for each particular patient and depends on multiple factors including, without limitation, the patient's physical and mental state, age, and tolerance to pain. The cells, polypeptides, or antibodies can be administered to any part of the animal's body including, without limitation, brain, spinal cord, bloodstream, muscle tissue, skin, peritoneal cavity, and the like. Thus, these therapeutic agents can be administered by injection (e.g., intravenous, intraperitoneal, intramuscular, subcutaneous, intracavity, or transdermal injection) or by gradual perfusion over time.

Preparations for administration can include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Other vehicles for adminstration include sodium chloride solution, Ringer's dextrose, dextrose and sodium chloride, lactated Ringer's intravenous vehicles containing fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Further, a deficiency in a neuron's IEG responsiveness to a stimulus can be treated by administering a therapeutically effective amount of a compound that directly interferes with the translation of IEG nucleic acid. For example, antisense nucleic acid or ribozymes could be used to bind to IEG mRNA or to cleave it. Antisense RNA or DNA molecules bind specifically with a targeted RNA message, interrupting the expression of the mRNA product. The antisense binds to the messenger RNA forming a double stranded molecule that cannot be translated by the cell. Typically, an antisense oligonucleotides is about 15–25 nucleotides in length. In addition, chemically reactive groups, such as iron-linked ethylenediaminetetraacetic acid (EDTA-Fe), can be attached to an antisense oligonucleotide, causing cleavage of the mRNA at the site of hybridization. These and other uses of antisense methods to inhibit the translation of nucleic acid are well known in the art (Marcus-Sakura, Anal. Biochem., 172:289 (1988)).

An oligonucleotide also can be used to stall transcription winding around double-helical DNA and forming a three-strand helix (Maher, et al., Antisense Res. and Dev., 1:227 (1991) and Helene, Anticancer Drug Design, 6:569 (1991)).

Ribozymes are RNA molecules possessing the ability to specifically cleave other single-stranded RNA in a manner analogous to DNA restriction endonucleases. By modifying nucleic acid sequences that encode ribozymes, it is possible to engineer molecules that recognize specific nucleotide sequences in an RNA molecule and cleave it (Cech, J. Amer. Med. Assn., 260:3030 (1988)). There are two basic types of ribozymes namely, tetrahymena-type (Hasselhoff, Nature, 334:585 (1988)) and "hammerhead"-type. Tetrahymena-type ribozymes recognize sequences that are four bases in length, while "hammerhead"-type ribozymes recognize sequences 11–18 bases in length. The longer the recognition sequence, the greater the likelihood that the sequence will occur exclusively in the target mRNA species. Consequently, "hammerhead"-type ribozymes are preferable to tetrahymena-type ribozymes for inactivating a specific mRNA species. In addition, 18-based recognition sequences are preferable to shorter recognition sequences. These and other uses of antisense methods to inhibit the in vivo translation of nucleic acid are well known in the art (DeMesmaeker et al., *Curr. Opin. Struct. Biol.* 5:343–355 (1995); Gewirtz et al., *Proc. Nat'l. Acad. Sci. U.S.A.,* 93:3161–3163 (1996); and Stein, *Chem. Biol.* 3:319–323 (1996)).

Delivery of nucleic acid, antisense, triplex agents, and ribozymes can be achieved using a recombinant expression vector such as a chimeric virus or a colloidal dispersion system. Various viral vectors that can be utilized for gene therapy include adenoviruses, herpesviruses, vaccinia viruses, and retroviruses. A retroviral vector can be a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. In addition, a nucleic acid sequence of interest along with another nucleic acid sequence that encodes a ligand for a receptor on a specific target cell can be inserted into a viral vector to produce a vector that is target specific. For example, retroviral vectors can be made target specific by inserting a nucleic acid sequence that encodes an antibody that binds a specific target antigen. Those of skill in the art can readily ascertain without undue experimentation specific nucleic acid sequences that can be inserted into a retroviral genome to allow target specific delivery of the retroviral vector containing the nucleic acid of the invention.

A colloidal dispersion system can be used to target the delivery of the nucleic acid of the invention. Colloidal dispersion systems include macromolecule complexes, nanocapsules, microspheres, beads, and lipid-based systems including oil-in-water emulsions, micelles, mixed micelles, and liposomes. Liposomes are artificial membrane vesicles that are useful as delivery vehicles in vitro and in vivo. It has been shown that large unilamellar vesicles (LUV) that range in size from 0.2–4.0 µm can encapsulate a substantial percentage of an aqueous buffer containing large macromolecules. Thus, nucleic acid, intact virions, polypeptides, and antibodies can be encapsulated within the aqueous interior and be delivered to cells in a biologically active form (Fraley et al., *Trends Biochem. Sci.,* 6:77 (1981)). In addition to mammalian cells, liposomes have been used to deliver nucleic acid to plants, yeast, and bacteria. In order for a liposome to be an efficient nucleic acid transfer vehicle, the following characteristics should be present: (1) encapsulation of the nucleic acid of interest at high efficiency while not compromising its biological activity; (2) preferential and substantial binding to a target cell in comparison to non-target cells; (3) delivery of the aqueous contents of the vesicle to the target cell cytoplasm at high efficiency; and (4) accurate and effective expression of the nucleic acid (Mannino et al., *Biotechniques,* 6:682 (1988).

The composition of a liposome is usually a combination of phospholipids, particularly high-phase-transition-temperature phospholipids, usually in combination with steroids, especially cholesterol. Other phospholipids or other lipids also can be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14–18 carbon atoms, particularly from 16–18 carbon atoms, and is saturated. Illustrative phospholipids include egg phosphatidylcholine, dipalmitoylphosphatidylcholine, and distearoylphosphatidylcholine.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. In general, the compounds bound to the surface of the targeted delivery system will be ligands and receptors that allow the targeted delivery system to find and "home in" on the desired cells. A ligand may be any compound of interest that will bind to another compound, such as a receptor or antibody.

Compounds that modulate IEG expression can be identified by contacting a test compound with an IEG nucleic acid, and determining whether the test compound effects expression. Likewise, compounds that modulate IEG polypeptide activity can be identified by contacting a test compound with an IEG polypeptide, and determining whether the test compound effects polypeptide activity. Contacting includes in solution and in solid phase, or in a cell. Any type of compound can be used as a test compound including, without limitation, peptides, peptidomimetics, polypeptides, chemical compounds, and biologic agents. In addition, the test compound can be a combinatorial library for screening a plurality of compounds. Compounds identified using the method of the invention can be further evaluated, detected, cloned, sequenced, and the like, either in solution or after binding to a solid support, by any method usually applied to the detection of a specific DNA sequence such as PCR, oligomer restriction (Saiki, et al., *Bio/Technology,* 3:1008–1012, 1985), allele-specific oligonucleotide (ASO) probe analysis (Conner, et al., *Proc. Nat'l. Acad. Sci. USA,* 80:278 (1983), oligonucleotide ligation assays (OLAs; Landegren, et al., *Science,* 241:1077 (1988), and the like.

The invention will be further described in the following examples, which do not limit the scope of the invention described in the claims.

EXAMPLES

Example 1

Construction of Subtracted cDNA Libraries

The mRNA used to prepare the cDNA libraries was obtained from the hippocampus of adult rats (male or female). Briefly, the hippocampus was dissected from naive or stimulated rats, and rapidly frozen in liquid nitrogen. The stimulation protocol used to stimulate the rats was as follows. Rats were injected intraperitoneally with 50 mg of the protein synthesis inhibitor cycloheximide (50 mg/ml stock in 50% ethanol) per kilogram of body weight 15 minutes prior to initiating repetitions of maximal electroconvulsive seizure (MECS). MECS was induced by passage of a constant current signal by means of an ECT unit (Ugo, Basil). The current signal lasted one second with a frequency of 100 Hz. Each pulse lasted 0.5 milliseconds, and the current was 90 milliamperes. This stimulus caused brief loss of consciousness and a tonic-clonic seizure lasting 30 seconds to one minute. MECS was administered about every 15 minutes for a total of 13 administrations over the course of 2.5 to 3 hours. Thirty (30) minutes after the last MECS, the rats were sacrificed by decapitation.

To collect total RNA, the tissue was homogenized in 4M guanidinium thiocynate using a polytron and then centrifuged through a CsCl cushion. To isolate polyA$^+$ RNA, the resulting total RNA was chromatographed on oligo(dT) columns using a commercial oligo(dT) resin and purification protocol (Fastback, Invitrogen). About 50 naive (control) and 50 stimulated rats were used to generate the polyA$^+$ mRNA needed to make the cDNA libraries and perform the Northern blot analysis.

A nonsubtracted cDNA library was made using polyA$^+$ RNA isolated from rats subjected to MECS. Briefly, cDNA was synthesized and cloned directionally into the Lambda ZAP vector yielding a library containing 3.6×10$^6$ recombinants. This library was designated the 3 hr MECS/CHX library. Differential screening of the 3 hr MECS/CHX library with control and stimulated rat hippocampal cDNA probes yielded several novel IEGs. Analysis of these IEGs revealed that they were relatively abundant.

The 3 hr MECS/CHX library was used as starting material for preparing a subtracted cDNA library highly enriched for IEGs. A subtracted cDNA library highly enriched for IEGs can allow for the detection of lower abundance novel IEGs. To make a subtracted cDNA library, DNA template was prepared from the 3 hr MECS/CHX library as follows.

The 3 hr MECS/CHX library was amplified and plated on 15 cm NZCYM agarose plates at a density of about 50,000 phage/plate. A total of 1.85×10$^6$ phage were plated on a total of 37 plates. The plates were overlaid with Suspension Media (SM) and the phage particles eluted by swirling at 4° C. overnight. The lysate was collected, and chloroform added to a final concentration of 5%. The lysate was clarified by centrifugation, and the phage containing supernatant collected and stored at 4° C. A 300 ml aliquot of the lysate was treated with RNaseA (final concentration of 1 μg/μl) and DNase I (final concentration of 1 μg/μl) for three hours at 37° C. Polyethylene glycol (PEG 6000) was added to a concentration of 10%, and NaCl added to a concentration of 1 M. After mixing well, the lysate was stored at 4° C. overnight to allow phage particles to precipitate. Phage particles were pelleted by centrifugation, resuspended in 20 ml of SM, and stored at 4° C. Phage particles were lysed by adding EDTA to a concentration of 10 mM and SDS to a concentration of 0.2% followed by a 20 minute incubation at 68° C. Polypeptides were removed by two extractions with phenol/chloroform/isoamyl alcohol (50:48:2) followed by two extractions with chloroform/isoamyl alcohol (24:1). The phage DNA contained within 40 ml of lysate was precipitated by adding 1/10th volume of 3M NaOAc (pH 5.2) followed by the addition of 2 volumes of 100% ethanol. After mixing, the solution was incubated at −20° C. overnight. DNA was pelleted by centrifugation, resuspended in 10 mM Tris, 1 mM EDTA pH 7.5 (TE), and reprecipitated overnight. After this second precipitation, the DNA was pelleted by centrifugation and resuspended in 12 ml of 10 mM Tris (pH 7.5), 5 mM EDTA, 300 mm NaCl. To remove residual RNA, RNase A (final concentration of 50 μg/ml) was added followed by incubation at 37° C. for 1 hour. To remove RNase A, SDS (final concentration of 0.5%) and then Proteinase K (final concentration of 50 μg/ml) was added followed incubation at 37° C. for 1 hour. The DNA lysate was extracted twice with phenol/chloroform/isoamyl alcohol (50:48:2) followed by one extraction with chloroform/isoamyl alcohol (24:1). After this extraction, the DNA lysate was dialyzed against 12 liters of TE for 2 days at 4° C. The 300 ml aliquot of phage lysate yielded 7254 μg of phage DNA. This phage DNA was then used to prepare in vitro polyA$^+$ RNA (cRNA).

To prepare in vitro cRNA, the phage DNA template was linearized at the 3' end of the cDNA insert using the restriction enzyme XhoI. Briefly, 1 mg of phage DNA was digested with 1000 U of XhoI for three hours at 37° C. After the three hour incubation, an additional 1000 U of XhoI was added and the 37° C. incubation continued an additional three hours. XhoI was removed by adding SDS to 0.5% and Proteinase K to 50 μg/ml followed by incubation at 37° C. for one hour. Polypeptides were removed by three extractions with phenol/chloroform/isoamyl alcohol (50:48:2) followed by one extraction with chloroform/isoamyl alcohol (24:1). The DNA was precipitated with 1/10th volume 3M NaOAc (pH 5.2) and 2 volumes 100% ethanol. The DNA was pelleted by centrifugation and resuspended in 500 μl TE (1.58 mg/ml final DNA concentration).

This linearized DNA was used as template to prepare in vitro cRNA from the sense strand of the cDNA inserts. This cRNA is representative of the initial in vivo population of RNA in the MECS/cycloheximide treated rat hippocampus. Forty (40) μg of DNA template was incubated with 40 mM Tris (pH 7.5), 6 mM MgCl$_2$, 2 mM spermidine, 10 mM NaCl, 10 mM DTT, 1 U/μl RNasin, 500 μM ATP, 500 μM CTP, 500 μM GTP, 500 μM UTP, and 2 U/μl T3 RNA polymerase in a final volume of 300 μl for two hours at 40° C. After two hours, an additional 2 U/μl of T3 RNA polymerase was added, and the reaction incubated for an additional two hours at 37° C. for a total time of four hours. The DNA template was removed by adding DNaseI (2 U/μg of template) and incubating the mixture at 37° C. for an hour. Polypeptides were removed by two extractions with phenol/chloroform/isoamyl alcohol (50:48:2) followed by one extraction with chloroform/isoamyl alcohol (24:1). The cRNA was precipitated at 20° C. with one half volume 7.5 M NH$_4$OAc and 2 volumes 100% ethanol. The cRNA was pelleted and resuspended in TE. The cRNA was chromatographed on sephadex G-50 columns (NICK columns; Pharmacia) to remove free nucleotides and the concentration of cRNA determined by UV absorbance at 260 A. Thirty (30) μg of DNA template yielded 68.6 μg of cRNA. The cRNA was either stored frozen at −20° C. or precipitated with 1/10th volume 2 M KOAc (pH 5) and 2 volumes 100% ethanol. The 68.6 μg of cRNA was further purified using oligo(dT) column chromatography to select polyA$^+$ cRNA. The cRNA was bound to oligo(dT) under high salt conditions, rinsed with low salt conditions, and eluted with TE (pH 7.5). This eluted cRNA was again passed over an oligo(dT) column under high salt conditions, rinsed with low salt conditions, and the polyA$^+$ cRNA eluted with TE (pH 7.5). The two passes on oligo(dT) cellulose yielded 34.2 μg of polyA$^+$ cRNA. This polyA$^+$ cRNA was then used as template for synthesis of first strand cDNA that was then subtracted against control brain and liver polyA$^+$ RNA.

Two cDNA synthesis reactions were performed to prepare first strand cDNA from the polyA$^+$ cRNA. One involved using 2 μg of cRNA with a small amount of $^{32}$P-dCTP to allow for the analysis of subtraction efficiency, and the other involved using 5 μg of cRNA with no radioactive dNTPs. The radioactive cDNA synthesis reaction was as follows. First, 2 μl cRNA (1 μg/μl in TE), 1 μl Xho(dT) primer (1.4 μg/μl), and 8 μl water was combined, and the mixture was incubated at 70° C. for ten minutes, quickly spun, and placed on ice. Second, 1 μl RNasin (40 U/μl), 5 μl 5×Reaction Buffer (BRL), 2.5 μl 0.1M DTT, 1.5 μl dNTP mix, and 2 μl $^{32}$P dCTP (3000 Ci/mmole) was added, and the mixture was incubated at room temperature for ten minutes. The dNTP mix contained 10 mM of each dATP, dGTP, and dTTP as well as 5 mM of methyl dCTP. After incubation, 2 µl of Superscript/MMLV RT mix (1:1) was added, and the mixture (25 µl total volume) was incubated at room temperature for five minutes followed by a 90 minute incubation at 40° C. The nonradioactive cDNA synthesis reaction was as follows. First, 5 µl cRNA (1 µg/µl in TE), 2 µl Xho(dT) primer (1.4 µg/µl), and 3 µl water was combined, and the mixture was incubated at 70° C. for ten minutes, quickly spun, and placed on ice. Second, 1 µl RNasin (40 U /µl), 5 µl 5×Reaction Buffer (BRL), 2.5 µl 0.1M DTT, and 1.5 µl dNTP mix was added, and the mixture was incubated at room temperature for ten minutes. After incubation, 5 µl of Superscript/MMLV RT mix (1:1) was added, and the mixture (25 µl total volume) was incubated at room temperature for five minutes followed by a 90 minute incubation at 40° C.

After completion, 3.2 µl of 0.5 M EDTA (pH 8.0) was added to the radioactive reaction, and then the radioactive and nonradioactive reactions were combined. For subtractive hybridizations, it was necessary to remove the cRNA template by alkaline hydrolysis. This was done by adding 25 µl of TE (pH 7.5) and 5.8 µl of 2 M NaOH. This resulted in a 20 mM final concentration of EDTA and a 138 mM final concentration of NaOH. The mixture was heated for 30 minutes at 68 to 70° C., and then 12.2 µl of 1 M Tris (pH 7.5) and 5.8 µl of 2 N HCl was added to neutralize the reaction. The final volume was 100 µl of which 2 µl was removed and counted to determine the percent incorporation of $^{32}$P-dCTP into cDNA. This analysis revealed that 7000 ng of cRNA was converted to 2598 ng of first strand cDNA. This first strand cDNA was subtracted against adult rat brain and liver polyA$^+$ RNA.

For the subtractive hybridizations, the first strand cDNA was chromatographed on a sephadex G-50 column (NICK, Pharmacia) to remove unincorporated dNTPs, especially the unincorporated $^{32}$P-dCTP in order to allow the efficiency of subtraction to be followed. After the cDNA was eluted from the NICK column, it was mixed with 60 µg of adult rat brain polyA$^+$ RNA that was coupled to biotin (2×Bio RNA). The cDNA and polyA$^+$ RNA mixture was precipitated by adding ¹⁄₁₀th volume 3M NaOAc (pH 5.2) and 2 volumes 100% ethanol. This mixture then was pelleted and resuspended in 20 µl TE (pH 7.5) and 20 µl 2×Subtraction Hybridization Buffer (100 mM Hepes (pH 7.6), 0.4% SDS, 4 mM EDTA, 1 M NaCl). The resuspended cDNA and polyA$^+$ RNA mixture was then incubated at 95 ° C. for two minutes, quickly spun, and submerged in a 60° C. water bath for 48 hours to allow hybrids to form between the cDNA and biotinylated polyA$^+$ RNA (BioRNA).

The cDNA/BioRNA complexes were removed as follows. First, 40 µl 1×Subtraction Hybridization Buffer lacking SDS and 20 µl Strepavidin (1 mg/ml) was added, and the resulting mixture incubated at room temperature for ten minutes. After incubation, the cDNA/BioRNA complexes were removed by extraction with phenol/chloroform/isoamyl alcohol. The phenol phase was back-extracted with 1×Subtraction Hybridization Buffer lacking SDS, and the aqueous phases pooled. Once pooled, 20 µl Strepavidin (1 mg/ml) was added, and the resulting mixture incubated at room temperature for ten minutes. After incubation, remaining cDNA/BioRNA complexes were removed by extraction with phenol/chloroform/isoamyl alcohol. The phenol phase was back-extracted with 1×Subtraction Hybridization Buffer lacking SDS, and the aqueous phases pooled. The pooled aqueous phases (about 400 µl) were extracted with chloroform/isoamyl alcohol. At this point, an aliquot of the aqueous phase was counted to determine the amount of cDNA remaining. Results revealed that 78% of the starting cDNA was removed with 22% remaining (572 ng).

To perform a second round of subtraction, the aqueous phase (about 400 µl) containing the non-hybridizing first strand cDNA was mixed with 30 µg of adult rat brain polyA$^+$ RNA coupled to biotin and 30 µg of adult rat liver polyA$^+$ RNA coupled to biotin. The cDNA and biotinylated polyA$^+$ RNA was co-precipitated and hybridized as described for the first round. In addition, the cDNA/BioRNA complexes were removed as described above, and the percentage of non-hybridizing cDNA remaining was determined. Results revealed that two rounds of subtraction removed 87.5% of the starting cDNA with 12.5% of the starting cDNA remaining.

A third round of subtraction similar to the second round was performed using the remaining cDNA. Analysis of the remaining cDNA revealed that the three rounds of subtraction had removed 90% of the starting cDNA leaving 10% of the starting cDNA (255 ng).

The remaining single stranded cDNA was used to synthesize double stranded cDNA for the subtracted cDNA library. First, the single stranded cDNA (300 µl) was alkali treated to remove any remaining RNA as follows. The final concentration of EDTA was adjusted to 20 mM by addition of 13 µl of 0.5M EDTA, and then 20 µl of 2M NaOH (120 mM final concentration) was added. This mixture was incubated at 68° C. for 30 minutes and then neutralized by adding 40 µl 1 M Tris (pH 7.5) and 20 µl 2 N HCl. The cDNA was precipitated by adding 10 µl glycogen (10 mg/ml), ¹⁄₁₀th volume 3M NaOAc (pH 5.2), and 2 volumes ethanol. The cDNA then was pelleted, resuspended in 100 µl of TE (pH 7.5), and purified on a sephadex G-50 column (NICK, Pharmacia). The purified cDNA was re-precipitated using glycogen, pelleted, and resuspended in TE (pH 7.5) as described. Second, 50 µl resuspended cDNA (single stranded, subtracted cDNA), 20 µl 5×Sequenase Buffer, and 13 µl water was combined, and the mixture incubated at 65° C. for five minutes, 37° C. for ten minutes, and room temperature for 30 minutes. After incubation, 5 µl dNTP mix, 5 µl 0.1 M DTT, 2 µl Sequenase (13 U/µl), and 2 µl Klenow (5 U/µl) was added, and the mixture (100 µl final volume) incubated at 37° C. for one hour. The dNTP mix contained 10 mM dATP, 10 mM dCTP, 10 mM dGTP, and 10 mM dTTP. The reaction was terminated by adding 3 µl of 0.5 M EDTA (pH 8.0) followed by two extractions with phenol/chloroform/isoamyl alcohol and a final extraction with chloroform/isoamyl alcohol. The double stranded cDNA was ethanol precipitated, pelleted by centrifugation, and resuspended in 86 µl TE (pH 7.5).

The double stranded cDNA was then restriction digested as follows. Eighty-six (86) µl cDNA, 10 µl 10×EcoRI Reaction Buffer (NEB), 2 µl EcoRI (20 U/µl), and 2 µl XhoI (20 U/µl) was combined, and the mixture (100 µl final volume) incubated at 37° C. for one hour. After this incubation, an additional 2 µl EcoRI (20 U/µl) and 2 µl XhoI (20 U/µl) was added, and the mixture again incubated at 37° C. for one hour. After digestion, the reaction was extracted twice with phenol/chloroform/isoamyl alcohol followed by one chloroform/isoamyl alcohol extraction. The digested cDNA was precipitated with ethanol, pelleted by centrifugation, and resuspended in 40 µl of 10 mM Tris (pH 7.5), 1 mM EDTA, 100 mM NaCl, and 20 µl loading buffer. The cDNA was divided into two aliquots, and each aliquot was size-fractionated on a 1 ml BioGel A-50 m column. The columns were rinsed with 10 mM Tris (pH 7.5), 1 mM EDTA, and 100 mM NaCl, with 50 µl fractions being collected. One column was run to select for only relatively long cDNAs while the other was run to select for all cDNAs. These separate pools were then extracted twice with phenol/chloroform/isoamyl alcohol followed by one chloroform/isoamyl alcohol extraction. The cDNA was precipitated by adding 5 µl yeast tRNA (1 µg/µl) and 2 volumes of 100% ethanol. The cDNA was pelleted by centrifugation and directionally cloned into lambda phage UniZAP as follows. For the regular cDNAs (all sizes), 4 µl water, 2 µl 5×Ligase Buffer (BRL), 2 µl UniZAP (500 ng/µl), and 2 µl T4 DNA Ligase (10 U/µl) was added to the pelleted cDNA, and the mixture (10 µl final volume) incubated at 14° C. overnight. For the large cDNAs, 2 µl water, 1 µl 5×Ligase Buffer (BRL), 1 µl UniZAP (500 ng/µl), and 1 µl T4 DNA Ligase (10 U/µl) was added to the pelleted cDNA, and the mixture (5 µl final volume) incubated at 14° C. overnight. The ligated cDNA was then packaged using packing extracts (Stratagene) and titered on XL1-Blue MRF cells. The subtracted 3 hr MECS/CHX cDNA library containing large cDNAs (designated IEG-Lg cDNA library) had 239,000 recombinants, and the subtracted 3 hr MECS/CHX cDNA library containing regular cDNAs (designated IEG-Reg cDNA library) had 4,992,000 recombinants. A portion of each library was rescued as pBluescript plasmid, and the cDNA inserts analyzed. Of 46 plasmids analyzed from the IEG-Lg cDNA library, all contained cDNA inserts with the average insert size being 1.36 kilobases. Of 44 plasmids analyzed from the IEG-Reg cDNA library, 43 contained cDNA inserts with the average insert size being 0.9 kilobases.

Duplicate southern blots containing cDNA from the 44 plasmids analyzed from the IEG-Reg cDNA library were probed with control and stimulated subtracted $^{32}$P-oligolabeled cDNA from rat hippocampus. Eleven of the 44 cDNA inserts gave a clear differential signal that was stronger with the 3 hour MECS/CHX cDNA probe than with the control cDNA probe. This result indicates that 1 in 4 of the clones in the IEG-Reg cDNA library is derived from an IEG.

Example 2

Preparation of Subtracted cDNA Probes

Subtracted cDNA was prepared using exactly the same protocol described in example 1 with the exception that rather than in vitro cRNA being used as the template for cDNA synthesis, polyA$^+$ RNA derived from control rat hippocampi or rat hippocampi from rats treated with the 3 hour MECS protocol was used. After first strand cDNA synthesis, the RNA template was denatured by alkaline hydrolysis, and the free nucleotides removed by chromotography on sephadex G-50 (NICK, Pharmacia). The cDNA was precipitated using ⅒th volume 3M NaOAc (pH 5.2), 2 µl glycogen (20 mg/ml), and 2 volumes ethanol, pelleted by centrifugation, and resuspended in TE (pH 7.5). The final concentration was 25 ng/µl. The single strand of cDNA was labeled to high specific activity (2–4×10$^9$ cpm/µg) by oligolabelling (Pharmacia) with $^{32}$P dCTP (3000 Ci/mmole). Free nucleotides were removed by chromotography on sephadex G-50 (NICK column, Pharmacia), and the purified $^{32}$P-labeled subtracted cDNA used to probe the subtracted cDNA libraries.

Example 3

Screen Subtracted Libraries

The IEG-Reg and IEG-Lg cDNA libraries were plated on NZCYM agarose plates at a density of 500–800 plaques/plate. Duplicate nitrocellulose filter lifts were prepared from each plate using standard techniques. The filters were prehybridized overnight at 68° C. in 5×SSPE (pH 7.4), 10% dextran sulfate, 0.2% SDS, 5×Denhardt's Solution, and 50 µg/ml boiled, sonicated salmon sperm DNA. The first lift from each plate was then hybridized with 4×10$^6$ cpm/ml of the control subtracted cDNA probe and the second lift with 4×10$^6$ cpm/ml of the 3 hour MECS stimulated subtracted cDNA probe. Hybridization was done in freshly prepared 5×SSPE (pH 7.4), 10% dextran sulfate, 0.2% SDS, 5×Denhardt's Solution, and 100 µg/ml boiled, sonicated salmon sperm DNA at 68° C. for three days. Filters were washed twice at room temperature for 30 minutes in 2×SSC/0.2% SDS, twice at 60° C. for two hours in 0.5×SSC/0.2% SDS, and then dried and exposed to X-Ray film for one to seven days. Clones exhibiting greater hybridization signals with the stimulated cDNA probe than those observed with the control cDNA probe were picked for further analysis.

The putative neuronal IEGs were analyzed by reverse northern analysis and northern analysis to confirm that they were true differentially hybridizing cDNAs. The nucleotide sequence from the ends of these cDNAs was determined, and those sequences not matching the sequences of known genes were used to obtain full-length cDNAs from cDNA libraries.

Example 4

Construction of a cDNA Library Enriched for Near Full-length IEG cDNAs

Since the initial isolates for all of the IEGs represented small cDNAs derived from the 3' regions of the corresponding RNA, it was necessary to rescreen other libraries to obtain full-length or near full-length cDNAs. For this purpose, a cDNA library enriched for neuronal IEGs with very long inserts was prepared from 3 hour MECS/CHX polyA$^+$ RNA isolated from rat hippocampi. This RNA was already relatively enriched for neuronal IEGs since the MECS/CHX stimulus produces a large induction of IEG expression. Further, the cDNA was synthesized in the presence of methylmercuric hydroxide to eliminate RNA secondary structure allowing for the synthesis of long cDNAs using Superscript II Reverse Transcriptase (BRL).

The basic protocol used to synthesize cDNA was as follows. First, RNA secondary structure was denatured with methylmercuric hydroxide which forms adducts with imino groups of uridine and guanosine in the RNA and disrupts Watson-Crick base pairing. Briefly, 22 µl polyA$^+$ RNA (0.5 µg/µl in either 10 mM Tris/1 mM EDTA (pH 7.0) or water) was incubate at 65 ° C. for five minutes and then cooled to room temperature over five minutes. Once cooled, 2.2 µl 100 mM CH$_3$HgOH (90 µl depc'd water plus 10 µl 1 M CH$_3$HgOH) was added, and the mixture incubated at room temperature for one minute. After incubation, 4.4 µl 700 mM 2-mercaptoethanol (190 µl depc'd water plus 10 µl 14 M 2-mercaptoethanol) was added, and the mixture (final volume 28.6 µl) incubated at room temperature for five minutes.

Second, the first strand of cDNA was synthesized as follows. The volume of the denatured RNA mixture was adjusted by adding 26.4 µl water such that the concentration of RNA was 0.2 µg/µl. In the radioactive reaction, 5 µl (1 µg) polyA$^+$ RNA, 2 µl 10×Strand 1 Buffer (Stratagene), 1.2 µl Strand 1 dNTP mix (Stratagene), 0.8 µl Xho/dT linker primer (1.4 µg/µl), 5 µl water, 3 µl dCTP$^{32}$ 3000 Ci/mmole (NEN), and 1 µl RNase Block (Stratagene) was combined, and the mixture (final volume 18 µl) incubated at room temperature for ten minutes to allow the primer to anneal to the RNA. In the nonradioactive reaction, 25 μl (5 μg) polyA+ RNA, 5 μl 10×Strand 1 Buffer (Stratagene), 3 μl Strand 1 dNTP mix (Stratagene), 2 μl Xho/dT linker primer (1.4 μg/μl), 9 μl water, and 1 μl RNase Block (Stratagene) was combined, and the mixture (final volume 45 μl) incubated at room temperature for ten minutes to allow the primer to anneal to the RNA. After the room temperature incubation, 2 μl and 5 μl of reverse transcriptase mix (4 μl Superscript II (BRL 200 U /μl) plus 1 μl MMLV RT (Stratagene)) was added to the radioactive and nonradioactive reactions, respectively. The reactions then were incubated at 40° C. for one hour and placed on ice. Two μl of cDNA was removed from the radioactive reaction and added to 18 μl $T_{10}E_1$ and 2 μl 0.5M EDTA. Two (2) μl of this mixture then was applied to a PEI strip to determine the percent incorporation and quantity of cDNA synthesized, while 18 μl was mixed with sample buffer and ran on a gel to assay cDNA quality.

Third, the second strand of cDNA was synthesized as follows. Both the radioactive and nonradioactive reactions were kept on ice to prevent "snapback" cDNA synthesis. For the radioactive reaction (18 μl), 10 μl 10×Second Strand cDNA Buffer, 3 μl Second Strand dNTP mix, 62.5 μl water, 1 μl RNaseH (1.5 U/μl), and 5.5 μl DNA Polymerase I (9 U/μl) was added, and the mixture (100 μl final volume) incubated at 16° C. for 2.5 hours. For the nonradioactive reaction (50 μl), 20 μl 10×Second Strand cDNA Buffer, 6 μl Second Strand dNTP mix, 111 μl water, 2 μl RNaseH (1.5 U/μl), and 11 μl DNA Polymerase I (9 U/μl) was added, and the mixture (200 μl final volume) incubated at 16° C. for 2.5 hours. Four (4) μl of cDNA was removed from the radioactive reaction and added to 18 μl $T_{10}E_1$ and 2 μl 0.5M EDTA. Two μl of this mixture then was applied to a PEI strip to determine the percent incorporation and quantity of cDNA synthesized, while 18 μl was mixed with sample buffer and ran on a gel to assay cDNA quality.

The cDNA from both the radioactive and nonradioactive reactions were extracted twice with phenol/chloroform/isoamyl alcohol followed by one extraction with chloroform/isoamyl alcohol. After extraction, the cDNA was precipitated with 100% ethanol, pelleted by centrifugation, and resuspended in 39.5 μl water. To blunt the cDNA ends, 5 μl 10×T4 DNA Polymerase Buffer (NEB), 2.5 μl dNTP mix (2.5 mM each dNTP), and 3 μl T4 DNA Polymerase (3 U/μl) was added to the 39.5 μl of cDNA, and the mixture (50 μl final volume) incubated at 16° C. for 30 minutes. After incubation, 350 μl TE (pH 7.5) was added, and the mixture (400 μl final volume) extracted twice with phenol/chloroform/isoamyl alcohol followed by one extraction with chloroform/isoamyl alcohol. After extraction, the cDNA was precipitated with 100% ethanol, pelleted by centrifugation, and resuspended in 17 μl water.

EcoRI/NotI adaptors were ligated to the cDNA, allowing for the quick identification of artifactual cDNAs generated by the ligation of two independent cDNAs prior to ligation into the lambda phage vector. To ligate the EcoRI/NotI adaptors to the cDNA, 3 μl 10×Ligase Buffer, 4 μl EcoRI/NotI Adaptors (1 μg/μl), 3 μl 10 mM ATP, and 3 μl T4 DNA Ligase (400 U/μl) was added to the 17 μl cDNA, and the mixture (30 μl final volume) incubated at 10° C. overnight. After the overnight incubation, 1 μl T4 DNA Ligase and 1 μl 10 mM ATP was added, and the mixture (32 μl final volume) again incubated at 10° C. overnight. After this second overnight incubation, 270 μl TE (pH 7.5) was added and the mixture extracted twice with phenol/chloroform/isoamyl alcohol followed by one extraction with chloroform/isoamyl alcohol. After extraction, the cDNA was precipitated with 100% ethanol, pelleted by centrifugation, and resuspended in 30 μl water.

To kinase the cDNA ends, 4 μl 10×T4 Polynucleotide Kinase Buffer, 4 μl 10 mM ATP, and 2 μl T4 Polynucleotide Kinase (10 U /μl) was added to the 30 μl of cDNA, and the mixture (40 μl final volume) incubated at 37° C. for 30 minutes. After incubation, 2 μl T4 Polynucleotide Kinase was added, and the mixture (42 μl final volume) incubated at 37° C. for 30 minutes. After this second 30 minute incubation, 170 μl TE (pH 7.5) was added, and the mixture extracted twice with phenol/chloroform/isoamyl alcohol followed by one extraction with chloroform/isoamyl alcohol. After extraction, the cDNA was precipitated with 100% ethanol, pelleted by centrifugation, and resuspended in 85 μl water.

To digest the 3' cDNA ends with XhoI, 10 μl 10×NEB Buffer #2 and 5 μl XhoI (20 U/μl) was added to the 85 μl of cDNA, and the mixture (100 μl final volume) incubated at 37° C. for 45 minutes. After incubation, 3 μl XhoI (40 U/μl) was added, and the mixture (103 μl final volume) again incubated at 37° C. for 45 minutes. After this second incubation, 120 μl TE (pH 7.5) was added, and the mixture extracted twice with phenol/chloroform/isoamyl alcohol followed by one extraction with chloroform/isoamyl alcohol. After extraction, the cDNA was precipitated with 100% ethanol, pelleted by centrifugation, and resuspended in 20 μl 10 mM Tris (pH 7.5), 1 mM EDTA, 100 mM NaCl, and 5 μl loading buffer. This resuspended cDNA then was size-fractionated on a 1 ml BioGel A-50m column to select large cDNAs. The column was rinsed with 10 mM Tris (pH 7.5), 1 mM EDTA, and 100 mM NaCl. Thirty-six (36) fractions (50 μl/fraction) were collected. Aliquots from individual fractions were electrophoreses on 1% agarose to identify fractions containing cDNAs longer than 2 kilobases. Such fractions were pooled, and the resulting mixture of pooled fractions was extracted twice with phenol/chloroform/isoamyl alcohol followed by one extraction with chloroform/isoamyl alcohol. After extraction, the cDNA was precipitated by adding 2 μl glycogen (20 mg/ml) and 2 volumes 100% ethanol, pelleted by centrifugation, and resuspended in 5 μl water.

To directionally clone the cDNA into UniZAP, 2 μl UniZAP (500 ng/μl), 1 μl 10×T4 DNA Ligase Buffer, 1 μl 10 mM ATP, and 1 μl T4 DNA Ligase (4000 U/μl) was added to the 5 μl of cDNA, and the mixture (10 μl final volume) incubated at 12° C. overnight. After incubation, the cDNA was packaged into phage particles. To package the cDNA, the ligation reaction (10 μl final volume) was divided into two packaging reactions with each containing 5 μl of ligation reaction together with a packaging extract (Stratagene). This mixture was incubated at 22° C. for 2 hours. After incubation, the two reaction mixtures were pooled and the library titered on IL1-Blue MRF cells.

This 3 hr MECS/CHX library (designated IEG-FL 3 hr MECS/CHX cDNA library) had a titer of $4.4 \times 10^6$ primary phage. The library was amplified and used to isolate full length cDNAs derived from novel neuronal IEGs. The relative abundance of near full length neuronal IEG cDNAs in this library was substantially higher than the levels experienced using other cDNA libraries. In a single cDNA library screen, full length cDNAs for four different novel IEGs were obtained. Three of the four IEG cDNAs were derived from mRNAs of 4 kilobases, while one was derived from an mRNA of 3 kilobases.

The nucleic acid sequencing of the IEG cDNAs was performed at Johns Hopkins School of Medicine and at Applied Biosciences, Inc., CA using the Sanger method with fluorescent dye termination.

Northern blot analysis was performed both to confirm that the cloned cDNAs represent tissue mRNA that is rapidly induced by brain activation and to assess the size of the mRNA transcript. The latter is essential information for the identification of authentic full length clones. Either 20–25 µg of total RNA or 2 µg of polyA$^+$ RNA was sized by denaturing agarose gel chromatography and transferred to nitrocellulose. Blots were then hybridized with [$^{32}$P]labeled cDNAs. Labelling was done using the random primer method (Pharmacia).

In addition, in situ hybridization was performed both to confirm that the cloned cDNAs represent tissue mRNA that is rapidly induced by brain activation and to confirm that the mRNA was induced in activated neurons. In situ hybridization was performed as described previously (Andreasson and Worley, *Neuroscience* 69: 781–796 (1995)).

Example 5

IEG Nucleic Acid

The following clones were identified as being IEG nucleic acid as described in Example 3. In addition, certain clones were identified by chip-hybridization between PCR fragments generated from rat hippocampus ESTs and $^{32}$P-dCTP-labeled cDNA derived from polyA$^+$ RNA of rat hippocampus from MECS treated animals and controls.

One IEG nucleic acid clone was designated A003. The first library screen produced a fragment (A003-1-1) of 1.6 kilobases (kb) with a polyA sequence at the 3'-end. A second round of screening was performed using a probe prepared from the 5'-end of A003-1-1. This screen produced two clones: A003-1 (2.8 kb) and A003-2 (1.3 kb). The fragments from the secondary screen were sequenced from both ends. These fragments formed a contig at their 3'-end with the A00-3-1-1 fragment. The following two nucleic acid sequences are within the A003 clone:
5'-TTGCAGATCAGCACCTTTTGATGATGCCTGCCC
AACAGTGGGTAATGCTNACAGCAAAG-
CACCACTTTAC
GCTTTTTAGTTGTGCTGGGTTCATG-
GCTGGACATACACCAACCAGCCTTGAC-
CCCACAGGAATGCCAAGTTG
GCTGGAATGTAACCCAACCTAGTTTCTGCGCTTC
GCTCCTCTCCCAGTGCAAGGTGCTAAACACCCAC
TCACAAGCCTGCTGTCAAGCTGCGACCTTGGGGG
CTGGTTAGAAAGGGCTGCCTCCTTCCAGCAATA
GAAGTTCATGAATTTGAGGCTGGAGATAGGTCA
AGACCACTGTGATAACTATAAAGACTGTAGCAGC
CACAAAGGAGACCCCCAAATAACTGGAGGCATG
GCACTGACGTACCAGATGAGGTTATGTTTGGAGC
TGAAGGCTTGCTCTGTGCTTCTTGGTAGCATCTT
TTGTCCTCTTGGGACATGGTTGACCCCATACTG
TCCACTGAGCTTGGGAGATGACAGTTGAATAA
AAAAAAAAAAAAAAA-3' (SEQ ID NO:1) and
5'-CGGCTTAATTAACCCTCACTAAAGGGAACAAA
AGCTGGAGCTCCACCGCGGTGGCGGC-
CGCTCTAGAACT
AGTGGATCCCCCGGGCTGCAGGATTCT-
GCGGCCGATTAAGAAGCCTGCTGATGTC-
CTTAGGCGAGGACATTAA
CTCCAGTCTCTGACAGACTTTTGGACATCCAGA
ATAAGTTCTTTTTGTATATCAGAGCACAGAGCCC
AGCTTTAGCCTCTGATGATGGACCTCAG-
GAACCAAG
AAGGAGGGACTTCCTTAACATTCTAGAGATGGG
ACTCTAACTCTAGCTCTTGTGTTAAGC-
CCTGAAGTCC
AGAAAGAAGTAGTTCTTTGACATTCTAGTGCCAA
GATCCAGCCTCTAAGAGAACTCTGATFTCTAAAG
AAAGTCTTTCATAGTCTAGNCCAGTCACCAGTG
AAGCTAAACACCTGAAAACTATTAGATTCTCTGG
AGCCAGGAATCCATCTCAAGTCTCTCATAAAG
CCCAAATGTCCCAGGAGAAGTTGACAATATAAA
GCCGTATCTCGATGGACTTTTGAAGAAGCTCAG
AAAAGGAGACCACCTTGGTAGTCTTGATCTAGG
ACTCTGGCTTGTTTGTCTCCAGGGACGTTTACAT
GTATAAAAAGAGGGACCTTTCTGATGATTCAGAA
CTGGGACTCCACCTCCATCCTTTGATCAAAGCTC
AAATGTCCAGAAAGAGGGGCCTCTCTGATATTCT
AGAGTAGGACCCTCCCTCCAGCCTTTGATGGTG
CCAGATGTCCAGAAAGAGGGGCCTCTCTGATGT
TCCAGACCTAGGGCCCTCCCTCCAGCCTTTGAT
GGTGTCCAGATGTCCAGAAAGAGGGACTTCTCT
GATGTTCCAGACCTAAGACTCTAGCTCCAGCCT
GATGAAGCTCAGATGTTCAGAAAGGGGGCCTC
CATGATGTTCTAGAACCAGGACTCCACCTCTAGC
CTTTGATGGTGTCCAGATGTCCAGAAAGAGGGT
CTTCCATGATTTCTAGGACCAAGACTTTACCTCC
AGCCTTCTATGCCTCCATGTCTCCAGTAAAGCT
TAGGTGTCCAGAAAAGAGCATTCTCAATGAATT
TATAGAACCAGGACTCTTTCTCCAGCCTTTGATA
GCGTTCAGATGTTCATAAAGAAGAACTTCCACA
ATGTACTAAAGCTATGACTCCATCTCCATCCTTT
GATGAAAAGGGACTTCCTTCCACTCTGTTCCAG
AAGCCTAGCTCCACCTCTAATCTTTGTTGATGTC
ATTATCCAGAAAGAGGGGGCCTTTAGAACAAA
GACTGTACTTTTATTCATTGATAAAGCACAGATT
CCAGAAGCACAGAAATCTAGAAAGAGGGTCCT
CCCTAACACGCTCGAGCTAGAACCCCGGTGCA
AGGGTCTGAAACTTAGACACCAGAAGACCGC
TTTGTCCTACAACAAGTCTGCATTTTCTAAATCTC
CAGGTGGCTGAT:CAGAAGGGTCCAGGAAGGTAT
GGGG-3' (SEQ ID NO:2).

Northern blot analysis using the 3'-end of A003 revealed the presence of two mRNA transcripts. The more abundant transcript was 2.2 kilobases in length, while the less abundant transcript was 4.8 kilobases in length. This analysis also revealed that the expression of A003 mRNA was marginally upregulated in response to the multiple MECS treatment. The multiple MECS treatment involved the induction of multiple maximal electroconvulsive seizures followed by the preparation of total RNA from rat hippocampus four hours post-seizure. This multiple MECS treatment was designed to mimic ischemia.

Another IEG nucleic acid clone was designated A013. The first library screen produced the clone designated A013-8. The 5'-end of A013-8 was used as a probe for the second round of screening. This second screening produced two additional clones: A013-4and A013-26. The A013-8, A013-4, and A013-26 clones were sequenced using either the gene specific primer used to generate the probe for the second round of library screening, or the T3 and T7 primers. Both A013-4 and A013-26 made a contig on their 3'-ends with the A-013-8 clone. In addition, the sequence from the 5'-ends of A013-4 and A013-26 revealed that they from contigs between each other. Further, the sequence data from the 5'-ends of A013-4 and A013-26 revealed the presence of an open reading frame of at least 720 basepairs (bp) Based on the combined length of the obtained clones, the A013 clone is at least 3.0 kb in length. The following two nucleic acid sequences are within the A013 clone:
5'-GGCACGAGATCACTCAGTGTCTTCACTGAAC CAAATCGTCATTTTTACAGAGAGATGCAAAGCTT
AGCGAAGACATTTAGCTTTTTTAAAATGTATAATT
CCTGTGGCTACATATGCAAGTAGGGTCCCATTAT
GTTTTTTTTCATTAGTGGAAACTAATCCTTTTGTG
CTGTGTTTAATCAGTATTAGCTTTATAGAATTATAA
ATGTATATTCTACTTCTTGATCAAAGAACGTAGTC
GGGTATTGGTTTTAGAAGTTCAAAGTGACACT
GTATAGGGCTTTCACGGTTTAATGGGATTGTTA
GCAAATCTTAAGGACATACAGCCAATGATTATCT
GAGGTTACTGGCTAACTGTTTTTCACTGAGTTA
CTCTGCCTTTTTGACATTTTTATTCTTTGTTTGTC
GAATCCAGAGCTTCAGGAGCCCAAATTTTTTAT
WCCGTATATATATATATATATAAATATCCATAAGCC
TGGTGAATTTGTATGCAATGCACTGCATCTATGT
ATTCTGATAGCATCTCATTGATTTTTTGTTTGAAA
AGAAAGAAAGATAGTATCCCAAATGAGTTATCT
TTAACAGAAAGCTGAGTTTAACTTTTATTACCTA
TATAATAATTGATATTGCCAATTACCATTCTGAAT
TTCATATAGTATAAGTTAGACATTGCTTAATCCCC
TTTTAAATGTATTTACATAGACATGAACACTCAA
ATTGCTGGATTTTTTAAATATATCTGACATAATTT
TTTCATCTGTTACATTCAAGTTAGCT-
TGTTTAGCCCA
GATTTCAGAATAGTAAAGGAGGAAAGGAACCGC
ATTCCAGGGAAACCTCTGAGGCCAAGTCAGAG
TCCAGAACTGTAAACACACAGGCCTGCAAGCCA
ACATTAGTCGTGAAATCCCTAACACGT-
CACTGGATTC
TCTCTGTCAGCGCAAGTGTCAGCTGCCAAAGA
ATAGACTTACATGAAGAAGTGCCCACAT-
GCTGGCAG
GGGCTGGCCGGCTCCGGCCAGCAGACACTGC
TAGATTGTAATATTAAGGTCGAGTTTCGACCTGT
GGTACACAGCTGTGCTGTGCTCAGTCAG-
CAACCTCAGAACTCTGAAAAAAACAT-
AAAAAAGAAAAAAAAA
AAAAAAAAAMATGCASCTGKYTCACTTGTGAA
TAGTGAATGTAAAGGAAAGAAAG-
GAAAACCAAAAG
CTTGTTCCATCACAGGTATGAGCTGCTATGATTCA
TGAAGAACATTCCATGGAGTATGTTTTAAAACCT
TGTTATATCTGAGAGGCTTTAAAAGCCAACTTAACT
GTTTCAGGGCAACCGCGGTACAGACGTGGTCTC
TGTGAGACTTCCACCTGACCCAAGTTTTAAGTGGT
ACGAATGTTGTGCATTTAATGTTAAGGACAGTCT
GCAATAATAAGTAAGTAGC-
CAGCGTGGGTGCCCAGC
AGTGCTGAGACCTGGCTGCTCTATTGTACGCTT
TGGAAACACAATTTATGCAACAGATGTC-
CAGATATGAT
TCTATTTATGGAAAAGTTTATATGTTTTACAAA
TGGTTTTACCATCTTATATTAAATGAC-
CTTTTGACAGG
TGTGCACTGTTTTGTCTCCAGTGAGCACATACC
ATGCGGATTTTATATGTACATCAGTAGT-
GTGAATCCA
CTGGCACAGTGTGTGTAAATGCCAGATGTGGTG
AGATTTTATCTTGTATATGTGATCAGATAAAATAA
CTCCTGACAGAAACTGTAAGGRAACCCAGCTGA
ATGGTTTGACCTGGATGRCYKRKRTKGTWTGGTT
TATGTTAAATGTATATTCTTTTAATCAATGAATAA
AGCATTAAAAAATGGGAAAAAAAAAACTCGTGC-3'
(SEQ ID NO:3) and
5'-TCTGCGGCCGCAGCATCCGGAACAACAGGAA
CCTCCAGAAGTTTAGTCTTTTTGGAGATATAAGT
GTCGTTCAGCAGCAAGGAAGTCTGTCCAGCACA
TACCTCAGCAGAGTAGACCCTGACGGCAAGAAG
ATTAAGCAAATTCAGCAGCTGTTTGAAGAGATA
CTGAGCAATAGTAGGCAACTAAAATGGCTGTCC
GTGGGTTTATGCTGGAAATAGTAACCCCATCATC
ACTGTCGTCTCTGTCTAACTCCATTGCCAACAC
CATGGAACACCTGAGTTTACTGGACAACAACAT
TCCTGGTAACAGCACGCTCATCACCGCAGTCGA
ACTAGAGCGCTTTGTAAATCTGCGCTCACTTGC
CCTGGATTTCTGTGACTTTACAGCTGAGATGGC
G
AGAGTCCTGACCGACAGCAACCATGTGCCTTTG
CAGCGACTGTCTCTTCTGGTCCACAATGCTTCA
GTGATGCTCAAGTCATTAGACAACATGCCAAAC
GATGAGCACTGGAAGGCCCTGTCAC-
GAAAGAGCTC
CAGCCTCCGGGTCTATCTAATGGCTTTTGATGTT
AAAAGTGAAGACATGCTAAAGATTCT-
GAAACCCAGT
ATACCACTTGAGAAGGGTTCACTTTGGACAGCT
ACGTCACTTGTGTCTCAAGGGGCTATTGGTTGATCT
TATATTCCAGGCAGTATTGACCAAGGTTTCCTYAA
CCCMWTTTWTATTGATGAATGATATGATTGATAC
GTCTGGTTTTCCGGATCTTAGTGACAACCGAAATG
AAGATCCATTGGTTTTATTGGCATGGCGGTG
CACAAAGCTCACTCTTTTGGCAATTCATGGTTA
CACCGTGTGGGCACACAACCTCATTGCCATTGC
TCGTCTTCGTGGCTYTTGACCTAAAAGTGCTTT
GGAAGTCACCSRAAGAAAGCATTGATTTTGACC
AAGGTGAACTAGCCCGACCAGGAATGTGGRWY
CCCGTACATAACCTTTCTTGGAGCAGGTATTCC
CTGGGGCCTTGGTCAAGTCTTGGCACG-3' (SEQ ID
NO:4).

Northern blot analysis using a sequence from the A013 clone revealed the presence of a 3.2 kb mRNA transcript. In addition, this analysis revealed that the expression of the A013 mRNA was strongly upregulated in response to the multiple MECS treatment. Specifically, A013 mRNA expression was induced 8.9 fold by the multiple MECS treatment as determined from Northern blot data using total RNA from rat hippocampus (Table I).

TABLE I

| Fold induction of mRNA expression after multiple MECS treatment | |
|---|---|
| Probe (rat cDNA) | Fold induction (normalized for the S26) |
| A013 | 8.9 |
| L094 | 7.3 |
| L100 | 17.2 |
| L119 | 17.8 |
| R113 | 7.0 |
| R286 | 2.4 |

Another IEG nucleic acid clone was designated A020. The following nucleic acid sequence is within the A020 clone:
5'-TCAAACCNTATCTCGGTCATTCNTTTGATTNAT
AAGGGATTTKSCCGATKTCCGGCNTATTGGTTAA
AAAWTGAGCTGATTTAACAAAAATTTAACGCGA
ATTTTAACAAAATATTAACGCTTACAATTTGCCAT
TCGCCATTCAGGCTGCGCAAYTGTTGGGAAGGG
CNATCGGTGCGGGCCTCTTCGCTATTACGCCAGC
TGGCGAAAGGGGGATGTGCTGCAAGGCGATTA
AGTTGGGTAACGCCAGGGTTTTCCCAGTCACGAC
TTGTAAAACGACGGCCAGTGAATTGTAATACGAC
TCACTATAGGGCGAATTGGGTACCGGGCCCCC
CCTCGAGGTCGACGGTATCGATAAGCTTGATATCG
AATTCGGCACGAGCGAAGCCAGGGCCTTGCAC
TTCCTAGGCAAGCGCTCTACCACTGAGCTAAAT
CCCCAACCCCTTGTTTTATTTTTAAAGCAAACGA
GATACATAATTTCARCCATGATAATTTAAGATTAT
CTTGAACTCTTAAGGAAATGTATATACTAAGCTA
TTATAGTTTTTATTTTCCCTAATTCAGTGGCATAAT ACCTTACCTTGAGTCGTTTACTACTTTCTTTGGT
TTCTAAAAACTCTACTGCTAAATTACAATGTAAA
AACATAGGGCTCGTATATACTGTAGAGTGCTGTAG
ATGTCCTCGTCATCAACTATGCAATAACAGTCTG
ATCGACACATTTCAGGAKCGATCACTCTTTGGTG
TGCTTCTTTAAATACTTTCAGAAGCTTAGGATGT
GCAAAGCAGGAAGACTGTGGGTGTAAATGTTT
ACTTATTTCTTTGAGAGTGTTAGTAAGTCTTTTC
DAAATTGCTTTTCTCTTCAAAATTATCGTTAACTT
AAATGATAATTATCTTTGAGGTTAAACAGAAGCT
CATTGACAAACTAAAGTGACTTTTTAGGGCATTC
TTTGAGATCATAGTCTTATATCTTGGGGACTAAA
ATGTCATTAGACCCTAATAGACTAACTTGTATGT
TTGTGTGGGGAAACGTTTTCCTCTCTCATTCAA
GGTAACTGTTTGCTGCCTGTTGTTACTTGTGTA
GCATTCTAGAAAATGGCTAGGTTTTTTATAAGAT
TTAAGACAATAGAAGTAGTTTTATATTATTATAGTT
CTGTTGGAATGTGATCCTGAAATTATTACTGAAA
ATTAGAATTTTTATTTCGCTAATGACAACCTTGAC
TCTCAGAGATGCAGTGTAAATTGATACCTCATCT
TTCCGAGAGTTCAGAGCACAGGGCGGCAGTATG
TGAAGCTGCTTTTGCACTGACGCATTTTGATAAG
TTTGGCTACTGTAATGGTAAAAGGCTCCTCAGG
CACTGACTGCATTTGGGTTCTTCCGATGGGGA
TGATCCGTTCTCGTGGTGCTGCTGGACTTATGC
ATTTTGGAGGTACTGCATGTATCTTCCACACTG
CTTGACATTTTCTCTGATCTGTGTGTTTGCACC
AACTCATTAAAAGAAATATGCAGAAATATCTTCC
TAATTCGTTGATCTTCGCTGTATGACAGTTTATA
ATATTAAACACTTGGGTTGATCCACTCTGTTTAC
ATTTATCTTTCTAAGCGTCAGAAAGGGACTAAC
TTGAAATTATATCTAGAGGCTTTGTATCATTTCAA
AAATTAAATTTCCTTGGATACTTTAGGCAATATC
TAAACAACTTTTTAATAAATTTAAATATTTATATTT
ACGTAAGCTAAAATATACATGAATGTGCTTTTTAA
TAAATTAAATACAGTTTATACTTATTTGCCAATTCA
CAAATAAAAAAAAAAAAAAAAAAAAAAAAA-3'
(SEQ ID NO:5). This clone is similar to GLGF-domain protein Homer (accession #U92079).

Another IEG nucleic acid clone was designated A021. The following nucleic acid sequence is within the A021 clone:
5'-TTTTTTTTTTTTTTTTTTTTAARGGGRCCACCC
CACCGSGCTAAAGGCCCAGGGGCCCCCCCCTTG
GAGMCCCAGGGGTTTTGGCCCMCCCCCTCACC
CAAATGGTCTGCCAATGACCCAGGTACTCACAA
C
ATGTTCCAGGAGGAGMCTGGGGCCAGGATTTT
GACCAGAGGGTATGGGAAGGGAAAGGGGAGA
AGAAATCGACATTTATTTTTATTATTTATTTAAAT
GTTTACAWTTTCTTTGTGTTGTTCCAAGCCCTG
AATAGAAACAGATAGCATTAAAGGACTCTGTTC
CCACCCCTTCTCTGTCTCTCTCTCCCCCACTTG
TGCTAACTTAGGATAACACTCTCTATTTCGTTTT
GTTTCTAAAGTGATTTGTGGACTTGTGCCGTGT
GAACTGCATTAAAAAGGTTCTGTTTTCAAAGA
TCGATTGTCGTTCCTGTGGGACAGTGGCTCCT
AAGAAATCTGCATTGTAGGAGAAGACAATGAAA
GACCCTGGCCCTGTCTCTCAAAACTTAACTCTCT
GTATGATTTAAAAAAAAATTCCATTTACTTTACT
TTGTGGTTACTTGATTTTGAGGAAGAAAATATTC
AACTTTGTATAAAGACTAGGTATCAGGGTTTCTT
TTGCAGTGGGAGTTGTATATATATCGTATTTTGGT
ATATCGTAGAAACTCAAGCTTTATGCATCCGTAT
TTGGGATATGTCAATGACGTGCAGTGAAATTTG
CTATTAGACCCTGGAGGCAAACGAGTTGTACAA
GGTTTTATGGCTCCATGGGGAATTCTAATTTCCT
TTCTGGGGACCTTTTGTCCCGTTTTTACAGTAA
TGGTGAAATGGTCCTAGGAGGGTCTCTCTAGTC
GAATTCTCCAGGCAGGACCACGTGCTCAAAAA
ATCTTTGTATAGTTTTAAATTTTTGAGGAGTATC
TCTGCTCAGAAGCATCTGTGGTGGTGTGTGTTG
CGTTGTTCTGTGTACTGTGTGTGACACAAGCCT
ACAGTATTTGCACTAAGGAAAGCTGTTTAGAGC
TTGCTGCTATGGAGGGAAGAACATATTAAAAC
TTATTTTCCCTCGGGGWTTRTWCWMGTTTTATGT
WCTTGTTGTCTTGTTGGCTTTCCTACTTTCCACT
AGTAGCATTTTGTAGAATAAAATGAATTAAGATC
AGMWTWTWTWTMAAAAAAAAAAAAAAAAAA
AAAAAAAAAAAAAAAAAAAAAAAAAAAAAA
AAAAAAAA-3' (SEQ ID NO:6). This clone is similar to fra2.

Another IEG nucleic acid clone was designated A024. The following two nucleic acid sequences are within the A024 clone:
5'-TCAGGCCTNAGCAATCCTCNTTAATTTGANCC
AAGNTTAACTCTTGGGGCGAATTCCTGTGNTTG
CTTTCTTTCCCCATANTTCCAGGCCCACAAANG
GTTTCTGTGANTCCGAGAATCGGCCCACCATGC
AGACCCACNGAGAGGATTCAGAATGTGTGTGAG
AGTGAGTGTGTGAGTGCGCGTGCGTGTGCTTTG
TATGTGTGTTTATAGATGTAGGACATTAAGTTCC
TTCTGACACAGGGAAGATGTGAGAAGGATGG
CCTGACATCAGATGACAAGAGGTCTTATAGCAC
ATCTCTGGGCTTTTCCCTACCCAGAGAAGAGCC
CCCTTTGATACAAATCAGTTGGATTTTCATATGCT
TCAAAGGCTTGATCTGTGAGTCACTCCAGTTTG
GGACATAGGTCTGTCTGTGGCTTTGAGAAAAGG
TACTTTCAAAAGAGGGCTTTCCAGAGCACAGCT
CACAGCCAGCTGTTAGGACCCCACCCTTCTCCTT
TATTGTGGAGGTGACTCACAGCAGACTGACAGT
GGTCAGACTGAGCTTTCTGCTAAGGTGGTGAGG
TAGCCAACACTGGCATGTCTCGGTAGTGGTTTG
GGCAAATTTCCGCAGGTCTCTTCCCCCAACCC
TGCCTCTGATGAATAAAGACAATGAGTACAGTT
CCTTAATTCAGGCTTTTGTGACTAGCTTACTACGG
AACCGAAAATGGTCCCCTTTGTACAAGCCGAGCT
GTTATGGAATCACGGTGAACCAGACCCAGGTCT
GTGGCACCTGTTTGTTTTTTTTTTTTTTTTTTTT
TTTTAGCTCTCATTTCTACGGCATGCTTTCCAAGG
AACCAAAGGAGGGTCTCAGAGATGCCCCAAACA
TCCCAAAGTACACAAAGCTAAGTAATCGATTGC
TTACTTATTGCACAGCTAGACACGGATTTTAAG
TCTATCTTAAAGCTTTGAAGCAAGCTTAGCTTC
TCAAAGGCCTAGCAGAGCCTTGGCACCCCAGGA
TCCTTTCTGTAGGCTAATTCCTCTTATCCAGCGG
CATATGGAGTATCCTTATTGCTAAAGAGGATTCT
GGCTCCTTTAAGGAAGTTTGATTTCTGATTCAGA
GTCCTTGTTTCCCTGACTTGCTCTGCCAGCCCTG
CACCAGCTTTTTCGAAGTGCACTATGCTTGTGTT
TAACTTCTCCCAGTTTTATTTGGGCATAAAAGTTG
TTGCCTTTATTTGTAAAGCTGTTATAAATATATAT
TATATAAATATATGACAAAGGAAAATGTTTCAGAT
GTCTATTTGTATAATTACTTGATCTACACAGTGAG
GAAAAAAATGAATGTATTTCTGTTTTTGAAGAG
AATAATTTTTTCTCTAGGGAGAGGAGAGGTTA
CAGTGTTTATATTTTGAAACCTTCCTGAAGGTGT
GAAATTGTAAATATTTTTATCTAAGTAAATGTTAA
GTAGTTGTTTTAAAAAGACTTAATAAAATAAGC
TTTTTCCTGTGAAAAAAAAAAAAAAAAAAAAA
AAAAAAAAAA-3' (SEQ ID NO:7) and
5'-GTGGCCCCTGCTCGCCGCATCATGGAGCGGAT
CCCCAGCGCGCAACCACCTCCTACCTGCCTGCC
CAAAACGCCAGGGCTGGAGCACGGAGACCTGT
CAGGGATGGATTTTGCCCACATGTACCAAGTGT
ACAAGTCCAGGCGGGGAATAAAACGGAGCGAG
GACAGCAAGGAAACTTACAAATTGCCGCACCG GTTGATTGAGAAAAAGAGACGTGACCGGATTAA
CGAGTGCATTGCCCAGCTGAAGGATCTCCTACCC
GAACATCTCAAACTTACTACTTTGGGTCACTTGG
AGAAAGCAGTGGTTCTCGAGCTGACGCTGAAG
CACGTGAAAGCATTGACAAACCTAATTGATCAG
CAGCAGCAGAAAATCATGGCCCTGCAGAGCGGT
TTACAAGCTGGTGATCTGTCGGGAAGAAATATTG
AGGCAGGACAAGAAATGTTCTGCTCCGGTTTCC
AGACCTGTGCCGGGAGGTACTTCAGTACCTGG
CCAAGCATGAAAACACTAGGGACCTGAAGTCTT
CCCAGCTTGTCACTCATCTCCACCGTGTGGTCT
CTGAACTCCTGCAGGGTAGTGCTTCCAGGAAA
CCATTGGACTCAGCTCCCAAACCCGTGGACTTC
AAAGAGAAGCCCAGCTTCCTAGCCAAGGGATC
AGAAGGCCCTGGGAAAAACTGTGTGCCAGTCAT
CCAGAGGACTTTTGCTCCCTCGGGCGGGAGCAG
AGTGGTAGTGACACGGACACAGACAGTGGCTA
CGGAGGCGAATTGGAGAAGGGTGACTTGCGCA
GTGAGCAACCCTACTTCAAGAGCGATCACGGA
CGCAGGTTCACCGTGGGAGAACGCGTCAGCAC
AATTAAGCAAGAATCTGAAGAGCCCCCCACCAA
AAGAGCCGAATGCAGCTCTCAGATGAGGAAGGC
CACTTCGTGGGCAGTGACCTGATGGGTTCCCCA
TTTCTTGGGCCTCACCCACATCAGCCTCCCTTTT
GCCTGCCCCTTCTATCTCATCCCACCATCGGCCA
CTGCCTATCTGCCTATGCTGGAGAAATGCTGGT
ATCCGACCTCTGTGCCACTGTTATACCCAAGCC
TCAACACCTCAGCAGCAGCCCTCTCCAGCTT
CATGAACCAGACAAGATCCAACTCCCTTGCTC
TGCCCAGAAATCCCTTCTCCCTTGGCACATTCG
TCCCTTGACTCTCAAGCCTGCTCAAGCCCTGA
AGCAGATCCCTCCTTAAACTTAGAAACAAAGAT
AACCTTGAGGGCAATCNCTGCGCCTTGCTTTCC
TTCCCACAATTCAAGACACAAAAGGTCTGTACT
CAAAACAGAGAGATCAGCCCACCCTGCAGAC
CCACAGAGAAGATTCAGAGTGTGTGTGAGAG
TGAGTGAGTGTGCGTGCGTGCGTGCTTGTATGT
ATGTTTGTATATGTAGGACAATAAGTTCCTTCTG
ACACAAGGGAGACACGAGAAGGATAGCCTGA
TCAGATGACAGACTGGAGGACTGTAGCACATCT
CTGGGCGTTTCCCTACCCAGAGAAGAGCC-3′ (SEQ
ID NO:8). This clone is similar to a basic helix-loop-helix
polypeptide.

Another IEG nucleic acid clone was designated L003. The
following nucleic acid sequence is within the L003 clone:
5′-GCACGAGGGAGTTTATTTCCACGTCTCTTAGG
AAAGCCTCGCTTGGTTACACATGGCAAT-
GATTGCAAGCAGATACACGTCTTAACAC-
CAGAGTACAGTACACACATTGAGCT-
GCCCTCGTCTAACAAGCAGTTGCAGTTTGTTTA
AATGTGAATATCTATGAAACGAGCAAAG-
CAACTTTCCAGAGTATAGCTTATCACA-
GAATAGTAACACATGGCCGCTACTG-
TATCATACAGAGTACAACTCTATAGCTTTTCATCC
CCGTGTGAGCATTTCCAAATCACTCAAT-
GAGCACCAAGCACGGACAAGTGAC-
TAAAAAGGCTAGTCCCAATCTCCCCG-
CAACCCTCGGCGGTAAGGGTAAAGAATTTTGTT
TCAAGTAAGTTTTCTC-
CTCGTCTCTCTCTTCTGAAGACCTGAG-
CAAAACCAACATTCTAAACCACCCCAA-
GATATGATACTAGAATTTAAAGGCCCGATGGCTT
CAACCCAGAACCTTAACCTACTA-
GATAAAATCTCTCCGAATCTGACTCACT-
GATGCTGTTAAGTCCGACAGTACAATCA-
CATAGTACCTCTTTGATACTGTCAAAGTTGGTTT
TAAAAATGCCCTAAGAAAACCAAAT-
CATTTTTGGGAGATGTTCTAAG-
CAAGCTTTCCAACATATAAAGAA-
CAAAACCATGTTACTAAAAACATGGTGCAGGT
CCTCACAAAACATTTACTGCTACTAC-
CAGGAAACCAAGCTACTCTTGGTTTGT-
GCTCCTGGTGATAACTGGTGAGCTTTG-
GACAGCTGCTGGCACATGTCCACTGTGTTCCGT
TTTATAATCAAGTGTCAGTTTTCCACTC-
GACAGAGATTAAAGACAATAGCT-
TAAAAGTGAAAATGAAATTTCAAGTA-
GAAGCTACAATTGAATGCTACTTGTTGAGACTTT
AACTTTCACATCCAAATATCAAAAACT-
TAACTTTGACGACACATGCACACAAACA-
CACCATTTGGGAAAGGGTCTTGTTATG-
CAGTTCAAGCTGGCCTTGAACTCATGATCTCCT
GCCTCAGTTTCTTGGGCAGTAGCACTG-
GACCTTACTGTGGGCAGAAAGTAT-
TGCTCCAATTAGAAAGCATTACTATA-
CACTTCACTTCGTCATGTGCCTAGTGTGGCTCTG
AAGGCATAGGAACAATGAAATTAAAT-
TCTTCAGCAGCTGAGGATTCTCTATACT-
TCAACATTCTGAACTTCAATCATGGCT-
TCACATTTGAGGCTGAGCTAGATACAAAAATATC
AAAACATCCCATAGAATTGTTTATTTC-
CCTATGTTACTGTTTACCCAAGGAATGT-
GAAGACTAAAAAGGACTCATTTGGT-
TGTTTAATTATGATTAAATTATGTAAATATACAAA
CATTTAACAAAGCCATCATATTC-
CAATCTTTTACGAATTCTAACTGCTAG-
CAGTTGAGCAGCTTTTAGATATCAC-
TAATAAAATATACAATTTAAAATAGTCGCATTCA
TCCTACTAACTTTATAAATAACTTCT-
TAGGTTAGACTTCTTCCTGCCTAAGTT-
TATAAGACAGTCTAAACCCAAAACTCAA-
CACATATTAAGCTTTTTAAAAACTCCATATAGTT
CTAAAGTAACCTCAATGTATTCCCAA-
GAACCGCCACCATCAATCAGCTCACTC-
CCTCACACCACTGACTTTAAGACGCTC-
CTGGGTGGAGAACTGCCAGGCAGAAGCTCTAC
CTTTCTAGTGTGTGTGGTGGTCTGCT-
GCTCCTAGTCCAGATCTGGACCACAT-
CAGCACAGCATCAGTGTGACTCAGCACT-
GAGGCCTTGAGCGCTCTTCCCCCCGATGGCCTGT
GTATAGAGGTGTCTAATTCCTTGTG-
TATAGATGGCCTGTATATAGAGGT-
GTCTAATTCCTTGGCTCTGTATGTATAG-
GTAATGTGATACTTTACCATTAAAGCACTATTTT
CTCCATTCAAGAATTTAGTGATATAG-
GAAAATGAGTGGACTTGCGAGACTCA-
GAAAAACAAAACATAACCTGTCTTGAAT-
TCAAAACAAACCATGGGTGTAGGGGGAACTG
ATGAAAGTTTATGGGTTTAACTCTAGG-
TAATTAACTAAGACAGTCACGAAACA-
CATTATCAAAATCCTTTCAGGCCCA-
GAGCTTGTACTGTACCCCACTGTGAGACCACAT
CACAACCCCGGATTGAGCTTTATCCA-
CAACACCTACACCATAGTAACGCAAAGT-
GCACAATGTACTAAAATAAATTCCTATT-
AGTTTTATGCAAACTATGGTATAAAATTATCACC
TGCCATACATATTTTGCCATGGCAC-
CAACTTCATATAATAAGCCAACG-
TATAATCAAAGTCCTTACCAGCACCAAT-
CAATGTCCTTGGCACCACTGGACACTCACCGTC
AGCTGTTCATCTAAGAGCCAGTCTGT-
TCTGACCTGAACAGTTGTGCATTCCAC-
CTTACCACACCCAAGTCTGTGAGCCGGA-
CAAGTGTTTAAATGCAGTTTTACATCTAACGGTG CAGGTTAAGCCGAGCACTTGAAACTGAT-
CACTCATTAATACCTGTCTCCCTCCATA-
CATGTACACCACATGTACACAGAACTAT-
GTGCTCTGACTTCAGAATAGCTCTTCCTGTTGGC
AAACACCACAGACATGAAGGGCCTAGT-
GTGAAGCGAGCTCACAGAATGTTGGATG-
GAACTTCGACTATAATGGAAACACCTG-
CAAAAGCTTTGCTAACCCAGCAAACACTCAAC
ACTTACCAAAGACAACAGGGAAGT-
TAAAGTTAGCTCGCCAA-
GAGATGGGCTGGGGAGGTGGGGGTG-
TAACTCAAAGAAAGCTTTAGCTAACAAAAACGA
ATGATGGACAACTTCAGAAATTC-
CCTAAAAACAGAACCTGAAAGTGCAGGT-
GAGGTTTTGTCCTTCAGTAACAAATGCA-
GACAGATTCCCAACAGGAATAAAACAGTCTGG
GCTTTGAAACCTGCTAGATGGAAACAC-
GAACTCAAAATGTGGAACCAAGGAAAAC-
CAAATACTTAAATGTGTAAGATAATT-
TATAATAGTAAAAAGTTGCAAATTGCTGTGACT
TGATTTGCCGAAAACATCTGTAAATCCA-
CACTGGCAGTTAGAAGACCAGTTCCCA-
CATTAACTCCTCTCTCAGCAGGTAAC-
CGTTTGTGCGCAGAAGTATCTGAAACATCGCAC
ACTGCTTATTTTATGGTGTATTGTGCA-
GAATCTGTACATGCTATTACAGACAATA-
CATATTTGTAAACCTGGTCATGCAAAAT-
CAGTGTGTACAAGGGGATATTGTTAAGCCTTATA
AGTGGTACTTTATTATCTTTGTGACGAT-
GCCAATCTCTCCGAAATATAGCATATCT-
TAAATGGATATTCTTTATCTGCCAGT-
TAAAATCATTTTATGTCACTGAAAGAAGAGGTT
TACAAGGAAAGAAACATGGTCCTTGTGT-
TGCAGAATTGATTTTAAATGAGAGAATT-
TACAAAACCAAGAAATCCATGGTCAT-
AAAGTTTTAACATTTTAATCCTACACATTACAGG
GCAAACAGATACTGGACCCTATTTCCA-
CATTCCATAAATCCAAACTTTAGTTC-
CCATTTCAAACGTTGCCCTAACCAC-
TAAAACCATCAGTGGTCTTACAACCTCTGGATTA
TGGAAATACAGATTTCTGAAGTAAAAGC-
TACAAAAACAACAATGGAAGAAAGCT-
GAACAAACTTCCCATGAAT-
GAAAATAAAAGTGGAACATCCTGAAGCTCTAGA
CACTTCTCTCCCGTGTCTATGGTCAACT-
TGTCGGTTCAGTGCACTGTGCGGT-
CAAATGTAATGGTCCTCATGTGGAACA-
CACGTCTAACTAGTGTCCATTGATTCCAAGTTAG
TGGACGAAGAATCTTTCTG-
GATACTTTCAAAGATGGCTGCCAGCTC-
CGGGTTGGAGCTGATCTGTGACTG-
GAACTCACTCATGAGAGGGCTCTTCTCTGCCTC
TATA-binding polypeptide (TIP120).

Another IEG nucleic acid clone was designated L048. The nucleic acid sequence of the L048 clone is as follows:
5'-TCGCCGCCCGAAGTCGCGCAGCTTCCCTGGC
GAACGCGGAAGCCCGAAGAGCGCCGTCCTCG
GGCCCTGTCGGCGCTCAGGCCCCTTCGCGCGC
CTCCTCGCTCGGCCGGGACGTTGCTGTGGAGGC
GTGAGGCGCCGGCGGTCGAGCACCTGGAGCGA
CGGTAGCCCGCGGCCTGCGGTTCTTCTCCTCCC
CCGCCGCCCTCCCACCCGAGCTGCGGCGGGGC
TCGGCCGCCTCGGTGCTTCTGCACGAACAAAG
GAGGCCCCGCGGCGCCGGCGCAGCTCCATCTG
CGGTCCGATCCACCCGGGCCCGCGGCGGCCGC
TAGCCAGCCCTTCCCGGAGGCCTCAGCCCGGCC
CACCGCCCGGCGTCGCGCGCCAGCTCGCTAGTG
CATCCGGGCCCCGCAGGCACAAAAATATGGCTC
AGGAGACTAACCAGACCCCAGGGCCCATGCTG
TGTAGTACTGGATGTGGCTTTTATGGGAATCCTAG
GACAAATGGAATGTGTTCTGTTTGCTACAAAG
ACATCTTCAGAGACAGCAGAATAGTGGCAGAA
GAGCCCAATGGGGACAGCTAGTGGTTCCAAC
AGTCCTACCTCAGACTCTGCGTCTGTACAAAGA
GCAGATGCTACTTTAAACAACTGTGAAGGTGCT
GCTGGCAGCACATCTGAAAAATCAAGAAATGT
CCTGTGGCTGCCTTGCCTGTAACTCAACAAATG
ACAGAAATGAGCATTTCAAGAGAGGACAAAAT
AACCTCCCCGAAAACAGAGGTGTCAGAGCCAGT
TGTCACTCAGCCCAGTCCATCAGTTTCTCAGCC
AGTTCTTCTCAAAGTGAAGAAAAAGCTCCTGAG
TTGCCCAAACCAAAGAAGAACAGATGTTTATG
TGTAGAAAGAAAGTTGGCCTTACAGGGTTTGA
CTGCCGATGTGGAAATTTGTTTTGTGGACTTC
ACCGTTACTCTGACAAGCACAACTGTCCTTATG
ATTACAAAGCAGAAGCTGCAGCAAAAATCAG
AAAAGAAAATCCAGTTGTTGTGGCTGAAAAA
ATCCAGAGAATATAAAATTACTACATGTGAAGAG
ACTGAAACTTTGTTTTTATTTTAATATATCGTAGG
AAAACATTAAAGAGCAGATGCATGGCCATTTTCC
TTTGATGTTCTCCAGAGTTTTGCTTTATACTTGTC
TGTCATATAATTGATATTTAGGATGTTTGGGTGT
TTGTTACAGGCAGAATTGGATAGATACAGCCCA
ACAAATGTATATGCCCTCCCCTCAGTAAAATTG
ACAAAAATATGCACAGCAAATTGAAATACACA
TATACTAGGAACAAAATTTAGTTCCATGTGCCA
AACTGAATGAAATCTCTGCATGTTTGCAGCATA
TCTGCCTTTTGGGAATGTAATCAAGGTATAATC
TTTGGCTAGTGTTATGTGCCTGTACTTTAAAAAA
TGGTACACCAGAAAAGGACTGGCAGTCTACT
ACCATAGTCAAACTTCACCTTAATTTCGACAT
GCTTTTGGAAGCAGGAAGAAAGCTACAAAAC
CAGTATTTGGTGCCATGTGTGAGCCTGGTTAA
ATTGGTCTTCTAAAAGCTGTCAATTAGGACATTC
TGCGAAAGGTAACATCACAACTGGTTCTGAGTA
AACCATCAAGTCAACAGCAGGGTGCCTGAGATA
TCTTTGAAGCTTATTGTGCTGGCCTGCACCAGA
GATATCTGCATTCTCATTACTAAAATTGTAGCACA
GAACTGCACTAGGATTTGTTTACAAGAAGAAAT
TAAAACTCTACGTTTGGTTTTCACATATAGCAGC
TCTGTTAAATAACATGCATCTGAATTTTAAGTTG
CAAAGGTATCTGAGCAGTTAGTTTTTCATGTGCA
TCTTTTGTTGAATGTTTTGGTTCAAGAAAGAAT
GTTTAAAGCTTTTTAAAGACTTCAGTTCTTAATG
AACTGTACCCTTCTGCATGGAAAATCATAACCAA
CATGGCTGCAGTAGACTTCTTTAGTGGTATCCAG
ACCACTTGCAGAGGGCTGCTTTATCATATTGTAT
TGGGTGTAGGACTCTAGTGTTCTTGGGTGTATTG
CATGGGCTGCATTATCTACAGCATTGTACAATAA
CAACTAGAAAAGGCAGTATACTTCACTGATGCTT
GTCTGGTAATATCACTTCTGTGTTATAATGGAAG
GTTTTTTGTGATGTATGAAACTTGTGTTTTTTATA
ATAAATGAGTATAGTTAGATTAGTGTTGTGGTA
ATGCCTGTTTTCATCTGTAAATAGTTAAGTATGT
ACACAAGGCACTACTTCTGATTTATTGCAGTGT
TCAGTCCTAGTTTTTCTTTATTAAAACATTCAGT
TTTGCTTCAATTTTATGTACTTTAGTTCTAAGTTA
GATTTGCAGATGTGTACAGATAGTTCATATTTAT
TATTGCACATAATCATGCTATTCAGCATTGATGCT
ATATTGTATTATGTAAATAATAAAAGCAGTGTAC
GAGGGAAAAAAAAACTCGTGC-3' (SEQ ID NO:10). In addition, the L048 clone contains an open reading frame (ORF) from basepair 414 through basepair 1055. This ORF encodes a polypeptide of 214 amino acid residues. The amino acid sequence of the L048 polypeptide is as follows: MAQETNQTPGPMLCSTGCGFYGNPRTNG-MCSVCYKEHLQRQQNSGRMSPMGTASG-SNSPTSDSASVQRADATLNNCEGAAGST-SEKSRNVPVAALPVTQQMT EMSISREDKITSPKTEVSEPVVTQPSPS-VSQPSSSQSEEKAPELPKPKKNRCFM-CRKKVGLTGFDCRCGNLFCGLHRY SDKHNCPYDY-KAEAAAKIRKENPVVVAEKIQRI (SEQ ID NO:11). In addition, the L048 polypeptide was found to be cysteine rich, having a motif with distant homology to that of polypeptides with Zn++-fingers.

Northern blot analysis using a sequence from the L048 clone revealed the presence of a 2.5 kb mRNA transcript. In addition, this analysis revealed that the expression of the L048 mRNA was strongly upregulated in response to the multiple MECS treatment.

Another IEG nucleic acid clone was designated L064. The following nucleic acid sequence is within the L064 clone:
5'-ATTCCAAAAATGCATAGATTACAAAGAAACA
CCAGACAAGCTCAAACTCAAGGATATTCTACA
AATAAACCAGTACCTTCAAAATGCCATGCTACCA
GGTACAGACAGGCGAGANACTGTTCCACACTG
AGGAAACTAACAAAGTATCCATGAAGTCCATAA
TTGTGGGTCAAATCCAGGACCTGCAAAGGGGA
TTTGGGGATAATTTTCAAAATTTGACTAAGGTCT
GCAGAGTAGAGAGACGAGGTCAATGCCAATGT
CCTGATTTTGACAGTAAGTATTTAAATATGCAG
GAGAACAACCTAACCAAGAGGCTGCCAACACAC
TTCCTGGCTGTGGCACAACTAGATTTAAAACC
AGCAATTTGTTGGTTCTTGTTCTCAAATATCAGT
TACCTGCAAGCACTCCATCGTGAAAGGATTGA
GAGCATGAGGTGATGTGTTGATGGTGAAAATGA
GAACTGACTGAGCACAGGAAAGAGTGGCATG
TGGGCAGGGAAAGGGGAGACAAAGGTCACAAG
GCATGCAACACTCAGTGAACTACAGGACACTC
CAAAAGGCACTCTGCTGTCTAGCTTGGATCTG
GAGGAGGATCAGNTATTAATAAGGGCCCTGGAA
GGGNCAAAGCTAGCCTCCCAGCTGCTGGCTTC
CCATCTGCT-3' (SEQ ID NO:12).

Another IEG nucleic acid clone was designated L067. The following nucleic acid sequence is within the L067 clone:
5'-GCCACCACCATTGTTAATGGAGGGAGGCTCT
CCCTTGTTATTTCTCAGAAGACTGAATGTCTGT
ACCAAAAGGCTCATGGCTTTCTCTGGGCCTTTC
CATTTAAGGTTATAGTTTTTTATGTAGTGTTACTA
AAATCTAGGCTTGTTACTAAAGTGGGCTTTGTA
TTATTGGTATCGGTGGATTTTTATGTTACTTGGAG
TCCAGAACAGGGAGAGCTCACCACAAACCTCT
CCTTTCCCTGGACCAAACACCCTCTCTGTCCTG
TGAACTCACCTTTTCTTCTCTGTGGGTCACTCC
CATTACCACACTGGTGAGCGAGCCAAATGGATGA
GAGACACAAAGACCGTAGTTCTGAGAGACATT
ATTTTTTTCAACTTTGTTTTTAAGAGATTTTATG
TGTTGATTTGTTTTGGTTTGGTTAAAGGGATTC
ATAGCTAACTTGGATTTTTGTTACCTCAGCTCT
GGAGAGGATTTTTGCTGAATGACTATTAATTACC
TGAGCATTGTTGCTCTGAGGTCATGGCATGCTA
GCCTATGTCTGTTACAGTCTCAGGCTGCCCTTG
TTTCCTCGTTCCTGTGCTATTGTGCTACACGCTC
AAGGGGCCTTGACTCTGCTTACACACATTAGGG
GCAGTGTGAGTAAATGTGCAGTGTCCACACTTG
AGGACATGAATGTCTGCACTGTCACTTTGCTCT
GGTGTGAAGTCCCTGGTCCCCTTGCTCCTGTAG
TTTCTTTTGATCGACTACTGGAACTCAACCCTGT
GTACAAGAGCAGCACTGCCTCTGGTGGGTGGT
GTTTGCAGCCAGGATTAGATGCCAGTCCTCGGG
TCCCTGGCCTTGTTGGAAAGGTGTGCTTCCTTGA
GGTCTGAGAATGGAAGGCTCTGCCTCACTCTAG
CTAGGAGGCGCAATGGGAAAGTATGAGTTCAG
GGCGTCAGGGCAGTGGCTCCTGAAGAGCCAG
CTGTGGACAGAGGGAGTGAGGCTTTATTTAA
AGTGACAGGAAGAAACATGGCGTTTTGGTATA
TTGGGAGCAATGCCAAGATTCCCTCCTGCCCT
ACATAGGTCACAGACACCTTCCCAACCATCC
CCTCCTCCACTTCCATAAATGAAGACAGCCCT
GATGACCCTCACCCCTTTTGCATAGGTCACTG
GATCCCACTGTCCTTCCTCGGTGCTTACACAC
TTTACAGACCCTTTAGGCGAGCCCTTGCATAGA
GCGTTATCTCAGTGCTCCATTCCAGTCCTGACTC
CCTGTGGCCATTGAGACTTTGGATTTAAGAA
TCACATTGCTAGGGAGAGGGGCTTTGCTGGGA
AGGTGACTCCTCTGTAACCTAGCCTCTTGTGCT
CCTCCATGACAGAAATGCTGGGTGGAGTTTTAC
ATTTGCCAATGGCCAGCTTGTGAATATCTTCATAT
ACACTTTCTATTCATGTTACTGTAGTTTCTGTTTT
GAAATAAAACTTCTGAATGT-3' (SEQ ID NO: 13). This clone is similar to a glucose transporter type III polypeptide.

Another IEG nucleic acid clone was designated L076. The following two nucleic acid sequences are within the L076 clone:
5'-CATATAAATGTACTTTATTGTTTTAAACAGAAC
GAAAGAAGAGGCAGAAAACATTTGCATGTAAG
TCCTAGCTTATAAATGTAGTTTTTAGTGGTGGCA
TCTCTAACACGTCGTTCAGGGACTGTTTCCTTT
TGCCTCCTTGTACTGTGAGCACTGACACTTGA
AAAAGCACATCTGGCGGACATATGTCTCCAGA
ACTGGAAGAACTTGGAGAGCAAACATTTTTCTT
AATTCCTCTAAGTAATCTTTAGTAAAACAAAAG
ATGATCTTTGGCATAGATTCATACTTTAAAGGCA
TTGATATGCATTTATATCAGGTAAGCAACTATAC
AGATCTGCTGAGAGCTTTCAAAAGAATCTGTT
ATCAGCTGAAAGGAAATAGGGGAAGCCTGAGTA
TCAGGGTCAACTTAAGATTTGCAAGTTCAGTG
TTGGGGTCAACATACTAGATGTGGGAAGAACA
TCCAGGCAAGGTCTTAGTCCTGTATTCACCTG
GTTCTTGATTTCTGGAAGAAGCATCCATGCGCT
AGGAAATGCTTATACAGCCGAGGTAAATGCAA
AAATGAGTAAAGTCACTTTTTCACTAACTTTGCC
CAATAGGRAACATGCCTTTCTGATAAGTAGATAC
CATACTCTTTATTCTTGAATACTTTATATTGAGA
AAGGTTGTAGTTGGTTAAAAGCAACTGGGAAC
TATAACTTCCTACTGATTCCCTAGCAGCACCAG
AATTATATTCTGCAAATGCTATTCTCCCTTACATA
GGAAATATCCTTCAGACAAAATTGCCTTTCCATT
AGTCTCTTAAGAGYTTAATTTTGAATGGACTTTT
CAAAGTTACAAGCAAAGTCAAGTGTGGTGGTA
GGAGCTAAGAGGCTGACACAAGTAGATGACTT
GAATCCAGAAGTTCAAGACTAGCCTGGACAACA
TAGAGAGACCCAGTCTCAAAATT-3' (SEQ ID NO:14) and 5'-GGCGGGGATCTCTCGGCTGGTAAGAAGGGGC
AGTGGTACCANGCGGGCACTTATTCAGTGTGCC
AAGGATATCGCCAAGGCCTCTGATGAGGTGACG
GGTTGGCCAAGGAGGTTGCCAAGCAGTGCAC
AGATAANGCGGNTTAGAACCAAATCTCTTACA
GGTCTGTGAGCGAATCCCAACTATAAGCACCCA
GCTCAAAATCCTGTCCACAGTGAAGGCCACCA
TGCTGGGCCGGACCAACATCAGTGACGAGGA
GTCTGAGCAGGCCACAGAGATGCTGGTTCATA
TGCCCAGAACCTCATGCAGTCTGTGNAAGAGA
CTGTGCGAGAGGCCGAAGCTGCTTCAATCAAG
ATTCGANCAGACGCCGGATTTACTCTGCGCTG
GTCAGAAAGACTCCCTGGTACCAGTAGGCAC
CTGGTCAGACCTGGCTGGTACACAGACCTCTG CTAATGANGANGTGACCATCTTGAGCTTCAGAA
CCATTCAGAGTTGCCAAGGGGTGGNAAATCA
ATCCCTGGTTTCACACACCAAGAAAGGGAAT
GGGGCCTCCTTCACATTAGAATAAACATTTATA
TCTTGTCATGGGACACTTTGAAAGTGTCTCTC
TACAAAACCCCTGGTACCTTTCAGGNTTACTCC
GGTNGCAANNTCCTCCCCCAAGGGGAATTTTTT
ACCAATAAAAGGCTCAAGGAATTAANGGCGNTT
GAAAACCAACNTNATCCAANGGGAAANGCCCC
CNTGGCCTTCTGGCCCCCTTGGGGGNACAATTT
TTCNTCCCNCTGGGTGTTTAAATGGGGTTTCAA
CCTTGGGGCTGGNCCTTTTTCCNCCCCCCCTTT
TAAGGGGCTTCCTCCGAAGGAACCTNAGAAAAC
TNAAGGGCCAAAGNTCCANTTTACNAATAACT
G-3' (SEQ ID NO:15). This clone is similar to vinculin.

Another IEG nucleic acid clone was designated L082. The following two nucleic acid sequences are within the L082 clone:
5'-TTTTTTTTTTTTTTTTCCTCCCTTAAAAGATA
AACTAATAAACTCTTCAATGGTCTTTTTCAGTAT
AGTTCTTATGTAGTTTAACATAGCTTATAAATTG
AGTTTAACAATAAACTCAAGAAGATAATTTTATA
AACCCTGTTTTCCAATCTGTCATTTACTTAAATT
ATTTTGGTTGTTTTCCCTTTTTTTCCTTCTTTCTC
ACCCCCTCCCTCTCCATGAAGATTCAGGTGCTTA
ACATATCATTTTTTCCCTGCTGGAATTTTAGCAT
TGATATGAACCATGGACAAGTATATTCTGCTGCC
ACAAAGACTGTAAAGTGCTTCATTTCAACAGCT
GAGGCAAGCCAAGTGATCATTAATAAAGCTTTT
CTTGCTTCCTTCAGTGGTGTTGGTAGTAAAATG
GTAGGTAAAAGTTAGGCTGCAAGTTCAATAAAT
GAGATTTACCTATCATTCCACCCTTGTGTATTCAT
TCACCTATCCTGGTTCAAGCAGTTTGAGTCAACT
AGGCATTTAAAGGCATTGTGTTTATTACTTTATG
GTTCCAACTTTACATACTTGTCAGGGATGAAGTC
TGATAGGTTAAGGACAGTAGAAATTTCTGTGCA
ACAAGCAGCAAC-3' (SEQ ID NO:16) and
5'-TTTTTTTTTTTTTTGGTTACAAAAGTATTTATT
TTATAAAACTTGTATTTAAAATAGAGCTTATCTG
TCTACTCACAAATCCTAATTTAAAACATAACAC
ATTATCCTTAGCTAATCTGATGTTAACCTTTACAA
TCAACACTCATTTTTGTAATTTTATTAAGAACCT
GTACTAAATGAAGTTTTTAATCAGAAAACATTC
CCTTTTATCTTAAAAGTGCTTCTTAAATGAAGGC
ACCAACAAGAACTACTTTCAGATGGTACAGAA
TCTTATTTCTTGAAGACTCTGTGGTTGACCACT
TCTTCATTAGTTACCTGCAGCAAGACACCTTCC
GCCAAAGGAAAAAAAAAAGTATCTGAAGAAGT
TTATCATGTTTGTCCAAAGAACCTAAGTAACTTC
AGTGGTGGTTTTAGGATTAAAGCAGACTCACTG
TGTGTATACGCCCTGAATATCACATTTCTGGAAA
GCAGTAAAGCCTAGAAATCAGAAGGCGGGCGGT
TTTAAAGAAATTTCAATAGCCAACCTACAACAN
TTTAGGGCAAAGATAATGGGCAAAAANTNC-3' (SEQ ID NO:17). This clone is potentially similar to a nRNP polypeptide A2/B1.

Another IEG nucleic acid clone was designated L094. The following two nucleic acid sequences are within the L094 clone:
5'-ACGATATMTAYWGARRTWYAWCTSTTHACTG
AATMWHATGCACAAATATTAACTAGTRRTTTATT
AAACAGATATSATTTAGAACAAGACTTAAWKAA
ATACAAATCCTTAGGTACGRTTTAATATCATGTT
CADGATGTTTGAAGAGTTTAAAAAGAATCACT
GATTAAGKKAAGCATCCBCACTTTTCTTTGAG
AABCCAAACCTTTTAGGNAAADACCCCATTCC
AAATTTTGTCCCCHATTTCAGRCCKKCAGAAAG TCTCTAACATSAAGAGTCCTCAACGGGGNGTAA
CTCAVAWCTCCTATCAAGTGCAGTAACCTAGCT
CTCCCGGDGGCCATGGCGT-3' (SEQ ID NO:18) and
5'-AAACTAAACAGTGTTTTGTTAATTCTTCTGCA
TTCGGACTATTGCAGGCATTAGAGCATCCAGAG
CTACGAAGGGCTGGCTGCAGCAGCACCGCCCT
TTGTAAGCCAGCAGACCAGCCTTAACTGTGGG
CTTGACTCCTGTGAGCTGGCCTCAGTGTGACTC
AGAAATGTTTGATTAGCAGATGAGAGAGCGAG
CACACCACGAGGGCTGCGTTCTCTTCCTCCAG
GCTGTGCAGGACAGTTTCTTCTCACCCTAGCC
TTTTTAAATGCACCAGAAGTACAGACAGTTGCA
TACACAAACCCTTTGAACACTTGTAGAAATCAG
TCCACCGTAGATTAGACAGAATCACCTTCCAAT
CCTTTGACTTCTTTTCCTTTCATTTGAACAATT
GTATAATAATTGATTATTGTCAAATTTTTCTGT
TGTGGTAGTATCGCTTTAATTTATCTTAGTACA
TCAACGTTTTGATTTAAAAAAGAATTAAAAC
AACAAAAAAAGTCACTTAGAAGCCATGAAC
TTTTTTTTTNGATNGGGAAATTTTCTTGTTTNG
AAAATTATCATTGGGGTTCCTCCGGAAANCT
GTAAGATTGGNTTATAAGGTACCTGGGANGT
TCANAACNGGTGGNTATACCCTTTTTAAGGG
AAATTAATGATTTNGAGTTTTTGGGCCAACTNC
GGGANTGGCAGGGAAACCANNCNGGGGNGG
GGTTTAAATTNTGTGAGGGTTTTTTGGGCCTN
AATTTTTTGCATAATTTTCACCTNGNAACCTTT
NAANNCTNGGAAAAAAAAAAAAACNT-3' (SEQ ID NO: 19).

Northern blot analysis using a sequence from the L094 clone revealed that the expression of the L094 mRNA was upregulated in response to the multiple MECS treatment. Specifically, L094 mRNA expression was induced 7.3 fold by the multiple MECS treatment as determined from Northern blot data using total RNA from rat hippocampus (Table I). In addition, developmental studies revealed that the transcriptional expression level of L094 was upregulated between day E15 and E18, and downregulated at day 0. The expression then increases again during post natal development.

Another IEG nucleic acid clone was designated L097. The 5'-end of the clone obtained from the first library screen was used to design an antisense primer. Using PCR, L097 DNA was amplified and inserted into the pCR2.1 vector. The L097 clone is about 4.4 kb in length. Sequence analysis of the first 4060 bases from the 3'-end revealed the presence of a coding region of at least 2351 bp. In addition, RT-PCR analysis revealed that the L097 clone was missing an adenosine at position 1166 from the 5'-end. The lack of this base results in a frame shift in the coding sequence. Further, the sequence at position 1358 was ambiguous. However, any base substitution at this particular position will not alter the encoded amino acid residue. Specifically, a serine residue will be encoded by the codon containing nucleic acid position 1358 regardless of the base at position 1358. The following nucleic acid sequence is within the L097 clone:
5'-TGCAGCCGCCCTTGGAACTGCATGTCAGGAA
GCATCCCTTTGTGTATGTCTGTGC-
TATATGTCTCAAGAAATTTGTCAGCT-
CAATCAGGCTGCGCTCCCATATC-
CGAGAGGTGCATGGGCGGCCCAGGAGACCTT
GGTTTTTACTAGCTCCATCAACCA-
GAGTTTCTGCCTCCTGGAGCCTGGTGGG-
GATATCCAGCAGGAAGCCTTGGGAAAC-
CAGCTATCACTGACAGCTGAGGAATTTGTGTG
TCCAGAAATTGATGTACGTAAGGGGGAG-
GTTTGTCCTGGGGAAGCTCAGCCTGAG- GTGGGGCTGAGGGAGTTGGAGGCCCCTG-
GAGAAGCATGTGCCCCAGCCGTGCCCTTG
GCCAACCCCAGAGTGTCAGTGTTTCCCTGTCC
CCCTGCAAACTGGAAACCACTGTGGTCAATTCC
GACCTCAACTCTCTTGGAGTGGTTTCAGATGAT
TTTTTACTGAAAACTGATACCTCTTCTGCTGAGC
CTCATGCTGCTGCTGAGCTAACCTCAGACACAC
AGCATCGAGGCTCAGCCCAGACTCAGGGTGAAG
AAGTCACACTGCTGCTGGCCAAGGCCAAAAGT
ACTGGACCAGACTCAGAGAGTCCTCCAAGTGG
AGGGCAGAATGTGGGTGCTCTGCCAGCCAGTGA
ATCTGACTCTAACAGGTGTCTCAGGGCAAACCCA
GCAGAGACCTCAGACCTCCTTCCTACAGTGGCT
GATGGAGGAGACCTCGGTGTGTGCCAGCCTGA
CTCTTGCACGTCGTCCTCTGAGCACCACCCTGG
CAGCACAGCATTCATGAAGGTCCTAGACAGTC
TCCAGAAGAAGCAGATGAACACCAGTCTTTGC
GAGCGGATCCGGAAGGTTTATGGAGACCTGGA
GTGTGAATACTGTGGCAAACTTTTTTGGTACCA
GTGCATTTTGACATGCATGTCCGCACCCACACC
CGGGAACATCTGTATTATTGCTCCCAGTGTCACT
ACTCTTCCATCACCAAAAACTGCCTTAAACGC
CATGTAATCAGAAACACAGTAACATCTTGCTG
AAGTGTCCCACTGACGGCTGTGACTACTCGACT
CCAGATAAATATAAGCTACAGGCCCACCTTAAA
GTTCACACAGAGCTGGACAAAAGGAGTTATTC
TTGTCCTGTATGTGAAAAATCTTTTTCAGAAGA
CCGATTGATAAAGTCACATATCAAGACTAATCA
TCCAGAGGTCTCCATGAATACCATTTCTGAGGT
TCTTGGGAGAAGAGTCCAGCTCAAAGGGCTA
TTGGAAAGCGAGCCATGAAGTGTCCGTATTGCG
ATTTCTATTTCATGAAGAATGGCTCAGACCTTCA
GCGGCACATCTCNGCTCACGAGGGTGTGAAGCC
TTCAAATGTTCTTTGTGTGAGTATGCAACTCGTA
GCAAGAGCAACCTCAAAGCTCATATGAATCGTCA
CAGCACTGAGAAGACTCACCTCTGTGACATGT
GTGGCAAGAAATTCAAATCCAAAGGGACATTAA
AGAGTCATAAGCTCCTTCACACATCTGATGGGA
AGCAATTCAAGTGCACGGTGTGTGACTACAC
AGCTGCCCAGAAACCACAGCTGCTGCGACACA
TGGAGCAGGATGCCTCCTTCAAGCCTTTCCGC
TGCGCTCACTGTCATTATTCATGTAACATCTCTG
GATCTCTGAAACGGCACTACAACAGGAAGCAC
CCAACGAGGAGTATGCCAACGTGGGCAGCGGG
GAGCTTGCAGCTGAAGCCCTCATCCAACAAGG
TGGTCTGAAGTGTCCTGTTTGCAGCTTTGTGTAT
GGAACCAAATGGGAGTTCAACAGACACTTGAA
GAACAAGCATGGCTTGAAGCCAGCGACAGAGA
CTCCCGAGGAGCCCTCCACCCAGTATCTCTACAT
CACCGAGGCTGAAGATGTTCAGGGGACACAAG
CAGCTGTAGCTGCACTTCAGGACCTGCGATATAC
CTCCGAGAGTGGTGATCGACTTGACCCCACAGC
GTGAATATCCTGCAGCAGATCATTGAACTGGGT
TCAGAGACTCACGATGCTGCTGCCGTGGCCTC
CGTGGTTGCCATGGCGCCTGGGACAGTGACTGT
TGTAAAGCAGGTCACCGATGAGGAACCCAATT
CCAACCATACAGTCATGATCCAGGAGACTCTGC
AGCAGGCCTCTGTGGAGTTGGCCGAGCAGCAC
CATCTGGTGGTGTCCTCTGATGACGTGGAGGGC
ATTGAGACAGTGACAGTGTACACACAGGGTGG
GGAGGCCTCAGAGTTCATCGTGTACGTGCAAG
AGGCTGTCCAGCCCATGGAGGAGCAGGTCGGG
GAGCAGCCAGCCACAGAACTCTAGAGAATCCC
TGCCTCCTTTGGCAGCCAGCCTTTGTGGGCCTG
AAGACCTCCTAACCCACCAGGTCCATCCCTGGC
TCTTCTTGCCCACTGGCCCCAGATAAATTTCTC
CATAACTGTCCTCTGTGTGGTCAAAGCCAGGA
GAGTATCATGAAGAGAGAGAGAGAGAGACT
AGTCTCCGAGTTTTTTTTTTT-3' (SEQ ID NO:20). In addition, the following amino acid sequence is within the L097 polypeptide: QPPLELHVRKHPFVYVCA-
ICLKKFVSSIRLRSHIREVH-
GAAQETLVFTSSINQSFCLLEPG-
GDIQQEALGNQLSLTAEEFVCPEIDVRKGEVCPG
EAQPEVGLRELEAPGEACAPAVPLAN-
PQSVSVSLSPCKLETTVVNSDLNSLGV-
VSDDFLLKTDTSSAEPHAAAELTS-
DTQHRGSAQTQGEEVTLLLAKAKSTGPDSESPPS
GGGQNVGALPASESDSNRCLRANPAETS-
DLLPTVADGGDLGVCQPDSCTSSSEHH-
PGSTAFMKVLDSLQKKQMNTSLCER-
IRKVYGDLECEYCGKLFWYQVHFDMHVRTHTR
EHLYYCSQCHYSSITKNCLKRHVIQKHS-
NILLKCPTDGCDYSTPDKYKLQAHLKVH-
TELDKRSYSCPVCEKSFSEDRLIKSHIK-
TNHPEVSMNTISEVLGRRVQLKGLIGKRAMKCPY
CDFYFMKNGSDLQRHISAHEGVKPFKCS-
LCEYATRSKSNLKAHMNRHSTEKTHLCD-
MCGKKFKSKGTLKSHKLLHTS-
DGKQFKCTVCDYTAAQKPQLLRHMEQDASFKPF
RCAHCHYSCNISGSLKRHYNRKHPNEEY-
ANVGSGELAAEALIQQGGLKCPVCS-
FVYGTKWEFNRHLKNKHGLKPATET-
PEEPSTQYLYITEAEDVQGTQAAVAALQDLRYTS
ESGDRLDPTAVNILQQIIELGSETH-
DAAAVASVVAMAPGTVTVVKQVTDEEPN-
SNHTVMIQETLQQASVELAEQHHLVVSS-
DDVEGIETVTVYTQGGEASEFIVYVQEAVQPMEE
QVGEQPAT EL (SEQ ID NO:21). Using tblast2x algorithms, nine Zn$^{++}$-fingers were identified by homology to motifs of Zn$^{++}$-finger containing polypeptides (accession #PIR2:A32368, S03677, A29634, S06571, and A60392). The presence of the multiple Zn$^{++}$-finger domains suggests that the L097 clone is a transcription factor, however, the size of the encoded polypeptide is in excess of 700 amino acids.

Northern blot analysis using a sequence from the L097 clone indicated that the L097 mRNA transcript is rather rare. In addition, this analysis revealed that the expression of the L097 mRNA was very weakly upregulated in response to the multiple MECS treatment. Another IEG nucleic acid clone was designated L099. The following four nucleic acid sequences are within the L099 clone: 5'-TGGATCTACTT
GTTAATGGTTTCATGGAAGCAATCAGCAATATGT
GATATGAACTGCTGCATTACTTATTATACTCGTGG
AACTGAGATATTTARMSRSMGCTTWWYTTTTTT
TTTYTTAGTGTAAAATACTTAAGCGTTTCCACTA
TTGGAAGAAAAGCATATATGGGTATTTTGTATTG
TAACTTGTTTAAAAGGACAGTCTTTTTAAYCTT
CCCACTTAAATGCTTTTAAAAATATGTAATACAAT
TTGAAGCTTGTTTAAAAAATAGAATTAAATGTCTT
AWATAGKGCTACKGTTTTGGAATTAGAAAGTGAT
CAAATACAAAACATTTTAAAATTAAGCCCAGA
AAACAAAATAGTGTTTAAAGTTAGTTTAGTATA
AAAGAAATTTATAAGATTTTTTCTTCAATATAAG
ATACCTCACTTGAAAATAAAGAAAGCACAGCAC
ATTAAAGTAATTCTCATGAGAACACCCCATTAGA
ATAATTGCTAAATCTAGGACACCTTTTGAGTTG
TGAGTTTGTGATACATGTAGTCACCATTAGCTTT
TCTGCTGGAAGGACTTCCCGTAGTAATTTAAG
CAGTGTAATAGTTCAATTACCCCACAGTTTCTAA
CCTGGGAAGGCAGTATGTGAATGGTCCCTTCT
GCAACTACGGAAACACATTAGCTACATTGAGC
TAACTCGATTGATAATTTTGCCAGTGCATATAGT TTTATGATTAAAATTGCTGTGGTTGGTTGCATTA
CACGACACACAAAACTGTCCTCTACCTCACAT
GAAATAAATATTTTATATGGTTTTACTAAAAAAAT
GACTCATCTATCTGGTTACTTAGTTTACAAATTTT
GGATTATATTTATTGAAACATGACATACTGTGCT
CTTAGCTTATACCTCAATCGTATTTTGTGCTGT
TTGCCATTTTCATGCCTTGTATATAACTTGTATA
GATTGGATGATATTCCCAATAAACACTTTTAATK
CCAAWRAAAAAAAAAAAAAAAAA-3' (SEQ ID
NO:22);
5'-TAATGTTTATGATACAAAGCTACTCACTCTGGA
GCCTTCTCATTACAGAATCTCTTGACTTTTATAC
ACCCAGCCTGTTGTTACTTTGTTCAGGTTGCAG
AATGAGTTTCCTCTGGTTTCCTCCTAGAGGAGT
TTTCCTGATGAAATGCTAGTAGCACCTCCCCGAC
ATACAGCGGGTGGGTGGGGCACACTTTGCTGT
GCTCTGATGGTACACACAAGAAGCAGTTTGTAA
TTGTCTTTCTGTTTAAGAGTGACCATAGCTAGAT
ATGTGTGTGTGACTTCAGAAAATTAAAATGCTT
TCCGAACTTTTCCTGTTAATAGAGGTGTGAAGT
ACTCATTCATGTGCATGAGGAAAGTGGATTCCA
CGGACGCACACCGCTTCCTATGTAACTCACAAT
GCTCTGTACAGTTTTTATATGTAGTCTTACAAAG
GTCTTATGAAATTTATATAATGGATTTTTTCTTTT
AAATTATAAAATACTAAATATCTTAAAGATTGT
TTGGACTTTTGTATGTTTAAATGTTATCTTAAAA
CTTGCACAAATGGACCATGATGACTCTTTGATC
TAAAAATCAGGAATTTACAGTCAGCTAAGAAA
AATGTGGATAGGTTAATAATCCACAGTGGGAGT
TCTGCTAGGAGCAGGAATTGTAGATGACATGA
TTCCGTGATTTGAGGAAGGGCAGCCTCTGCAC
TTTTCTTTGTTTTTGTTTTTGCACATGAAGTC
GACATTTTACCATCGAATTTCACATTACTAGATG
GTTGGCTTGGGATTTACCTAGGGGAAATTCTTA
CAACTTTGTACTTTTGTTGTTTGTTCTGTTTG
TCTCCAGCTTGCAGAGACCCTCTTGCCTCTGTC
TCCCAAGTGTTGGGTTGGCAGGATGAGCCCCA
CCACCGCTGGCCCTGTGCAGTTCTTTTGGGATG
TCCCTGAAAGCAGCTGTGGCATTATCTTCTGTT
TCATGTGTCCCGAGCTGTCTCATGGTACTACATG
CAGTGACCTGAGATCTGCGTTAAGGAATAACTTA
GGAGAAAACGGCTGTCACTGTCCTCCCCGCTGT
GAGACACCAGAGTTATCACACCTGTTATGGTCA
TACTTTGTGTTATGATACTGATGTCTAAGGCAA
TTTTTCTACTTTCCAAAAGGGAGTTTGTTTCCT
ATATATTGTGACCTAAATGTGGTTTTATTCTGC
TATGTTCTATAATTTATGTATGACTTTTGTAACCT
CCTTGGGAGAAACATGTTAAGTGGCACAGGGA
CCATATATGTCATTTATTTTAGCTCTGGAGAAGG
AAACCACAGGCGTTTGTAAAATAGCATTAGCTT
AGATGTCAGTCATTGTGCTTGGCTGTGTGGGAG
GCAGACTCAAGGACTTGCACCATTTATTTTCT
GACAGAAGTGTTCTGCTTATGTGCTGCTTAGTA
GTGTGATTTTTCTAGTCTTGATGAAACTTGCCTC
GTGACATTGTTGAGCGTAGTCTTCACTTTCCAGA
AGATGAAATGATGTGCCATCATTTTCTGTCTAAA
CTTCCTTTAAAGTAATTTTTAATCAGCTGTAAATA
TCATATCTCCTACTGTTGAAAGTAACTTTAATTTA
CATTGCACCATATAGCTTGAAAACCAACTTTGAA
ATTCTGTACTCCTCCACAAGTGACCTCCGCTAAA
ATACCCATAGGAAGCTTACTTTGTGCATGCNT
GCTTTGTGTGCCGGTTGCCGTCCTAANGGTTGC
TTTGGG-3' (SEQ ID NO:23);
5'-TTTTTTTTTTTTTTTTTAGTGTAAAATACTTAA
GCGTTTCCACTATTGGAAGAAAAGCATATATGG
GTATTTTGTATTGTAACTTGTTTAAAAGGACAGT
CTTTTTTAATCTTCCCACTTAAATGCTTTTAAAA
TATGTAATACAATTTGAAGCTTGTTTAAAAAATAG
AATTAAATGTCTTATATAGTGCTACTGTTTTGGA
ATTAGAAAGTGATCAAATACAAAACATTTTAAA
ATTAAGCCCAGAAAACAAAATAGTGTTTAAAG
TTAGTTTAGTATAAAAGAAATTTATGAGATTTT
TTCTTCAATATAAGATACCTCACTTGAAAATAAA
GAAAGCACAGCACATTAAAGTAATTCTCATGAG
AACACCCCATTAGAATAATTGCTAAATCTAGGA
CACCTTTTGAGTTGTGAAGTTTGTGATACATGT
AGTCACCATTAGCTTTTCTGCTGGAAGGACTTC
CGTAGTAATTTTAAAGNAGTGTAATAAGTTCA
ATTANCCCACAAGTTTCTAANCTGGGAAAGNAA
NTATGGTGAATGGNCCCTTCTGCAACTACGGGA
ACACA-3' (SEQ ID NO:24); and
5'-TTTTTTTTTTTTTTTTTTGGCATTAAAAGTG
TTTATTGGGAATATCATCCAATCTATACAAGTTA
TATACAAGGCATGAAAATGGCAAACAGCACAA
AATACGATTGAGGTATAAGCTAAGAGCACAGTA
TGTCATGTTTCAATAAATATAATCCAAAATTTGT
AAACTAAGTAACCAGATAGATGAGTCATTTTTT
TAGTAAAACCATATAAAATATTTATTTCATGTGA
GGTAGAGGACAGTTTTGTGTGTCGTGTAATGC
ACCAACCACAGCAATTTTAATCATAAAACTATA
TGCACTGGCAAAATTATCAATCGAGTTATGCTC
AATGTAGCTAATGTGTTTCCGTAGTTGCAGAAG
GGACCATTCACATACTGCCTTCCCAGGTTAGA
AACTGTGGGGTAATTGAACTATTACACTGCCT
TAAAATTACTACGGGAAGTCCTTCCAGCAGAA
AGCTAATGGTGACTACATGTATCACAAACTCAC
ACTCAAAAGGTGTCCTAGATTTAGCAATTATTC
TAATGGGGTGTTCTCATGAGAATTACTTTAATGT
CTGTGCTTTCTTTATTTCAAGTGAGGTATCTTAT
ATTGAAGAAAAAATCCATAA-3' (SEQ ID NO:25). This
clone is similar to sno I.

Another IEG nucleic acid clone was designated L100. The
L100 clone is 2924 bp in length and has a nucleic acid
sequence as follows:
5'-TGCGGCCGCCGGGGCCGGGGCTGAGCCAGT
CTCTCCCGCCGCCGCCGGACGCGCAGACCTGG
GCAGGCTGCACCGACGGCCGCCTGGCCGAGCG
CACTGCAGGTCGCTGCGCGCGCTGCGACCCC
GGGGCCCGGACGCGAGTGGCTGCGGTGTCCT
GGGCGAGCACTGCTAGTTTAGGCCGTCTGTCC
TCAGCTGCTTGGAACCCCTACATCCCACCATG
GCTGGGATACAGAAGAGGAAGTTTGACCAGCT
GGAAGAGGACGACTGCAGCTCCTCCTCCTTGT
CTCTGGCGATCTCTCTCCCTCTCCTCCCAGCTCT
TCTGCCTCCCCTGCCTGGACCTCTGAGGAGGA
GGGACTGGGTGATCAGCCACCCCAGCCTGATC
AGGACTCCAGTGGCATCCAGAGTTTAACGCCC
CCATCCATCCTGAAGCGGGCTCCTCGGGAGCG
TCCGGGTCACGTGGCCTTCGATGGCATCACTG
TCTACTATTTCCCGCGGTGCCAGGGATTCACCA
GTGTGCCCAGCCATGGTGGCTGTACCCTGGGC
ATGGCTTCTCGTCATAGCACCTGCCGCCTCTTCT
CCTTAGCCGAGTTTAAACAGGAGCAGTTCCGG
GCTCGGCGTGAGAAGCTCCGTCGGCGTTTAA
AGGAGGAGAAGCTAGAGATGCTGAAATGGAAG
CTTTCAGTGTCCGGAGTTCCGGAGGCAGGGG
CAGACGTGCCGCTCACAGTGGACGCCATCGA
TGACGCTTCTGTAGAGGAGGACTTGGCAGTGG
CCGTGGCAGGTGGCCGCCTGGAGGAAGCGAA
TTTCCTACAGCCCTATCCACCTCGGCAGCGACGG
GCCCTACTTCGCGCTTCCGGTGTTCAAGGATT
GACCGAGAGGAGAAGCACGAGCTGCAGGC
TACGCCAATCCCGGGAGGATTGTGGTTGTCA
CTGTGATGGCGTCTGTGACCCTGAGACCTGC AGTTGCATCCTGGCGGGCATTAAATGCCAGAT
GGATCACACGTCCTTCCCCTGTGGCTGCTGCA
GCGAGGGCTGTGAGAACCCCCATGGTCGAGTG
GAATTCAATCAGGCGAGAGTTCAGACACACTT
CATCCACACGCTCACCCGCCTGCAGATGGAGCA
GGGTGCGGAGAGTTTGGGGGACCCGGAGTCC
CCCATGGAGGACGTTCCTGTCGAACAAACCGT
GGTTTCCCCCTTTCCTCCTTCCAAACCCACTA
TGAGCAATGACCTGGGGGACAGCAGCTGTGGC
AGCGACATGACAGACTCTTCCACGACCTACTCC
TCTGGCGGCAGTGGCAGCCGCAGCGAGGCTCC
AACCATCTTGCCCACCCCAGCCTGCCAGGTTCC
AGCTTCCGGTCTGGCATAGATGAAGACAGCCTG
GAACAGATCCTGAATTTCAGTGACTCTGACCTC
GTATTGAGGAAGAAGAGGAGGAGGGAGGGAG
TGTGGGCAACTTGGATAACCTCAGCTGTTTCAT
TTGGCTGACATCTTTGGTACCGGTGACCCCGGCA
GCCTGGCTAGCTGGACACACAGCCAGTTTGGCT
TAGCCTTCCATCGGGCATCCTAGATGAGAATGCC
AACCTGGACGCCAGCTGCTTCCTAAGCAGCGGA
CTCGAAGGGTTGAGAGAAGGTAGCCTCCCCAGC
GTTCTGGGTCCCCTGAGGGGGAAGCCGCCCAG
AGCAGCTCCTTGGACCTCAGTTTATCCTCCTGT
GACTCCTTTGAGCTTCTCCAATCTCTGCCAGATTA
TAGTCTGGGGCCTCACTATACTTCCCGAAGGGT
ATCTGGCAGCCTGGACAGCCTTGAGACCTTCC
ACCCTTCGCCCAGCTTCTCTCCACCGAGGGATGC
AGCTTCCTGGATTCTCTCATAGGCCTGTCTGAGC
CGGTTACAGATGTCCTGGCGCCCCTTCTGGAGA
GCCAGTTTGAGGACACTGCTGTGGTGCCTTTGG
ACCCTGTGCCTGTGTAAGGATTGAGATGACTTTT
TCCTGCCCTGAGACCCTGTTGCTGCTTTTTATGT
GATCTTGGTGTCCCCCAAGGTCTGTGTATGTAAC
GGTCTCCCGTGGGCTGGTTCTGCCCCCGTGCCA
TGTGGGCAATCCTCTATTTTTACAGTAACACTCTA
GATTTATTTATTTTTTATGTTTTTCTGTACTGAA
GGGAGGGTGGGAAGGGTATCCCTCTTTCAATGC
CTGGCCTCTATGTCCAAACAGAGGTCTCCCACC
TCCTACTGTATGCCTGGAGGAGGAAGGGGCGGG
GTTCACATCCCCTCTTTCTGTACTGTAAAATGC
TCCTTGGTCCAAAGACAGCTGAAAAGCAGGC
CTTAGGGTTTCCTGTGGACCGTGGGAGCTAGG
TCTTCTGGACTCTGAAGATGTAATTTATTTCTGT
AATTTATTTGGGGACTGAGACAGCAGTGGTTGG
GCCTCTCTGGCAGGTGGGCGGTGTTGAGGCA
ATCTTCGGTGTCCCCGCCGGTCTGGGCTTCGG
TGTGGCGTGTAGGTTCGAGCTGAGCAGACGGA
GGCTGTGCTTGACCATCGGTGATCAAAACTCCC
TCTGCCCCCTGCCCAGACGCTCTAACATGCCT
CTGTCCATTTCCCTCTCCCCAAGGCCATGGGTTA
TAAAGGCCCTATGTAGGATGGGGAGCCAGAGG
CCCTAAGACATGAAGCACACCCCAGATCACTGT
CTCTAGCCTTTCTGGGCACTGAATCCATCCTGA
CCCACCACACACCCCCCGGCCAGTTGGCAAGAA
GAGGTGGCTCTTGGGGGCTTTTATGCCCTTCATT
AGCTGATGTTGGATTTTATATGCATTTTTATATTGT
CTCTAAGTGTCAGAACTATAATTTATTCATTTCTCT
GTGTGTGTGTGTGCCAAGAAACGCAGGCTCTG
GGCCTGCCTCCTTGCCCAGGAGGCCTTGCCAGC
CTGTGTGCTTGTGAGAACACATTGTACCTGAGC
TGACAGGTACCAATAAAGACACTCTATTTTTAAA
AAAAAAAAAAAAAAAA-3' (SEQ ID NO:26). In addition, the L100 clone contains an ORF from basepair 145 through basepair 1890. This ORF encodes a polypeptide of 582 amino acid residues. The translational start site was assigned to the first methionine residue in the ORF. The amino acid sequence of the L100 polypeptide is as follows:

MAGIQKRKFDQLEEDDCSSSSLSSGDL-
SPSPPSSSASPAWTSEEEGLGDQPPQP-
DQDSSGIQSLTPPSILKRAPRERPGH-
VAFDGITVYYFPRCQGFTSVPSHGGCTL
GMASRHSTCRLFSLAEFKQEQFRARREK-
LRRRLKEEKLEMLKWKLSVSGVPEAGAD-
VPLTVDAIDDASVEEDLAVAVAGGRLEE-
ANFLQPYPPRQRRALLRASGVRRIDREEKHELQ
ALRQSREDCGCHCDGVCDPETC-
SCILAGIKCQMDHTSFPCGCCSEGCEN-
PHGRVEFNQARVQTHFIHTLTRLQMEQ-
GAESLGDPESPMEDVPVEQTVVSPFPPSKPTMSND
LGDSSCGSDMTDSSTTYSSGGSGSRSEA-
PNHLAHPSLPGSSFRSGIDEDSLEQILN-
FSDSDLGIEEEEEGGSVGNLDNLSCF-
HLADIFGTGDPGSLASWTHSQFGSSLPSGILDEN
ANLDASCFLSSGLEGLREGSLPSSSG-
SPEGEAAQSSSLDLSLSSCDSFELLQS-
LPDYSLGPHYTSRRVSGSLDSLETF-
HPSPSFSPPRDASFLDSLIGLSEPVTDVLAPLLESQ
FEDTAVVPLDPVPV (SEQ ID NO:27). This amino acid sequence was found to contain numerous cysteine residues, forming a motif that has features of a methalothionein-like motif. Alignment analysis revealed that the L100 methalothionein-like motif exhibits higher similarity with the methalothionein motif from *C. elegans* than with the methalothionein motif from mouse.

Northern blot and in situ analysis using a sequence from the L100 clone revealed that L100 mRNA is weakly expressed in wild-type rat brain. For in situ hybridization, Dig-labeled cRNA probes were used as described elsewhere (Kuner et al., *Science* 283:5398 (1999)). Specifically, this weak L100 mRNA expression was observed in the pyramidal cell layers as well as the dentate gyrus of the hippocampus, thalamus, cortex, cerebellar granule cell layers, and several fiber tracts including the fimbria hippocampus and the cingulum. In addition, Northern blot analysis revealed that the expression of the L100 mRNA was strongly upregulated in response to the multiple MECS treatment. Specifically, L100 mRNA expression was induced 17.2 fold by the multiple MECS treatment as determined from Northern blot data using total RNA from rat hippocampus (Table I).

The mRNA expression pattern of L100 demonstrated a compelling overlap with neuronal populations known to release Zinc into the synapse via synaptic vesicles and to take-up Zinc post-synaptically. Briefly, synaptic release and uptake of Zinc may participate in the induction and maintenance of epileptic seizures and the neuronal cell death following epileptic seizures and ischemia. The L100 metallothionine-like motif most likely enables the L100 polypeptide to bind Zinc or other divalent cations in vivo. The expression of L100 mRNA in Zinc-containing neuronal populations in the brain indicates that L100 polypeptide may sequester Zinc in brain.

In addition, when acute seizures were induced by kainate treatment, the expression of L100 mRNA was strongly upregulated (Tables II and III). Kainate-induced seizures is a model used to study epilepsy. Briefly, 300–350 g male Sprague-Dawley rats were intrapertoneally injected with either 10 mg/kg body weight of kainate or PBS. RNA samples from the hippocampus, cortex, and cerebellum were prepared from treated rats at 1.5, 6, and 24 hours post-injection. This RNA then was used to measure mRNA expression by Northern blot and RT-PCR analysis. Control mRNA measurements included c-fos, GAPDH, NO-38, and ATF-4 for the Northern blot analysis, and Hsp70, c-jun, Zif268, c-fos, Clathrin, and β-actin for the RT-PCR analysis. A Phosphoimager FLA2000 (Fuji) was used to analyze the data, which was expressed as the Integral PSL—background PSL (1D evaluation with Aida version 2.0).

At six hours following kainate injection, strong upregulation of the L100 mRNA was observed, by in situ hybridization, in the dentate gyrus and areas CA3 and CA4 of the hippocampus as well as the associated entorrhinal cortex, the cingulum, and fimbria, which are brain areas known to be highly excited in and which mediate Kainate-induced seizures. Moderate upregulation of the L100 mRNA also was found in the thalamic nuclei, temporal, parietal, frontal, medial orbital, and cingulate cortex as well as in the cerebellar granule cells. Thus, the data presented herein indicates that L100 participates in cellular mechanisms mediating kainate-induced epileptic seizures and the consequent neurodegeneration.

TABLE II mRNA expression normalized to GADPH expression

| Clone | 1.5 hour PBS | 1.5 hour kainate | 6 hour PBS | 6 hour kainate | 24 hour PBS | 24 hour kainate |
|---|---|---|---|---|---|---|
| Hippocampus: | | | | | | |
| L100 | 4622 | 85251 | 7847 | 15444 | 3940 | 16551 |
| L119 | 2816 | 69982 | 4597 | 11519 | 2787 | 12944 |
| Cortex: | | | | | | |
| L100 | — | — | 81 | 290 | 86 | 131 |
| L119 | — | — | 255 | 1262 | 538 | 505 |

TABLE III

Fold increase in mRNA expression upon kainate treatment

| | Hippocampus | | | Cortex | | |
|---|---|---|---|---|---|---|
| Clone | 1.5 hour | 6 hour | 24 hour | 1.5 hour | 6 hour | 24 hour |
| A013 | 9.8 | — | — | | | |
| L094 | 3.6 | — | — | | | |
| L100 | 18.44 | 1.97 | 4.20 | | 3.58 | 1.52 |
| L119 | 24.85 | 2.51 | 4.64 | | — | |
| R113 | 2.0 | — | — | | | |
| R286 | — | — | — | | | |

In addition, when acute seizures were induced by pentylenetetrazole (PTZ) treatment, the expression of L100 mRNA was strongly upregulated (Tables IV and V). PTZ-induced seizures is a model used to study epilepsy and ischemia. Briefly, 300–350 g male Sprague-Dawley rats were intrapertoneally injected with either 50 mg/kg body weight of PTZ or PBS. Total RNA samples from the hippocampus, cortex, and cerebellum were prepared from treated rats at 20 minutes, 6 hours, and 24 hours post-injection. This RNA then was used to measure mRNA expression by Northern blot analysis. Control mRNA measurements included c-fos and GAPDH. A Phosphoimager FLA2000 (Fuji) was used to analyze the data, which was expressed as the Integral PSL—background PSL (1D evaluation with Aida version 2.0).

TABLE IV mRNA expression normalized to GADPH expression

| Clone | 20 min PBS | 20 min PTZ | 6 hour PBS | 6 hour PTZ | 24 hour PBS | 24 hour PTZ |
|---|---|---|---|---|---|---|
| Hippocampus: | | | | | | |
| L100 | 534 | 1637 | 854 | 1992 | 966 | 1903 |
| L119 | 342 | 965 | — | — | — | — |
| Cortex: | | | | | | |
| L100 | 958 | 2719 | 1162 | 3740 | 1175 | 1825 |
| L119 | 577 | 1605 | — | — | — | — |

TABLE V

Fold increase in mRNA expression upon PTZ treatment

| | Hippocampus | | | Cortex | | |
|---|---|---|---|---|---|---|
| Clone | 20 min | 6 hour | 24 hour | 20 min | 6 hour | 24 hour |
| L100 | 3.1 | 2.33 | 1.97 | 2.84 | 3.22 | 1.55 |
| L119 | 2.82 | — | — | 2.78 | — | — |
| R113 | — | 2.0 | — | | | |
| R286 | — | 2.6 | — | | | |

In another study, the expression pattern of L100 and L119 was determined using two models for ischemia. Briefly, neurons degenerate in brain and spinal cord after acute insults (e.g., stroke, cardiac arrest, and trauma) and during progressive, adult-onset diseases (e.g., amyotrophic lateral sclerosis, and Alzheimer's disease). Impaired energy metabolism plays an important role in neuronal cell death after brain ischemia, and apoptosis has been implicated in cell death induced by metabolic impairment. The irreversible inhibitor of succinate dehydrogenase in the mitochondria, 3-nitroproplonic acid (3-NP), inhibits oxidative phosphorylation and causes intracellular hypoxia. Thus, one model used to study ischemia involves intrastriatal injections of 3-NP, which is known to produce selective cell death similar to that observed in transient ischemia and Huntington's disease (McLaughlin et al., *J. Neurochem* 70:2406–2415 (1998)). The other model is a global ischemic paradigm that involves a 15 minute insult by complete occlusion of the carotis.

In the 3-NP study, 220–300 g Wistar rats were intraperitoneally injected with 20 mg/kg body weight. Three hours post-injections, the brain was removed and total RNA prepared. In the global ischemia study, 220–300 g Wistar rats were received a 15 minute insult (bilateral occlusion of the Carotis/arterial pressure=35 mm Hg). One hour later, the rats received a reperfusion followed by immediate brain dissection and total RNA preparation. Untreated rats were used as controls for each study. Ten (10) μg of total rat brain RNA (without cerebellum) was loaded per lane and blotted. Probes were prepared from the 3' untranslated regions of L100 and L119. The Northern blot data was collected using a Phosphoimager (FLA2000 Fuji, Tina software) and expressed as PSL—background.

L119 mRNA expression was upregulated 6-fold by global ischemia while L100 mRNA expression was not inducible by global ischemia (Table VI). This result indicates that only seizure related stimuli alter the expression level of L100 and that L100 is not a general marker for stress response of the cell like c-fos.

TABLE VI mRNA expression after 3-NP or global ischemia treatment.

| Probe | Untreated | 3-NP | Global Ischemia |
|---|---|---|---|
| c-fos | 18.1 | 26.64 | 216.22 |
| GAPDH | 487.02 | 587.51 | 593.31 |
| L100 | 30.95 | 43.82 | 40.15 |
| L119 | 55.48 | 41.94 | 332.73 |

Northern blot analysis using multiple tissues from rat revealed that the expression of L100 and L119 mRNA was not brain specific (Table VII). Briefly, fragments from the 3' untranslated region of L100 and other IEG clones were labeled with $^{32}$P-dCTP. The denatured probe was hybridized with 10 µg total RNA from rat brain, liver, lung, muscle, intestine, eye, heart, testis, and kidney in the Quik Hyb-solution (Stratagene) at 68° C. and washed with 0.1×SSC at 60° C. For L100, after one day of exposure, signals were detected at the 3 kb position in brain. In addition, a weaker signal was detected in heart and a faint signal detected in kidney. A strong signal was detected in testis but this signal was at a position corresponding to a size smaller than 3 kb. For L119, a strong signal was detected in heart and weaker signal in brain. In addition, only very faint signals were detected in liver, kidney, and testis.

TABLE VII mRNA expression in various rat tissues.

| Probe | Brain | Liver | Lung | Heart | Kidney | Muscle | Intestine | Testis | Eye |
|---|---|---|---|---|---|---|---|---|---|
| A013 | (+) |  | (+) |  | (+) |  | (+) |  |  |
| L094 | + |  | + | (+) | + | (+) | + |  |  |
| L100 | +++ |  |  | ++ | + |  |  | +++(*) |  |
| L119 | ++ |  |  | +++ |  |  |  |  |  |
| R113 | (+) | (+) | (+) | (+) | (+) | (+) | (+) |  |  |
| R286 | +++ | (+) | +++ | (+) | + | (+) | (+) |  | ++ |

(*)smaller transcript

Another IEG nucleic acid clone was designated L111. The first round of screening produced a clone (designated L111-5) that contained a 3.0 kb fragment of L111. A second round of screening using the coding region of L111-5 as a probe produced several additional clones. The following nucleic acid sequence is within the L111 clone:
5'-ATTCGGCACGAGCCAGAGTGAAGGGGCATGGA
GAAGTGGACGGCCTGGGAGCCGCAGGGCGCCG
ATGCGCTGCGGCGCTTTCAAGGGTTGCTGCTG
GACCGCCGCGGCCGGCTGCACTGCCAAGTGTT
GCGCCTGCGCGAAGTGGCCCGGAGGCTCGAGC
GTCTACGGAGGCGCTCCTTGGCAGCCAACGTAG
CTGGCAGCTCTCTGAGCGCTGCTGGCGCCCTAG
CAGCCATCGTGGGGTTATCACTCAGCCCGGTCA
CCCTGGGAGCCTCGCTCGTGGCGTCCGCCGTGG
GCTTAGGGGTGGCCACCGCCGGAGGGGCAGTC
ACCATCACGTCCGACCTCTCTCTGATCTTCTGC
AATTCCCGGGAGGTACGGAGGGTGCAAGAGATC
GCCGCCACCTGCCAGGACCAGATGCGCGAACTC
CTGAGCTGCCTTGAGTTCTTCTGTCAGTGGCAG
GGGCGCGGGGACCGCCAGCTGCTGCAGAGCGG
GAGGGACGCCTCCATGGCTCTTTACAACTCTGT
CTACTTCATCGTCTTCTTCGGCTCGCGTGGCTT
CCTCATCCCCAGGCGTGCGGAGGGGGCCACCA
AAGTCAGCCAGGCCGTGCTGAAGGCCAAGATT
CAGAAACTGTCTGAGAGCCTGGAGTCCTGCAC
TGGTGCCCTGGATGAACTTAGTGAGCAGCTGGA
ATCCCGGGTCCAGCTCTGTACCAAGGCCGGCCG
TGGTCACAACCTCAGGAACTCCCCTGATCTGGA
TGCAGCGTTGTTTTTCTAAGAGCATCCTCTAGC
TGTGTGGAATGTTCTAGATTCGCAGCATCCACAA
GGAAGTGCTACATGGGCGGAGTGCAAAGGAT
TCAGAAGCTCTTCTTGCAGGGCATCAGTCCGTA
GCTCCTTGTGTGTGCGAAAGACTTTTCACTTG
TGTAATCCCAACTGAGTATGTGACCCTAAACAGT
CACTTTGGGGACTCCCCAAATCCTTTTTAGCT
GCACACAGCTTGTCAGACTGTCCTTCAATTA
GAGTTATTGGGGTGGGGGGGCTTGATGGCTTG
AGTAATAGAGGTCTGGCGAGGTGTCTCCCT
CTTGGACCTCTTATGTGTTGTTACTAGAATCCT
AGATTCTCAAATGTTGGTGAGAGGAGACTTT
TACTTTTCAACTTTGCTTCGGCAGTTTCCGATA
CACAGGACTCCAGAATCCAGAACAAGAAAG
AAGAACCTTGTGTTTGTAGGGTGTGCAGACCC
AGACGGGGCCGAGGAGCTGACTTGCTCAGCT
CTCACACGCAGCCAGTTTATCCACTCACAGACC
AACCTGGCTACTGCATAGACTGTTCCAGTGTG
GCTTCAAATCCACACCTCTAGGTACCCTGAG
AAGGAAAGCCACCTGAAGAGTCACTCTAATCC
CAACACGCTCACCCCCTTCACGTCCATAAA
GGAGCTGGGCAAGGGGTGAGATGAAGACCCTGA
CAATTTTAAATGACTGTAGCATAGAGAGCCAT
GGCCTTTGAGTTTAAGAGTCTTGATCCCAGG
TTCTGTCCCCACTGTCCTGTGACTTAGCC
ACCTTGTCTTGCTACAGATGGTGGTAGGAGGCC
CCCTGTTGCGAAGTCCTGAGATAATGACAAA
CACAGAGGCTAGCTCACAAAAATGTACTTC
TGGCCTGGCTTCTGAAGGGTTAACTGTTGGGC
TCCATCCCAGATTTCTGAGATCAGGAACTCC
AAATATGAGGCCCGCCTCTGGCTGATTCTGAT
GCCCCATAAATGTTTGAAAATGACACAGCA
AAGGTTCATCTCCAGCCAGGTGTGGTGGG
ACACACCTGTAAGGCCAGCGCTTGGAGATGG
AGACAOGGGGGACCAGTAGTTCAGGGTC
ATTCTTGGCTACATAGCAAACTCAAGGCCAC
CCTGGTCTCAAAAACCAAAACAAAAAGCCATC
TCTGACTCCCTTCAATTGTTCAAAGCCTTTCCAG
GGCCTTCAGAATCACGCTCAGAGTGTTCTGGGA
GATTAGCCCAGAAGCCAGAGAAAGAGTACGCTG
TGTGCTTGTAAAGCCAGTTACTCTGTCCCCTGT
AACTAGGAGACAGAGCACTTCCGACCCTATAGA
GGGCAGTAGTGGCCATTCCTTGTAGGGGACTGG
TATAGAAGTAATGTGAACTATTTAAAAATAGTT
ATTTAATTGCTGCCTTCACATTTGATTTTATTTAA
CCTTCACATTATTTAGAAAATAATAAGAGTAG
TAAGTGTCTGAATAGGAAGGGAGTCTCTTAAG
GCTCTTTCCAAGAGCTCAGGTTTGGATTTCTAG
AGTCCCCCGACCCCAGAGAGGACTCTTTAGTG
TTGACACGGTCTTTGTAAGTAAGATGGGGAGTC CTGGAGAGAGAGACCAAGCTGATTTTTAAACTA
GGAAATGGAGTCTTGAACTGTGGAAGATTTGA
AAAGTTAAGCCTATGTGTCTTGAAGGTACTTGGC
CAGAAAAGCACTTGGCTTGAAAAAGAAAACCT
GTTTAATTCAGGGGTGGAGGAATAGAGACAGATG
AAGAAAGCATTTAGACCTCGGAAACCTGATGTC
CTATGAAATTCTGTTTTTATAAAATTGTGTTATGG
TGGAGATCTGTTGCATTTCGACTTTGTGGCTGTA
AGAAACCTGTTATCTATGTTTAAGAAAGTACTT
TAATTTATTCAATGTCTTCCTAAATTATCCTTTAA
AAAAAAAAGTTGGAAAGTCTATGAGACCGTACC
TAAGAAACCTTGACTGTGTATTTAAGTTATTTAAT
GCCATGCATTTGTGAAGCCCCTTCCCAGTGATGG
CTGTGGTGTGTCTGAGGAAATGTAAGTTTGGCAT
AGGGGGAGGGGCTGCTGTTTCTATATTTGTTTTT
GTTTTCTATAAACAGTAATCAGGATGTATCCTGGT
TTCATTTGACATTGAAAAAAAAAAAAAAACTCG
TGCCGAATTC-3' (SEQ ID NO:28). The L111-5 clone contained 0.5 kb of the 3'-end of an ORF.

Northern blot analysis using a sequence from L111 revealed the presence of a 4.0 kb mRNA transcript. This analysis also revealed that the expression of L111 mRNA was marginally upregulated in response to the multiple MECS treatment.

Another nucleic acid clone was designated L117. The L117 clone is 2460 bp in length and has a nucleic acid sequence as follows:
5'-TACGGCTGCGAGAAGACGACAGAAGGGGAGC
GGAGCCAAGATGGCGGCGGAGCTGGAATACG
AGTCTGTGCTGTGTGTGAAGCCCGACGTCAG
CGTCTACCGGATTCCGCCGCGGGCCTCCAACCG
CGGTTACAGGGCATCTGACTGGAAGCTAGACCA
CCTGATTGGACTGGTCGCCTCCGAATCACTTCA
AAAGGGAAGATTGCCTACATCAAACTGGAAGAT
AAAGTTTCAGGGGAGCTCTTCGCTCAGGCGCCA
GTAGAGCAGTACCCTGGGATTGCTGTGGAGACT
GTGGCCGACTCCAGCCGCTACTTTGTGATCAGG
ATCCAGGATGGCACCGGGCGCAGTGCGTTTAT
TGGCATCGGCTTCACGGACCGGGGAGATGCC
TTCGACTTTAATGTCTCCCTGCAAGATCACTTCA
AGTGGGTAAAGCAGGAAACCGAGATCTCCAAAG
AATCGCAGGAAATGGATAGTCGTCCCAAGTTGGA
TTTAGGCTTCAAGGAAGGGCAAACCATCAAGC
TGAGTATTGGGAACATTACAGCCAAGAAAGGG
GGTACTTCTAAGCCCCGGGCCTCAGGAACGGGG
GGCCTGAGCTTACTCCCACCTCCTCCTGGAGGC
AAAGTCACTATCCCCCCACCGTCCTCCTCCGTT
GCCATCAGCAACCACGTCACCCCACCACCCATT
CAAAATCTAACCATGGAAGTAATGATTCAGATAT
CCTGTTAGATTTGGATTCTCCAGCTCCTGTCCCG
ACTTCAGCACCAGCTCCAGCTCCAGCTTCTACA
AGCAATGACTTGTGGGAGACTTAGCACTGCAT
CCAGCTCTGTTCCAAACCAGGCACCACAGCCA
TCTAACTGGGTCCAGTTTTGAGTCGCATTGGCA
AGAAGTTGAGGACACTTGAAGAATAAAAATGA
TCAAGGGCACCATTCTATGAGGGAGTTGAGGG
ACGGCTTAATTTCCCAGGACCCAAATCAGTGGTC
AGTCTTTCCTGTAGCTTCTCTGTGCATTCAGGCT
GGATTTTTTTTTTTTTTTTTTTGGTTACCTCTGT
GTTACTTGCTGTATATCCAGGAGACAATCTGCTG
TTTCCTGCTCAGAACCAAGCAAGGGAGTAGTGG
GTATTATCACACTGACTGACTTTGCAGAGTTCA
GAAGGCCAACTTGATGAGTGGGAGTGACCTCGA
ACGTATGTAAATCCTTGAACTTATTTCAGAATCA
TCTCATGATTCCCTAGTTAGCAATTTCAGGAGAG
ACAAATGCCTTGAAACTGTCTTCTCCACTAATC
CGAGACTAAATATGGTCAGGCTGGCCCCAGGA
CTCATGAAGTTAGGGTTTTCATGGGGGTAGATT
TGGAGAAAGCTGTGTCCCGGCTCTCTTCTGTAA
GCCTCCTTCAGGCTTACCCCATGCAGTGAACTT
CCCGTGCTGGGTGGAGCCCCATCACCTTCTTGT
GTGTTTACATGTTGTTTCCTTTGACAAGAGGGTT
ATGTTGGTGGCACCTCACTGTTTTCTTGTTGAA
TAGTGCAGCATCTTTGACCAGTGAATATTTCTGAG
ATGAAGGGGTCAAGGGGCTGTGCTTTCCATGGT
GTAGTCTACAGAAGTGTTTAATTTCTTGCGGCCC
CACGGGATTGCTGCACTGACGCATAGAATTGAT
TATACTCACCCTGTGTTTGACCTGAAGAGTTTTA
CTTGATGTGTAGAGCAGAGAGCTGGAAGCACT
AAGTTCCCATTCAGTACCCACAATGCCTTGCTGC
CTGGTTTGACTCCTTTTCATAAACATTTCATTTC
AGTCCATCTAGCACTTCTGTGGAAAGCTGCTGTT
GATTGTGTCAGTGTGAAGGAGGTGAAGTCACA
CTTTCTTTACCTATGACAGTTAGGCTTTGCACTA
GACGTTGATACCAGCTAGGATATCTTAAAGGAA
GTTACCGCCCCATCACTCTCCAGTCTCTGGCCG
CATTCCTTTTACAGTGCTGTGAAGAGCGTCCTC
TGAGGTCGGTGGGTACTGTCTCCTGTTGGTCGG
GCAGTTtGAGGGAGGAGTGGGAGGACTCACACT
CCTGCAGGTACCTGTTTGGGTAGCACACTGGC
TGCAGAGAGTCCTTTCAGATATATTGTTTCTCAAT
TTCTTCGTAGCTTTTTCTAACTTCGGGTCCATTT
TTCCCATCGCCTCTTCCCATTCCCAGGCAGCTCT
CTTGTTGCAGAGCCATGGCAGGACGTTTAAGT
TCCAATAAAAACACTAAGAAGAAAGTATAGAAT
CACTAGTGACTGTTGGGAAACCTATTTTCTCAAT
CTTCCTCCATTTTGTGTTCTTTGTATTCTTAAGA
TGATAATATATTATGTATTTGAATTGCTGAAAATT
GAAAATGAAGTTGAAGATATATGTATATAAGCG
TATGCTGTATTGGTGCAATAATGGTAATTAAAG
ATATTAAAAAAGAAAAAAAAAAAAAAAAAAAA
AAAAAAAAAAAAAAAAAAAAAAAAAAAAAAAA
AAAAAAAAAAAAAAAAAAAAAAAAAAAAAA
AAAAAAAAAAA-3' (SEQ ID NO:29). In addition, the L117 clone contains an open reading frame (ORF) from basepair 42 through basepair 875. This ORF encodes a polypeptide of 278 amino acid residues. The amino acid sequence of the L117 polypeptide is as follows: MAAELEYESVLCVKPD-VSVYRIPPRASNRGYRASDWKLDQPDWT-GRLRITSKGKIAYIKLEDKVSGEL-FAQAPVEQYPGIAVETVADSSRYFVIRIQDGTGRS AFIGIGFTDRGDA DFNVSLQDHFKWVKQETEISKESQEMD-SRPKLDLGFKEGQTIKLSIGNITAKKG-GTSKPRASGTGGLSLLPPPPGGKVTIP-PPSSSVAISNHVTPPPIPKSNHGSNDSDILLDLDSP APVPTSAPAPAPASTSNDLWGDF-STASSSVPNQAPQPSNWVQF (SEQ ID NO:30).

Using tblast2x algorithms, the L117 polypeptide was found to have homology with expressed sequence tags (ESTs) from mouse, mouse embryo, human hNT neurons, human tumors, drosophilia, drosophilia embryo, C. elegans, and Arabidopsis thaliana, a plant organism. Although the sequence of ESTs can be questionable, the identified ESTs were aligned for comparison. The comparison of consensus sequences from each species provided evidence that the L117 clone or a L117 motif has a very strong pressure for conservation during evolution since it is conserved in a variety of very distant species. In addition, this alignment indicated that the first methionine residue in the ORF of the L117 clone is the true initiation site for translation since most of the homology between the ESTs begins around this position, and the C. elegans, drosophilia, and human hNT ESTs each contain a methionine residue that is in a very close proximity to that of the L117 clone. Further, the relation between these ESTs and the L117 clone was supported by an exactly matching stop codon in the human EST, mouse EST, and L117.

Northern blot analysis revealed that the expression of the L117 mRNA was not upregulated in response to the multiple MECS treatment in either the hippocampus or cortex. Analysis using a total RNA extract, however, revealed a small upregulation upon MECS stimulus.

Another IEG nucleic acid clone was designated L119. The L119 clone is 2900 bp in length and has a nucleic acid sequence as follows:
5'-ATTCGGCACGAGCCAGAGTGAAGGGGCATGG
AGAAGTGGACGGCCTGGGAGCCGCAGGGCGCC
GATGCGCTGCGGCGCTTTCAAGGGTTGCTGCT
GGACCGCCGCGGCCGGCTGCACTGCCAAGTGT
GCGCCTGCGCGAAGTGGCCCGGAGGCTCGAGC
GTCTACGGAGGCGCTCCTTGGCAGCCAACGTA
GCTGGCAGCTCTCTGAGCGCTGCTGGCGCCCT
AGCAGCCATCGTGGGGTTATCACTCAGCCCGG
TCACCCTGGGAGCCTCGCTCGTGGCGTCCGCC
TGGGCTTAGGGGTGGCCACCGCCGGAGGGGC
AGTCACCATCACGTCCGACCTCTCTCTGATCTTC
GCAATTCCCGGGAGGTACGGAGGGTGCAAGA
GATCGCCGCCACCTGCCAGGACCAGATGCGCGA
ACTCCTGAGCTGCCTTGAGTTCTTCTGTCAGTG
GCAGGGGCGCGGGGACCGCCAGCTGCTGCAGA
CGGGAGGGACGCCTCCATGGCTCTTTACAACT
TGTCTACTTCATCGTCTTCTTCGGCTCGCGTGGC
TTCCTCATCCCCAGGCGTGCGGAGGGGGCCAC
CAAAGTCAGCCAGGCCGTGCTGAAGGCCAAGA
TTCAGAAACTGTCTGAGAGCCTGGAGTCCTGC
CTGGTGCCCTGGATGAACTTAGTGAGCAGCTGG
AATCCCGGGTCCAGCTCTGTACCAAGGCCGGCC
GTGGTCACAACCTCAGGAACTCCCCTGATCTGG
ATGCAGCGTTGTTTTCTAAGAGCATCCTCTAGCT
GTGTGGAATGTTCTAGATTCGCAGCATCCACAAG
AAGTGCTACATGGGCGGAGTGCAAAGGATTTC
GAAGCTCTTCTTGCAGGGCATCAGTCCGTAGCT
CCTTGTGTGTGCGAAAGACTTTTCACTTGTGTA
TCCCAACTGAGTATGTGACCCTAAACAGTCACT
TGGGGACTCCCCAAATCCTTTTTAGCTGCACAC
AGCTTGTCAGACTGTCCTTCAATTAGAGTTATTG
GGGTGGGGGGGCTTGATGGCTTGAGTAATAGAG
TCTGGCGAGGTGTCTCCCTCTTGGACCTCTTATGT
GTTGTTACTAGAATCCTGAGATTCTCAAATGTT
GGTGAGAGGAGACTTTTACTTTTCAACTTTGCT
TCGGCAGTTTCCGATACACAGGACTCCAGAATC
CAGAACAAGAAAGAAGAACCTTGTGTTTGTAG
GTGTGCAGACCCAGACGGGGCCGAGGAGCTG
ACTTGCTCAGCTCTCACACGCAGCCAGTTTATCC
ACTCACAGACCAAACCTGGCTACTGCATAGAC
TGTTCCAGTGTGGCTTCAAATCCACACCTCTAG
GTACCCTGAGAAGGAAAGCCACCTGAAGAGTC
ACTCTAATCCCAACACGCTCACCCCCTTCACG
TCCATAAAGGAGCTGGGCAAGGGGTGAGATGA
AGACCCTGACAATTTTAAATGACTGTAGCATAGA
AGCCATGGCCTTTGAGTTTAAGAGTCTTGATC
CCAGGTTCTGTCCCCCACTGTCCTGTGACTTAGC
CACCTTGTCTTGCTACAGATGGTGGTAGGAGGC
CACCCTGTTGCGAAGTCCTGAGATAATGACAA
ACACAGAGGCTAGCTCACAAAAATGTACTTCC
TGGCCTGGCTTCTGAAGGGTTAACTGTTGGGCT
CCATCCCAGATTTCTGAGATCAGGAACTCCAAA
TATGAGGCCCGCCTCTGGCTGATTCTGATGCCCC
ATAAATGTTTGAAAATGACACAGCAAAGGTTC
ATCTCCAGCCAGGTGTGGTGGGACACACCTGTA
AGGCCAGCGCTTGGAGATGGAGACAGGGGGAC
CAGTAGTTCAGGGTCATTCTTGGCTACATAGCA
AACTCAAGGCCACCCTGGTCTCAAAAACCAAA
ACAAAAAGCCATCTTCTGACTCCCTTCAATTGT
TCAAAGCCTTTCCAGGGCCTTCAGAATCACGCT
AGAGTGTTCTGGGAAGATTAGCCCAGAAGCC
AGAGAAAGAGTACGCTGTGTGCTTGTAAAGCC
AGTTACTCTGTCCCCTGTGAACTAGGAGACAGA
GCACTTCCGACCCTATAGAGGGCAGTAGTGGCCA
TTCCTTGTAGGGGACTGGTATAGAAGTAATGTG
AACTATTTAAAAATAGTTATTTAATTGCTGCCTT
CACATTTGATTTTATTTAACCTTCACATTATTTAG
AAAATAATAAGAGTAGTAAGTGTCTGAATAGGA
AGGGAGTCTCTTAAGGCTCTTTCCAAGAGCTCA
GGTTTGGATTCTAGAGTCCCCCCGACCCCAGA
AGGACTCTTTAGTGTTGACACGGTCTTTGTAAG
AAGATGGGGAGTCCTGGAGAGAGAGACCAAG
TGATTTTTAAACTAGGAAATGGAGTCTTGAACT
GTGGAAGATTTGAAAAGTTAAGCCTATGTGTCT
TGAAGGTACTTGGCCAGAAAAGCACTTGGCTT
GAAAAAGAAAACCTGTTTAATTCAGGGGTGGA
GAATAGAGACAGATGAAGAAAGCATTTAGAC
CTCGGAAACCTGATGTCCTATGAAATTCTGTTTT
TATAAAATTGTGTTATGGTGGAGATCTGTTGCAT
TTCGACTTTGTGGCTGTAAGAAACCTGTTATCT
ATGTTTAAGAAAGTACTTCTAATTTATTCAATGT
CTTCCTAAATTATCCTTTAAAAAAAAAAAGTTG
GAAAGTCTATGAGACCGTACCTAAGAAACCTT
GACTGTGTATTTAAGTTATTTAATGCCATGCATT
TGTGAAGCCCCTTCCCAGTGATGGCTGTGGTGT
GTCTGAGGAAATGTAAGTTTGGCATGAGGGG
GAGGGGCTGCTGTTTCTATATTTGTTTTTGTTTT
CTATAAACAGTAATCAGGATGTATCCTGGTTTC
ATTTGACATTGAAAAAAAAAAAAAAAA-3' (SEQ ID NO:31). In addition, the L119 clone contains an ORF from basepair 28 through basepair 768. This ORF encodes a polypeptide of 247 amino acid residues. The translational start site was assigned to the first methionine residue in the ORF. The arnino acid sequence of the L119 polypeptide is as follows: MEKWTAWEPQGADALRRFQGLLL-DRRGRLHCQVLRLREVARRLERLRRRS-LAANVAGSSLSAAGALAAIVGLSL-SPVTLGASLVASAVGLGVATAGGAVTI TSDLSLIFCNSREVRRVQEIAATCQDQM-RELLSCLEFFCQWQGRGDRQLLQSGR-DASMALYNSVYFIVFFGSRGFLIPRRAE-GATKVSQAVLKAKIQKLSESLESCTGALDELSEQL ESRVQLCTKAGRGHNLRNSPDL DAALFF (SEQ ID NO:32). Hydropathy plot analysis revealed a stretch of about 50 hydrophobic amino acid residues, possibly indicating that the L119 polypeptide is a type II transmembrane protein.

Northern blot analysis using a sequence from the L119 clone revealed that the expression of the L119 mRNA was strongly upregulated in response to the multiple MECS treatment. Specifically, L119 mRNA expression was induced 17.8 fold by the multiple MECS treatment as determined from Northern blot data using total RNA from rat hippocampus (Table I).

Another IEG nucleic acid clone was designated R010. The R010 clone is 1280 bp in length and has the following nucleic acid sequence:
5'-GCTTTGGAAACCGGACTGCAGGCTAAACTGG
CTTCTTTTGAATCCTTGGAAGCATAAAGGACAA
TAGCAGGGCTCGCAGTCTTCCATTTGTCACTGG
AGAAGAACTTATAATTCAGAAGATCTGGGTCT
GACCCAGGCTGACCACTTTGGAGCTTTGAGAC TCTGGGATTGTGATCCAGTTCTGAGCTGGTGAT
AAACACTCCTTGTGACTTTTGGTCAATTCAGCT
ACCAGATTCCAGCCAACATGACCCTCGCAGCC
TATAAGGAGAAGATGAAGGAACTCCCACTAGTG
TCTCTGTTCTGCTCCTGTTTTCTGTCTGATCCC
CTGAATAAATCATCCTACAAATATGAAGGCTGGT
GTGGGAGACAGTGTAGGAGGAAAGGTCAAAG
CCAGCGGAAAGGCAGTGCTGACTGGAGAGAAA
GAAGAGAACAGGCAGATACGGTAGACCTGAACT
GGTGTGTCATCTCTGATATGGAAGTCATCGAGCT
GAATAAGTGTACCTCGGGCCAGTCCTTTGAAGTC
ATCCTGAAGCCACCTTCCTTTGACGGGGTGCCTG
AGTTTAATGCCTCCCTCCCAAGACGTCGAGACC
CATCGCTAGAAGAGATACAGAAGAAGCTAGAAG
CAGCAGAGGAGCGAAGGAAGTACCAGGAAGCT
GAGCTCCTAAAACACCTTGCAGAGAAACGAGA
GCATGAGCGTGAGGTAATCCAGAAAGCTATCGA
GGAAAACAACAACTTCATCAAGATGGCGAAAG
AGAAGCTGGCCCAGAAGATGGAGTCCAATAAG
GAAAACCGGGAGGCCCATCTGGCTGCCATGTTG
GAGCGGCTGCAAGAGAAGGACAAGCACGCAG
AGGAGGTGCGGAAAAACAAGGAGCTGAAGG
AAGAGGCCTCCAGGTAAAGCCCANAGGCCAAG
GAAGTTTCCAGGACAGCCGGACAGCTCCCGCA
CAACCTGGTTCCAGCAGCATCGGCCGCTGGCTG
TCTCCCAGCACTGGGGTTCGGGGGGAGGGGG
TGGCCAAAGGGGCGTTTCCTCTGCTTTTGGTGT
TGTACATGTAAAAGATTGACCAGTGAAGCCATC
CTATTTGTTTCTGGGGAACAATGATGGGGTGGGA
GAGGGGACAGAGAGTGTTTGGAAAAGGAGGTG
AAGATGAGCCCGAGGACTTTGTGACACTGTCCA
CTGACTGCAGACTTGGGCCAAGGCCCCCGCTTT
TCACGGCTCTGCCTGGACATTCGGCCTCCAGGT
TCCTAGTGGAGAGAAGATGTGACAGAAGTTCAG
AGTGAAGGGCCGAGTCCTGGTGGGGTGGTGTGC
AGGGCCAGCAGGACGAGCCCGTCTGGATGGAGT
GAAACCTACCCTGAGCGGGTGGGATAAGGTCTG
GTGCGTCTGTTCATTGTCATCTTTTGATCATCATG
ACCAACGAAACATTTAAAAAAAAAAAAAAAAAA
AAAAA-3' (SEQ ID NO:33). Two genomic R010 clones
were also obtained. The nucleic acid sequence for these
genomic R010 clones is as follows:
5'-GATAAACACTCCTTGTGACTTTTGGTCAATTC
AGCTACCAGATTCCAGCCAACATGAC-
CCTCGCAGGTAGGTACATGCACCAGT-
CAGTGATGAACACCATAACACAAGC-
CATTTTCTATCTCTGTGTGTGTCCATGTGTATTA
GGTGCATCCGTGTGTGTGATACACACG-
TAGGTGCATGGCATGCATGTGTGTG-
CAAATGCATATACAAGTCCAAGGA-
CAGGGGTTGGGGATTTAGCTCANTGGTAGAGCA
CTTGCCTANGAAGCGCAAGGCCCTGGGT-
TCGGTCCCCAGCTCCGAAAAAAGAAC-
CAAAAAAAAAAAAAAAAAAAAAAAAAAAAAT
TTCCANGGACAACCCCAAATTTCCTTTC-
NCNAAANCCANCCANCTTCCATT-
NAAAAAAAANGGGTCNCNCNTGGGT-
TAAACCATTTNNAAANGGCNAACCTNACNGGCC
AKTGAKTGCCAGGAATCTTCTTTATYCCT-
GCCCWACCTCCAATGTCTTTCACATGT-
GAATGCTGAGGGTCAGAACTTGTGCTTA-
CAAGGCAGACATTTTGCCAGCTCTCCGGCCATC
TTCTCTATGTATGTACACTCACAGATG-
CACAGGAAGAGAGGGTAGAGAAGCCAA-
GAGGCAAAGTCATTTCTGGGTG-
GTGGGTGGGATCACAGCTGAATTCTTCTTCCTCA
TTTGCTCTGTGTGTATTATTTAATTT-
TAAAATAATACCTTTATAATAGTATC-
GAAACTATGCTTTCAAGTTTGTAA-
GAGAAAGTGATCACTGGGCTGTGTAGTGAGGG
GTCTTTATATTATGCATATAACATGGTG-
CAATGGGAAGGACTGGCAGAGGCCTC-
CATGATGACCTATGACTTCTAGG-
GAGACTCAGTCGTGTCAAGGGTACATTCCTACTC
GCAGACAGCTTCTCCCTGGTTTGATTC-
CTGTGCTGGGAAGATTTGAGGAGTCTTC-
CAGCCTGACCTCTTCTACAGTGGGCCTG-
GACTTTAAGGAGAGTAGCAAGGAAGTCTTTTTA
TTAATCTCTTACCCTTTAGGCAGCAGT-
GTCAAGTACTTTTAGCAGAAT-
TAAATATAGATTTCCTACAAACTA-
CAAACTTCAAAGCCCTGGTTTATCCTTGGGTGGG
AGTAGGAGATGGAGGGCCAGGGT-
CAGGGCACTGCACTTGGGATCTTTACT-
TGAGGGTACTCAACGCTTGGTAGTAA-
CAAAAAGTGGGGTGAGTGACAATGTTAATTTTC
AACTGGGAGGTAGCCCAGGCTTGGG-
TACTTTGGAGCCAGAAAGCCTGGGCT-
GACTCACAGAAGTGGTGCTCTCTCTTGY-
AGCCTATAAGGAGWWGATGAAGGAACTCCCACT
AGTGTCTCTGTTCTGCTCCTGTTTTCT-
GTCTGATCCCCYGRATAAATCATCCTA-
CAAATATGAAGGTGAGTAGGGGCTAG-
GCTGGGATAGAAAAGGGTGGAGGCTTCTGTGTC
CTGTGMGTSGGTGCCCACATTGACTC-
CTATCTTGTAAAACTGTCCTGGTCG-
CAGTGTGTCTTATTTCCCAGAGGCTGAG-
GAGTCTGAGCCCAGGGGGATGTAGCCTGGGTGCC
AAGCAGCCTCCAGGGATCTGGATTGGGC-
CCTCCTGGAGCACTTGCTCCTAGAGTC-
CCTTTTRCACATTCCTTGACACCACA-
GAGGACACCAGGATAAGCCAGACACAAGTTTTG
AGATTCCATTCATGGAGGCCCAGAACA-
GAAAAAGAAAACTTAGTGTGTTCAC-
CAGGGCTTCTAGGGACAGGTAGAGAT-
GCTCCTAGACAGGTCCAGGGTGGGAATAGCACT
TCTAACCTGGATGGTGACAGTTCGAGC-
CCCTAGACCCTATCAGAGAGTACTGGAT-
TGTCATGCTGTCAGGAGGAGTGGT-
CAGGGGACAGATAGGTCATCTCTTCATTTCTGTTT
GCCAGGAAGGGATGGGTTTGGTCTGT-
CAATAAGAGAGATGGGTGTTTGGATGAC-
CTGAGTCTGTTTTTTCCATTTAGGCTG-
GTGTGGGAGACAGTGTAGGAGGAAAGGTCAAA
GCCAGCGGAAAGGCAGTGCTGACTG-
GAGAGAAAGAAGAGAACAGGGTAGGCCG-
GAGCCAGGGGAGAGGTCCACAAGCCAT-
CAGAGGGACAGGGCAAGGAGGGGCTGGCGGT
GGGGATGGGTGAAATGAACTGGTGTCT-
GTCACCAGCGAGGAACAACAGCAGCTG-
GTGCTATCACAAATCACAGCTCCCTGCT-
TACCCTGTAAAAGCCATTGACCTTAGGGTCCAA
CGTTCAGGATCGACCAGACCCCTAGT-
CATTGGTGTGCCTTGGGACCCT-
CAGCTTTCCTGTGTCTGTGTGCATGTA-
CACATGCTCATTGGGGCCCCAGCTGCTCCTCAG
AAGGTGAGCAGCCCCAACTCTGCCCTC-
CATAGCAGATACGGTAGACCTGAACTG-
GTGTGTCATCTCTGATATGGAAGTCATC-
GAGCTGAGTAAGTGTACCTCGGGCCAGTCCTTTG
AAGTCATCCTGAAGCCACCTTC-
CTTTGACGGGGTGCCTGAGTTTAAAGC-
CTCCCTCCCAAGACGTCGAGAC-
CCATCGCTAGAAGAGATACAGAAGAAGCTAGA AGCAGCAGAGGAGCGAAGGAAGGTTAGT-
GTAGCCCCATGTCACTTCCTCCCATC-
CCAGCGGGAGCAGGAAGTGCAGCTC-
CATATCTCTTCCTCCCATCCCAGTGGGAGTGGGA
AGGATATTTAGACAGCACCTCCTGAGT-
GCTGGGCATAGACCGGTAGTTCTCAAC-
CTTCTTAGTGCTGTAACCCT-
TAATATATATATATATATATATATATATATATATATATA
TAGTTCCTCATGTTGTGATTAC-
CCCCCATACCATAAACTTATCCCGT-
TGCTCTTTATGTCTTCATAAT-
TATAATTTTGCTACTGTTATGAATTGTGATACAA
CTATCAGACCTGCACCCCCTAATGGCAG-
CAGCCCACGTGTTGAGAACCACTG-
GCATAGATGTAGACTAAGATACCACCT-
GAAGGGGACAAGACTATGACTATGCACTGGGTG
AGCTTACAGTGTGGCTAATGGCTAAAAT-
GTCACAGTCCTCACAAAGCTGCCTTTG-
TATGCAGCTTCCTTGTTCCCCATTGAT-
TCTMGTCCSTCAGCTCAGATGCCCATTTTTTAAT
GTGAGTGTTTCTTNACCTTTCACAAANA-
CAAAACAAAACAACCCAGCTTTCTC-
CACTNAATTGTGTGGTCCCTCCCTT-
TAAATATCCAAAGCATTTATCACACCCAGGTCT
GNGTCCANTATNTATTGATATGCGTGTT-
TATTTNNACTAGGGCAATTNTCTCCNT-
TCCCTGGTGTCTGGAGTTGTGAGGGCCT-
TGAGGTTTATAGAAGATCACTTAGTACTTGTGAA
TGAACGCGAGGAAAAGGAGAAAA-
GAGACTCAGAAGCTACTTNGGAAAGGGC-
TACNAAAGCCAAATATGACGGAAAG-
GTTTGCAGTCCATGNCGTTGTTCTCTGCTTCTGG
GACAGAGGACCAGGTTCATCT-
CATCTGGGCATGGCACTGTTCAGCTGTG-
GTGGTAGAAATCCACTCTAAAGGGTCNT-
TCTCTTTCTTTTGNTGCCCTAGTACCAGGAAGCT
GAGCTCCTAAAACACCTTGCAGAGAAAC-
GAGAGCATGAGCGTGAGGTAATCCA-
GAAAGCTATCGAGGAAAACAACAACT-
TCATCAAGATGGCGAAAGAGAAGCTGGCCCAGA
AGATGGAGTCCAATAAGGAAAACCGG-
GAGGCCCATCTGGCTGCCATGTTG-
GAGCGGCTGCAAGAGAAGGTAAGAGGTC-
CTGGATTGGCAGGAGGCTCCTTCCATGGCAAGA
ACGTGCAACCTACACATCACTCTGGAG-
GAAGCGGCCTATGCAGGAATTGAAAT-
GTTTCTACCAGGCAGGGTCCTCATTGT-
TCTAAGGGGAAGATTTGGGAAGTCATAGGCAAG
AAGCTCACACC addition, the R010 clone contains an ORF from basepair 80 through basepair 727. This ORF encodes a polypeptide of 216 amino acid residues. The translational start site was assigned to the first methionine residue in the ORF. The amino acid sequence of the R010 polypeptide is as follows: MTLAAYKEKMKELPLVSLFC-
SCFLSDPLNKSSYKYEGWCGRQCR-
RKGQSQRKGSADWRERREQADTVDLN-
WCVISDMEVIELNKCTSGQSFEVILKPPSFDGVPE
NASLP
RRRDPSLEEIQKKLEAAEERRKYQE-
AELLKHLAEKREHEREVIQKAWEENNN-
FIKMAKEKLAQKMESNK ENREAHLAAMLER-
LQEKDKHAEEVRKNKELKEEASR (SEQ ID NO:36).
The R010 clone was found to have homology to the stathmin family of polypeptide, including stathmin, SCG10, and XB-3. In addition, the R010 polypeptide was found to contain a unique 27 amino acid sequence (encoded by exon 3) that is alternatively spliced to lead to the formation of two distinct mRNA transcripts.

Northern blot analysis using a sequence from the R010 clone revealed that the expression of L119 mRNA was restricted to brain. In addition, R010 expression was found to be developmentally regulated. Further, R010 expression was found to be rapidly induced in vivo in the dentate gyrus in response to the multiple MECS treatment and LTP stimulation, and rapidly induced in vitro by NGF treatment of PC12 cells.

Another IEG nucleic acid clone was designated R042. The R042 clone is 3978 bp in length and has a nucleic acid sequence as follows:
5'-CGGCGATGGCGGCGGCTGCTGTGGTGGCAGC
GACGGTCCCCGCGCAGTCGATGGGCGCG-
GACGGCGCGTCCTCCGTGCACTGGTTC-
CGCAAAGGACTACGGCTCCACGACAAC-
CCCGCGCTGTTAGCTGCCGT
GCGCGGGGCGCGCTGTGTGCGCTGCGTCTACAT
CCTCGACCCGTGGTTCGCGGCCTCCTCGTCAGT
GGGCATCAACCGATGGAGGTTCCTACTGCAGTC
TCTAGAAGATCTGGACACAAGCTTAAGAAAGCT
GAATTCCCGTCTGTTTGTAGTCCGGGGTCAGCC
AGCTGATGTGTTCCCAAGGCTTTTCAAGGAATGG
GGGGTGACCCGCTTGACCTTTGAATATGACTCCG
AACCCTTTGGGAAAGAACGGGATGCAGCCATTA
TGAAGATGGCCAAGGAGGCGGGTGTGGAGGTGG
TGACTGAGAACTCTCACACCCTTTATGACTTAGA
CAGAATCATCGAACTGAATGGGCAGAAACCACCC
CTTACCTACAAGCGCTTTCAGGCTCTCATCAGCC
GTATGGAGCTGCCCAAGAAGCCAGTGGGGGCT
GTGAGCAGCCAGCATATGGAGAACTGCAGAGC
TGAGATCCAGGAGAACCATGATGACACCTATGG
CGTGCCTTCCTTAGAGGAACTGGGATTCCCCACA
GAAGGACTTGGCCCAGCTGTTTGGCAAGGAGG
AGAGACAGAAGCTCTGGCCCGCCTGGATAAGC
ACTTGGAACGGAAGGCCTGGGTTGCCAACTAT
GAGAGACCTCGGATGAATGCCAATTCCTTGCTG
GCCAGCCCCACAGGCCTCAGCCCCTACCTGCGC
TTTGGCTGCCTCTCCTGCCGCCTCTTCTACTAC
CGCCTGTGGGACTTGTACAGAAAGGTGAAGAG
GAACAGCACACCCCCCTCTCCTTATTTGGACA
ACTCCTATGGCGAGAATTCTTCTATACAGCGGC
CACCAACAACCCCAGGTTTGACCGAATGGAGGG
GAACCCCATCTGCATCCAGATCCCCTGGGACCG
CAACCCCGAAGCCCTGGCCAAGTGGGCCGAGG
GCAAGACAGGCTTCCCTTGGATTGACGCCATCA
TGACCCAACTGAGGCAGGAGGGCTGGATCCAC
CACCTGGCCCGGCACGCTGTGGCCTGCTTCCT
CACCCGAGGGGACCTCTGGGTCAGCTGGGAG
AGCGGGGTCCGGGTATTTGATGAGTTGCTCCTG
GATGCAGATTTCAGCGTGAATGCAGGCAGCTG
GATGTGGCTGTCCTGCAGTGCTTTCTTCCAACAG
TTCTTCCACTGCTACTGCCCTGTGGGCTTTGGCC
GACGCACGGACCCCAGTGGGGACTACATCCGGC
GATACCTGCCCAAACTGAAAGGCTTCCCCTCT
GATATATCTATGAGCCCTGGAATGCTCCCGAGTC
GGTTCAGAAGGCCGCTAAGTGCATCATTGGCGTG
GACTACCCACGGCCCATCGTCAACCACGCAGAG
ACTAGTCGGCTCAACATTGAGCGGATGAAGCAGA
TCTACCAACAGCTGTCACGATACCGGGGGCTCTG
TCTGTTGGCATCTGTCCCTTCCTGTGTAGAAGAC
CTCAGTCACCCTGTGGCAGAGCCTGGTTCTAGCC
AGGCTGGGAGCATCAGCAACACAGGCCCCAGAC
CACTGTCCAGTGGCCCAGCCTCCCCCAAACGCA
AGCTGGAAGCAGCTGAGGAACCTCCAGGTGAA
GAACTGAGCAAGCGGGCTAGAGTGACAGTGAC
TCAGATGCCTGCCCAGGAGCCACCAAGCAAGGA
CTCCTGAGACTGGAGAGCCATTGCTCCGTGAGC AAAGCCCAGGTGCCTGAGCTGCCATGGCCACAG
AGAAGACATGGAACCTACAGAGAAGACAGTCAC
CAACAGACAGAGCGAGCGACTGTGTGTGTGCA
GAGGGAGGTGTGGTGTGCCGTTTGCGTGTGCAT
GCATCTGTTTACACTCTCATGATCCTGAATGTTGC
CTGTGCTGGAGGAGCCCCTAGATCATGCCTTCTT
ACCAGGGCTGTTTCTTGACTTCCAGACATAAGAC
TAGAACCCGCAGCAGTAACCGTCAGCCCAAATCT
GCCCCTGGGAGCCCCAATAGGGTGGTAAGACCCT
AGCTTGAATTCTGGTCTCTGCCTCCCCAGACTCTT
CTTCCTCCCTCCTTTTAACAAGGAGCTGGAGGG
CACATTTTTTGACTCTCATCTAAAGCATGGAGT
TTCAGAGGCAGTCAGAGTCCTGCTGACTTAGTT
CCCACTTTTCTGACACTAGAACCTGAGCAGGCT
GGAATAGATGTGTCCTGTTGATCTTAAACAGCCT
GGCCAGTCTTCTTATAAAATCCTGTGCCATTAACA
GGCTTCCCTGATGTCTAAGGCTACAGACTAGTGT
GTTGTGTGCCCAGTACTGCTTATGTCAGCCTCAG
ACATAATATCAGTCTTTGTAGAACCTTCTAAAAA
AAACCACATGGGGAATAGACTCCCAGTCTTCTGT
CCCTTCCCTAGCAGCTAAGGTCCAGTCTCGACCT
TCTAGAAGCTGTGGACAGGCTAGGGTCTGAACT
GGTGAAAGAAACCCAGGTCCCACAGCTGCAGGG
CCCCTGGTTCCTCTGGCTGTACTCCTGACACCAC
ATGCTCCAGCCAGTACTGCTGATATCCAGCCAGG
CAAGCTGGACAGCCTGGCTGGTCAGCACCTGCCC
TGCAGTGTCAGCTGCCCAGGACTGAGCTTCCGG
AGACTCAGACAGACTTAGGGGTGGAGCACTGCC
TCTGGCAGTTGGCGAGAGGTCAGAGACCATGCC
TGGCACATCAACATCTTCGCAGAGCAGCAGTGA
AGGATTGACATAGAGAAGTCAAGCCTTGCTTTCC
AGGGGAGCCAACTCTCCCTCCCACTGTTGGGTC
ATATGGAGAAAGAAGTTATGAAAGGATCTGGGGG
TACCTGAGCAAGTCTTCCTTCCACCCCGTGGCC
GCATTTGAGCCACAGTGTGTGTGTGTGTGTGTG
TGTGTGTGTGTGTGTGTGTGTGTGTGTGTGTGTG
TGTGTGTGTGTAGAGAGAGAGAGAGAGAGAGA
GAGAGAGAGAGAGAGAGAGAGAGAGAGAGAG
AGAGAGTTTGTTTCTGTTTGGATTTTTGTTCTCA
CATGTAACATTAAGCTGGCCTCTGGGCCTTTTCCT
CTCTACCTCCCCTGTGACCTTTCCTAGCCTCAGA
GTTGTTAATGCCCTTGGCCCTGGCCTTTTTTTTGT
GTCAGACCAGAACCCTGGGGTCAGGCTCCCCCC
TCCAGCTGTCTAGCACATCTGACAGGCTTCTTTT
TGAGATGGCCTCAGGTTTTCTCAGCAGAGAGCTG
CCTTTAGTCCAACTGTTTATGTTCATCATCCTGAC
AGAAGCATCCTACGATTGTGTGAAGAAACGGCAT
CTGTGATGCCATGTTCAGAGTCATGGGGTGTGGC
CTCCCTGTCCCTAGCCCCAGGCCAAGAGGAAAG
GGCCAAAGGCTCTTGCTGGAGGGACAGTAGAA
TGCGTCTGGAGAACTGGTCCCAGAGGAGCAAA
GCTTATTCTGGGGCCAGTATTTATTTTGCAACATC
TTCAGCTATGGGGACAATGGCCTTCTCTGCTTTT
TTGATGATGGCTCTCTCCTCAAGGTACAAGTTG
GCAAGGTCATCTGTCCTTCCACCTCCTTGACATG
TTGGCCCATTTCCAGGACAGCCTTCCAGTGAATG
GAGCAGACTATTCCACAGCTGTGGGATAGAGTG
TCTTGGAGCCCTGGAATGACTTCATGCCTCCTTT
GCCTAGCCTGAGTGGCCCTGAGGACTGTCACAG
AACAGTGCCCCATGTCCTGCTCCTGGGCCCGAG
TGGGGAAGAGATGGTTGCAGGCAAGAGCACTTT
ACAGCATTCCCCATTGCTGGGAAGGTTGTTTCTC
ACAGTGTGTGAATACTTACCTGTTTTATAAATGTC
TGATCCTGTCTGAGTAAAAAAAAAAAAAAAAA
AAAAA-3' (SEQ ID NO:37). In addition, the R042 clone contains an ORF from basepair 51 through basepair 1790. This ORF encodes a polypeptide of 580 amino acid residues.

The amino acid sequence of the R042 polypeptide is as follows: MGADGASSVHWFRKGLRLHDNPAL-
LAAVRGARCVRCVYILDPWFAASSS-
VGINRWRFLLQSLEDLDTSLRKLNSR-
LFVVRGQPADVFPRLFKEWGVTRLTFEYDSEPFGK
ERDAAIMKMAKEAGVEVVTENSHTLY-
DLDRIIELNGQKPPLTYKRFQALIS-
RMELPKKPVGAVSSQHMENCRAEIQEN-
HDDTYGVPSLEELGFPTEGLGPAVWQGGETEALA
RLDKHLERKAWVANYERPRMN-
ANSLLASPTGLSPYLRFGCLSCRLFYYR-
LWDLYRKVKRNSTPPLSLFGQLLWR-
EFFYTAATNNPRFDRMEGNPICIQIPWDRNPEAL
AKWAEGKTGFPWIDAIMTQLRQEGWI-
HHLARHAVACFLTRGDLWVSWES-
GVRVFDELLLDADFSVNAGSWMWLSC-
SAFFQQFFHCYCPVGFGRRTDPSGDYIRRYLPKLK
GFPSRYIYEPWNAPESVQKAAKCI-
IGVDYPRPIVNHAETSRLNIERMK-
QIYQQLSRYRGLCLLASVPSCVEDLSHP-
VAEPGSSQAGSISNTGPRPLSSGPASPKRKLEAAEE
PPGEELSKRARVTVTQMPAQEPPSKDS (SEQ ID NO:38). The R042 clone was found to be a photolyase receptor based on sequence alignment data. In fact, the R042 clone was found to be the rat paralog of human and mouse clones based on the following observation. The identity between the human and the mouse clones is considerably higher (97%) than between either the human clone and R042 (72%) or the mouse clone and R042 (71%). This lack of a higher identity between the mouse clone and the rat R042 clone is more than that expected from species-to-species differences. Thus, the R042 clone most likely is a different member of the family of photolyase/blue-light receptor homologues. The translational start site was assigned to the second methionine residue from the 5' end based on the alignment data using the human and mouse members of the photolyase/blue-light receptor family.

The R042 clone potentially has two differentially spliced forms at the 3'-end. The difference between these two forms is 142 bp. The shorter form was found in four clones while the longer form was found in one clone.

Northern blot analysis using a sequence from the R042 clone revealed that the expression of the R042 mRNA was strongly upregulated in response to the multiple MECS treatment.

Another IEG nucleic acid clone was designated R053. The primary library screen produced 40 positive signals that were isolated. The following nucleic acid sequence is within the R053 clone:
5'-TTGGCACACAAGTCTGTCTTCAGGACAGCTGATC
CATTTTACTTACRAATTCAGAAAGTAAACATTGG
CAGTATGGATCTGGTTACTTCATGGTAACTGCTCT
AGAATTTACGCCAAGGCCATCTCTTTTGCCTCAC
TGTTTAGTGACCGGAGTAAAGCATGGGGCCACT
GAAACTCCACTTTACAATTGGGCTTCTAAATTTA
AGGAAAAATTTTTTGATTTAACCACAACTGGATT
CCAAAGTTCATCTTATTCYAAATTAGGCCCACTGA
GCCTGTGATGTTTTGGAATATATGATTAGTCCACT
TGGTTCACTGGATGTTACCTATCATGTTATGTAG
AGAAACAGCCATAACTATTGGTCACGATGTCGTC
CTCCGAATTGGGAATGGCTCTGTTGTTGGAAAC
AAAGTATTTGTAAACACGTTGATCAAAGCGGTGT
GCTTTGGCCTTTCCGGGAATCACTGATTATGTTTG
AAAACTTCCTTTAATTGTATTTGCAATAAGCTAT
TNTCCCTTNTNATGNCNCTGCCATGCTTCCTTGC
TTTGCACTGTGGTCGCATGCCATCNGCTGGTTAA
CCCANGATGGCTTGCTGCNCTGATATNCACCATG
CNAAATACCACTTCT-3' (SEQ ID NO:39).

Northern blot analysis using a sequence from the R053 clone revealed the presence of a 4.9 kb mRNA transcript. In addition, this analysis revealed that the expression of the R053 mRNA was marginally upregulated in response to the multiple MECS treatment.

Another IEG nucleic acid clone was designated R055. The first library screen produced a clone designated R055-7 having a 1.7 kb fragment. A second library screening using the 5'-end of the R055-7 as a probe produced several additional clones having fragments of about 3.0 kb. The following nucleic acid sequence is within the R055 clone:
5'-TGAATTGCAGTAACTAGCCTTGCCTTTCTATTCT
GTAGAAATGACAGGGTCTTCACAATCCT-
TCACCAGTGGCTACTAAGCTATAATT-
AGCTGAATAGAAAGAATGTGGAAGTG-
GTCTGAGGCATATAGAGCATATGCCAAGAACACT
ACCATATATGGCATCAGCTTTGGTTAC-
CAGAGAAATTTTCTTAGTCATTAGAC-
CATATAACAGTAATATATCATATG-
TAAATCTTTAGATTTCAAT
TTGAGAATCCTCCAAAAAAAAGGAG-
CAAAGAATGC
ATAAGCTATGTGTTGGCAAAAGTAATTTATATTAA
AATTTTTGACCTGCCTTTGTAAGATTAAGTGGTA
AATGTCATAGTGGTGGGTTTTTACGTCTTAACCA
ATCTCTGAGGTTTATTTCTCCTGCAGGGGATGGT
TCATGGCCTCTCTTCCCGCTGTAGGAAGATAGCAG
AAGGATGAGGATTAATTGTAGCATTTCACTGATC
CTCGTCCCAGGGACTAGGGACAATAGAAATCTGC
AAACATGGAGAGTCTGTCATAAATATTTGCTTTT
TGAAGGTGTTGGTCTTTGTTGATTTCTGTCAGA
AAATGGCATTATACAAATTATGGGGAGCAACCA
ACTTTTCTGTTCTGTTTTTGAAGTGCTACTATGA
ACCATTCAGAGTCGTATTTTTTTTTTTAAAATTT
TGGCCAGATATCCCCAGCTAATGAAAAATAG:TC
ACCATTCCTTGAAAAAGTTGGAAGCTAGAACCC
CCAATTCCAAATTATTGTTGAAGATGTTTCTCAG
CTACTGTATATAGAAATAATGTTTTTAAGAAAAA
CAAAGAGAGGAGAAAAAAAAAACCTATGCAGA
GACCCTACTACTTTGTGGTTTCTATTGTCCCTATA
CATCATTTCAGCAAATCTACTGGCAGTTCTTGTCA
GCAAGTCCTTCAGTGCATATGCTGCACAAAACA
AAACAAAAATCTGCATGGCACCAAAAACCAAAC
AAGCAAACCAAAAACCCAGACACCCTATGTATCT
GTTGGAGGCATGTAGGTGGTACAAATGACTAGC
CATGAGCACACATGGCTTCTTGTCATGTCACTTT
TCATAATTATTTACTGCAAAATGATTGAGAGGCT
TTTGGTGCAGGCAGCCATTAGCCTGCTTCCTTTGT
TACCTCTGGATCACTTTCAGTAAATTGCAGGTCTT
TTAAAAGATTCAAGCTTCGGTTTTCTCAAAACAA
AACAATTATCCTGTCTTACCTGAAAATGCAGGGTT
GTGGGCAAAAGAGGCTGGTTATAATAATGCCCTC
ATATTGAGTGGTCTGTAAATGGCTGCACACTTCA
GGCACTAGAGTTGCCGAGGATGCGTTGTTAATGT
GACCTTGACTGGCTTTACAGGGGTGTAGAACAGT
CTACACGGGCGACTATTTGCATCCATCTTGCTCTCG
AGGTGGATGGAAATAAGAAAAGGCTGGAGTGTG
TAAGTCATGCACATAAGTATTCACTGTAAATTTAT
TTTCATTTTTAACCCAATTATGGTACTTTGTCCAA
TGCACAACTGATCTCTCAGTAGATATTCATTTGA
AAATAGTGTGGCCTTGACCAGCGAGAAGGGGAA
GAAGTGACTTAGCTTGTGTTAAGATGACCTGTTT
GCTGAGAGTGGTCATTCTGCAGCACCCTAATGTC
TGGTTTTGATTAGGGAGAGTTAATGTTTTTGACC
CTGAATTGAGTTTTCTTCTATTTTTAGGAAGTATC
AGAATTGCTCTGATGAGTAACAAAGTTGACTGTT
TTGATGTCCAATCTCAGGTTTTAAAATAGAGTGG
TATAAAAGTCCACTGTTACTAATTCTTAAGACAAT
TTTGATTTAGTGTGCCCTAAAAGTCACGTGCATA
ATAAGGCCTGCTCAGAGGGCAGGGCCTCCATCT
TTTGCTCCTTTCCATGTTGTACGCACTTCACTTGA
AAAGGTGTCAAGTGACTTTGCATTGTAGATTTCCA
TTTTAACCCCAACATAGTTCTCAAAGATAAAGCA
CTTTTTGAACATGAAATACATGGGTAATGTGTGAT
GTGGATCATGGTTTCTCAGGCCCCTAGATAATCC
ACTTCTGAGTATTGTTCTATGTAAGGAGAATAGAG
GTCTTCGCTAATGTTCGAGTTTGTATTCCTGAATG
GAATGCACTTGCTAGTTTCCAATGGATGGGAGAG
TAAACACTGCTGCATTCACAATTTATACGTTGCTT
TCCCTTGAGCCTTAAGGTAACTTTTCTTTTCTGTC
AACAACAGCACTGAAGTTCTAGTAAGTGAATGA
GATTATCTGTTTTCAGGGTTGGTTTTAGAGTACTG
TAAATTAATTAGCTGTCTTCCTAAAGAGGAACTCC
CTTTAACTCCCTTCGATAGACTGAAAGTGGGTGT
GGGGAGGGGGAGGGAAGAGAGGGAGGTAGTTT
GTAGAAAAAAAAAAAAAAAAAAAAAAAAAAA-3'
(SEQ ID NO:40).

Northern blot analysis using a sequence from the R055 clone revealed the presence of a 7.3 kb mRNA transcript. In addition, this analysis revealed that the expression of the R055 mRNA was marginally upregulated in response to the multiple MECS treatment.

Another IEG nucleic acid clone was designated R061. The following nucleic acid sequence is within the R061 clone:
5'-GGCCCCCCCTANAAGGTCGAGGNTATCGATAA
GCTTNAATATCGAATTCGGCACGAGGCCACCAGG
TCTTTGCATTGTCTCTTTAAAAGTGGTGTATAAG
GGGGAAATTGGCAAGACAGACATTTCTAAACA
GAGGGGAACACAGACAGACAGACAGACAGAC
AGACACACAAACACACAAACACACACACACA
CACACACACACACACACACACACACACACACAC
ACACACACACACACACACCCCAGACTGCGTATG
TGGCATAACATACAGCTTGCATGGGAAGCAGCCC
CCTGCRCATTGCTTATACATCCTCGAGTCCTTTC
ATCTTTTTTCCTAAAACGTGTGCACCCGCTATAAA
GTGGGTGATGGGCTCGTCAGAGCTGGGCTGATT
CTGTGGCCGGTGACCACCATGCCTCAGGTCCCTC
AACCTCCATCACCCATGGCCCAATCCATAACTGC
CACCCTTGAAAACCCAAAGCAGTCTGAGGGTG
CTCTCTGCCTGTCACTCAGAGGCCTGGGACGTT
GAACCCAAAAAAGCTAAACTTATGAAAGCCGGG
CTGAAATGGGGCCCGGGGCCTGGGATAGCTCAG
GCAGGGGTTTTCCACTCTGATGTTTCCACTGGGC
CAGTTTTTGTTTCTTTGTCTCTATTTTCTCTGTT
CATCCCGCTGAGTGTTTTGTATCCATGATGATTCC
AGCATGAAGTACGTAGCACACTCCAGTTAGGAG
AAATTTTTTTAAAGATACAAGACTAGCGTGGTGG
TGAGATGAGATAGTCTTCTCGTGCTCGCAGCAAC
CTGAAGGGGCAATAAGGACAAAGAAGGCCATGT
GGCAGGGTTAGCCCCCTCCAGACCAGGGGTACA
ACGGACAGTTGTGGTGAGCCTCGGAAAGGCAGG
GGTAACCTTCCCTCTCCGTTCTTCACCCATGGCCA
GAGCAAGGCAGGTAGTGAAAGGGATATGCTTGA
TGCAGAAAAGCCAGCTCAGGCATGGCAGGTGGG
ATTTATAGCTGGTTTTGTTTAAAGCGAAGGCCTGA
TATTTGATAAATGCAGTAACCAGCGGTTGAGAGT
GACAAGCCCTTAAATGCGAACATTAATCAAAGGA
GAACTTAAACGGCCCCCTTTACAGAAGGACTT-3'
(SEQ ID NO:41).

Northern blot analysis using a sequence from the R061 clone revealed the presence of a 4.9–5.0 kb mRNA transcript. In addition, this analysis revealed that the expression of the R061 mRNA was marginally upregulated in response to the multiple MECS treatment.

Another IEG nucleic acid clone was designated R066. The following nucleic acid sequence is within the R066 clone:
5'-CGAGTTTTTTTTTTTATGTACTTTGAAAATAT
ATTTAAAAACATTAAAAATTCTATATTTAAAACA
TATATTATATGTTAATTGGTACACTTAAATAGAAC
CTGTATTTACAATAGGCTTCTGATGTGGTTAAGT
TTTAATGCCAATTTTTTTTTCAATAACATAATTAT
ATAAATATACTAAAATACAATAAATATTTTTCTTG
TTTTACATGGTGAATAATATCTTTACCATAGAGAG
AACAAGGCCACAGACATTTACTTACAGTTTCAAT
GGGAATCACTATAAAAAGCATCAGGCCTGCTGCC
ATGCATGAAACACTTCTGCCAAAAAGAGACCAC
AGCAAGACTTTCAGAACAGAACAGAACAGAACA
GGACGGAAACAGAACGAACAGAAACAGAGGAG
AGATTTTAACAAATCAATCTCAGGTCAACATAAAC
CACCGACATGGAGCTATGATGTATCTTAGTGGGTA
TGAGAGCCAGCCACTGACCACACAGTTGCGGAG
GGTCTCCTATGAAGCCACCTAATCGACCTGGCCC
TTCGAATACCGTGAGATTGTGATGGGGCTCCTTT
TATTTGTTTGACTAACGTCTCTCAGAATGAAGCT
GCAAAAAGTTAGCATATAGCAGATATTCAAAGCA
TTCCTTAATAGGTTAAAAATGATGACAGAGATTAA
TGTTGTCAAACGGCACAAAACAATCTAGGCTAC
GTGAAGTCTTCCAAAAACAGGGGATTCAGTGGG
ACTCCAGAAGACAGACTAGTTCTAAAGGAACAG
TTGAACAAAAAGAAACTATTTGCTGATGGTATCT
TCACTCCCTGAGTCACAGTGGACAGCCACTTTG
TTTCACCCTTTCCACTCCTAAGATGAAGCAATTG
TTTGCCTCTTTTTCTGATGCCCAGGAGCCCAGTCA
GGTAACCACTAACACATTCGCGCTGGCGGAAAA
CCTCACTAGGGAAATGGGCTTAACACTAGTTCT
CATTGGGGCCATTCATTCAGGCTTCCAGCTTGAC
TTCTCCTAACCCCAAGAGGTAAAGTGTAGAAGGG
ACCCTTGTGCTGAATGGACAGAACTATCAGGAGC
TTTCTGTGCTCTTCACTTAAGCAGTATTTCCTCCT
GTGTTCTTGTCTCTTTCACAGTGAAAGCACCTTC
CTATGCCTTGTCATTCTAGCCCTTACAGACAGAC
ATTGCTCATTCTGCCTAAGTTTTGGTGCTTTTTCT
GGTTTTGTTTGTTTGTTTTCTTCTTTCTTTTTCTTTC
ACCAAAATGTCTCAAAAAAATAAATAAATAAAA
CCTAGGCTTCCTGAAGTCTAAGCGCAAAGAAAG
TTAAGTCTCTTCACAGCAAACATTTCCCATCATGC
TGCACTGATAGCATCACTGCTATGCCATATTTGGA
TCCAAAGCTGCTCCAGGTTAATCCAACTTTATCC
ATAATTATTTAAAATGGGATGGAGGCCATAAATGG
ATTTGAG-3' (SEQ ID NO:42). This clone is similar to BDNF.

Another IEG nucleic acid clone was designated R089. The first library screen produced a clone having an insert of 0.5 kb. A primary screen with a portion of this clone produced seven positive signals that were isolated. The following nucleic acid sequence is within the R089 clone:
5'-AGTCTGGGACTAAAACGTCACAGCAGAAAA
AAAATAAAAAAAAATAATTTGCTTTTTCTTTCTTT
CATTTAGCAGCATAAATAAGTTTGGCCACTGGGA
GTACAGTACAGGGGTGGGACAACGATCCCGTAT
TGAAGACCTACTTCTAGCACCAGCATCAAGAAC
TAAATCCACCTCAGGACTCACAGAACCCAGGAC
AACTTGCCATCTTTGAGCAACATATGCATTGAAG
AGTGTATATAGAAGCAACAGTAAATAGATTAACA
GAGGCTAATACTGTGATTGATTGACATTGGCAATG
GTTGGCAAAAAAAAAAAAAAAAAAAAA-3' (SEQ ID NO:43). A portion of R089 was found to be highly homologous to a region within an EST from GenBank representing a cDNA clone from ae87b04.s1 Stratagene human schizo brain S11 (accession #AA774778).

Northern blot analysis using a sequence from the R089 clone revealed the presence of a 3.8 kb mRNA transcript. In addition, this analysis revealed that the expression of the R089 mRNA was marginally upregulated in response to the multiple MECS treatment.

Another IEG nucleic acid clone was designated R095. The first library screen produced a clone having an insert of 2.0 kb. A primary screen with a portion of this clone produced 53 positive signals that were isolated. The following nucleic acid sequence is within the R095 clone:
5'-ACTTGATAAATTGTATTTTTTTTTCTACAGTCAT
TTGTACAATTTGTTACAAAACCATAGAAGACTAC
AACTTGTTTTAAATCATTTTTGGTCTGCAAATATG
TAAAATCTGTGGTGCAATTATCATGTATTTACAGG
GCCTTGTTAGTCATTTTCAATGATTATTTCAACAA
TGTCACACTCTCAACATAAGACATGGCTTAAGAC
AAATATATTAGTACATANATATTCTGAGAACATATT
TCCATNAATGGAAAGTNGCTGCTAATACANATAC
AGAATATACATAAGNTGTTTTCTAGCTTTTTAAAAC
AGTTTTTAAAATGGNAANGTGAAAAAAGAGCCC
CTAGGANCATTTTATCCCAAAAAAATCCTTACNA
AATATTNAAGGGGCCAGGGGGGGAATTAAAAAT
CTAAAAANGGTGGTC-3' (SEQ ID NO:44).

Northern blot analysis using a sequence from the R095 clone revealed the presence of two mRNA transcripts: one 2.5 kb and the other 3.2 kb. In addition, this analysis revealed that the expression of the R095 mRNA was extremely strongly upregulated in response to the multiple MECS treatment.

Another IEG nucleic acid clone was designated R113. The following two nucleic acid sequences are within the R113 clone:
5'-AARGGGRCCACCCCACCGSGCTAAAGGCCCAG
GGGCCCCCCCCTTGGAGMCCCAGGGGTTTTGGC
CCMCCCCCTCACCCAAATGGTCTGCCAATGACC
CAGGTACTCACAACATGTTCCAGGAGGAGMCTG
GGGCCAGGATTTTGACCAGAGGGTATGGGAAGG
GAAAGGGGAGAAGAAATCGACATTTATTTTTATT
ATTTATTTTAAATGTTTACAWTTTCTTTGTGTTGT
TCCAAGCCCTGAATAGAAACAGATAGCATTAAAG
GACTCTGTTCCCACCCCTTCTCTGTCTCTCTCTCC
CCCACTTGTGCTAACTTAGGATAACACTCTCTATT
TCGTTTTGTTTCTAAAGTGATTGTGGACTTGTGC
CGTGTGAACTGCATTAAAAAGGTTCTGTTTTCAA
GATCGATTTGTCGTTCCTGTGGGACAGTGGCTC
CTAAGAAATCTGCATTGTAGGAGAAGACAATGA
AAGACCCTGGCCCTGTCTCTCAAAACTTAACTC
TCTGTATGATTTAAAAAAAAATTCCATTTACTTTA
CTTTGTGGTTACTTGATTTTGAGGAAGAAAATAT
TCAACTTTGTATAAAGACTAGGTATCAGGGTTTC
TTTTGCAGTGGGAGTTGTATATATATCGTATTTTG
GTATATCGTAGAAACTCAAGCTTTATGCATCCGTA
TTTGGGATATGTCAATGACGTGCAGTGAAATTTGC
TATTAGACCCTGGAGGCAAACGAGTTGTACAAG
GTTTTATGGCTCCATGGGGAATTCTAATTTCCTTTC
TGGGGACCTTTTGTCCCGTTTTTACAGTAATGGT
GAAATGGTCCTAGGAGGGTCTCTCTAGTCGAAT
TCTCCAGGCAGGACCACGTGCTCAAAAAATCTT
TGTATAGTTTTAAATTTTTGAGGAGTATCTCTGCTC
AGAAGCATCTGTGGTGGTGTGTGTTGCGTTGTTC
TGTGTACTGTGTGTGACACAAGCCTACAGTATT
TGCACTAAGGAAAGCTGTTTAGAGCTTGCTGCT
ATGGAGGGAAGAACATATTAAAACTTATTTTCCC
CGGGGWTTRTWCWMGTTTTATGTWCTTGTTGTC
TTGTTGGCTTTCCTACTTTCCACTGAGTAGCATTT
TGTAGAATAAAATGAATTAAGATCAGMWRWRWR
MAAAAAAAAAAAAAAAAAAAAAAAAAAAAAA
AAAAAAAAAAAAAAAAAAAAAAAAA-3' (SEQ ID NO:45) and
5'-AATTCCCCATGGAGCCATAAAACCTTGTACAAC TCGTTTGCCTCCAGGGTCTAATAGCAAATTTCACT
GCACGTCATTGACATATCCCAAATACGGATGCAT
AAAGCTTGAGTTTCTACGATATACCAAAATACGA
TATATATACAACTCCCACTGCAAAAGAAACCCTG
ATACCTAGTCTTTATACAAAGTTGAATATTTTCTTC
CTCAAAATCAAGTAACCACAAAGTAAAGTAAAT
GGAATTTTTTTTAAATCATACAGAGAGTTAAGTT
TTGAGAGACAGGGCCAGGGTCTTTCATTGTCTT
CTCCTACAATGCAGATTTCTTAGGAGCCACTGTC
CCCACAGGAACGACAATCGATCTTTGAAAACAG
AACCTTTTTAATGCAGTTCACACGGCACAAGTC
CACAAATCACTTTNGAAACAAAACGAAATAGA
GAGTGTTATCCTAAGTNAGCACAAGTGGGGGN
GAGNGAGACAGAGAAGGGGTGGGAACAGAGTC
CTTTAATGCNATCTGTTTCTATTCAGGCTTGGAAC
AACACAAAGAAATGTAAACATTTAGNATAAATAA
TAGAATAAATGTCGGGTTCTTCTCCCCTGTCCCTT
CCCATACCCNCTGGCAAAATCTGNCCCAGGTCCT
CCCGGAACATGGTGNGAGTACCTGGGTCCATTG
NAGNCCATTTGGNGAGGGCGTGGCCAA-3' (SEQ ID
NO:46).

Northern blot analysis using a sequence from the R113 clone revealed that the expression of the R113 mRNA was upregulated in response to the multiple MECS treatment. Specifically, R113 mRNA expression was induced seven fold by the multiple MECS treatment as determined from Northern blot data using total RNA from rat hippocampus (Table I). In developmental studies, the expression level of R113 was found to be low and unchanged in embryonic as well as post natal development.

Another IEG nucleic acid clone was designated R114. The R114 clone is 3318 bp in length and has a nucleic acid sequence as follows:
5'-GGCACGAGCCGAGGCTCAGCACAGCACGGAT
AGGGGCGCGGAGCGCACTGAGAACCCTACTTTC
CCGTGAGCCCGAGCCCGGCAAATGGGCGAATG
AAGAAGGAGAGCAGGGACATGGACTGCTATCTG
CGTCGCCTCAAACAGGAGCTGATGTCCATGAAG
GAGGTGGGGGATGGCTTACAGGATCAGATGAAC
TGCATGATGGGTGCACTTCAAGAACT-
GAAGCTCTTA
CAGGTGCAGACAGCATTGGAACAGCTGGAGATC
TCTGGAGGCGCGCCCACCTTCAGCTGC-
CCTAAGAGC
TCACAGGAACAGACCGAGTGCCCTCGCTGGCA
GTAGTGGAGGGCCTGCTGGGCTTGCTGC-
CTGTCCCT
CCTCCAGTCAACCATCTTTTGACGGCAGCCCCAA
GTTTCCATGCCGTAGGAGTATCTGTGGGAAGGAG
CTGGCTGTCCTTCCCAAGACCCAGATGCCAGAGG
ACCAGAGCTGTACCCAACAAGGGATAGAGTGGGT
GGAGCCAGATGACTGGACCTCCACGTTGATGTCA
CGGGGCAGAAATCGGCAGCCTCTGGTGTTGGGA
GACAATGTTTTCGCAGACCTGGTGGGCAACTGGC
TAGACTTACCAGAACTGGAAAAGGGCGGGGAGA
GGGGTGAGACTGGGGGATCCGGTGAACCCAAA
GGAGAAAAAGGTCAGTCCAGAGAGCTGGGTCG
TAAGTTTGCCCTAACTGCAAACATTTTTAGGAAGT
CTTGCGTAGTGTGCGGCCTGACCGAGACCGGCT
GCTCAAGGAGAAGCCTGGTTGGATGACTCCTATG
GTTTCTGAGTCACGAGCAGGACGCTCGAAGAAA
GTCAAGAAGAGGAGCCTTTCTAAGGGCTCGGGA
CGGTTCCCTTTTTCCAGCACAGGAGAGCCCAG
ACATATTGAAACCCCGGCCACAAGCAGTCCCAAG
GCTTTAGAACCCTCCTGTAGGGGCTTTGACATT
AACACAGCTGTTTGGGTCTGAATTCGAGAGAT
GCTCACTGACCTAAAATGCAGACTTGTGAGGGC
CCTGGGGGAGGGTGGGCAGATGGCATGGTCTT
CAGGCCAGATGCAAGTTCCCATCCTCAGAAAGA
AAGCAGAGTTCTTAGTCAGGCCTCAGTAGAACA
GTGGAGAGAGGCTGTCACAGGCCAGGCTGAGCT
GAGTCCCTGGAGAGAATGTGTGTATTTGTGTGTGT
GTGTGTGTGTGTGTGTGTGTGTGTGTGTGTGT
GTGTATGTGTGTGTGTATGCGTGTGCATGCACTGTT
GTTGTTAGAGGCTGGATGTGACAATAATTGGGAGA
GGCAGGAAAGGAGTCCAGGACAAGCCTATGATAT
TCCTCCATTACCTTACCCAAGACCTCATTTGAACAT
TCTATATGCAAAGGGGCATTTAGCCCTCAGGTTTC
CCAGAGGAACTCCCAATAAAGACCTGTCTCAGGG
ACCCCCAACCATTTTTTAATGGTCTGCTTCCCTGA
CAAGGCACTGATGCAGGCAAGGGGTTTGTTTTTGT
TTTAAGGGTTGGTATCCCAGAATGGAGCACCGGAA
ATAGGAAAATCCCTATTTATAGCCCTTCCTAGGACC
AAGATTTCACCCATGGCTGGGTGCTGGGGACGCA
GAACAAGCAGAGGGGTGTGCGTGCGTGCGTGCGT
GCGTGCGTGCATGTGGTGTTGAGGAAGCCTGAGA
TGCTCCCAGATCTCTAAAGTGCAGAGGAGAAGCA
ATGTGCGTTCACCCCGGTGATTCCATAAGCAGCCA
TCTCTGAGAGCACACTCGGCTGCCAGGAGGAAA
AACAGGTCAGGCCAATCTCATGGTTATCAATGGAC
CCTAGAGTCATACGCTGCCTGGTCCAGCAGTGAG
AGCCCATCCTGACTCCCTGTTGCCTATCTTAATGCT
CCTGCAGGGCAGCAGATGGTTGGGGTGAACCCA
GAGATAATACCCATACATTGAGAACATTTCTTAGTC
TACATCTCATAGTCATTCAGCGAACTGGACACATC
ACCCGCATCACCCTGGAGGTCAACAGGGGACCC
TGAGGGTGGGGCTGATGCCAGGCACTTTATATAG
TGAGCAGGCGTGCAAGTCTGGGACCCAGGGAATC
CATCTCAGCCCCCACCCCTTAGCCAGGAGAGAAC
AAAGTAGGCCCCTGTTCAAGCCCAGCTCGGAGGC
TGCCTTAGCTCCTCCTTCGCCCCCTCCTGCAGACC
CAGCTCAGCTTGATGAGGTGTGACAACTGCAATTA
GAGGCAAGCCGCCTGCTGCCCCAGAGCATTAAG
AGCAAATTAGAGAAGAAAAATCACAAGAGAAGC
TCTTCTGCCTGCAGTCTAGACTCCCAGGGGACTG
GGTGGAGGAAGGAAGAGCTTAGGGCATAGGGAT
GAGGAGGTAAAAGTAACAGCAGGAAGGGTCACC
TGCAAGTTCCCACGCAGTTAAATGATAGGTGGCCT
TTTTTTTTTTTTTTTAATCTGTAGCTTTTTGTCAGG
CAATGTGCCTATCTCTTTCAGAACAATTAATCAGT
GGGGTCAAAGGGCCCTGCCATGCTGGCTGCCCC
CATCAGGCTACTCAAAAAGGAAAGCAGTTCCAA
GCTCCAGCCTGTGGGCATCAGGCCTATCTGCTCT
GGCCTGGTGTTTATCAGCTAGGCTCGCTCTTTCTG
GTCAAATGGGTCCTCATCCATTCTGTCCCACTG
AACTTCTGTCTCTGGTGAAGGAAGGTAACTGTAG
CTGCCTCTGATGGCTGCTGCAATGTGTGTGGAGA
ATGAACATGTGAAAACCCCACACCCTGAAGGGTG
GCACATATGACACATTTACTCAAGAGGACACAGG
ACTGGGACGGTGTAGGAAGCCAACTCATTTGTTT
TGTGGACTAGTCACTGTTCACATTATTTAAATCGA
CTGACGTGACAGACTCCTTCTTTGACTGGGCACT
GTGACAGAAGGAGAGAACTCAGCAATGGGAAAG
CTGGCCTCCACAGCTACCAAGGCACACAAAGAA
ATCCAGTTAACCACCACCTGGCCAGAAAAGGGTC
AAGGGACCAAAACAAAATGATTAGCAAGTAATTT
TGGCTTCTAAGAGAACCCACAGGTGTCTGTCACC
TGATCTTTATTTTTCTGCTACACCCAGGAAATGGT
TGCTCATTTTACCCAGTAGACTCGGAGAAGTTAAT
GCTTTCAAGGTCACACAGTACAAAGCTGGGATT
GAAACAGTTTGTAACTGACTTCCAATCTTGTGTT
CATGCTACCTGGCAAACTGTCCATATTTGCTCCAC
AGCCAGATCCAGAATAACATTTGTCTCCTCTCGTG
CAAAAAAAAAAAAAAAAAAAA-3' (SEQ ID NO:47). In addition, the R114 clone contains an ORF from basepair 94 through basepair 993. This ORF encodes a polypeptide of 300 amino acid residues. The translational start site was assigned to the first methionine residue in the ORF. The amino acid sequence of the R114 polypeptide is as follows: MKKESRDMDCYLRRLKQELMSMKEVGDG-LQDQMNCM-MGALQELKLLQVQTALEQLEISGGAPTF-SCPKSSQEQTECPRWQGSGGPAGLAACPSSSQPSFD SPKFPCRRSICGKELAVLPK-TQMPEDQSCTQQGIEWVEPDDWTSTLM-SRGRNRQPLVLGDNVFADLVGNWLDL-PELEKGGERGETGGSGEPKGEKGQSRELGRKFALT ANIFRKFLRSVRPDRDRLLKEKPGWMTP-MVSESRAGRSKKVKKRSLSKGSGRF-PFSSTGEPRHIETPATSSPKALEPSCRGFDINTAVWV (SEQ ID NO:48). A portion of R114 from base position 111 to position 210 was found to have 98 percent identity with the mouse G protein-coupled receptor EBI 1 (accession #L31580). This homology, however, ends with position 210. In addition, the 100 bp region of 98 percent identity in the EBI 1 clone appears to be an artifact produced while PCR cloning EBI 1. This "identity" region in R114, however, is not an artifact, since RT-PCR with primers located in the 3' untranslated region of R114 and the middle of the "identity" region (139–164 bp) was used to obtain portions of the R114 clone. In addition, a portion of R114 from base position 143 to 601 was found to have very strong homology with a human EST obtained from prostate tumor (accession #AA595469). This indicates that the entire "identity" region is from one gene and not a product of concatamerization of the R114 clone and EPI 1.

The alignment of the human EST obtained from prostate tumor with R114 revealed a very high level of identity at the 5' and 3' ends of the overlapping region and a somewhat lower homology in the middle. In addition, 13 base insertions and deletions were identified between the EST sequence and R114. After excluding 7 of the 13 differences because they would have caused a frame shift, the two sequences were translated and compared. This comparison revealed an 81% homology at the nucleic acid level and an 85% homology at the amino acid level. Interestingly, no homology was found between the two sequences before position 143 of R114. Position 143 is six bp before the third methionine residue. Thus, the translational start site of R114 may be the third methionine residue in the ORF.

Further, 95% homology was found to exist at the nucleic acid level (98% at the amino acid level; there is a one base deletion in the EST that is probably an error of sequencing) between the 3' end of the R114 ORF from position 580 to about 987 and the full length of an EST from mouse mammary gland (accession #AA472513).

Northern blot analysis using a sequence from the R114 clone revealed that the expression of the R114 mRNA was moderately upregulated in response to the multiple MECS treatment.

Another IEG nucleic acid clone was designated R198. The following two nucleic acid sequences are within the R198 clone:
5'-TTTKTTTKTAATTATTTTTTTTTTTGGGTTGAT TCCTTGTNTTTTANTTGCCAAATNTTACCGATCA NTGANCAAAGCAAGCACAGCCAAAATCGGACCT CACCTTAATTCCGTCTTCACACAAAAATAAAAA AACGGCAAACTCACCCCCATTTTTAATTTTGTTT TTAATTTTACTTACTTATTTTATTTATTTATTTTTGG CAAAAAAATCTCAGGAATGGCCCTGGGCCACCTA TATATTAATCATTTTGATAACATGAAAAATGATGGG CTCCTCCTAATGAAAAASCAAGGAAAGGAAAAGG CCAGGGGAATGAGCTCAAAATTGATGCCCACKTG GGGAGCATCTGGTGAATAATCGCTCACKTCTTTCT TCCACAGTACCTTGTTTTGATCATTTCCACAGCAC ATTTCTCCTCCARAAACSCGAAAAAACACAASCGTK TGGGTTCTGCATTTTTAAGGATAARARARARAAAG AGGTTGGGTATAGTAGGACAGGTTGTCAGAAGAG ATGCTGCTATGGTCACGAGGGGCCGGTTTCACCTG CTATTGTTGTCGCCTCCTTCAGTTCCACTGCCTTTA TGTCCCCTCCTCTCTCTTGTTTTAGCTGTTACACA TACAGTAATACCTGAATATCCAACGGTATAGTTCA AAGGGGGTAATCAATGTTAAATCTAAAATAGAATTT AAAAAAAAAAAGATTTTGACATAAAAGAGCCTTGA TTTTAAAAAAAAAAGAGAGAGATGTAATTTAAAA AGTTTATTATAAATTAAATTCAGCAAAAATTTGCTA CAAAGTATAGAGAAGTATAAAATAAAAGTTATYHG TTTCAAAMTAVCDTRTCGAMCTCVTCVABCCCGR GGAAKCCMCTASKKCBARHSCGGCCCCCACCSCS SYSKAKMTYCATKCTTTTGAWWCCCTTTAGTGAG GGTTAANAA-3' (SEQ ID NO:49) and 5'-CAGCCTCTCACTCTCTNGCTCTCTTTCTGTCTC TTCCTCGCTCCCTCTCTTTCTCTCCTCCCTCTGC CTTCCCAGTGCATAAAGTCTCTGTCGCTCCCGGAA CTTGTTGGCAATGCCTATTTTTCAGCTTTCCCCCG CGTTCTCTAAACTAACTATTTAAAGGTCTGCGGTC GCAAATGGTTTGACTAAACGTAGGATGGGACTTA AGTTGAACGGCAGATATATTTCACTGATCCTCGCG TGCAAATAGCTTACCTGGTGCAGGCCGTGAGAGC GCAGGCAAGTGCGATGCAGTCTTTAAGGGCTTTT CAGACTGTTTGCTCAAGCTGGGTGACAGCATGGC CAACTACCCGCAGGGCCTGGACGACAAGACGAAC ATCAAGACCGTGTGCACATACTGGGAGGATTTCCA CAGCTGCACGGTCACAGCTCTTACGGATTGCCAG GAAGGGGCGAAAGATATGTGGGATAAACTGAGA AAAGAATCGAAAAAACCTCAATATCCAAGGCAGCT TATTCGAACTCTGCGGCAGCGGCAACGGGGCGGC GGGGTCCCTGCTCCCGGCGCTTTCCGTGCTCCTG GTGTCTCTCTCGGCAGCTTTAGCGACCTGGCTTTC CTTCTGAGCACGGGGCCGGGTCCCCCCTCCGCTC ACCCACCCACACTCACTCCATGCTCCCGGAAAATC GAGAGGAAAGAGCCATTCGTTCTCTAAGGACGTT GTTGATTCTCTGTTGATATTGAAAACACTCATATGG GGATTGTTGGGNAAATCCTGTTTCTCTC-3' (SEQ ID NO:50). This clone is similar to neuretin (accession #U88958).

Another IEG nucleic acid clone was designated R233. The following nucleic acid sequence is within the R233 clone:
5'-AAACCNAGAACCCCCCTTTGNAGAACCNTTGT TTCCTTTCAAGCCCAAGGAAGGCGGGGCCCAA CCTTTGGTGTTNTTTGAACAGGCCTTGAACAGGA GGNTWAGGAGAAATTTCCGGTTGTGGAACCCCA ACAGGAACCCCTTGGCACCCCTGGCCCCAAGGTT GTGMAACTTTGGTTTGCTTAATTTGGACCGTTTTT GCCTTGAGGATTCATGACTTTTTTTTGKGCCCTTGT GAGCCAAGATGTTGGGTTTTCCCATCAACAWTAA TAACCCCTTGCTTTTTGGGGTGATTCCCCTGGGGA TTTCCTGATGAAATTCCCCCACAGCTCCTGGGGTTT TCATCTTGTTCTTACTGTTGTCTGGATTAGGAGGG CGGAGAGGGTGGACTCCCTGAGACAAGATAAGCA GGTGGAGACATAGAAGAGGGAGGGACATTTAACA TAGTAACATTTTCAGAGGTGACAGAGATGATACAC GGGCAGCTGGAMTTTTGTGAAGGACAGAGGAG CTGGCAGACCCACAGGGCCATACCTTTGAGGGAC AGGTGAATGGCTGGTTACCAGAGACAGGACTGGT AGACAGTCAAGTACCTCACTACGATGTGCCAAGA GATYTGGGATCCTGGGAAATGTGTGGAGAAGAGG ATTTGACACTCCCCACCCCCAAGGCCCTTCCCCTT
TGCTGACAGCATTGCTGTGGTCGTGGCCTGTTGCC
TTGTCCTCTGTCCCTGGGTGGGGCACACCCTCCTG
TGCTGTGCTTGCCTTGTGCATCAATAAACCAC-3'
(SEQ ID NO:51). This clone is similar to KIAA0273
(accession #D87463).

Another IEG nucleic acid clone was designated R241.
The first library screen produced a clone designated R241-4.
This R241-4 clone contained a 2.0 kb fragment and a polyA
tail. A second library screen using 5'-end of R241-4 as a
probe produced an additional clone designated R241-12.
The following nucleic acid sequence is within the R241
clone:
5'-GCANTTTGGAGTTATTGCTTAAAACCAGGNTA
AGGCACTTTGTCCCACAGGACCCAGGAATCNTAA
ANGGGTTGAAATTGGGNCGGGGAACCCCAGGAT
ATAATGCNACTTTTGTTAGGGGGAGAGTTCAGCT
CTAACTGGTAGTAGTGTGAAAGTAAGCACCTTGA
CTTCAATTTTGGAAAGCACTTGGTAAATGGAGAG
AACTTTGGAGTTTCCCTATCATCTATATCAGTCTTT
GAACACACCCTCAAGTCCCAGCCTCAAGGCTCA
ATAAAGGACCACATAGCAGGTCTGAGGCTCACTG
CTCTCAGCCCTTAACACAGGGCAGTGGAGAGCA
GGGTGATCTTCCCTCTCTGGAGCTTCTCCTTGGC
CTTCTTCTCCACTTGGGCTTCTGCTCAGCAGCAG
ATATATTCTGGGTTCCATAAGGAATCCAGCTGTCC
CAGTGGCTTGACCCTGTCAAGGCAAGATATCAACT
CTGAGGATGACCCAGTCATGGAGGAAGAGAGT
GTGACAAGATCCGCAGTTTGAAGCAAAACTGTG
TTTGGTCTTTTCAAGAAACAAATGGGCACATTGA
GTTCTGTTCAGTGTCAGAGGATATCTTTCCCTTTG
CTCCCAGATTTCCAGAAATGGATAATGTTTTCATT
TCTGTGGGAAGGGTCAAGAAACATAAAATTGCTC
AACAATGCTTGCTTCCCTTGAGGGTTGTTGAGCA
AAGGCCGATATGCCTCCCTGCATTCTCTTCTACCT
CAAGATTTTGGAATTCAATTCTGGAACAGAAATTT
ATTTACACAAGAACACTTGTTGTCAGCCTTGGTTA
CTGTGGGAGTTACATAAGGGTGACAGTCTGTATC
TTCTAARTTAAACAGGAACTGGGCTTTGGCGGCC
TATTGACCCAGTTTATATCTAAATATAACTGTGGC
TCCAAATGATTGGCCAATAACATTCCCTTTACCTT
CAAAGTTTTCTCCATCAGTCATTTCTGTGGCAGC
ACAGTTCCAATGTCATATGCCCC:TGCAAATTGTG
AAAGTAATTAGTGACAAAATAACCCTCCCCCCTTT
CAGTGGCCAAACTGTCAGCTGTAGCAGCGCTGCG
AAAGCGAGTACTACACTATGTACGGAAAG:CCTGT
TCCTTATCACGGACTAGACTCAAGAAATGCCATC
TCCGAACGGTGGCATTCAAGGTGGTAGTCGTTTG
AATGGAACAGTCATCTATGTGGACATTGTTAAAGT
TTTTAAAGAGTATTTTGAAAATTAAGTTTACATTT
CAACTGCTTTATTTTATTGAAACAATTGTATATAA
ATATTACCCTCTTTCACTGTTAATTAAAGTAAACCT
AGACCTTGTAGACAAGTGGGTCAACTGATATGTA
AGAAGCTGTGATGTAGACAATACCTTTCTCTTGTG
TAAATGGTCATAAATATAGCTGTTCCTGTGTTTTA
TAAGTTGAGGGTATTTTGTTGTTTTATAACAACAA
AATTTATTGCATTTGAAATGGTTTTTATGTAATAGA
ATCATGCAAACAGTGAAGGATTATAACATGGTAT
ATGTAAATGTATAAACTTTAGAAAGAAATAAATAC
AACAAATTCAAAAAAAAAAAAAAAAAAA-3' (SEQ ID
NO:52).

Northern blot analysis using the 3'-end the R241 clone as
a probe revealed the presence of two mRNA transcripts: one
about 7.0–8.0 kb and the other 4.8 kb. In addition, this
analysis revealed that the expression of the R241 mRNA
was marginally upregulated in response to the multiple
MECS treatment.

Another IEG nucleic acid clone was designated R256.
The first library screen produced a clone designated R256-8.
This R256-8 clone contained a 1.8 kb fragment. A second
library screen using 5'-end of R256-8 as a probe produced
two additional clone designated R256-2 and R256-3. These
additional clones contained each contained a 3.0 kb fragment. The following nucleic acid sequence is within the
R256 clone:
5'-GGCACGAGGACAGATTCTGAGATGGAAACTTA
AATTACATCCCAGAGGCAGGGAAACTATGAAGTC
ACCGTTCCTAGACCACCCCTTACTGAGGTTCCAC
GGTCACACTGACGGCAGGACCCACAAGGGCAGG
TATTGGTCTGCCCTCCTTTCTCCTGTCTGTCTGAC
TTACCTAACTTTGGTCTCGGCTGCTGACACTTGGA
AAGGACCAAATTACTTGATAGTATTTCCCCCTGTT
TGTGTAATAGCCTGAAACCTTGGAGAGGTTCCAG
AATACTTCTGTATATAGGGCACAGGTGAAGACATT
GTCCAAAGCTTATTTATTTATCTATTTATTTACCCT
GGCTGAGTAACCACACCAGTAGGGGGAAAACTA
AAATGTGTTGAGTGTAAACAAAGTCACCAGCCT
GGCTAGAAATTCTCCCTGGAAAACATCCATTTTGA
TACAATGTAAACGTTAGTGTTCACCCTTAGATACAT
GTTGAAAGAGAGCTTTGGTACGCGGAAGTGGCAT
CTTTGGTCACACACCATGCCAAAGTGAAGAGGTG
GCCAGTGGAGGTCTTCCGGTCCTGTCGGGATCATT
TGTGAATACATTCTTTGCCCCTCTTAAGTACTTGTT
ACTAAACATGTGCAGTGGTAGGTATTAGTGTTAG
ATCACAGTGGGCACTTCCCTGGGGATCTGGGGAA
GACCAGAGCTTGCAACTCTGCCTGTTTTGATCCC
TATTTCTCACAGTGCTGTATTAAAAAAAATAGGAT
TTAAGACAGATAACCACCTTTACATTGTGAGTGTG
TTTGCCTTGTCTAACGACAGATAATTCCTTAACATT
TCTCTTCACCTTAGTACTTTAGGCTAATTATACACG
TCTGTCTATGCCATGAGTAAGTGGACTGTAGTCGG
ACCAAAAGAAAACAAATGAGCCGTTGGACCATT
GTGCAGTCAGTTTCTGGTCCTTAGATGTATCCTAA
GCAGTAAGTGTCTGATTGTACCCTGGTGGTATGAT
AGTTGTCTCGTAGCTGTCTCAGCTCCACAGTTTAC
AATGCAAATCTGTCTCAAGATCTTCACGTCACTGC
TGCTGAGAGCAGGGAGAATTCTCTGCAGCTGTTT
AAAGTTGTGGCCCGGCCTTGAATCCTCTGTTAATT
ACTGTGTGAGCCAGAGGGAGCTGCCCAGCAAGG
GTGGGCCCCCAGCCGGCAGGGGAACTTTCTAGA
CTCCCCGCTCATTCAATTGATCTAGGCATTCGGGC
CTGCTACTTGACCATTCTCGCCCTGTGAAATGTCC
CACACTTTGAAGCAAATACAATTCACAGCACAGT
ACACACAAAAACCCTGGCATAAGACAGGGGAGG
TTCTTCTTATTTTGTGAGCCGGTTGCCCTGGAAA
CGGATAACAAAGGGCAGCCTTCCACTTCTGGCAT
AATGGTGGAGCCTCTTTTCTCAGGCTTGACACCT
GTCTGAATAAGAGTGATTAGAGCCGCATAATATCC
CTCTCTTGGCTATTGAATATGTGGTTCACATACCAA
ACCCTGTAGAAGTTAGAAGACGGTCGTGTTCGTAT
GTTGTTTGCTTCCACTACATTTTTGAGGTTTGTA
AAACTGTTATTTTTTTTCACGATGTGAAACTGAAG
GTCAATAAATTATTAGAGATTTTCAAAAAAAAAA
AAAAAAAAAAA-3' (SEQ ID NO:53).

Northern blot analysis using a sequence from the R256
clone as a probe revealed the presence of a 4.0–4.8 kb
mRNA transcript. In addition, this analysis revealed that the
expression of the R256 mRNA was moderately upregulated
in response to the multiple MECS treatment.

Another IEG nucleic acid clone was designated R261.
The first library screen produced a clone containing a 1.0 kb
fragment with a polyA signal and tail. A second library
screen using a portion of this clone as a probe produced 41
positive signals that were isolated. In addition, PCR using T3 or T7 primers along with a R261 sequence specific primer resulted in the 850 bp of additional sequence from a solution containing the phage plug from a first screen. The following nucleic acid sequence is within the R261 clone:
5'-CTTAAAACCCCTAGATTTCCTGTTACATACTAA
CACAGGTCTTCCCTTTCACTCCAACCCCAGGTT
TCAGGCCTCAGAGCCATGCTGGGGTTGGAGAAA
ACTGCATTCCTATGAGGGTAAAAAGTAGCTGCCC
TCTCTGACCCTTTCTTGCTAGGCTTCATGCGGGAT
GGAGAGGGTATCCCCAGGATGGGGACAGAGGAA
GCCTGGCTAGGGCCTTCTAGCCCAATAAGCCAA
ACAGGAACTATAAGCAGATCAAAATCCTACACTA
GCTTATTAGGGCCCTGTTAGTTGAAAACCTTGTT
CTGTCCCAAGTTCTTCAGTTACAACCGAGTACACT
TACTCTTCCAACTGTCCTAAGGGTCACTACCCAG
CCAGCTTTGGATCTTCAGCACTTTTAAAAGCTGAA
ACTCCCTCTTGCCCTTCTTGTCTATTCCTCACTGCC
AGTTGGGGCCTAGGCTCAGTCCTGGGCAAATGCC
CATGATCCTGCTGCTGTGGGAAGTTTGATAGGGCA
TTTGGCTCAAATTTCAAAAGGCCTCGCTCCTGAC
CTGATTTCTCGAAGCTCCAGTAGTTCTAGACCCCT
CCAATCTCTCATCTGACTGGTTGCAAGGCTTATTT
TTCTTTTGTACTTTCCTATAGAGCATTTCTGTAGCA
TTTGAGTGTGGCGATATTTTTTGTTGTGTGTAGAT
TTCTAAGAACCAACACTACTCAGTCTCCTGCTAGT
CTGACTCCTGAAGCATCAGACCTCGTCATACGGTA
TTGACTGTGTATGTGCCTTTCACCTTGAGCATGCT
TCAGGATTTTTTTTCTTAAACCACAGAACTTGAA
CACAAGGGAACCAGAATTCACAAAGTCCTATGC
AACCCTAGACAGGAGGAGGTTAGAGAGTCTGTCT
TGATTGGTGATTTCAGAGACCCNAGAGAAATTTG
TACCAGTTTGTATTAATGTCAGTACTACCAGCACT
TTGCCAAAACTAAGGATGTCAGAGGGACCTGTTT
TAGAGTGAGTCCCAATTACATCAAAGGGCAACTT
ACAGCTTTCTCCAGTAAGTCTGAGTGGTTCTCTT
GAGCTGGTGTCACTTTCTAACCTTTGCCAGTCTAG
CCCAGCAGGGCCCTGTGTGTGTGAGTGCAGTTT
GGTGCTGTTTTGGAGTATGCCTGCTCCCCAGCCT
GGAACCCTCTCAGCAACTTGCTGGGACCTATAAT
GTCTTAGGTGCAACAAGGACCCTACCAGAGCTCC
TGGGTGGCTTTCAAGATCCACGTAGCTTTGTGTG
AGGGGACTGAATGCAGACAAACCACAGCCTGCT
TCAAATACCTTCTTTCCCTACCACCTAGTTCCAA
ATGGAACCAACAAGTTGAGTGCATCTCTGTTGGG
TGTTTTGTGTTGAGACTGGCTGAAGTGAAAACTC
TTTGACTGACCATGTTGTGATGTGTCGACAGACTC
AAGGACACAACCACCTCGAGCTGGTCATGTGGCA
TGCCTGTGTATGTGTGTAACAGGATTCTGAATGT
AGGTTGTAATGCTATTCCTGTATGGGAGAAAAAA
ATAATATAAACAAATAAAAATCTATTTAAAGCACA
AAAAAAAAA-3' (SEQ ID NO:54). Sequence analysis revealed the presence of some homology with EST sequences including that of a cDNA clone from ae69b04.s1 Stratagene schizo brain S11 (accession #AA774320).

Northern blot analysis using a sequence from the R261 clone as a probe revealed the presence of a 4.0 kb mRNA transcript. In addition, this analysis revealed that the expression of the R261 mRNA was marginally upregulated in response to the multiple MECS treatment.

Another IEG nucleic acid clone was designated R272. The first library screen produced a clone that was used in a second library screen. This second library screen produced two additional clones designated R272-1 and R272-2. Clone R272-1 contained a 2.0 kb fragment while clone R272-2 contained a 1.7 kb fragment. The following two nucleic acid sequences are within the R272 clone:
5'-CCATGGGGACTGGTTTGTCACCNATTGCCCATG
GNTTGGTTGGTAGGTGTTTTTTGGTGGACATTTTT
GTTTCNCGTTTTGAACTCCAGATTATTGGGTTTTT
GTTTTAATTTATTTTTGTCAGAGGAAAAATAATTT
AACATCCATCTCACAGGCTTGCTTGACTGTTCAG
TTCCAAGGTCCTGCTCACTTTTTCTTGTCTTGCCT
CTGCTCTGGCTTTCTTCATGATAGTGCTGGACGTG
GAGCTGAGAGTCTCGTTTACTCTAGGCAAACCCT
CTACCTGAAGCCAGAGCCCAGCACTCCGTACCAC
CACAGACTTCTGAAGCTGGCAAAGTTTTAGAAGCT
GGGAGTTTTCTGATTCTCTCATTATTAAGTTTCTCC
TCAGTCTTTAGATAGAGGTAAATGTGGGCTTGTAA
GAAAAGAAACGAAAGCACGTAATGTACACCTATT
CTGAATTATGCAAATTAGCTCTTACTCAGGGTCAA
CTAAATTACTTCAACTCGCCCTTAGTTTACTCTTAA
TTTGCAAAAAGAGAAAAAAGAAGGAAAACTAA
ATAGGACTATGATTTGGGGAGCCAAATTGATAATC
TGATGTAAAAGTTGCTGTGTTAAACATAAATTATT
AAGTGTAGACTTTTTTCCTAGGATATTGTATTCATT
TTGTGATATCGCCTAGAATGATGTATTAGATAAAAA
TCAATTTTGTAAGTATGTAAATATGTCATAAATAA
ATACTTTGACTTATTTCTCAAAAAAAAAAAAAAA
AAAAAAA-3' (SEQ ID NO:55) and
5'-GATTTTATATTCAATGTTGTTTATTTAATCCATTG
CAGTTGGTGAATGCCTTTTCCTCCTAGACACCCTG
TATTATACCATTTGGGGATTAAGTCAAAGTTAAGT
ATATTTTTTTCTTACTTGAGCTCTATATATGCAATT
CAGATATCTTCCTGATGACAGTTTTATATGTAAATG
TAATTTAACTTTCTTTCCGTGTTGACGAAGTTCTG
TAGGTGTTAGGGTTAGAAGTCTCAGCACTCACTT
CTCTCACTGGATGTGCAGTGTGCCTGCCATGGCG
CACGGCTTCTCAGTAATGATGCCATCTCTGCTACT
TTTACAGAAGGAGAAGTTTACTTTTGAGGTGGGT
ATGTGTTGATATCTAAACACTGTGTGTTGCTTGCT
AGATAGGCAAGACACACTGCTGTGCGTGGCTCCT
GTGGTGCACCTAGCCCAGGGGAACGTAGCCTCA
GTACTTCCGCTGGCTTCTTCATGCCTAAGAAGCAG
GGCCTTTCTTGTTTGCTGGGCTCTGGCTTTAAAA
GTTGTCCTTTGGGTCTGGAGATGTAGCTCTGTGA
CAGAACACCAGCTAATGTCAGGTCCTGCGGTCA
TCTCTGGTACACACAAGCGCACACTCACATGATG
GGGGATGAAAGGCTGTCCTTGTAACAGTATTC
GATGGGCGTTGCCTGGATGACGATGTTTATGTAC
TCTGAAGGCAGATCCTGAAGGCACCCTGTTCTTC
CCTTCCTTGTGTAACTGAGTCTGCACTAGCTTAG
CCACTGTTTAGAGGCCATCCTAGTGGGCGAAC
AGGAGGCATCGCACTGGGTGATGGTTTGCCTTC
AGTCCTCAAGTAACAGCGGCCGACTTATGCCGA
TGGCTTGTTTGAAATCAAATATTACCAAGTTGGCC
TAGTCTGCCTTCTGTGAAGAAGGGGAGAAAGG
AAGGGTGGAAAGGTGGATGGAAAGCCTTTGGGG
AACTAGTCTGATCTCTCAAGGG-3' (SEQ ID NO:56).

Northern blot analysis using a sequence from the R272 clone as a probe revealed the presence of a 1.0 kb mRNA transcript. There appears to be a discrepancy in the length of the R272 mRNA since the Northern blot data indicates a message of 1.0 kb while the cloning data reveals a message length around 2.0 kb. Regardless, the Norther blot data indicated that the R272 mRNA expression level was moderately upregulated in response to the multiple MECS treatment.

Another IEG nucleic acid clone was designated R280. The following nucleic acid sequence is within the R280 clone:
5'-CTTCAGTTCCTTTGAGGGGNCTTTCCTTCGAA
GGATACGCCTACCTTTCACGAGTTGCGCAGTTTG
CTGCAAGACTCTATGAAGCAGATAAGCGATAA
GTTTGCTCAACATCTTCTCGGGCATAAGTCGGA CACCATGGCATCACAGTATCGTGATGACAGAGGCA
GGGAGTGGGACAAAATTGAAATCAAATAATGATTT
TATTTTGACTGATAGTGACCTGTTCGTTGCAACAA
ATTGATAAGCAATGCTTTTTTATAATGCCAACTTAG
TATAAAAAAGCTGAACGAGAAACGTAAAATGATA
TAAATATCAATATATTAAATTAGATTTTGCATAAAA
AACAGACTACATAATACTGTAAAACACAACATAT
GCAGTCACTATGAATCAACTACTTAGATGGTATTA
GTGACCTGTAACAGAGCATTAGCGCAAGGTGATT
TTTGTCTTCTTGCGCTAATTTTTTGTCATCAAACCT
GTCGCACTCCAGAGAAGCACAAAGCCTCGCAAT
AGTGCAAAGCTTGCATGCCTGCAGGTCGACTCAT
ATGCGGTGTGAAATACCGCACAGATGCGTAAGGA
GAAAATACCGCATCAGGCGGCCATCGCCCTGATA
GACGGTTTTTCGCCCTTTGACGTTGGAGTCCACG
TTCTTAATAGTGGACTCTTGTTCCAAACTGGAAC
AACACTCAACCCTATCTCGGTCTATTCTTTATTTAT
AAGGGATTTTGCCGATTCGGCCTATTGGTTAAAA
AATGAGCTGATTTAACAAAAATTTAACGCGAATT
TTAACAAAATATTAACGCTTACAATTTTCCATTCG
CCATTCAGGCTGCGCAACTGTTGGGAAGGGCGA
TCGGTGCGGGCCTCTTCGCTATTACGCCAGCTGG
CGAAAGGGGGATGTGCTGCAAGGCGATTAAGTT
GGGTAACGCCAGGGGTTTTCCCAGTCACGACGT
TGTAAAACGACGGCCAGTGAATTGTAATACGACT
CTATAGGGCGAATTGGGTACCGGGCCCCCCCTCG
AGGTCGACGGTATCGATAAGCTTGATATCGAATT
GGCACGAGCCGCAGCCGATATGCAGTCCCCGGC
GGTGCTCGTCACCTCCAGGCAAGTTCAGAATGCG
ACACGGGYCTCGACCTGACTGTACCACAGCACC
AGGAGGTGCGGGGTAAGATGATGTCAGGCCATGT
GGAGTACCAGATCCTGGTGGTGACCCGGTTGGCT
TGTTCAAGTCAGCCAAGCACCGGCCCGAGGATG
CGTCCAGTTCTTGGTCTCCAAAAAATACAGCGA
GATCGAGGAGTTTTACCAGAAACTGTACAGTCGT
TACCCAGAAGCCAGCCTGCCCCCACTGCCTAGGA
AGGTCCTGTTTGTCGGGGAGTCTGACATCCGGGA
AGGAGAGCCATGTTTGATGAGATTCTACGCTGTG
TCCAAGGATGCCCAGTTGGCGGGCAGCCCAGAG
CTGCTAGAATTCTTAGGCACCAGGTCCCCGGGGG
CTACAGGCTTTGCCACCCGAGATCCCTCTGTCTT
GGGATGACGACAGCCAGCCGGCCAGGGGACAGT
ATGAGGCTTTTGACTTCTTTGAGCAACAGGGATG
AAGTGCAAGCCACCCACATTGGGCCTGAGCAAC
AANGAAATGTTGAGAAGGTCCNTGGAAGGAANG
GGAGGGAAGGGAGGAAGGANGATAACTTGGGAT
CCCCCTTGGGGCAATCAATGCGGCCTCCCAAAGG
AAAGNCCCTAAAG-3' (SEQ ID NO:57).

Northern blot analysis using a sequence from the R280 clone revealed that the expression of the R280 mRNA was upregulated in response to the multiple MECS treatment.

Another IEG nucleic acid clone was designated R286. The first library screen produced a clone that was used as a probe for a second library screening. Briefly, the $^{32}$P-labeled probe was used to screen a UniZAP rat hippocampal oligo (dT) primed library (Stratagene). This second screening produced a clone having a 4.7 kb full-length R286 cDNA sequence. The nucleic acid sequence of this rat version of R286 is as follows:
5'-CTGCCAGCCGAGGCTCCTGCCGCTGTGACCCGC
GCTCCGCCCGCCGCCGGGCCGGGACCCT-
GATAGCTAATGTCAGAAGAAAGT-
GACTCTGTGAGAACCAGCCCCTCTGTG-
GCCTCACTCTCCGAAAATGAGCTGCCACCCCTC
CCCCGGAACCTCCRGCTACGTGT-
GCTCGCTGACAGAAGACTTGGTCAC-
CAAGGCCAOGGGAAGAGCTTCAG-
GAGAAGCCCGAGTGGAGACTCCGGGATGTGCAG
GCCCTTCGAGACATGGTACGGAAGGAG-
TACCCATACCTGAGTACATCGCTGGAT-
GATGCCTTCCTGTTGCGCTTTCT-
GAGGGCCCGAAAGTTTGATTATGACCGGGCCCTG
CAGCTGCTGGTCAACTACCATGGCTG-
CAGGCGGAGCTGGCCAGAGGTCTTCAG-
CAACCTGAGGCCATCAGCCCTGAAA-
GACGTTCTTAACTCTGGATTCCTCACAGTGCTGCC
CCACACAGACCCCAGGGGCTGCCATGTC-
CTCTGCATCCGACCAGACAGATGGATAC-
CGAGCAACTACCCGATCACCGAGAA-
CATCCGCGCCATCTACTTGACGTTAGAAAAACTCA
TCAGTCCGAGGAGACCCAGGT-
GAACGGGGTTGTAATCCTCGCCGACTA-
CAAGGGAGTGAGCTTATCAAAGGCGTCT-
CACTTTGGCCCCTTTATCGCCAGAAAGGTGATTG
GCATCCTTCAGGATGGCTTCCCCATTCG-
GATAAAAGCAGTTCACATAGTAAAC-
GAACCTCGGATATT-
TAAGGGCATTTTCGCCATCATAAAACCATTTCTGA
AGGAGAAAATTGCAAACAGGTTCTTC-
CTCCATGGGTCTGACCTGAGCTCTCTG-
CACACGAGCCTTCCAAGGAATATCCTC-
CCCAAAGAGTATGGGGGCACCGCTGGGGAGCTG
GACACTGCCAGCTGGAACGCGGTGCT-
GCTGGCCTCGGAGGATGATTTGTGAAA-
GAGTTCTGCCAGCCTGAGTCTGGCTGC-
GATGGTCTCTTGGGCCAGCCCCTGCTGCCTGAGG
GCTGATCTCAGACGCGCAGTGTGAC-
GACTCCATGCGAGCCATGAAGTC-
CCAGCTCTACTCCTGCTATTAGCCCTCT-
TCCGGGAGAATCACCATGTGTAATTCCTTCCTTCT
TCGAATGCACAGGCTGAAGATGCCAG-
GACCTCGGTCTTGCTCCATCACAGTG-
CAGCACGGAGCTGCCTGCAGAGATT-
TAAGGAGAGCCCATCACAGGCAGACCTCTGACC
AGCTAGGTTATTCCAAGAAGACATG-
GAAATTGCCCTGGTGATTCCCAGAT-
GTCTGTACTCTAAGTCTGCAACTGT-
TACTCTGGAAGCTGCATCTGTTTCTTATGCATCTT
GGAAAGAACTAGGGTCAAAGTCACTCT-
GAAGTGACCAGGAGTAGACAACTTGAT-
TGATCATGAGTCTGAAACAATTGC-
CAATCCTGAAAGGTGGCCATGCGTGAGACTTTG
TCTCTTTCCCATAAACTGTAGGTGT-
TGACTACTGCTGCTTATCTGCAAAGGT-
CAGGGTTCAGGCCCCAGTTGGCAT-
TGCTGGGTCTGGGAAGCACTGCTAACTGAGTGGT
AGAAACGCCAGGCCCAGGCAGCACT-
TAAAGGTTAAAGGTCAAATTTG-
GAAGCTAAGGCTATAAATCATCCTGGGT-
TCCAGGCTTAAATCTTGCAATGGACACTCTCCCC
AAACCATAAAGCCTTAGCTCTGGTTCTC-
CATGGAATCATGCAGGTCAACAT-
AAAATACTGGATTCTTGGACTGCGTG-
GCTAAAAGCACTTAGACTARGAGTCCAGTGTGTG
ACTGGATGGATAGGGGCCTCAGCTTGT-
CAACTCTAAGTTAGMGMTCCATGGAAT-
GAAGGCCTTGRGGGCTGCTCAAGTTCT-
GTTAGGTTTCTGCTTGGAAAGATGACCACCTGGA
GGTGGCCGGGCCTTTTTGGTTTGGCTTG-
GTTTGTGTTATAGACACAAGCCTTATG-
GAAAGGAACCGTCTGGCCTTTAAA-
GAAATTACTATGTTCCTGGGAGTTGGTGGTAACCA
GCTGCTTTTGCAGATGATGGGTGAACTG-
GAAAGGGATGGCTTTTGTGAGGCTGAC- CAAGTCTTGTACGCGGATGTTGTACA-
GATTCCTCCCACACCGGAGACATTCGTACTATATT
AGAAACAGCCACGGACTTGT-
GCTCTTTCAGTTTGTGTCCCTGGAAA-
CATACGGGGGGCAGGCTGTTGCTGGT-
TCACCTGGGGGCCCTGCCCTCCCAGACACGGGAG
TGCTTGTCTAGCGTGGGAGGGCCAGTTG-
GCCAGATTGTTAGCTCTGCGTTGGGGT-
GTCGTAGACAACTGACAGGATTTTAGC-
CTTAACCCAAGCACTGAGTGAGGTGATTTTTCCC
TTGGCTTTTGGCGTGTCTTTGGTAT-
TCACCATGTATTGTGGTGTCAGGTAGT-
GTCAGGTACTGTTGGCTGTGTGTCTC-
CTAGACTAAGCGGGCGTTGSATACAGCTTACATAC
TGCTTGGAGACCAAAGGTCAGTTGGTTG-
TAATAAGCTGGTCCACCCTTAACAGACT-
TCCCAAACATYACAAGAGCTYTTATGGM-
CCTTACCTAATAATGCCAATTCTGGAGGACACTCT
TTTACCATAGAWKCSAATCCTTGATCTC-
CTGGCTCCTGGTTGAGCTTCCGCACT-
GATACACCCTCTTGRCTGCCCAT-
CAGGGCCATTTGCTGCTGAGTTCTGCATTGCTTA
CTSCKGSYGYTTTCTGCCTAAAGGGATG-
GCCACCCAGACACCTAAAAAGACCCGG-
GATGGCTCTCTAGCCTTGGTG-
GAGAGTCTTATTAGAAGTTTTCTTTGGGGGATTGG
GGATTGGCTCAGTGGTAGAGCGCTTGC-
CTGGCAAGCACAAGGCCCTGGGTTCG-
GTCCCCAGCTCT-
TAAAAAAAAAAAAAGTTTTCTTTGGTAGTTGGGG
AAAGGCAGAAGGAAAAAAACAAAGG-
GAAAGATGAATCTCTCAGTCCTACCTG-
GTTCCCTAAATTTAAATCGTGTCATGT-
GACTAGTTAAGTCTCTTTGACTTAACAAAGGGAC
ACCAGGTTCTTGGGGAGAAATCTCAGAG-
CAAAATGTTGCCTGTTGSTAACCTTCTG-
GTAACCARAGGARCCTTGATAARCTTAR-
GAGYKGACTGTATGTCCATGCTCTTGTGACTCTA
AGACTCTGGCACCTCAGGTTNAAGCAG-
GCTGTGAGCCAGATGTCCTGGTGCCAAG-
CAACCCCACTGTTGAGCAGCAGGGGCAC-
CATAGGCCTCAGCTAGGGGAGCGCACTGGTAGAG
CAGCAAGTGAGCAGGAATCTGACTT-
TAGGGTAAAAATCTAGACAGTTCTGA-
CAGCTGGAAGTCAACTTTTCCTCCAT-
TCAAAGTCATGTGGCATTGGGAAGGGGCTAGGG
AAATAGAAGTGGGTTCCAGCTTTATCT-
TCCTACACAGTCTCGAGTATAGCATTAA-
CACCGAGTGCTGGACAGAGGTTGTCT-
GCTGAACACTCAATCCTGCTCCTGACTGACTCTG
GAAATAAGGACATTCCACTCTGCTTG-
GCGCGGAGATGCCCTAGTGTGCGGC-
CGCGGGGGCTTCTCTTTCTCAAGTCCTC-
TACAGNACTTCCAGGCAGTTCATCTTCCTAGGAA
AAGGTATGGAGGTTCTGCCTTCATGGTA-
GAAACACAGGATAAAATCTACAGTAAA-
CAACCGGTAAGTGCTGGCTTCTTACGC-
CTTGGCTTCTCCAGGCACAGGTGGGTTCGACTAC
TCCCATTTCATCTTTGTAAGCACCTCAG-
GTTATAGGGCAGTTTCTTCAGAGT-
TGGGGGGACTGGAGCCATTCCCCCTG-
TAATGCCTGAGGTGGCCTTACCACCTAGCAGCCA
GTTTGGCCAGCAACAGCCACACTGCTGT-
TATGGTATCATAATACCTCATC-
CTCGGGTTTCCTTCAGAAAGGRAAAWGCTAAC portion of the human R286 nucleic acid sequence, specific primers were designed to amplify the human R286 homo ogue. After RT-PCR using human hippocampal RNA and the specific primers, the PCR product was subcloned in the TA-cloning vector (InVitrogen) and sequenced with SP6 and T7 primers. The following nucleic acid sequence is the ORF for human R286:
5'-ATGTCCGAAGAAAGGGACTCTCTGAGAACCAG
CCTTCTGTGGCCTCACTCTCTGAAAATGAGCTGC
CACCACCACCTGAGCCTCCGGGCTATGTGTGCTC
ACTGACAGAAGACCTGGTCACCAAAGCCCGGGA
AGAGCTGCAGGAAAAGCCGGAATGGAGACTTCG
GATGTGCAGGCCCTTCGTGACATGGTGCGGAAGG
AGTACCCCAACCTGAGCACATCCCTCGACGATGC
CTTCCTGCTGCGCTTCCTCCGAGCCCGCAAGTTT
TGATTACGACCGGGCCCTGCAGCTCCTCGTCAAC
TACCACAGCTGTAGAAGAAGCTGGCCCGAAGTCT
CAATAACTTGAAGCCATCAGCCTTAAAAGATGTC
CTTGCTTCCGGGTTCCTCACCGTGCTGCCCCAC
ACTGACCCCAGGGGCTGCCATGTCGTCTGCATCC
GCCCAGACAGATGGATACCAAGCAACTATCCAAT
TACTGAAAACATCCGAGCCATATACTTGACCTTA
GAAAAACTCATTCAGTCTGAAGAAACCCAGGTG
AATGGAATTGTAATTCTTGCAGACTACAAAGGA
GTGAGTTTATCAAAAGCATCTCACTTTGGCCCTTT
TATAGCCAAAAAGGTGATTGGCATCCTCCAGGAT
GGTTTCCCCATTCGGATAAAAGCAGTCCATGTGG
GAATGAACCTCGAATATTTAAAGGCATTTTTGCC
ATCATAAAACCATTTCTAAAGGAGAAAATAGCAA
ACAGATTCTTCCTCCATGGGTCTGACTTGAACTCT
CTCCACACAAACCTTCCAAGAAGCATCCTCCCCA
AGGAGTATGGGGGCACGGCTGGGGAGCTGGACA
CTGCCACCTGGAACGCAGTACTGCTGGCTTCAGA
AGACGATTTTGTGAAAGAGTTCTGCCAACCTGTT
CCTGCCTGTGACAGCATCCTGGGCCAGACGCTG
CTGCCCGAGGGCCTGACCTCAGATGCACAGTGTG
CGACTCCTTGCGAGCTGTGAAGTCACAGCTGTA
CTCCTGCTACTAG-3' (SEQ ID NO:60). The R286 clones were found to be homologous to a family of transfer proteins for hydrophobic ligands (such as lipid soluble vitamins and phospholipids). Thus, R286 is a lipid transfer polypeptide. The amino acid sequence of the rat R286 polypeptide is as follows: MSEESDSVRTSPSVASLSENELPPP-
PPEPPXYVCSLTEDLVTKAREELQEKPE-
WRLRDVQALRDMVRKEYPYLSTSLD-
DAFLLRFLRARKFDYDRALQLLVNYHGCRRSWPE
VFSNLRPSALKDVLNSGFLTVLPHTD-
PRGCHVLCIRPDRWIPSNYPITE-
NIRAIYLTLEKLIQSEETQVNGVVILA-
DYKGVSLSKASHFGPFIARKVIGILQDGFPIRIKAV
IVNEPRIFKGIFAIIKPFLKEKIANRF-
FLHGSDLSSLHTSLPRNILPKEYGG-
TAGELDTASWNAVLLASEDDFVKEFC-
QPESGCDGLLGQPLLPEGLISDAQCDDSMRAMKS
QLYSCY (SEQ ID NO:61). The amino acid sequence of the human R286 polypeptide is as follows: MSEERDSL-
RTSPSVASLSENELPPPPEPPGYVCSLT-
EDLVTKAREELQEKPEWRLRDVQALRDM-
VRKEYPNLSTSLDDAFLLRFLRARKFDYDRALQLL
VNYHSCRRSWPEVFNNLKPSALKDVLAS-
GFLTVLPHTDPRGCHVVCIRP-
DRWIPSNYPITENIRAIYLTLEKLIQ-
SEETQVNGIVILADYKGVSLSKASHFGPFIAKKVIGI
LQDGFPIRIKAVHVVNEPRIFKGIFAI-
IKPFLKEKIANRFFLHGSDLNSLHTNL-
PRSILPKEYGGTAGELDTATWNAVL-
LASEDDFVKEFCQPVPACDSILGQTLLPEGLTSDA
QCDDSLRAVKSQLYSCY (SEQ ID NO:62).

Northern blot and in situ analysis using a sequence from the R286 clone as a probe revealed the presence R286 mRNA throughout rat brain. For in situ hybridization, Dig-labeled cRNA probes were used as described elsewhere (Kuner et al., *Science* 283:5398 (1999)). Specifically, R286 mRNA expression was the highest in the cortex and hippocampus while being moderately high in the cerebellar granule cells, brainstem nuclei, several lateral and medial thalamic nuclei, olfactory bulb, and striatum. In addition, this analysis revealed that the expression of the R286 mRNA was upregulated in response to the multiple MECS treatment. Briefly, a probe from the 3' untranslated region of R286 was used to hybridize a Northern blot containing 2 μg polyA$^+$ RNA from hippocampus from brains of untreated rats as well as rats receiving the multiple MECS treatment. After one day of exposure using the phosphoimager FLA2000 (Fuji), an upregulation of R286 mRNA was detected in the hippocampus (3.72 fold induction) collected four hours after the last MECS treatment. An additional Northern blot analysis using 10 μg total RNA from hippocampus from untreated rats and rats receiving the multiple MECS treatment was performed. In this experiment, the probe was the ORF of R286 and the level of expression was found to be induced 2.4 fold in the MECS treated animals (Table I).

In addition, rats that developed seizures following intraperitoneal injection of kainate or PTZ were analyzed for the expression of R286 mRNA in addition to the mRNA of other LEG clones (Tables III and V). R286 mRNA expression was observed, by in situ hybridization, to be mildly upregulated in the hippocampal pyramidal cell layer, cortex, thalamus, and cerebellar Purkinje cell layer at 6 hours post-kainate injection. At 6 hours post-PZT injection, R286 mRNA expression was observed to be mildly upregulated in these brain structures, while no upregulation was observed at 20 minutes post-PTZ injection or at 1.5 hours post-kainate injection.

Other IEG nucleic acid clones included L073 (concatamer with Krox-20), L125 (oxoglutarate carrier protein), L201 (concatamer), R094 (fra2), and R217 (diacylglycerol kinase; accession #D78588).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated nucleic acid comprising at least 60 bases in length, and that hybridizes to the sense or antisense strand of a second nucleic acid under highly stringent hybridization conditions, wherein said second nucleic acid has a sequence as set forth in SEQ ID NO:31, wherein the isolated nucleic acid is expressed in response to seizure or ischemia and wherein said hybridization conditions include 1–15 ng/mL of isolated nucleic acid probe hybridizing to said second nucleic acid bound to a nitrocellulose filter, hybridization in 25 mM $KPO_4$ (pH 7.4), 5×SSC, 5×Denhart's solution, 50 µg/mL denatured sonicated salmon sperm DNA, 50% formamide, 10% Dextran sulfate at 42° C., with washes at 50° C. in 0.2×SSC and 0.1% SDS.

2. An isolated nucleic acid that encodes an amino acid sequence set forth in SEQ ID NO:32.

3. An isolated nucleic acid comprising a nucleic acid sequence at least 90 percent identical to the sequence set forth in SEQ ID NO:31 and that is expressed in response to seizure or ischemia.

4. An isolated nucleic acid, wherein said isolated nucleic acid comprises a nucleic acid sequence that encodes an amino acid sequence at least 70 percent identical to the sequence set forth SEQ ID NO:32 and that is expressed in response to seizure or ischemia.

5. An isolated nucleic acid comprising a nucleic acid sequence as set forth in SEQ ID NO:31.

6. A host cell containing an isolated nucleic acid of claim 1.

7. The host cell of claim 6, wherein said host cell is a eukaryotic cell.

8. The isolated nucleic acid of claim 2 wherein said isolated nucleic acid is expressed at elevated levels within one hour following global ischemia or seizure.

9. The isolated nucleic acid of claim 3 wherein said nucleic acid sequence is at least 95 percent identical to said sequence set forth in SEQ ID NO: 31.

10. The isolated nucleic acid of claim 9 wherein said isolated nucleic acid is expressed at elevated levels within one and one half hour following seizure or global ischemia.

11. An isolated nucleic acid comprising a nucleic acid sequence that encodes an amino acid sequence at least 85 percent identical to the sequence set forth in SEQ ID NO: 32 wherein said nucleic acid is expressed in reponse to seizure or ischemia.

12. A host cell containing an isolated nucleic acid of claim 9 or 11.

13. The isolated nucleic acid of claim 1, wherein said isolated nucleic acid hybridizes to said sense or antisense strand of said second nucleic acid under highly stringent conditions, wherein said highly stringent hybridization conditions include for 1–15 ng/mL of isolated nucleic acid probe hybridizing to said second nucleic acid bound to a nitrocellulose filter, hybridization in 25 mM $KPO_4$ (pH 7.4), 5×SSC, 5×Denhart's solution, 50 µg/mL denatured sonicated salmon sperm DNA, 50% formamide, 10% Dextran sulfate at 42° C., with washes at 65° C. in 0.2×SSC and 0.1% SDS.

* * * * *

SEQUENCE LISTING

```
<160> NUMBER OF SEQ ID NOS: 62

<210> SEQ ID NO 1
<211> LENGTH: 527
<212> TYPE: DNA
<213> ORGANISM: Eukaryote
<220> FEATURE:
<221> NAME/KEY: misc_feature
<222> LOCATION: (1)...(527)
<223> OTHER INFORMATION: n = A,T,C or G

<400> SEQUENCE: 1
ttgcagatca gcaccttttg atgatgcctg cccaacagtg ggtaatgctn acagcaaagc      60
accactttac gcttttagt tgtgctgggt tcatggctgg acatacacca accagccttg      120
accccacagg aatgccaagt tggctggaat gtaacccaac ctagtttctg cgcttcgctc      180
ctctcccagt gcaaggtgct aaacacccac tcacaagcct gctgtcaagc tgcgaccttg      240
ggggctggtt agaaagggct gcctccttcc agcaatagaa gttcatgaat ttgaggctgg      300
agataggtca agaccactgt gataactata aagactgtag cagccacaaa ggagaccccc      360
aaataactgg aggcatgggc actgacgtac cagatgaggt tatgtttgga gctgaaggct      420
tgctctgtgc ttcttggtag catcttttgt cctcttggga catggttgac cccatactgt      480
ccactgagct tgggagatga cagttgaata aaaaaaaaaa aaaaaaa                   527

<210> SEQ ID NO 2
<211> LENGTH: 1485
<212> TYPE: DNA
<213> ORGANISM: Eukaryote
<220> FEATURE:
<221> NAME/KEY: misc_feature
<222> LOCATION: (1)...(1485)
<223> OTHER INFORMATION: n = A,T,C or G

<400> SEQUENCE: 2
```

-continued

```
cggcttaatt aaccctcact aaagggaaca aaagctggag ctccaccgcg gtggcggccg        60
ctctagaact agtggatccc ccgggctgca ggattctgcg gccgattaag aagcctgctg       120
atgtccttag gcgaggacat taactccagt ctctgacaga ctttggacat ccagaataag       180 ttcttttttgt atatcagagc acagagccca gctttagcct ctgatggacc tcaggaacca      240
agaaggaggg acttccttaa cattctagag atgggactct aactctagct cttgtgttaa       300
gccctgaagt ccagaaagaa gtagttcttt gacattctag tgccaagatc cagcctctaa       360
gagaactctg atgtctaaag aaagtctttc atagtctagn ccagtcacca gtgaagctaa       420
acacctgaaa actattagat tctctggagc caggaatcca tctcaagtct ctcataaagc       480
ccaaatgtcc caggagaagt tgacaatata agccgtatc tcgatggact tttgaagaag        540
ctcagaaaag gagaccacct tggtagtctt gatctaggac tctggcttgt ttgtctccag       600
ggacgtttac atgtataaaa agagggacct ttctgatgat tcagaactgg gactccacct       660
ccatcctttg atgaaagctc aaatgtccag aaagaggggc ctctctgata ttctagagta      720
ggaccctccc tccagccttt gatggtgtcc agatgtccag aaagaggggc ctctctgatg       780
ttccagacct agggccctcc ctccagcctt tgatggtgtc cagatgtcca gaaagaggga      840
cttctctgat gttccagacc taagactcta gctccagcct ttgatgaagc tcagatgttc       900
agaaaggggg gcctccatga tgttctagaa ccaggactcc acctctagcc tttgatggtg       960
tccagatgtc cagaaagagg gtcttccatg atttctagga ccaagacttt acctccagcc     1020
ttctatgcct ccatgtctcc agtaaagctt aggtgtccag aaaagagcat tctcaatgaa      1080
tttatagaac caggactctt tctccagcct tgatgacgt tcagatgttc ataaagaaga       1140
acttccacaa tgtactaaag ctatgactcc atctccatcc tttgatgaaa agggacttcc     1200
ttccactctg ttccagaagc ctagctccac ctctaatctt tgttgatgtc caattatcca      1260
gaaagagggg gcctttagaa caaagactgt acttttattc attgataaag cacagattcc      1320
agaagcacag aaatctagaa agagggtcct ccctaacacg ctcgagctag aaccccggtg      1380
caagggtctg aaacttagac accagaagac cgctttgtcc tacaacaagt ctgcattttc      1440
taaatctcca ggtggctgat cagaagggtc caggaaggta tgggg                     1485
```

<210> SEQ ID NO 3
<211> LENGTH: 1854
<212> TYPE: DNA
<213> ORGANISM: Eukaryote
<220> FEATURE:
<221> NAME/KEY: misc_feature
<222> LOCATION: (1)...(1854)
<223> OTHER INFORMATION: r = G or A
      y = C or T
      m = A or C
      k = G or T
      s = G or C
      w = A or T

<400> SEQUENCE: 3

```
ggcacgagat cactcagtgt cttcactgaa ccaaatcgtc attttacag agagatgcaa         60 agcttcagcg aagacattta gcttttttaa aatgtataat tcctgtggct acatatgcaa      120
gtagggtccc attatgtttt ttttcattag tggaaactaa tccttttgtg ctgtgtttaa      180
tcagtattag ctttatagaa ttataaatgt atattctact tcttgatcaa agaacgtagt      240
cgggtattgg ttttagaagt tcaaagtgac actgtatagg gctttcacgg ttaatgggat     300
tgttagcaaa tcttaaggac atacagccaa tgattatctg aggttactgg ctaactgttt     360
```

```
ttcactgagt tactctgcct ttttgacatt tttattcttt gtttgtcaga atccagagct    420
tcaggagccc aaatttttt atwccgtata tatatatata tataaatatc cataagcctg    480
gtggatttgt atgcaatgca ctgcatctat gtattctgat agcatctcat tgattttgt    540 ttgaaataga aagaaagata gtatcccaaa tgagttatct ttaacagaaa gctgagttta    600
acttttatta cctatataat aattgatatt gccaattacc attctgaatt tcatatagta    660
taagttagac attgcttaat ccccttttaa atgtatttac atagacatga acactcaaat    720
tgctggattt tttaaatata tctgacataa ttttttttcat ctgttacatt caagttagct    780
tgtttagccc agatttcaga atagtaaagg aggaaaggaa ccgcattcca gggaaacctc    840
tgaggccaag tcagagtcca gaactgtaaa cacacaggcc tgcaagccaa cattagtcgt    900
gaaatcccta acacgtcact ggattctctc tgtcagcgca agtgtcagct gccaaagaat    960
agacttacat gaagaagtgc ccacatgctg cagggctg gccggctccg gccagcagac    1020
actgctagat tgtaatattt aaggtcgagt ttcgacctgt ggtacacagc tgtgctgtgc    1080
tcagtcagca acctcagaac tctgaaaaaa acataaaaaa gaaaaaaaaa aaaaaaaam    1140 atgcasctgk ytcacttgtg aatagtgaat gtaaaggaaa gaaaggaaaa ccaaaagctt    1200
gttccatcac aggtatgagc tgctatgatt catgaagaac attccatgga gtatgtttta    1260
aaaccttgtt atatctgaga ggctttaaaa gccaacttaa ctgtttcagg gcaaccgcgg    1320
tacagacgtg gtctctgtga gacttccacc tgacccaagt tttaagtggt acgaatgttg    1380
tgcatttaat gttaaggaca gtctgcaata ataagtaagt agccagcgtg ggtgcccagc    1440
agtgctgaga cctggctgct ctattgtacg ctttggaaac acaatttatg caacagatgt    1500
ccagatatga ttctatttat ggaaaaagtt tatatgtttt acaaatggtt ttaccatctt    1560
atattaaatg acctttgac aggtgtgcac tgttttgtct ccagtgagca cataccatgc    1620
ggattttata tgtacatcag tagtgtgaat ccactggcac agtgtgtgta aatgccagat    1680
gtggtgagat tttatcttgt atatgtgatc agataaaata actcctgaca gaaactgtaa    1740
ggraacccag ctgaatggtt tgacctggat grcykrkrtk gtwtggttta tgttaaatgt    1800
atattctttt aatcaatgaa taaagcatta aaaaatggga aaaaaaaaac tcgt          1854
```

<210> SEQ ID NO 4
<211> LENGTH: 1030
<212> TYPE: DNA
<213> ORGANISM: Eukaryote
<220> FEATURE:
<221> NAME/KEY: misc_feature
<222> LOCATION: (1)...(1030)
<223> OTHER INFORMATION: r = G or A
      y = C or T
      m = A or C
      s = G or C
      w = A or T

<400> SEQUENCE: 4

```
tctgcggccg cagcatccgg aacaacagga acctccagaa gtttagtctt tttggagata    60
taagtgtcgt tcagcagcaa ggaagtctgt ccagcacata cctcagcaga gtagaccctg    120
acggcaagaa gattaagcaa attcagcagc tgtttgaaga gatactgagc aatagtaggc    180
aactaaaatg gctgtcctgt gggtttatgc tggaaatagt aaccccatca tcactgtcgt    240
ctctgtctaa ctccattgcc aacaccatgg aacacctgag tttactggac aacaacattc    300
ctggtaacag cacgctcatc accgcagtcg aactagagc ctttgtaaat ctgcgctcac    360
ttgccctgga tttctgtgac tttacagctg agatggcgag agtcctgacc gacagcaacc    420
```

```
atgtgccttt gcagcgactg tctcttctgg tccacaatgc ttcagtgatg ctcaagtcat      480
tagacaacat gccaaacgat gagcactgga aggccctgtc acgaaagagc tccagcctcc      540
gggtctatct aatggctttt gatgttaaaa gtgaagacat gctaaagatt ctgaaaccca      600
gtataccact tgagaagggt tcactttgga cagctacgtc acttgtgtct caagggcta       660 ttggttgatc ttatattcca ggcagtattg accaaggttt cctyaacccm wtttwtattg      720
atgaatgata tgattgatac gtctggtttt ccggatctta gtgacaaccg aaatgaagat      780
ccattggttt tattggcatg gcggtgcaca aagctcactc ttttggcaat tcatggttac      840
accgtgtggg cacacaacct cattgccatt gctcgtcttc gtggctyttg acctaaaagt      900
gctttggaag tcaccsraag aaagcattga ttttgaccaa ggtgaactag cccgaccagg      960
aatgtggrwy cccgtacata acctttcttg gagcaggtat tccctggggc cttggtcaag     1020
tcttggcacg                                                            1030

<210> SEQ ID NO 5
<211> LENGTH: 1824
<212> TYPE: DNA
<213> ORGANISM: Eukaryote
<220> FEATURE:
<221> NAME/KEY: misc_feature
<222> LOCATION: (1)...(1824)
<223> OTHER INFORMATION: r = G or A
      y = C or T
      k = G or T
      s = G or C
      w = A or T
      d = A, G, or T; not C
      n = A,T,C or G

<400> SEQUENCE: 5
tcaaaccnta tctcggtcat tcntttgatt nataagggat ttksccgatk tccggcntat       60
tggttaaaaa wtgagctgat ttaacaaaaa tttaacgcga atttaacaa aatattaacg       120 cttacaattt gccattcgcc attcaggctg cgcaaytgtt gggaagggcn atcggtgcgg      180
gcctcttcgc tattacgcca gctggcgaaa ggggatgtg ctgcaaggcg attaagttgg       240
gtaacgccag ggttttccca gtcacgacgt tgtaaaacga cggccagtga attgtaatac      300
gactcactat agggcgaatt gggtaccggg ccccccctcg aggtcgacgg tatcgataag      360
cttgatatcg aattcggcac gagcgaagcc agggccttgc acttcctagg caagcgctct      420
accactgagc taaatcccca accccttgtt ttattttttaa agcaaacgag atacataatt     480
tcarccatga taatttaaga ttatcttgaa ctcttaagga aatgtatata ctaagctatt     540 atagtttttta ttttccctaa ttcagtggca taataccta ccttgagtcg tttactactt    600
tctttggttt ctaaaaactc tactgctaaa ttacaatgta aaaacatagg gctcgtatat     660
actgtagagt gctgtagatg tcctcgtcat caactatgca ataacagtct gatcgacaca     720
tttcaggakc gatcactctt tggtgtgctt ctttaaatac tttcagaagc ttaggatgtg    780
caaagcagga agactgtggg tgtaaatgtt tacttatttc tttgagagtg ttagtaagtc    840
ttttcdaaat tgcttttctc ttcaaaatta tcgttaactt aaatgataat tatctttgag    900
gttaaacaga agctcattga caaactaaag tgactttta gggcattctt tgagatcata    960
gtcttatatc ttggggacta aaatgtcatt agaccctaat agactaactt gtatgtttgt   1020
gtggggaaac gttttcctct ctcattcaag gtaactgttt gctgcctgtt gttacttgtg   1080
tagcattcta gaaaatggct aggtttttta taagatttaa gacaatagaa gtagttttat   1140
```

| attattatag ttctgttgga atgtgatcct gaaattatta ctgaaaatta gaattttat | 1200 |
| ttcgctaatg acaaccttga ctctcagaga tgcagtgtaa attgatacct catctttccg | 1260 |
| agagttcaga gcacagggcg gcagtatgtg aagctgcttt tgcactgacg cattttgata | 1320 |
| agtttggcta ctgtaatggt aaaaggctcc tcaggcactg actgcatttg ggttcttccg | 1380 |
| atggggatg atccgttctc gtggtgctgc tggacttatg cattttggag gtactgcatg | 1440 |
| tatcttccac actgcttgac attttctctg atctgtgtgt ttgcaccaac tcattaaaag | 1500 |
| aaatatgcag aaatatcttc taattcgttg atcttcgctg tatgacagtt ataatattaa | 1560 |
| acacttgggt tgatccactc tgtttacatt tatctttcta agcgtcagaa agggactaac | 1620 |
| ttgaaattat atctagaggc tttgtatcat tcaaaaatt aaatttcctt ggatacttta | 1680 |
| ggcaatatct taaacaactt tttaataaat ttaaatattt atatttacgt aagctaaaat | 1740 |
| atacatgaat gtgcttttta ataaattaaa tacagtttat acttatttgc caattcacaa | 1800 |
| ataaaaaaaa aaaaaaaaa aaaa | 1824 |

<210> SEQ ID NO 6
<211> LENGTH: 1230
<212> TYPE: DNA
<213> ORGANISM: Eukaryote
<220> FEATURE:
<221> NAME/KEY: misc_feature
<222> LOCATION: (1)...(1230)
<223> OTHER INFORMATION: r = A or G
     m = A or C
     s = G or C
     w = A or T

<400> SEQUENCE: 6

| tttttttttt tttttttttt aargggrcca ccccaccgsg ctaaaggccc aggggcccc | 60 |
| cccttggagm cccaggggtt ttggcccmcc ccctcaccca aatggtctgc caatgaccca | 120 |
| ggtactcaca acatgttcca ggaggagmct ggggccagga ttttgaccag agggtatggg | 180 |
| aagggaaagg ggagaagaaa tcgacattta ttttttattat ttattttaaa tgtttacawt | 240 |
| ttctttgtgt tgttccaagc cctgaataga aacagatagc attaaaggac tctgttccca | 300 |
| ccccttctct gtctctctct cccccacttg tgctaactta ggataacact ctctatttcg | 360 |
| ttttgtttct aaagtgattt gtggacttgt gccgtgtgaa ctgcattaaa aaggttctgt | 420 |
| tttcaaagat cgattgtcgt tcctgtgggg acagtggctc ctaagaaatc tgcattgtag | 480 |
| gagaagacaa tgaaagaccc tggccctgtc tctcaaaact taactctctg tatgatttaa | 540 |
| aaaaaaattc catttacttt actttgtggt tacttgattt tgaggaagaa aatattcaac | 600 |
| tttgtataaa gactaggtat cagggtttct tttgcagtgg gagttgtata tatatcgtat | 660 |
| tttggtatat cgtagaaact caagctttat gcatccgtat ttgggatatg tcaatgacgt | 720 |
| gcagtgaaat ttgctattag accctggagg caaacgagtg gtacaaggtt ttatggctcc | 780 |
| atggggaatt ctaatttcct ttctggggac cttttgtccc gttttttacag taatggtgaa | 840 |
| atggtcctag gagggtctct ctagtcgaat tctccaggca ggaccacgtg ctcaaaaaat | 900 |
| ctttgtatag ttttaaattt ttgaggagta tctctgctca gaagcatctg tggtggtgtg | 960 |
| tgttcgttg ttctgtgtac tgtgtgtgac acaagcctac agtatttgca ctaaggaaag | 1020 |
| ctgtttagag cttgctgcta tggagggaag aacatattaa aacttatttt ccctcggggw | 1080 |
| ttrtwcwmgt tttatgtwct tgttgtcttg ttggctttcc tactttccac tgagtagcat | 1140 |
| tttgtagaat aaaatgaatt aagatcagmw rwrwrmaaaa aaaaaaaaaa aaaaaaaaaa | 1200 |

<210> SEQ ID NO 7
<211> LENGTH: 1516
<212> TYPE: DNA
<213> ORGANISM: Eukaryote
<220> FEATURE:
<221> NAME/KEY: misc_feature
<222> LOCATION: (1)...(1516)
<223> OTHER INFORMATION: n = A,T,C or G

<400> SEQUENCE: 7

| | | | | | |
|---|---|---|---|---|---|
| tcaggcctna | gcaatcctcn | ttaantttga | nccaagntta | actcttgggg | cgaattcctg | 60 |
| tgnttgcttt | ctttccccat | anttccaggc | ccacaaangg | tttctgtgan | tccgagaatc | 120 |
| ggcccaccat | gcagacccac | ngagaggatt | cagaatgtgt | gtgagagtga | gtgtgtgagt | 180 |
| gcgcgtgcgt | gtgctttgta | tgtgtgttta | tagatgtagg | acattaagtt | ccttctgaca | 240 |
| cagggaagat | gtgagaagga | tggcctgaca | tcagatgaca | agaggtctta | tagcacatct | 300 |
| ctgggctttt | ccctacccag | agaagagccc | cctttgatac | aaatcagttg | gattttcata | 360 |
| tgcttcaaag | gcttgatctg | tgagtcactc | cagtttggga | cataggtctg | tctgtggctt | 420 |
| tgagaaaagg | tactttcaaa | agagggcttt | ccagagcaca | gctcacagcc | agctgttagg | 480 |
| accccaccct | tctcctttat | tgtggaggtg | actcacagca | gactgacagt | ggtcagactg | 540 |
| agctttctgc | taaggtggtg | aggtagccaa | cactggcatg | tctcggtagt | ggtttgggca | 600 |
| aatttccgca | ggtctcttcc | cccaaccctg | cctctgatga | ataaagacaa | tgagtacagt | 660 |
| tccttaattc | aggcttttgt | gactagctta | ctacggaacc | gaaaatggtc | ccctttgtac | 720 |
| aagccgagct | gttatggaat | cacggtgaac | cagacccagg | tctgtggcac | ctgtttgttt | 780 |
| tttttttttt | tttttttttt | ttagctctca | tttctacggc | atgctttcca | aggaaccaaa | 840 |
| ggagggtctc | agagatgccc | caaacatccc | aaagtacaca | aagctaagta | atcgattgct | 900 |
| tacttattgc | acagctagac | acggatttta | agtctatctt | aaagctttga | agcaagctta | 960 |
| gcttctcaaa | ggcctagcag | agccttggca | ccccaggatc | ctttctgtag | gctaattcct | 1020 |
| cttatccagc | ggcatatgga | gtatccttat | tgctaaagag | gattctggct | cctttaagga | 1080 |
| agtttgattt | ctgattcaga | gtccttgttt | ccctgacttg | ctctgccagc | cctgcaccag | 1140 |
| ctttttcgaa | gtgcactatg | cttgtgttta | acttctccca | gttttatttg | ggcataaaag | 1200 |
| ttgttgcctt | tatttgtaaa | gctgttataa | atatatatta | tataaatata | tgacaaagga | 1260 |
| aaatgtttca | gatgtctatt | tgtataatta | cttgatctac | acagtgagga | aaaaaatgaa | 1320 |
| tgtatttctg | tttttgaaga | gaataatttt | tttctctagg | gagaggagag | gttacagtgt | 1380 |
| ttatatttg | aaaccttcct | gaaggtgtga | aattgtaaat | attttatct | aagtaaatgt | 1440 |
| taagtagttg | ttttaaaaag | acttaataaa | ataagctttt | tcctgtgaaa | aaaaaaaaa | 1500 |
| aaaaaaaaaa | aaaaaa | | | | | 1516 |

<210> SEQ ID NO 8
<211> LENGTH: 1534
<212> TYPE: DNA
<213> ORGANISM: Eukaryote
<220> FEATURE:
<221> NAME/KEY: misc_feature
<222> LOCATION: (1)...(1534)
<223> OTHER INFORMATION: n = A,T,C or G

<400> SEQUENCE: 8
gtggcccctg ctcgccgcat catggagcgg atccccagcg cgcaaccacc tcctacctgc    60

-continued

```
ctgcccaaaa cgccagggct ggagcacgga gacctgtcag ggatggattt tgcccacatg    120
taccaagtgt acaagtccag gcggggaata aaacggagcg aggacagcaa ggaaacttac    180
aaattgccgc accggttgat tgagaaaaag agacgtgacc ggattaacga gtgcattgcc    240
cagctgaagg atctcctacc cgaacatctc aaacttacta ctttgggtca cttggagaaa    300
gcagtggttc tcgagctgac gctgaagcac gtgaaagcat tgacaaacct aattgatcag    360
cagcagcaga aaatcatggc cctgcagagc ggtttacaag ctggtgatct gtcgggaaga    420
aatattgagg caggacaaga aatgttctgc tccggtttcc agacctgtgc ccgggaggta    480
cttcagtacc tggccaagca tgaaaacact agggacctga agtcttccca gcttgtcact    540
catctccacc gtgtggtctc tgaactcctg cagggtagtg cttccaggaa accattggac    600
tcagctccca acccgtggaa cttcaaagag aagcccagct cctagccaa gggatcagaa    660
ggccctggga aaaactgtgt gccagtcatc cagaggactt tgctccctc gggcggggag    720
cagagtggta gtgacacgga cacagacagt ggctacggag gcgaattgga agggtgac     780
ttgcgcagtg agcaacccta cttcaagagc gatcacggac gcaggttcac cgtgggagaa    840
cgcgtcagca caattaagca agaatctgaa gagccccca ccaaaaagag ccgaatgcag    900
ctctcagatg aggaaggcca cttcgtgggc agtgacctga tgggttcccc atttcttggg    960
cctcacccac atcagcctcc cttttgcctg cccttctatc tcatcccacc atcggccact   1020
gcctatctgc ctatgctgga gaatgctgg tatccgacct ctgtgccact gttatacca   1080
agcctcaaca cctcagcagc agccctctcc agcttcatga accagacaag atccaactcc   1140
cttgctctgc ccagaaatcc cttctcccctt ggcacattcg tcccttgact ctcaagcctg   1200
ctcaagccct gaagcagatc cctccttaaa cttagaaaca aagataaacc ttgagggcaa   1260
tcnctgcgcc ttgctttcct tcccacaatt caagacacaa aagtctgta ctcaaaacag   1320
agagatcagc ccaccctgca gacccacaga gaagattcag agtgtgtgtg agagtgagtg   1380
agtgtgcgtg cgtgcgtgct tgtatgtatg tttgtatatg taggacaata agttccttct   1440
gacacaaggg agacacgaga aggatagcct gacatcagat gacagactgg aggactgtag   1500
cacatctctg ggcgtttccc tacccagaga agag                                1534
```

<210> SEQ ID NO 9
<211> LENGTH: 5470
<212> TYPE: DNA
<213> ORGANISM: Eukaryote

<400> SEQUENCE: 9

```
gcacgaggga gtttatttcc acgtctctta ggaaagcctc gcttggttac acatggcaat     60
gattgcaagc agatacacgt cttaacacca gagtacagta cacacacatt gagctgccct    120
cgtctaacaa gcagttgcag tttgtttaaa tgtgaatatc tatgaaacga gcaaagcaac    180
tttccagagt atagcttatc acagaatagt aacacatggg ccgctactgt atcatacaga    240
gtacaactct atagcttttc atccccgtgt gagcatttcc aaatcactca atgagcacca    300
agcacggaca agtgactaaa aaggctagtc ccaatctccc cgcaaccctc ggcggtaagg    360
gtaaagaatt ttgtttcaag taagttttct cctcgtctct ctcttctgaa gacctgagca    420
aaaccaacat tctaaaccac cccaagatat gatactagaa tttaaaggcc cgatggcttc    480
aacccagaac cttaacctac tagataaaat ctctccgaat ctgactcact gatgctgtta    540
agtccgacag tacaatcaca tagtacctct ttgatactgt caaagttggt tttaaaaatg    600
```

-continued

| | |
|---|---|
| ccctaagaaa accaaatcat ttttgggaga tgttctaagc aagctttcca acatataaag | 660 |
| aacaaaacca tgttactaaa acatggtgc aggtcctcac aaaacattta ctgctactac | 720 |
| caggaaacca agctactctt ggtttgtgct cctggtgata actggtgagc tttggacagc | 780 |
| tgctggcaca tgtccactgt gttccgtttt ataatcaagt gtcagttttc cactcgacag | 840 |
| agattaaaga caatagctta aaagtgaaaa tgaaatttca agtagaagct acaattgaat | 900 |
| gctacttgtt gagacttta actttcacat ccaaatatca aaacttaac tttgacgaca | 960 |
| catgcacaca acacaccat tgggaaagg gtcttgttat gcagttcaag ctggccttga | 1020 |
| actcatgatc tcctgcctca gtttcttggg cagtagcact ggaccttact gtgggcagaa | 1080 |
| agtattgctc caattagaaa gcattactat acacttcact tcgtcatgtg cctagtgtgg | 1140 |
| ctctgaaggc ataggaacaa tgaaattaaa ttcttcagca gctgaggatt ctctatactt | 1200 |
| caacattctg aacttcaatc atggcttcac atttgaggct gagctagata caaaaatatc | 1260 |
| aaaacatccc atagaattgt ttatttccct atgttactgt ttacccaagg aatgtgaaga | 1320 |
| ctaaaaagga ctcatttggt tgtttaatta tgattaaatt atgtaaatat acaaacattt | 1380 |
| aacaaagcca tcatattcca atcttttacg aattctaact gctagcagtt gagcagcttt | 1440 |
| tagatatcac taataaaata tacaatttaa aatagtcgca ttcaatccta ctaactttat | 1500 |
| aaataacttc ttaggttaga cttcttcctg cctaagttta taagacagtc taaacccaaa | 1560 |
| actcaacaca tattaagctt tttaaaaact ccatatagtt ctaaagtaac ctcaatgtat | 1620 |
| tcccaagaac cgccaccatc aatcagctca ctccctcaca ccactgactt taagacgctc | 1680 |
| ctgggtggag aactgccagg cagaagctct acctttctag tgtgtgtggt ggtctgctgc | 1740 |
| tcctagtcca gatctggacc acatcagcac agcatcagtg tgactcagca ctgaggcctt | 1800 |
| gagcgctctt ccccccgatg cctgtgtat agaggtgtct aattccttgt gtatagatgg | 1860 |
| cctgtatata gaggtgtcta attccttggc tctgtatgta taggtaatgt gatactttac | 1920 |
| cattaaagca ctattttctc cattcaagaa tttagtgata taggaaaatg agtggacttg | 1980 |
| cgagactcag aaaaacaaaa cataacctgt cttgaattca aaacaaacca tgggtgtagg | 2040 |
| ggggaactga tgaaagttta tgggttaac tctaggtaat taactaagac agtcacgaaa | 2100 |
| cacattatca aaatccttc aggcccagag cttgtactgt accccactgt gagaccacat | 2160 |
| cacaaccccg gattgagctt tatccacaac acctacacca tagtaacgca aagtgcacaa | 2220 |
| tgtactaaaa taaattccta ttagtttat gcaaactatg gtataaaatt atcacctgcc | 2280 |
| atacatattt tgccatggca ccaacttcat ataataagcc aacgtataat caaagtcctt | 2340 |
| accagcacca atcaatgtcc ttggcaccac tggacactca ccgtcaagct gttcatctaa | 2400 |
| gagccagtct gttctgacct gaacagttgt gcattccacc ttaccacacc caagtctgtg | 2460 |
| agccggacaa gtgttaaat gcagttttac atctaacggt gcaggttaag ccgagcactt | 2520 |
| gaaactgatc actcattaat acctgtctcc ctccatacat gtacaccaca tgtacacaga | 2580 |
| actatgtgct ctgacttcag aatagctctt cctgttggca aaacaccaca gacatgaagg | 2640 |
| ggcctagtgt gaagcgagct cacagaatgt tggatggaac ttcgactata atggaaacac | 2700 |
| ctgcaaaagc tttgctaacc cagcaaacac tcaacactta ccaaagacaa cagggaagtt | 2760 |
| aaagttagct cgccaagaga tgggctgggg aggtggggt gtaactcaaa gaaagcttta | 2820 |
| gctaacaaaa acgaatgatg gacaacttca gaaattccct aaaaacagaa cctgaaagtg | 2880 |
| caggtgaggt tttgtccttc agtaacaaat gcagacagat tcccaacagg aataaaacag | 2940 |
| tctggggctt tgaaacctgc tagatggaaa cacgaactca aaatgtggaa ccaaggaaaa | 3000 |

```
ccaaatactt aaatgtgtaa gataatttat aatagtaaaa agttgcaaat tgctgtgact    3060
tgatttgccg aaaacatctg taaatccaca ctggcagtta gaagaccagt tcccacatta    3120
actcctctct cagcaggtaa ccgtttgtgc gcagaagtat ctgaaacatc gcactactgc    3180
ttattttatg gtgtattgtg cagaatctgt acatgctatt acagacaata catatttgta    3240
aacctggtca tgcaaaatca gtgtgtacaa ggggatattg ttaagcctta taaagtggta    3300
ctttattatc tttgtgacga tgccaatctc tccgaaatat agcatatctt aaatggatat    3360
tctttatctg ccagttaaaa tcattttatg tcactgaaag aagaggttat acaaggaaag    3420
aaacatggtc cttgtgttgc agaattgatt ttaaatgaga gaatttacaa accaagaaa    3480 tccatggtca taaagtttta acattttaat cctacacatt acagggcaaa cagatactgg    3540
accctatttc cacattccat aaatccaaac tttagttccc atttcaaacg ttgccctaac    3600
cactaaaacc atcagtggtc ttacaacctc tggattatgg aaatacagat ttctgaagta    3660
aaagctacaa aaacaacaat ggaagaaagc tgaacaaact tcccatgaat gaaaataaaa    3720
gtggaacatc ctgaagctct agacacttct ctcccgtgtc tatggtcaac ttgtcggttc    3780
agtgcactgt gcggtcaaat gtaatggtcc tcatgtggaa cacacgtcta actagtgtcc    3840
attgattcca agttagtgga cgaagaatct ttctggatac tttcaaagat ggctgccagc    3900
tccgggttgg agctgatctg tgactggaac tcactcatga gagggctctt ctctgcctct    3960
ggaatggtga gcagtgcagc tactgccctc atggccgagc gctttaactc gtcctgcttt    4020
tcaaactcct gctttacaga gttcgccttc accttagttg tacacgtagc tcgtagtggc    4080
tcaacaagcc ggtccaacct ctgtagtact gcacttggac aaagggtaga tagtctcacc    4140
aacattaaaa atgttagcat cttaatatca taatggtcct tcaaaccatc ttccacatga    4200
tttagaaatt caaagatatc cagtctgtca agacagctgt ctagaagtgt gtacatacac    4260
tcaaaagctg cctttctaat gtccaggccg tcatcaaccg tgtgcttaaa cgggcccatc    4320
tctacctctc ttataagttc cttcctaact tttgtctcat tgtaaagatg tggaagaaca    4380
gaatccagaa ggtcccgtat cagtgacggc ttgttatggg ctgcagaatt gaatgtgacc    4440
aaggccactc ttcttacatt caaatctggg tcttccaacg ttttagaaa atcacctatg    4500 cagttcttga gcagtggatc ttcttgacat cttgaataaa ctgacctact acagccggtc    4560
cctctttagg gcatgctcga gtaagggcag ctacacattt ggcaatggaa tagtaagact    4620
gcttatgagt aagagctgtg ctctgagagt aaactggacc cgttagcatg cgcagcaaat    4680
ccatgtatcc tagattgttt gttccagtga caaccaaagc ttggaagaag tctagcatgg    4740
cactaagagc tcctccctgc agcagaggtg accttacaag tccaatcagt tcattgagaa    4800
tagatccgct tatctttgaa agggaggagg gatatacttt tgccagggta gtaaggaagc    4860
tgatagccat ctgggacacg tgcatatcac tttcgctgat aagaggaggg agctcatcca    4920
gaactgcatc aatcatggcg gccgtcaaac tgtcactata gttttttaatg agaatatcta    4980 gggcagagag ggtcccccagt ttcaaagctc tctgattttt cctgagaaat gaagcaagga    5040
tagggactcc ctctcccagc acaggcctca gatctatctt caaaggtgac ccagcaatca    5100
gggtcagtgc tttcactgtc gttagccggg tgatttcatt cttgagtctc tccaagaaaa    5160
tctgaagtgt atttgataag tcagggccca aattgtctcc aagattgcaa ataatctgtc    5220
ccatacagga aatagccctc tccttgactt cctgatcaat gtcagctgct tttaagcgct    5280
taattgtaca agtgaagaga tctttgatgt aaggcgttgc atcgaaggag gagggttggt    5340
```

```
ccagaggacg gattactttg acaagctgct gagtgacaag aagggcttct gatgtgatct   5400
tgtaaaatgg gtcaccaaca caagccacca ctggagggac caaagcctga acatgcgggt   5460
ggaaaacttg                                                         5470
```

<210> SEQ ID NO 10
<211> LENGTH: 2515
<212> TYPE: DNA
<213> ORGANISM: Eukaryote
<220> FEATURE:
<221> NAME/KEY: CDS
<222> LOCATION: (414)...(1055)

<400> SEQUENCE: 10

```
tcgccgcccg aagtcgcgca gcttccctgg cgaacgcgga agcccgaaga gcgccgtcct     60
cgggccctgt cggcgctcag gccccttcgc gcgcctcctc gctcggccgg gacgttgctg    120
tggaggcgtg aggcgccggc ggtcgagcac ctggagcgac ggtagcccgc ggcctgcggt    180
tcttctcctc ccccgccgcc ctcccacccg agctgcggcg gggctcggcc gctcggtgc     240 ttctgcacga acaaaggagg ccccgcggg gccggcgcag ctccatctgc ggtccgatcc     300
acccgggccc gcggcggccg ctagccagcc cttcccggag gcctcagccc ggcccaccgc    360
ccggcgtcgc gcgccagctc gctagtgcat ccgggccccg caggcacaaa aat atg       416
                                                            Met
                                                            1 gct cag gag act aac cag acc cca ggg ccc atg ctg tgt agt act gga      464
Ala Gln Glu Thr Asn Gln Thr Pro Gly Pro Met Leu Cys Ser Thr Gly
        5                  10                 15 tgt ggc ttt tat ggg aat cct agg aca aat gga atg tgt tct gtt tgc      512
Cys Gly Phe Tyr Gly Asn Pro Arg Thr Asn Gly Met Cys Ser Val Cys
     20                  25                 30 tac aaa gaa cat ctt cag aga cag cag aat agt ggc aga atg agc cca      560
Tyr Lys Glu His Leu Gln Arg Gln Gln Asn Ser Gly Arg Met Ser Pro
 35                  40                 45 atg ggg aca gct agt ggt tcc aac agt cct acc tca gac tct gcg tct      608
Met Gly Thr Ala Ser Gly Ser Asn Ser Pro Thr Ser Asp Ser Ala Ser
 50                  55                 60                 65 gta caa aga gca gat gct act tta aac aac tgt gaa ggt gct gct ggc      656
Val Gln Arg Ala Asp Ala Thr Leu Asn Asn Cys Glu Gly Ala Ala Gly
         70                  75                 80 agc aca tct gaa aaa tca aga aat gtg cct gtg gct gcc ttg cct gta      704
Ser Thr Ser Glu Lys Ser Arg Asn Val Pro Val Ala Ala Leu Pro Val
     85                  90                 95 act caa caa atg aca gaa atg agc att tca aga gag gac aaa ata acc      752
Thr Gln Gln Met Thr Glu Met Ser Ile Ser Arg Glu Asp Lys Ile Thr
100                 105                 110 tcc ccg aaa aca gag gtg tca gag cca gtt gtc act cag ccc agt cca      800
Ser Pro Lys Thr Glu Val Ser Glu Pro Val Val Thr Gln Pro Ser Pro
115                 120                 125 tca gtt tct cag ccc agt tct tct caa agt gaa gaa aaa gct cct gag      848
Ser Val Ser Gln Pro Ser Ser Ser Gln Ser Glu Glu Lys Ala Pro Glu
130                 135                 140                 145 ttg ccc aaa cca aag aag aac aga tgt ttt atg tgt aga aag aaa gtt      896
Leu Pro Lys Pro Lys Lys Asn Arg Cys Phe Met Cys Arg Lys Lys Val
                150                 155                 160 ggc ctt aca ggg ttt gac tgc cga tgt gga aat ttg ttt tgt gga ctt      944
Gly Leu Thr Gly Phe Asp Cys Arg Cys Gly Asn Leu Phe Cys Gly Leu
            165                 170                 175 cac cgt tac tct gac aag cac aac tgt cct tat gat tac aaa gca gaa      992
His Arg Tyr Ser Asp Lys His Asn Cys Pro Tyr Asp Tyr Lys Ala Glu
        180                 185                 190
```

-continued

```
gct gca gca aaa atc aga aaa gaa aat cca gtt gtt gtg gct gaa aaa      1040
Ala Ala Ala Lys Ile Arg Lys Glu Asn Pro Val Val Val Ala Glu Lys
        195                 200                 205 atc cag aga ata taa aattactaca tgtgaagaga ctgaaacttt gtttttattt      1095
Ile Gln Arg Ile
210 taatatatcg taggaaaaca ttaaagagca gatgcatggc cattttcctt tgatgttctc    1155
cagagttttg ctttatactt gtctgtcata taattgatat tttaggatgt ttgggtgttt    1215
gttacaggca gaattggata gatacagccc aacaaatgta tatgccctcc cctcagtaaa    1275
attggacaaa aatatgcaca gcaaattgaa atacacatat actaggaaca aaatttagtt    1335
ccatgtgcca aactgaatga aatctctgca tgtttgcagc atatctgcct tttgggaatg    1395
taatcaaggt ataatctttg gctagtgtta tgtgcctgta ctttaaaaaa atggtacacc    1455
agaaaaggac tggcagtcta ctaccatagt caaacttcac cttaatttcg acatgctttt    1515
ggaagcagga agaaagctac aaaaccagta tttggtgcca tgtgtgagcc tggttaaatt    1575
ggtcttctaa aagctgtcaa ttaggacatt ctgcgaaagg taacatcaca actggttctg    1635
agtaaaacca tcaagtcaac agcagggtgc ctgagataat ctttgaagct tattgtgctg    1695
gcctgcacca gaagatatct gcattctcat tactaaaatt gtagcacaga actgcactag    1755
gatttgttta caagaagaaa ttaaaactct acgtttggtt ttcacatata gcagctctgt    1815
taaataacat gcatctgaat tttaagttgc aaaggtatct gagcagttag ttttcatgt     1875
gcatcttttg ttgaatgttt tggttcaaga agaatgtttt aaagcttttt aaagacttca    1935
gttcttaatg taactgtacc cttctgcatg gaaaatcata accaacatgg ctgcagtaga    1995
cttctttagt ggtatccagc accacttgca gagggctgct ttatcatatt gtatttgggt    2055
gtaggactct agtgttcttg ggtgtattgc atgggctgca ttatctacag cattgtacaa    2115
taacaactag aaaaggcagt atacttcact gatgcttgtc tggtaatatc acttctgtgt    2175
tataatggaa ggttttttgt gatgtatgaa acttgtgttt tttatatata aatgagtata    2235
gttagattag tgttgtggta atgcctgttt tcatctgtaa atagttaagt atgtacacaa    2295
ggcactactt ctgatttatt gcagtgttca gtcctagttt ttctttatta aaacattcag    2355
ttttgcttca atttttatgta ctttagttct aagttagatt tgcagatgtg tacagatagt   2415
tcatatttat gtattgcaca taatcatgct attcagcatt gatgctatat tgtattatgt    2475
aaataataaa agcagtgtac agagggaaaa aaaaactcgt                          2515
```

<210> SEQ ID NO 11
<211> LENGTH: 213
<212> TYPE: PRT
<213> ORGANISM: Eukaryote

<400> SEQUENCE: 11

```
Met Ala Gln Glu Thr Asn Gln Thr Pro Gly Pro Met Leu Cys Ser Thr
1               5                   10                  15

Gly Cys Gly Phe Tyr Gly Asn Pro Arg Thr Asn Gly Met Cys Ser Val
            20                  25                  30

Cys Tyr Lys Glu His Leu Gln Arg Gln Gln Asn Ser Gly Arg Met Ser
        35                  40                  45

Pro Met Gly Thr Ala Ser Gly Ser Asn Ser Pro Thr Ser Asp Ser Ala
    50                  55                  60

Ser Val Gln Arg Ala Asp Ala Thr Leu Asn Asn Cys Glu Gly Ala Ala
65                  70                  75                  80
```

```
Gly Ser Thr Ser Glu Lys Ser Arg Asn Val Pro Val Ala Ala Leu Pro
                85                  90                  95

Val Thr Gln Gln Met Thr Glu Met Ser Ile Ser Arg Glu Asp Lys Ile
            100                 105                 110

Thr Ser Pro Lys Thr Glu Val Ser Glu Pro Val Val Thr Gln Pro Ser
        115                 120                 125

Pro Ser Val Ser Gln Pro Ser Ser Ser Gln Ser Glu Glu Lys Ala Pro
    130                 135                 140

Glu Leu Pro Lys Pro Lys Lys Asn Arg Cys Phe Met Cys Arg Lys Lys
145                 150                 155                 160

Val Gly Leu Thr Gly Phe Asp Cys Arg Cys Gly Asn Leu Phe Cys Gly
                165                 170                 175

Leu His Arg Tyr Ser Asp Lys His Asn Cys Pro Tyr Asp Tyr Lys Ala
            180                 185                 190

Glu Ala Ala Ala Lys Ile Arg Lys Glu Asn Pro Val Val Val Ala Glu
        195                 200                 205

Lys Ile Gln Arg Ile
    210
```

<210> SEQ ID NO 12
<211> LENGTH: 660
<212> TYPE: DNA
<213> ORGANISM: Eukaryote
<220> FEATURE:
<221> NAME/KEY: misc_feature
<222> LOCATION: (1)...(660)
<223> OTHER INFORMATION: n = A, T, G, or C

<400> SEQUENCE: 12
attccaaaaa tgcatagatt acaaagaaac accagacaag ctcaaactca aggatattct      60
acaaataaac cagtaccttc aaaatgccat gctaccaggt acagacaggc gaganactgt     120
tccacactga ggaaactaac aaagtatcca tgaagtccat aattgtgggt caaatccagg     180
acctgcaaag gggatttggg gataattttc aaaatttgac taaggtctgc agagtagaga     240
gacgaggtca atgccaatgt cctgattttg acagtaagta tttaaatatg caggagaaca     300
acctaaccaa gaggctgcca acacacttcc tggctgtggc acaactagat ttaaaaccag     360
caatttgttg gttcttgttc tcaaatatca gttacctgca agcactccat cgtgaaagga     420
ttgagagcat gaggtgatgt gttgatggtg aaaatgagaa ctgactgagc acaggaagaa     480
gtggcatgat gggcagggaa aggggagaca aagtcacaa gagcatgcaa cactcagtga     540
actacaggac actccaaaag gcactctgct gtctagcttg gatctggagg aggatcagnt     600
attaataagg gccctggaag ggncaaagct agcctcccag ctgctggctt cccatctgct     660

<210> SEQ ID NO 13
<211> LENGTH: 1475
<212> TYPE: DNA
<213> ORGANISM: Eukaryote

<400> SEQUENCE: 13
gccaccacca ttgttaatgg agggaggctc tcccttgtta tttctcagaa gactgaatgt      60
ctgtaccaaa aggctcatgg ctttctctgg gcctttccat ttaaggttat agttttttat     120
gtagtgttac taaaatctag gcttgttact aaagtgggct ttgtagttat tggtatcggt     180 ggattttttat gttacttgga gtccagaaca gggagagctc accacaaacc tctcctttcc     240
ctggaccaaa caccctctct gtcctgtgaa ctcacctttt cttctctgtg ggtcactccc     300

-continued

```
attaccacac tggtgagcga gccaaatgga tgagagacac aaagaccgta gttcttgaga      360
gacattattt ttttcaactt tgttttttaa gagattttat gtgttgattt gttttggttt      420
ggtttaaagg gattcatagc taacttggat ttttgttacc tcagctctgg gagaggattt      480
ttgctgaatg actattaatt acctgagcat tgttgctctg aggtcatggc atgctagcct      540
atgtctgtta cagtctcagg ctgcccttgt ttcctcgttc ctgtgctatt gtgctacacg      600
ctcaaggggc cttgactctg cttacacaca ttaggggcag tgtgagtaaa tgtgcagtgt      660
ccacacttga ggacatgaat gtctgcactg tcactttgct ctgggtgtga agtccctggt      720 cccccttgctc ctgtagcttt cttttgatcg actactggaa ctcaaccctg tgtacaagag      780
cagcactgcc tctggtgggt ggtgtttgca gccaggatta gatgccagtc ctcgggttcc      840
ctggccttgt tggaaaggtg tgcttccttg aggtctgaga atggaaggct ctgcctcact      900
ctagctagga ggcgcaatgg gaaagtatga gttcagggcg tcaggcagt ggctcctgaa      960 gagccagctg tggacagagg gagtgaggct ttatttaaag tgacaggaag aaacatggcg     1020
ttttggtata ttgggagcaa tgccaagatt ccctcctgcc ctacataggt cacagacacc     1080
ttcccaacca tcccctcctc cacttccata aatgaagaca gccctgatga ccctcacccc     1140
ttttgcatag gtcactggat cccactgtcc ttcctcggtg cttacacact ttacagaccc     1200
tttaggcgag cccttgcata gagcgttatc tcagtgctcc attccagtcc tgactccctg     1260
tggccattga ctttggat ttaagaactc acattgctag ggagaggggc tttgctggga      1320
aaggtgactc ctctgtaacc tagcctcttg tgctcctcca tgacagaaat gctgggtgga     1380
gttttacatt tgccaatggc cagcttgtga atatcttcat atacactttc tattcatgtt     1440
actgtagttt ctgttttgaa ataaaacttc tgaat                                1475
```

<210> SEQ ID NO 14
<211> LENGTH: 953
<212> TYPE: DNA
<213> ORGANISM: Eukaryote
<220> FEATURE:
<221> NAME/KEY: misc_feature
<222> LOCATION: (1)...(953)
<223> OTHER INFORMATION: r = A or G
      y = C or T

<400> SEQUENCE: 14

```
catataaatg tactttattg ttttaaacag aacgaaagaa gaggcagaaa acatttgcat       60
gtaagtccta gcttataaat gtagttttta gtggtggcat ctctaacacg tcgttcaggg      120
actgtttcct tttgcctcct tgtactgtga gcactgacac ttgagaaaag cacatctggc      180
ggacatatgt ctccagaact ggaagaactt ggagagcaaa cattttttctt aattcctcta      240 agtaatcttt agtaaaacaa aagatgatct ttggcataga ttcatacttt aaaggcattg      300
atatgcattt atatcaggta agcaactata cagatctgct gagagctttc aaaagaatct      360
gttatcagct gaaaggaaat aggggaagcc tgagtattca gggtcaactt aagatttgca      420
agttcagtgt tggggtcaac atactagatg tgggaagaac atccaggcaa ggtcttagtc      480
ctgtattcac ctggttcttg atttctggaa gaagcatcca tgcgctagga aatgcttata      540
cagccgaggt aaatgcaaaa atgagtaaag tcacttttc actaactttg cccaataggr      600
aacatgcctt tctgataagt agataccata ctctttattc ttgaatactt tatattgaga      660
gaaggttgta gttggttaaa agcaactggg aactataact tcctactgat ttttccctag      720
cagcaccaga attatattct gcaaatgcta ttctccctta cataggaaat atccttcaga      780
```

| | |
|---|---|
| caaaattgcc tttccattca gtctcttaag agyttaattt tgaatggact tttcaaagtt | 840 |
| acaagcaaag tcaagtgtgg tggtaggagc taagaggctg acacaagtag atgacttgaa | 900 |
| tccagaagtt caagactagc ctggacaaca tagagagacc cagtctcaaa att | 953 |

<210> SEQ ID NO 15
<211> LENGTH: 911
<212> TYPE: DNA
<213> ORGANISM: Eukaryote
<220> FEATURE:
<221> NAME/KEY: misc_feature
<222> LOCATION: (1)...(911)
<223> OTHER INFORMATION: n = A, T, C, or G

<400> SEQUENCE: 15

| | |
|---|---|
| ggcggggatc tctcggctgg taagaagggg cagtggtacc angcgggcac ttattcagtg | 60 |
| tgccaaggat atcgccaagg cctctgatga ggtgacgagg ttggccaagg aggttgccaa | 120 |
| gcagtgcaca gataangcgg nttagaacca atctcttaca ggtctgtgag cgaatcccaa | 180 |
| ctataagcac ccagctcaaa atcctgtcca cagtgaaggc caccatgctg ggccggacca | 240 |
| acatcagtga cgaggagtct gagcaggcca cagagatgct ggttcataat gcccagaacc | 300 |
| tcatgcagtc tgtgnaagag actgtgcgag aggccgaagc tgcttcaatc aagattcgan | 360 |
| cagacgccgg atttactctg cgctgggtca gaaagactcc ctggtaccag taggcacctg | 420 |
| gtcagacctg gctggtacac agacctctgc taatgangan gtgaccatct tgagcttcag | 480 |
| aagccattca gagttgccaa ggggtggnaa atcaatccct ggtttcacac accaagaaag | 540 |
| ggaatggggc ctccttcaca ttagaataaa catttatact cttgtcatgg gacactttga | 600 |
| aagtgtctct cctacaaaac ccctggtacc tttcaggntt actccnggtn gcaanntcct | 660 |
| cccccaaggg gaattttta ccaataaaag gctcaaggaa ttaanggcgn ttgaaaacca | 720 |
| acntnatcca anggaaaang ccccntggc cttctggccc ccttgggggn acaattttc | 780 |
| ntcccnctgg gtgttttaaa tggggtttca accttgggc tggnccttt tccnccccc | 840 |
| cttttaaggg gcttcctccg aaggaacctn agaaaacttn aagggccaaa gntccanttt | 900 |
| acnaataact g | 911 |

<210> SEQ ID NO 16
<211> LENGTH: 621
<212> TYPE: DNA
<213> ORGANISM: Eukaryote

<400> SEQUENCE: 16

| | |
|---|---|
| tttttttttt tttttttcc tcccttaaaa gataaactaa taaactcttc aatggtcttt | 60 |
| tcagtatagt tcttatgtag tttaacatag cttataaatt gagtttaaca ataaactcaa | 120 |
| gaagataatt ttataaaccc tgttttccaa tctgtcattt acttaaatta ttttggttgt | 180 |
| tttccctttt tttccttctt tctcacccc tccctctcca tgaagattca ggtgcttaac | 240 |
| atatcatttt tttccctgct ggaattttag cattgatatg aaccatggac aagtatattc | 300 |
| tgctgccaca aagactgtaa agtgcttcat ttcaacagct gaggcaagcc aagtgatcat | 360 |
| taataaagct tttcttgctt ccttcagtgg tgttggtagt aaaatggtag gtaaaagtta | 420 |
| ggctgcaagt tcaataaatg agatttacct atcattccac ccttgtgtat tcattcacct | 480 |
| atcctggttc aagcagtttg agtcaactag gcatttaaag gcattgtgtt tattacttta | 540 |
| tggttccaac tttacatact tgtcagggat gaagtctgat aggttaagga cagtagaaat | 600 | ttctgtgcaa caagcagcaa c                                          621

<210> SEQ ID NO 17
<211> LENGTH: 567
<212> TYPE: DNA
<213> ORGANISM: Eukaryote
<220> FEATURE:
<221> NAME/KEY: misc_feature
<222> LOCATION: (1)...(567)
<223> OTHER INFORMATION: n = A, T, C, or G

<400> SEQUENCE: 17 ttttttttttt ttttggtta caaaagtatt tattttataa aacttgtatt taaaatagag    60
cttatctgtc tactcacaaa tcctaattta aaacataaca cattatcctt agctaatctg   120
atgttaacct ttacaatcaa cactcatttt tgtaatttta ttaagaacct gtactaaatg   180
aagtttttaa tcagaaaaca ttcccttta tcttaaaagt gcttcttaaa tgaaggcacc   240
aacaagaact actttcagat ggtacagaat ttcttatttc ttgaagactc tgtggttgac   300
cacttcttca ttagttacct gcagcaagac accttcctgc caaggaaaaa aaaaaagtat   360
ctgaagaagt ttatcatgtt tgtccaaaga acctaagtaa cttcagtggt ggttttagga   420
ttaaagcaga ctcactgatg tgtatacgcc ctgaatatca catttctgga aaggcagtaa   480
agcctagaaa tcagaaggcg ggcggtttta aagaaatttc aatagccaac ctacaacant   540
ttagggcaaa gataatgggc aaaaant                                        567

<210> SEQ ID NO 18
<211> LENGTH: 346
<212> TYPE: DNA
<213> ORGANISM: Eukaryote
<220> FEATURE:
<221> NAME/KEY: misc_feature
<222> LOCATION: (1)...(346)
<223> OTHER INFORMATION: r = A or G
        y = T or C
        m = A or C
        k = G or T
        s = G or C
        w = A or T
        b = G, C, or T; not A
        d = A, G, or T; not C
        h = A, C, or T; not G
        v = A, G, or C; not T
        n = A, T, G, or C

<400> SEQUENCE: 18
acgatatmta ywgarrtwya wctstthact gaatmwhatg cacaaatatt aactagtrrt    60
ttattaaaca gatatsattt agaacaagac ttaawkaaat acaaatcctt aggtacgrtt   120
taatatcatg ttcadgatgt ttgaagagtt taaaaagaat cactgattaa gkkaagcatc   180
cbcacttttc tttgagaabc caaaccttttt aggnaaadac cccattccaa attttgtccc   240
chatttcagr cckkcagaaa gtctctaaca tsaagagtcc tcaacggggn gtaactcava   300
wctcctatca agtgcagtaa cctagctctc ccggdggcca tggcgt                   346

<210> SEQ ID NO 19
<211> LENGTH: 803
<212> TYPE: DNA
<213> ORGANISM: Eukaryote
<220> FEATURE:
<221> NAME/KEY: misc_feature
<222> LOCATION: (1)...(803)
<223> OTHER INFORMATION: n = A, C, T, or G

<400> SEQUENCE: 19

```
aaactaaaca gtgttttgtt aattcttctg cattcggact attgcaggca ttagagcatc      60
cagagctacg aagggctggc tgcagcagca ccgccctttg taagccagca gaccagcctt     120
aactgtgggc ttgactcctg tgagctggcc tcagtgtgac tcagaaatgt ttgattagca     180
gatgagagag cgaggacaca ccacgagggc tgcgttctct tcctccagcg ctgtgcagga     240
cagtttcttc tcaccctagc cttttaaat gcaccagaag tacagacagt tgcactacac      300 aaacccttg aacacttgta gaaatcagtc caccgtagat tagacagaat caccttccaa      360
tcctttgact tcttttcctt tcatttgaac aattgtataa taattgatta ttgtcaaatt     420
tttgtctgtg gtagtatcgc tttaatttat cttagtacat caacgttttg atttaaaaaa     480
gaattaaaac aacaaaaaaa gtcacttaga agccatgaac ttttttttttt ngatngggaa    540 attttcttgt ttngaaaatt atcattgggg ttcctccgga aacttgtaa gattggntta     600 taaggtacct gggangttca naacngtgg ntataccctt ttttaaggga aattaatgat     660
ttngagtttt tgggccaact ncgggantgg cagggaaacc anncnggggn ggggtttaaa    720
ttntgtgagg gtttttttggg cctnaatttt ttgcataatt ttcacctngn aacctttnaa    780
nnctnggaaa aaaaaaaaaa cnt                                             803

<210> SEQ ID NO 20
<211> LENGTH: 2540
<212> TYPE: DNA
<213> ORGANISM: Eukaryote
<220> FEATURE:
<221> NAME/KEY: CDS
<222> LOCATION: (3)...(2348)
<221> NAME/KEY: misc_feature
<222> LOCATION: (1)...(2540)
<223> OTHER INFORMATION: n = A,T,C or G

<400> SEQUENCE: 20 tg cag ccg ccc ttg gaa ctg cat gtc agg aag cat ccc ttt gtg tat        47
   Gln Pro Pro Leu Glu Leu His Val Arg Lys His Pro Phe Val Tyr
     1               5                  10                  15 gtc tgt gct ata tgt ctc aag aaa ttt gtc agc tca atc agg ctg cgc       95
Val Cys Ala Ile Cys Leu Lys Lys Phe Val Ser Ser Ile Arg Leu Arg
             20                  25                  30 tcc cat atc cga gag gtg cat ggg gcg gcc cag gag acc ttg gtt ttt      143
Ser His Ile Arg Glu Val His Gly Ala Ala Gln Glu Thr Leu Val Phe
         35                  40                  45 act agc tcc atc aac cag agt ttc tgc ctc ctg gag cct ggt ggg gat      191
Thr Ser Ser Ile Asn Gln Ser Phe Cys Leu Leu Glu Pro Gly Gly Asp
     50                  55                  60 atc cag cag gaa gcc ttg gga aac cag cta tca ctg aca gct gag gaa      239
Ile Gln Gln Glu Ala Leu Gly Asn Gln Leu Ser Leu Thr Ala Glu Glu
 65                  70                  75 ttt gtg tgt cca gaa att gat gta cgt aag ggg gag gtt tgt cct ggg      287
Phe Val Cys Pro Glu Ile Asp Val Arg Lys Gly Glu Val Cys Pro Gly
 80                  85                  90                  95 gaa gct cag cct gag gtg ggg ctg agg gag ttg gag gcc cct gga gaa      335
Glu Ala Gln Pro Glu Val Gly Leu Arg Glu Leu Glu Ala Pro Gly Glu
            100                 105                 110 gca tgt gcc cca gcc gtg ccc ttg gcc aac ccc cag agt gtc agt gtt      383
Ala Cys Ala Pro Ala Val Pro Leu Ala Asn Pro Gln Ser Val Ser Val
        115                 120                 125 tcc ctg tcc ccc tgc aaa ctg gaa acc act gtg gtc aat tcc gac ctc      431
Ser Leu Ser Pro Cys Lys Leu Glu Thr Thr Val Val Asn Ser Asp Leu
    130                 135                 140
```

```
aac tct ctt gga gtg gtt tca gat gat ttt tta ctg aaa act gat acc      479
Asn Ser Leu Gly Val Val Ser Asp Asp Phe Leu Leu Lys Thr Asp Thr
145                 150                 155 tct tct gct gag cct cat gct gct gct gag cta acc tca gac aca cag      527
Ser Ser Ala Glu Pro His Ala Ala Ala Glu Leu Thr Ser Asp Thr Gln
160                 165                 170                 175 cat cga ggc tca gcc cag act cag ggt gaa gaa gtc aca ctg ctg ctg      575
His Arg Gly Ser Ala Gln Thr Gln Gly Glu Glu Val Thr Leu Leu Leu
                180                 185                 190 gcc aag gcc aaa agt act gga cca gac tca gag agt cct cca agt gga      623
Ala Lys Ala Lys Ser Thr Gly Pro Asp Ser Glu Ser Pro Pro Ser Gly
            195                 200                 205 ggg cag aat gtg ggt gct ctg cca gcc agt gaa tct gac tct aac agg      671
Gly Gln Asn Val Gly Ala Leu Pro Ala Ser Glu Ser Asp Ser Asn Arg
        210                 215                 220 tgt ctc agg gca aac cca gca gag acc tca gac ctc ctt cct aca gtg      719
Cys Leu Arg Ala Asn Pro Ala Glu Thr Ser Asp Leu Leu Pro Thr Val
    225                 230                 235 gct gat gga gga gac ctc ggt gtg tgc cag cct gac tct tgc acg tcg      767
Ala Asp Gly Gly Asp Leu Gly Val Cys Gln Pro Asp Ser Cys Thr Ser
240                 245                 250                 255 tcc tct gag cac cac cct ggc agc aca gca ttc atg aag gtc cta gac      815
Ser Ser Glu His His Pro Gly Ser Thr Ala Phe Met Lys Val Leu Asp
                260                 265                 270 agt ctc cag aag aag cag atg aac acc agt ctt tgc gag cgg atc cgg      863
Ser Leu Gln Lys Lys Gln Met Asn Thr Ser Leu Cys Glu Arg Ile Arg
            275                 280                 285 aag gtt tat gga gac ctg gag tgt gaa tac tgt ggc aaa ctt ttt tgg      911
Lys Val Tyr Gly Asp Leu Glu Cys Glu Tyr Cys Gly Lys Leu Phe Trp
        290                 295                 300 tac caa gtg cat ttt gac atg cat gtc cgc acc cac acc cgg gaa cat      959
Tyr Gln Val His Phe Asp Met His Val Arg Thr His Thr Arg Glu His
    305                 310                 315 ctg tat tat tgc tcc cag tgt cac tac tct tcc atc acc aaa aac tgc     1007
Leu Tyr Tyr Cys Ser Gln Cys His Tyr Ser Ser Ile Thr Lys Asn Cys
320                 325                 330                 335 ctt aaa cgc cat gta att cag aaa cac agt aac atc ttg ctg aag tgt     1055
Leu Lys Arg His Val Ile Gln Lys His Ser Asn Ile Leu Leu Lys Cys
                340                 345                 350 ccc act gac ggc tgt gac tac tcg act cca gat aaa tat aag cta cag     1103
Pro Thr Asp Gly Cys Asp Tyr Ser Thr Pro Asp Lys Tyr Lys Leu Gln
            355                 360                 365 gcc cac ctt aaa gtt cac aca gag ctg gac aaa agg agt tat tct tgt     1151
Ala His Leu Lys Val His Thr Glu Leu Asp Lys Arg Ser Tyr Ser Cys
        370                 375                 380 cct gta tgt gaa aaa tct ttt tca gaa gac cga ttg ata aag tca cat     1199
Pro Val Cys Glu Lys Ser Phe Ser Glu Asp Arg Leu Ile Lys Ser His
    385                 390                 395 atc aag act aat cat cca gag gtc tcc atg aat acc att tct gag gtt     1247
Ile Lys Thr Asn His Pro Glu Val Ser Met Asn Thr Ile Ser Glu Val
400                 405                 410                 415 ctt ggg aga aga gtc cag ctc aaa ggg cta att gga aag cga gcc atg     1295
Leu Gly Arg Arg Val Gln Leu Lys Gly Leu Ile Gly Lys Arg Ala Met
                420                 425                 430 aag tgt ccg tat tgc gat ttc tat ttc atg aag aat ggc tca gac ctt     1343
Lys Cys Pro Tyr Cys Asp Phe Tyr Phe Met Lys Asn Gly Ser Asp Leu
            435                 440                 445 cag cgg cac atc tcn gct cac gag ggt gtg aag ccc ttc aaa tgt tct     1391
Gln Arg His Ile Ser Ala His Glu Gly Val Lys Pro Phe Lys Cys Ser
        450                 455                 460
```

```
ttg tgt gag tat gca act cgt agc aag agc aac ctc aaa gct cat atg      1439
Leu Cys Glu Tyr Ala Thr Arg Ser Lys Ser Asn Leu Lys Ala His Met
    465                 470                 475 aat cgt cac agc act gag aag act cac ctc tgt gac atg tgt ggc aag      1487
Asn Arg His Ser Thr Glu Lys Thr His Leu Cys Asp Met Cys Gly Lys
480                 485                 490                 495 aaa ttc aaa tcc aaa ggg aca tta aag agt cat aag ctc ctt cac aca      1535
Lys Phe Lys Ser Lys Gly Thr Leu Lys Ser His Lys Leu Leu His Thr
                500                 505                 510 tct gat ggg aag caa ttc aag tgc acg gtg tgt gac tac aca gct gcc      1583
Ser Asp Gly Lys Gln Phe Lys Cys Thr Val Cys Asp Tyr Thr Ala Ala
            515                 520                 525 cag aaa cca cag ctg ctg cga cac atg gag cag gat gcc tcc ttc aag      1631
Gln Lys Pro Gln Leu Leu Arg His Met Glu Gln Asp Ala Ser Phe Lys
        530                 535                 540 cct ttc cgc tgc gct cac tgt cat tat tca tgt aac atc tct gga tct      1679
Pro Phe Arg Cys Ala His Cys His Tyr Ser Cys Asn Ile Ser Gly Ser
    545                 550                 555 ctg aaa cgg cac tac aac agg aag cac ccc aac gag gag tat gcc aac      1727
Leu Lys Arg His Tyr Asn Arg Lys His Pro Asn Glu Glu Tyr Ala Asn
560                 565                 570                 575 gtg ggc agc ggg gag ctt gca gct gaa gcc ctc atc caa caa ggt ggt      1775
Val Gly Ser Gly Glu Leu Ala Ala Glu Ala Leu Ile Gln Gln Gly Gly
                580                 585                 590 ctg aag tgt cct gtt tgc agc ttt gtg tat gga acc aaa tgg gag ttc      1823
Leu Lys Cys Pro Val Cys Ser Phe Val Tyr Gly Thr Lys Trp Glu Phe
            595                 600                 605 aac aga cac ttg aag aac aag cat ggc ttg aag cca gcg aca gag act      1871
Asn Arg His Leu Lys Asn Lys His Gly Leu Lys Pro Ala Thr Glu Thr
        610                 615                 620 ccc gag gag ccc tcc acc cag tat ctc tac atc acc gag gct gaa gat      1919
Pro Glu Glu Pro Ser Thr Gln Tyr Leu Tyr Ile Thr Glu Ala Glu Asp
    625                 630                 635 gtt cag ggg aca caa gca gct gta gct gca ctt cag gac ctg cga tat      1967
Val Gln Gly Thr Gln Ala Ala Val Ala Ala Leu Gln Asp Leu Arg Tyr
640                 645                 650                 655 acc tcc gag agt ggt gat cga ctt gac ccc aca gct gtg aat atc ctg      2015
Thr Ser Glu Ser Gly Asp Arg Leu Asp Pro Thr Ala Val Asn Ile Leu
                660                 665                 670 cag cag atc att gaa ctg ggt tca gag act cac gat gct gct gcc gtg      2063
Gln Gln Ile Ile Glu Leu Gly Ser Glu Thr His Asp Ala Ala Ala Val
            675                 680                 685 gcc tcc gtg gtt gcc atg gcg cct ggg aca gtg act gtt gta aag cag      2111
Ala Ser Val Val Ala Met Ala Pro Gly Thr Val Thr Val Val Lys Gln
        690                 695                 700 gtc acc gat gag gaa ccc aat tcc aac cat aca gtc atg atc cag gag      2159
Val Thr Asp Glu Glu Pro Asn Ser Asn His Thr Val Met Ile Gln Glu
    705                 710                 715 act ctg cag cag gcc tct gtg gag ttg gcc gag cag cac cat ctg gtg      2207
Thr Leu Gln Gln Ala Ser Val Glu Leu Ala Glu Gln His His Leu Val
720                 725                 730                 735 gtg tcc tct gat gac gtg gag ggc att gag aca gtg aca gtg tac aca      2255
Val Ser Ser Asp Asp Val Glu Gly Ile Glu Thr Val Thr Val Tyr Thr
                740                 745                 750 cag ggt ggg gag gcc tca gag ttc atc gtg tac gtg caa gag gct gtc      2303
Gln Gly Gly Glu Ala Ser Glu Phe Ile Val Tyr Val Gln Glu Ala Val
            755                 760                 765 cag ccc atg gag gag cag gtc ggg gag cag cca gcc aca gaa ctc          2348
Gln Pro Met Glu Glu Gln Val Gly Glu Gln Pro Ala Thr Glu Leu
```

-continued

```
                770              775              780
tagagaatcc ctgcctcctt tggcagccag cctttgtggg cctgaagacc tcctaaccca    2408
ccaggtccat ccctggctct tcttgcccac tggccccaga taaatttctc cataactgtc    2468
ctctgtgtgg tcaaagccag gagagtatca tgaagagaga gagagagaga gactagtctc    2528 cgagttttt tt                                                         2540
```

<210> SEQ ID NO 21
<211> LENGTH: 782
<212> TYPE: PRT
<213> ORGANISM: Eukaryote

<400> SEQUENCE: 21

```
Gln Pro Pro Leu Glu Leu His Val Arg Lys His Pro Phe Val Tyr Val
 1               5                  10                  15

Cys Ala Ile Cys Leu Lys Lys Phe Val Ser Ser Ile Arg Leu Arg Ser
            20                  25                  30

His Ile Arg Glu Val His Gly Ala Ala Gln Glu Thr Leu Val Phe Thr
        35                  40                  45

Ser Ser Ile Asn Gln Ser Phe Cys Leu Leu Glu Pro Gly Gly Asp Ile
    50                  55                  60

Gln Gln Glu Ala Leu Gly Asn Gln Leu Ser Leu Thr Ala Glu Glu Phe
65                  70                  75                  80

Val Cys Pro Glu Ile Asp Val Arg Lys Gly Glu Val Cys Pro Gly Glu
                85                  90                  95

Ala Gln Pro Glu Val Gly Leu Arg Glu Leu Glu Ala Pro Gly Glu Ala
            100                 105                 110

Cys Ala Pro Ala Val Pro Leu Ala Asn Pro Gln Ser Val Ser Val Ser
        115                 120                 125

Leu Ser Pro Cys Lys Leu Glu Thr Thr Val Val Asn Ser Asp Leu Asn
    130                 135                 140

Ser Leu Gly Val Val Ser Asp Asp Phe Leu Leu Lys Thr Asp Thr Ser
145                 150                 155                 160

Ser Ala Glu Pro His Ala Ala Ala Glu Leu Thr Ser Asp Thr Gln His
                165                 170                 175

Arg Gly Ser Ala Gln Thr Gln Gly Glu Glu Val Thr Leu Leu Leu Ala
            180                 185                 190

Lys Ala Lys Ser Thr Gly Pro Asp Ser Glu Ser Pro Pro Ser Gly Gly
        195                 200                 205

Gln Asn Val Gly Ala Leu Pro Ala Ser Glu Ser Asp Ser Asn Arg Cys
    210                 215                 220

Leu Arg Ala Asn Pro Ala Glu Thr Ser Asp Leu Leu Pro Thr Val Ala
225                 230                 235                 240

Asp Gly Gly Asp Leu Gly Val Cys Gln Pro Asp Ser Cys Thr Ser Ser
                245                 250                 255

Ser Glu His His Pro Gly Ser Thr Ala Phe Met Lys Val Leu Asp Ser
            260                 265                 270

Leu Gln Lys Lys Gln Met Asn Thr Ser Leu Cys Glu Arg Ile Arg Lys
        275                 280                 285

Val Tyr Gly Asp Leu Glu Cys Glu Tyr Cys Gly Lys Leu Phe Trp Tyr
    290                 295                 300

Gln Val His Phe Asp Met His Val Arg Thr His Thr Arg Glu His Leu
305                 310                 315                 320

Tyr Tyr Cys Ser Gln Cys His Tyr Ser Ser Ile Thr Lys Asn Cys Leu
```

```
                    325                 330                 335
Lys Arg His Val Ile Gln Lys His Ser Asn Ile Leu Leu Lys Cys Pro
                340                 345                 350
Thr Asp Gly Cys Asp Tyr Ser Thr Pro Asp Lys Tyr Lys Leu Gln Ala
                355                 360                 365
His Leu Lys Val His Thr Glu Leu Asp Lys Arg Ser Tyr Ser Cys Pro
        370                 375                 380
Val Cys Glu Lys Ser Phe Ser Glu Asp Arg Leu Ile Lys Ser His Ile
385                 390                 395                 400
Lys Thr Asn His Pro Glu Val Ser Met Asn Thr Ile Ser Glu Val Leu
                405                 410                 415
Gly Arg Arg Val Gln Leu Lys Gly Leu Ile Gly Lys Arg Ala Met Lys
                420                 425                 430
Cys Pro Tyr Cys Asp Phe Tyr Phe Met Lys Asn Gly Ser Asp Leu Gln
                435                 440                 445
Arg His Ile Ser Ala His Glu Gly Val Lys Pro Phe Lys Cys Ser Leu
        450                 455                 460
Cys Glu Tyr Ala Thr Arg Ser Lys Ser Asn Leu Lys Ala His Met Asn
465                 470                 475                 480
Arg His Ser Thr Glu Lys Thr His Leu Cys Asp Met Cys Gly Lys Lys
                485                 490                 495
Phe Lys Ser Lys Gly Thr Leu Lys Ser His Lys Leu Leu His Thr Ser
                500                 505                 510
Asp Gly Lys Gln Phe Lys Cys Thr Val Cys Asp Tyr Thr Ala Ala Gln
                515                 520                 525
Lys Pro Gln Leu Leu Arg His Met Glu Gln Asp Ala Ser Phe Lys Pro
                530                 535                 540
Phe Arg Cys Ala His Cys His Tyr Ser Cys Asn Ile Ser Gly Ser Leu
545                 550                 555                 560
Lys Arg His Tyr Asn Arg Lys His Pro Asn Glu Glu Tyr Ala Asn Val
                565                 570                 575
Gly Ser Gly Glu Leu Ala Ala Glu Ala Leu Ile Gln Gln Gly Gly Leu
                580                 585                 590
Lys Cys Pro Val Cys Ser Phe Val Tyr Gly Thr Lys Trp Glu Phe Asn
                595                 600                 605
Arg His Leu Lys Asn Lys His Gly Leu Lys Pro Ala Thr Glu Thr Pro
        610                 615                 620
Glu Pro Ser Thr Gln Tyr Leu Tyr Ile Thr Glu Ala Glu Asp Val
625                 630                 635                 640
Gln Gly Thr Gln Ala Ala Val Ala Ala Leu Gln Asp Leu Arg Tyr Thr
                645                 650                 655
Ser Glu Ser Gly Asp Arg Leu Asp Pro Thr Ala Val Asn Ile Leu Gln
                660                 665                 670
Gln Ile Ile Glu Leu Gly Ser Glu Thr His Asp Ala Ala Ala Val Ala
                675                 680                 685
Ser Val Val Ala Met Ala Pro Gly Thr Val Thr Val Lys Gln Val
                690                 695                 700
Thr Asp Glu Glu Pro Asn Ser Asn His Thr Val Met Ile Gln Glu Thr
705                 710                 715                 720
Leu Gln Gln Ala Ser Val Glu Leu Ala Glu Gln His His Leu Val Val
                725                 730                 735
Ser Ser Asp Asp Val Glu Gly Ile Glu Thr Val Thr Val Tyr Thr Gln
                740                 745                 750
```

```
Gly Gly Glu Ala Ser Glu Phe Ile Val Tyr Val Gln Glu Ala Val Gln
        755                 760                 765

Pro Met Glu Glu Gln Val Gly Glu Gln Pro Ala Thr Glu Leu
    770                 775                 780

<210> SEQ ID NO 22
<211> LENGTH: 1012
<212> TYPE: DNA
<213> ORGANISM: Eukaryote
<220> FEATURE:
<221> NAME/KEY: misc_feature
<222> LOCATION: (1)...(1012)
<223> OTHER INFORMATION: r = G or A
      y = C or T
      m = A or C
      k = G or T
      s = G or C
      w = A or T

<400> SEQUENCE: 22
tggatctact tgttaatggt ttcatggaag caatcagcaa tatgtgatat gaactgctgc      60
attacttatt atactcgtgg aactgagata tttarmsrsm gcttwwyttt ttttttttytt    120 agtgtaaaat acttaagcgt ttccactatt ggaagaaaag catatatggg tattttgtat    180
tgtaacttgt ttaaaaggac agtcttttt aaycttccca cttaaatgct tttaaaatat     240
gtaatacaat ttgaagcttg tttaaaaata gaattaaatg tcttawatag kgctackgtt    300
ttggaattag aaagtgatca aatacaaaac attttaaaat taagcccaga aaacaaaata    360
gtgtttaaag ttagtttagt ataaaagaaa tttataagat ttttttcttca atataagata   420 cctcacttga aaataaagaa agcacagcac attaaagtaa ttctcatgag aacaccccat    480
tagaataatt gctaaatcta ggacaccttt tgagttgtga gtttgtgata catgtagtca    540
ccattagctt ttctgctgga aggacttccc gtagtaattt taaggcagtg taatagttca    600 attacccccac agtttctaac ctgggaaggc agtatgtgaa tggtcccttc tgcaactacg   660
gaaacacatt agctacattg agcataactc gattgataat tttgccagtg catatagttt    720
tatgattaaa attgctgtgg ttggttgcat tacacgacac acaaaactgt cctctacctc    780
acatgaaata aatattttat atggttttac taaaaaaatg actcatctat ctggttactt    840
agtttacaaa ttttggatta tatttattga acatgacat  actgtgctct tagcttatac    900
ctcaatcgta ttttgtgctg tttgccattt tcatgccttg tatataactt gtatagattg    960
gatgatattc ccaataaaca cttttaatkc caawraaaaa aaaaaaaaaa aa           1012

<210> SEQ ID NO 23
<211> LENGTH: 1747
<212> TYPE: DNA
<213> ORGANISM: Eukaryote
<220> FEATURE:
<221> NAME/KEY: misc_feature
<222> LOCATION: (1)...(1747)
<223> OTHER INFORMATION: n = A,T,C or G

<400> SEQUENCE: 23
taatgtttat gatacaaagc tactcactct ggagccttct cattacagaa tctcttgact      60
tttatacacc cagcctgttg ttactttgtt caggttgcag aatgagtttc ctctggtttc     120
ctcctagagg agttttcctg atgaaatgct agtagcacct ccccgacata cagcgggtgg    180
gtggggcaca ctttgctgtg ctctgatggt acacacaaga agcagttgta atttgtcttt    240
ctgtttaaga gtgaccatag ctagatatgt gtgtgtgact tcagaaaatt aaaatgcttt    300
```

-continued

```
ccgaactttt cctgttaata gaggtgtgaa gtactcattc atgtgcatga ggaaagtgga      360
ttccacggac gcacaccgct tcctatgtaa ctcacaatgc tctgtacagt ttttatatgt      420
agtcttacaa aggtcttatg aaatttatat aatggatttt ttcttttaaa ttataaaata      480
ctaaatatct taaagattgt tttggacttt tgtatgttta aatgttatct taaaacttgc      540
acaaatggac catgatgact ctttgatctt aaaatcagga atttacagtc agctaagaaa      600
aatgtggata ggttaataat ccacagtggg agtatctgct aggagcagga attgtagatg      660
acatgaattc cgtgatttga ggaagggcag cctctgcact tttctttgtt tttgtttttt      720
gcacatgaag tctgacattt ttaccatcga atttcacatt actagatggt tggcttggga      780
tttacctagg ggaaattctt agcaactttg tactttgttg tttttgttct gtttggtctc      840
cagcttgcag agaccctctt gcctctgtct cccaagtgtt gggttggcag gatgagcccc      900
accaccgctg gccctgtgca gttctttttgg gatgtccctg aaagcagctg tggcattatc      960
ttctgtttca tgtgtcccga gctgtctcat ggtactacat gcagtgacct gagatctgcg    1020
ttaaggaata acttaggaga aaacggctgt cactgtcctc cccgctgtga gacaccagag    1080
ttatcacacc tgttatggtc atactttgtg ttatgatact gatgtctaag gcaattttttc    1140 tactttccaa aagggagttt gtttcctaaa tatattgtga cctaaatgtg gttttattct    1200
gctatgttct ataatttatg tattgacttt tgtaacctcc ttgggagaaa catgttaagt    1260
ggcacaggga ccatatatgt catttttattt agctctggag aaggaaacca caggcgtttg    1320
taaaatagca ttagcttaga tgtcagttca ttgtgcttgg ctgtgtggga ggcagactca    1380
aggacttgca ccatttattt ttctgacaga agtgttctgc ttatgtgctg cttagtaagt    1440 gtgattttc tagtcttgat gaaacttgcc tcgtgacatt gttgagcgta gtcttcactt    1500
tccagaagat gaaatgatgt gccatcattt tctgtctaaa cttcctttaa agtaattttt    1560
aatcagctgt aaatatcata tctcctactg ttgaaagtaa ctttaattta cattgcacca    1620
tatagcttga aaaccaactt tgaaattctg tactcctcca caagtgacct ccgctaaaat    1680
acccatagga agcttacttt gtgcatgcnt gctttgtgtg ccggttgccg tcctaanggt    1740
tgctttg                                                              1747
```

<210> SEQ ID NO 24
<211> LENGTH: 571
<212> TYPE: DNA
<213> ORGANISM: Eukaryote
<220> FEATURE:
<221> NAME/KEY: misc_feature
<222> LOCATION: (1)...(571)
<223> OTHER INFORMATION: n = A,T,C or G

<400> SEQUENCE: 24

```
tttttttttt ttttttttag tgtaaaatac ttaagcgttt ccactattgg aagaaaagca       60
tatatgggta ttttgtattg taacttgttt aaaaggacag tctttttttaa tcttcccact      120 taaatgcttt taaatatgt aatacaattt gaagcttgtt taaaaataga attaaatgtc      180
ttatatagtg ctactgtttt ggaattagaa agtgatcaaa tacaaaacat tttaaaatta      240
agcccagaaa acaaaatagt gtttaaagtt agtttagtat aaaagaaatt tatgagattt      300
tttcttcaat ataagatacc tcacttgaaa ataaagaaag cacagcacat taaagtaatt      360
ctcatgagaa cacccccatta gaataattgc taaatctagg acacctttg agttgtgaag      420 tttgtgatac atgtagtcac cattagcttt tctgctggaa ggacttcccg tagtaatttt      480
```

-continued

```
aaagnagtgt aataagttca attanoccac aagtttctaa nctgggaaag naantatggt    540 gaatggncoc ttctgcaact acgggaacac a                                   571
```

<210> SEQ ID NO 25
<211> LENGTH: 619
<212> TYPE: DNA
<213> ORGANISM: Eukaryote

<400> SEQUENCE: 25

```
ttttttttt ttttttttt tggcattaaa agtgtttatt gggaatatca tccaatctat      60
acaagttata tacaaggcat gaaaatggca acagcacaa aatacgattg aggtataagc    120
taagagcaca gtatgtcatg tttcaataaa tataatccaa aatttgtaaa ctaagtaacc   180
agatagatga gtcatttttt tagtaaaacc atataaaata tttatttcat gtgaggtaga   240
ggacagtttt gtgtgtcgtg taatgcaacc aaccacagca attttaatca taaaactata   300
tgcactggca aaattatcaa tcgagttatg ctcaatgtag ctaatgtgtt tccgtagttg   360
cagaagggac cattcacata ctgccttccc aggttagaaa ctgtgggta attgaactat    420 tacactgcct taaaattact acgggaagtc cttccagcag aaaagctaat ggtgactaca   480
tgtatcacaa actcacaact caaaaggtgt cctagattta gcaattattc taatggggtg   540
ttctcatgag aattacttta atgtgctgtg ctttctttat ttcaagtgag gtatcttata   600
ttgaagaaaa aatccataa                                                619
```

<210> SEQ ID NO 26
<211> LENGTH: 2995
<212> TYPE: DNA
<213> ORGANISM: Eukaryote
<220> FEATURE:
<221> NAME/KEY: CDS
<222> LOCATION: (218)...(1960)

<400> SEQUENCE: 26

```
tgcggccgcc ggggccgggg ctgagccagt ctctcccgcc gccgccggac gcgcagacct     60
gggcaggctg caccgacggc cgcctggccg agcgcactgc aggtcgctgc gcgcgctgcg    120 accccgggc cggacgcga gtggctgcgg tgtcctgggc gagcactgct agtttaggcc     180
gtctgtcctc agctgcttgg aaccctaca tcccacc atg gct ggg ata cag aag     235
                                        Met Ala Gly Ile Gln Lys
                                          1               5 agg aag ttt gac cag ctg gaa gag gac gac tgc agc tcc tcc tcc ttg     283
Arg Lys Phe Asp Gln Leu Glu Glu Asp Asp Cys Ser Ser Ser Ser Leu
           10                  15                  20 tcc tct ggc gat ctc tct ccc tct cct ccc agc tct tct gcc tcc cct     331
Ser Ser Gly Asp Leu Ser Pro Ser Pro Pro Ser Ser Ser Ala Ser Pro
       25                  30                  35 gcc tgg acc tct gag gag gag gga ctg ggt gat cag cca ccc cag cct     379
Ala Trp Thr Ser Glu Glu Glu Gly Leu Gly Asp Gln Pro Pro Gln Pro
   40                  45                  50 gat cag gac tcc agt ggc atc cag agt tta acg ccc cca tcc atc ctg     427
Asp Gln Asp Ser Ser Gly Ile Gln Ser Leu Thr Pro Pro Ser Ile Leu
55                  60                  65                  70 aag cgg gct cct cgg gag cgt ccg ggt cac gtg gcc ttc gat ggc atc     475
Lys Arg Ala Pro Arg Glu Arg Pro Gly His Val Ala Phe Asp Gly Ile
                75                  80                  85 act gtc tac tat ttc ccg cgg tgc cag gga ttc acc agt gtg ccc agc     523
Thr Val Tyr Tyr Phe Pro Arg Cys Gln Gly Phe Thr Ser Val Pro Ser
            90                  95                 100
```

-continued

| | | |
|---|---|---|
| cat ggt ggc tgt acc ctg ggc atg gct tct cgt cat agc acc tgc cgc<br>His Gly Gly Cys Thr Leu Gly Met Ala Ser Arg His Ser Thr Cys Arg<br>          105                  110                  115 | 571 |
| ctc ttc tcc tta gcc gag ttt aaa cag gag cag ttc cgg gct cgg cgt<br>Leu Phe Ser Leu Ala Glu Phe Lys Gln Glu Gln Phe Arg Ala Arg Arg<br>      120                  125                  130 | 619 |
| gag aag ctc cgt cgg cgt tta aag gag gag aag cta gag atg ctg aaa<br>Glu Lys Leu Arg Arg Arg Leu Lys Glu Glu Lys Leu Glu Met Leu Lys<br>135                    140                  145                  150 | 667 |
| tgg aag ctt tca gtg tcc gga gtt ccg gag gca ggg gca gac gtg ccg<br>Trp Lys Leu Ser Val Ser Gly Val Pro Glu Ala Gly Ala Asp Val Pro<br>                155                  160                  165 | 715 |
| ctc aca gtg gac gcc atc gat gac gct tct gta gag gag gac ttg gca<br>Leu Thr Val Asp Ala Ile Asp Asp Ala Ser Val Glu Glu Asp Leu Ala<br>      170                  175                  180 | 763 |
| gtg gcc gtg gca ggt ggc cgc ctg gag gaa gcg aat ttc cta cag ccc<br>Val Ala Val Ala Gly Gly Arg Leu Glu Glu Ala Asn Phe Leu Gln Pro<br>          185                  190                  195 | 811 |
| tat cca cct cgg cag cga cgg gcc cta ctt cgc gct tcc ggt gtt cga<br>Tyr Pro Pro Arg Gln Arg Arg Ala Leu Leu Arg Ala Ser Gly Val Arg<br>200                    205                  210 | 859 |
| agg att gac cga gag gag aag cac gag ctg cag gcg cta cgc caa tcc<br>Arg Ile Asp Arg Glu Glu Lys His Glu Leu Gln Ala Leu Arg Gln Ser<br>215                    220                  225                  230 | 907 |
| cgg gag gat tgt ggt tgt cac tgt gat ggc gtc tgt gac cct gag acc<br>Arg Glu Asp Cys Gly Cys His Cys Asp Gly Val Cys Asp Pro Glu Thr<br>                235                  240                  245 | 955 |
| tgc agt tgc atc ctg gcg ggc att aaa tgc cag atg gat cac acg tcc<br>Cys Ser Cys Ile Leu Ala Gly Ile Lys Cys Gln Met Asp His Thr Ser<br>              250                  255                  260 | 1003 |
| ttc ccc tgt ggc tgc tgc agc gag ggc tgt gag aac ccc cat ggt cga<br>Phe Pro Cys Gly Cys Cys Ser Glu Gly Cys Glu Asn Pro His Gly Arg<br>          265                  270                  275 | 1051 |
| gtg gaa ttc aat cag gcg aga gtt cag aca cac ttc atc cac acg ctc<br>Val Glu Phe Asn Gln Ala Arg Val Gln Thr His Phe Ile His Thr Leu<br>280                    285                  290 | 1099 |
| acc cgc ctg cag atg gag cag ggt gcg gag agt ttg ggg gac ccg gag<br>Thr Arg Leu Gln Met Glu Gln Gly Ala Glu Ser Leu Gly Asp Pro Glu<br>295                    300                  305                  310 | 1147 |
| tcc ccc atg gag gac gtt cct gtc gaa caa acc gtg gtt tcc ccc ttt<br>Ser Pro Met Glu Asp Val Pro Val Glu Gln Thr Val Val Ser Pro Phe<br>              315                  320                  325 | 1195 |
| cct cct tcc aaa ccc act atg agc aat gac ctg ggg gac agc agc tgt<br>Pro Pro Ser Lys Pro Thr Met Ser Asn Asp Leu Gly Asp Ser Ser Cys<br>          330                  335                  340 | 1243 |
| ggc agc gac atg aca gac tct tcc acg acc tac tcc tct ggc ggc agt<br>Gly Ser Asp Met Thr Asp Ser Ser Thr Thr Tyr Ser Ser Gly Gly Ser<br>345                    350                  355 | 1291 |
| ggc agc cgc agc gag gct ccg aac cat ctt gcc cac ccc agc ctg cca<br>Gly Ser Arg Ser Glu Ala Pro Asn His Leu Ala His Pro Ser Leu Pro<br>360                    365                  370 | 1339 |
| ggt tcc agc ttc cgg tct ggc ata gat gaa gac agc ctg gaa cag atc<br>Gly Ser Ser Phe Arg Ser Gly Ile Asp Glu Asp Ser Leu Glu Gln Ile<br>375                    380                  385                  390 | 1387 |
| ctg aat ttc agt gac tct gac ctc ggt att gag gaa gaa gag gag gag<br>Leu Asn Phe Ser Asp Ser Asp Leu Gly Ile Glu Glu Glu Glu Glu Glu<br>                395                  400                  405 | 1435 |
| gga ggg agt gtg ggc aac ttg gat aac ctc agc tgt ttt cat ttg gct<br>Gly Gly Ser Val Gly Asn Leu Asp Asn Leu Ser Cys Phe His Leu Ala<br>          410                  415                  420 | 1483 |

```
gac atc ttt ggt acc ggt gac ccc ggc agc ctg gct agc tgg aca cac       1531
Asp Ile Phe Gly Thr Gly Asp Pro Gly Ser Leu Ala Ser Trp Thr His
            425                 430                 435 agc cag ttt ggc tct agc ctt cca tcg ggc atc cta gat gag aat gcc       1579
Ser Gln Phe Gly Ser Ser Leu Pro Ser Gly Ile Leu Asp Glu Asn Ala
        440                 445                 450 aac ctg gac gcc agc tgc ttc cta agc agc gga ctc gaa ggg ttg aga       1627
Asn Leu Asp Ala Ser Cys Phe Leu Ser Ser Gly Leu Glu Gly Leu Arg
455                 460                 465                 470 gaa ggt agc ctc ccc agc agt tct ggg tcc cct gag ggg gaa gcc gcc       1675
Glu Gly Ser Leu Pro Ser Ser Ser Gly Ser Pro Glu Gly Glu Ala Ala
                475                 480                 485 cag agc agc tcc ttg gac ctc agt tta tcc tcc tgt gac tcc ttt gag       1723
Gln Ser Ser Ser Leu Asp Leu Ser Leu Ser Ser Cys Asp Ser Phe Glu
            490                 495                 500 ctt ctc caa tct ctg cca gat tat agt ctg ggg cct cac tat act tcc       1771
Leu Leu Gln Ser Leu Pro Asp Tyr Ser Leu Gly Pro His Tyr Thr Ser
        505                 510                 515 cga agg gta tct ggc agc ctg gac agc ctt gag acc ttc cac cct tcg       1819
Arg Arg Val Ser Gly Ser Leu Asp Ser Leu Glu Thr Phe His Pro Ser
520                 525                 530 ccc agc ttc tct cca ccg agg gat gcc agc ttc ctg gat tct ctc ata       1867
Pro Ser Phe Ser Pro Pro Arg Asp Ala Ser Phe Leu Asp Ser Leu Ile
535                 540                 545                 550 ggc ctg tct gag ccg gtt aca gat gtc ctg gcg ccc ctt ctg gag agc       1915
Gly Leu Ser Glu Pro Val Thr Asp Val Leu Ala Pro Leu Leu Glu Ser
                555                 560                 565 cag ttt gag gac act gct gtg gtg cct ttg gac cct gtg cct gtg           1960
Gln Phe Glu Asp Thr Ala Val Val Pro Leu Asp Pro Val Pro Val
            570                 575                 580 taaggattga gatgactttt tcctgccctg agaccctgtt gctgcttttt atgtgatctt     2020
ggtgtccccc aagtctgtg  tatgtaacgg tctcccgtgg gctggttctg ccccgtgcc      2080 atgtgggcaa tcctctattt ttacagtaac actctagatt tatttatttt tttatgtttt    2140
tctgtactga agggagggtg ggaagggtat ccctctttca atgcctggcc tctatgtcca    2200
aacagaggtc tcccacctcc tactgtatgc ctggaggagg aagggggcggg gttcacatcc   2260 cctctttctg tactgtaaaa tgctccttgg tccaaagaca gctgaaaagc aggccttagg    2320
gtttcctgtg gaccgtggga gctaggtctt ctggactctg aagatgtaat ttatttctgt    2380
aatttatttg gggactgaga cagcagtggt tgggcctctc tggcaggtgg gcggtgttga    2440
ggcaaagtct tcggtgtccc ccgccggtct gggcttcggt gtggcgtgta ggttcgagct    2500
gagcagacgg aggctgtgct tgaccatcgg tgatcaaaac tccctctgcc cctgcccag    2560 acgctctaac atgccctctg tccatttccc tctccccaag gccatgggtt ataaaggccc    2620
tatgtaggat ggggagccag aggccctaag acatgaagca cccccagat cactgtctct    2680 agcctttctg ggcactgaat ccatcctgac ccaccacaca ccccccggcc agttggcaag   2740
aaagaggtgg ctcttggggg cttttatgcc cttcattagc tgatgttgga ttttatatgc    2800
atttttatat tgtctctaag tgtcagaact ataatttatt catttctctg tgtgtgtgtg    2860
tgccaagaaa cgcaggctct gggcctgcct ccttgcccag gaggccttgc cagcctgtgt    2920
gcttgtgaga acacattgta cctgagctga caggtaccaa taaagacact ctatttttaa    2980
aaaaaaaaaa aaaaa                                                     2995
```

<210> SEQ ID NO 27

-continued

```
<211> LENGTH: 581
<212> TYPE: PRT
<213> ORGANISM: Eukaryote

<400> SEQUENCE: 27

Met Ala Gly Ile Gln Lys Arg Lys Phe Asp Gln Leu Glu Glu Asp
 1               5                  10                  15

Cys Ser Ser Ser Leu Ser Ser Gly Asp Leu Ser Pro Ser Pro Pro
                20                  25                  30

Ser Ser Ser Ala Ser Pro Ala Trp Thr Ser Glu Glu Glu Gly Leu Gly
            35                  40                  45

Asp Gln Pro Pro Gln Pro Asp Gln Ser Ser Gly Ile Gln Ser Leu
        50                  55                  60

Thr Pro Pro Ser Ile Leu Lys Arg Ala Pro Arg Glu Arg Pro Gly His
65                  70                  75                  80

Val Ala Phe Asp Gly Ile Thr Val Tyr Tyr Phe Pro Arg Cys Gln Gly
                85                  90                  95

Phe Thr Ser Val Pro Ser His Gly Gly Cys Thr Leu Gly Met Ala Ser
                100                 105                 110

Arg His Ser Thr Cys Arg Leu Phe Ser Leu Ala Glu Phe Lys Gln Glu
            115                 120                 125

Gln Phe Arg Ala Arg Arg Glu Lys Leu Arg Arg Leu Lys Glu Glu
    130                 135                 140

Lys Leu Glu Met Leu Lys Trp Lys Leu Ser Val Ser Gly Val Pro Glu
145                 150                 155                 160

Ala Gly Ala Asp Val Pro Leu Thr Val Asp Ala Ile Asp Asp Ala Ser
                165                 170                 175

Val Glu Glu Asp Leu Ala Val Ala Val Ala Gly Gly Arg Leu Glu Glu
            180                 185                 190

Ala Asn Phe Leu Gln Pro Tyr Pro Pro Arg Gln Arg Ala Leu Leu
    195                 200                 205

Arg Ala Ser Gly Val Arg Arg Ile Asp Arg Glu Glu Lys His Glu Leu
210                 215                 220

Gln Ala Leu Arg Gln Ser Arg Glu Asp Cys Gly Cys His Cys Asp Gly
225                 230                 235                 240

Val Cys Asp Pro Glu Thr Cys Ser Cys Ile Leu Ala Gly Ile Lys Cys
                245                 250                 255

Gln Met Asp His Thr Ser Phe Pro Cys Gly Cys Ser Glu Gly Cys
            260                 265                 270

Glu Asn Pro His Gly Arg Val Glu Phe Asn Gln Ala Arg Val Gln Thr
            275                 280                 285

His Phe Ile His Thr Leu Thr Arg Leu Gln Met Glu Gln Gly Ala Glu
    290                 295                 300

Ser Leu Gly Asp Pro Glu Ser Pro Met Glu Asp Val Pro Val Glu Gln
305                 310                 315                 320

Thr Val Val Ser Pro Phe Pro Pro Ser Lys Pro Thr Met Ser Asn Asp
                325                 330                 335

Leu Gly Asp Ser Ser Cys Gly Ser Asp Met Thr Asp Ser Ser Thr Thr
            340                 345                 350

Tyr Ser Ser Gly Gly Ser Gly Ser Arg Ser Glu Ala Pro Asn His Leu
            355                 360                 365

Ala His Pro Ser Leu Pro Gly Ser Ser Phe Arg Ser Gly Ile Asp Glu
    370                 375                 380

Asp Ser Leu Glu Gln Ile Leu Asn Phe Ser Asp Ser Asp Leu Gly Ile
```

```
385                 390                 395                 400
Glu Glu Glu Glu Glu Glu Gly Gly Ser Val Gly Asn Leu Asp Asn Leu
                405                 410                 415
Ser Cys Phe His Leu Ala Asp Ile Phe Gly Thr Gly Asp Pro Gly Ser
            420                 425                 430
Leu Ala Ser Trp Thr His Ser Gln Phe Gly Ser Ser Leu Pro Ser Gly
            435                 440                 445
Ile Leu Asp Glu Asn Ala Asn Leu Asp Ala Ser Cys Phe Leu Ser Ser
            450                 455                 460
Gly Leu Glu Gly Leu Arg Glu Gly Ser Leu Pro Ser Ser Ser Gly Ser
465                 470                 475                 480
Pro Glu Gly Glu Ala Ala Gln Ser Ser Ser Leu Asp Leu Ser Leu Ser
                485                 490                 495
Ser Cys Asp Ser Phe Glu Leu Leu Gln Ser Leu Pro Asp Tyr Ser Leu
            500                 505                 510
Gly Pro His Tyr Thr Ser Arg Arg Val Ser Gly Ser Leu Asp Ser Leu
            515                 520                 525
Glu Thr Phe His Pro Ser Pro Ser Phe Ser Pro Arg Asp Ala Ser
            530                 535                 540
Phe Leu Asp Ser Leu Ile Gly Leu Ser Glu Pro Val Thr Asp Val Leu
545                 550                 555                 560
Ala Pro Leu Leu Glu Ser Gln Phe Glu Asp Thr Ala Val Val Pro Leu
                565                 570                 575
Asp Pro Val Pro Val
            580

<210> SEQ ID NO 28
<211> LENGTH: 2938
<212> TYPE: DNA
<213> ORGANISM: Eukaryote

<400> SEQUENCE: 28
attcggcacg agccagagtg aaggggcatg gagaagtgga cggcctggga gccgcagggc     60
gccgatgcgc tgcggcgctt tcaagggttg ctgctggacc gccgcggccg gctgcactgc    120
caagtgttgc gcctgcgcga agtggcccgg aggctcgagc gtctacggag cgctccttg    180
gcagccaacg tagctggcag ctctctgagc gctgctggcg ccctagcagc catcgtgggg    240
ttatcactca gcccggtcac cctgggagcc tcgctcgtgg cgtccgccgt gggcttaggg    300
gtggccaccg ccggagggc agtcaccatc acgtccgacc tctctctgat cttctgcaat    360
tcccgggagg tacggagggt gcaagagatc gccgccacct gccaggacca gatgcgcgaa    420
ctcctgagct gccttgagtt cttctgtcag tggcaggggc gcggggaccg ccagctgctg    480
cagagcggga gggacgcctc catggctctt tacaactctg tctacttcat cgtcttcttc    540
ggctcgcgtg gcttcctcat ccccaggcgt gcggaggggg ccaccaaagt cagccaggcc    600
gtgctgaagg ccaagattca gaactgtct gagagcctgg agtcctgcac tggtgccctg    660
gatgaactta gtgagcagct ggaatcccgg gtccagctct gtaccaaggc cggccgtggt    720
cacaacctca ggaactcccc tgatctggat gcagcgttgt ttttctaaga gcatcctcta    780
gctgtgtgga atgttctaga ttcgcagcat ccacaaggaa gtgctacatg gcggagtgc    840
aaaggatttc agaagctctt cttgcagggc atcagtccgt agctccttgt gtgtgcgaaa    900
gacttttcac ttgtgtaatc ccaactgagt atgtgaccct aaacagtcac tttggggact    960
ccccaaatcc ttttagctg cacacagctt gtcagactgt ccttcaatta gagttattgg   1020
```

-continued

```
ggtgggggggg cttgatggct tgagtaatag aggtctggcg aggtgtctcc ctcttggacc      1080
tcttatgtgt tgttactaga atcctgagat tctcaaatgt tggtgagagg agacttttac      1140
ttttcaactt tgcttcggca gtttccgata cacaggactc cagaatccag aacaagaaag      1200
aagaaccttg tgtttgtagg gtgtgcagac ccagacgggg ccgaggagct gacttgctca      1260
gctctcacac gcagccagtt tatccactca cagaccaaac ctggctactg catagactgt      1320
tccagtgtgg cttcaaatcc acacctctag gtaccctgag aaggaaagcc acctgaagag      1380
tcactctaat cccaacacgc tcaccccctt cacgtccata aaggagctgg gcaaggggtg      1440
agatgaagac cctgacaatt ttaaatgact gtagcataga gagccatggc ctttgagttt      1500
aagagtcttg atcccaggtt ctgtccccca ctgtcctgtg acttagccac cttgtcttgc      1560
tacagatggt ggtaggaggc caccctgttg cgaagtcctg agataatgac aaacacagag      1620
gctagctcac aaaaatgtac ttcctggcct ggcttctgaa gggttaactg ttgggctcca      1680
tcccagattt ctgagatcag gaactccaaa tatgaggccc gcctctggct gattctgatg      1740
ccccataaat gtttgaaaat gacacagcaa aggttcatct ccagccaggt gtggtgggac      1800
acacctgtaa ggccagcgct tggagatgga gacaggggga ccagtagttc agggtcattc      1860
ttggctacat agcaaactca aggccaccct ggtctcaaaa accaaaacaa aaagccatct      1920
tctgactccc ttcaattgtt caaagccttt ccagggcctt cagaatcacg ctcagagtgt      1980
tctgggaaga ttagcccaga agccagagaa agagtacgct gtgtgcttgt aaagccagtt      2040
actctgtccc ctgtgaacta ggagacagag cacttccgac cctatagagg gcagtagtgg      2100
ccattccttg taggggactg gtatagaagt aatgtgaact atttaaaaat agttatttaa      2160
ttgctgcctt cacatttgat tttatttaac cttcacatta tttagaaaat aataagagta      2220
gtaagtgtct gaataggaag ggagtctctt aaggctcttt ccaagagctc aggtttggat      2280
ttctagagtc cccccgaccc cagagaggac tctttagtgt ttgacacggt ctttgtaagt      2340
aagatgggga gtcctggaga gagagaccaa gctgattttt aaactaggaa atggagtctt      2400
gaactgtgga agatttgaaa agttaagcct atgtgtcttg aaggtacttg gccagaaaag      2460
cacttggctt gaaaaagaaa acctgtttaa ttcaggggtg gaggaataga gacagatgaa      2520
gaaagcattt agacctcgga aacctgatgt cctatgaaat tctgtttta taaaattgtg      2580 ttatggtgga gatctgttgc atttcgactt tgtggctgta agaaacctgt tatctatgtt      2640
taagaaagta cttctaattt attcaatgtc ttcctaaatt atccttaaaa aaaaaagtt      2700 ggaaagtcta tgagaccgta cctaagaaac cttgactgtg tatttaagtt atttaatgcc      2760
atgcatttgt gaagcccctt cccagtgatg gctgtggtgt gtctgaggaa atgtaagttt      2820
ggcatgaggg ggaggggctg ctgtttctat atttgttttt gttttctata aacagtaatc      2880
aggatgtatc ctggtttcat ttgacattga aaaaaaaaaa aaaactcgtg ccgaattc       2938
```

<210> SEQ ID NO 29
<211> LENGTH: 2527
<212> TYPE: DNA
<213> ORGANISM: Eukaryote
<220> FEATURE:
<221> NAME/KEY: CDS
<222> LOCATION: (41)...(871)

<400> SEQUENCE: 29

```
tacggctgcg agaagacgac agaaggggag cggagccaag atg gcg gcg gag ctg      55
                                             Met Ala Ala Glu Leu
                                              1               5
```

-continued

| | |
|---|---|
| gaa tac gag tct gtg ctg tgt gtg aag ccc gac gtc agc gtc tac cgg<br>Glu Tyr Glu Ser Val Leu Cys Val Lys Pro Asp Val Ser Val Tyr Arg<br>          10                    15                  20 | 103 |
| att ccg ccg cgg gcc tcc aac cgc ggt tac agg gca tct gac tgg aag<br>Ile Pro Pro Arg Ala Ser Asn Arg Gly Tyr Arg Ala Ser Asp Trp Lys<br>             25                    30                  35 | 151 |
| cta gac cag cct gat tgg act ggt cgc ctc cga atc act tca aaa ggg<br>Leu Asp Gln Pro Asp Trp Thr Gly Arg Leu Arg Ile Thr Ser Lys Gly<br>      40                    45                  50 | 199 |
| aag att gcc tac atc aaa ctg gaa gat aaa gtt tca ggg gag ctc ttc<br>Lys Ile Ala Tyr Ile Lys Leu Glu Asp Lys Val Ser Gly Glu Leu Phe<br>     55                    60                  65 | 247 |
| gct cag gcg cca gta gag cag tac cct ggg att gct gtg gag act gtg<br>Ala Gln Ala Pro Val Glu Gln Tyr Pro Gly Ile Ala Val Glu Thr Val<br>70                    75                  80                  85 | 295 |
| gcc gac tcc agc cgc tac ttt gtg atc agg atc cag gat ggc acc ggg<br>Ala Asp Ser Ser Arg Tyr Phe Val Ile Arg Ile Gln Asp Gly Thr Gly<br>             90                    95                 100 | 343 |
| cgc agt gcg ttt att ggc atc ggc ttc acg gac cgg gga gat gcc ttc<br>Arg Ser Ala Phe Ile Gly Ile Gly Phe Thr Asp Arg Gly Asp Ala Phe<br>        105                 110               115 | 391 |
| gac ttt aat gtc tcc ctg caa gat cac ttc aag tgg gta aag cag gaa<br>Asp Phe Asn Val Ser Leu Gln Asp His Phe Lys Trp Val Lys Gln Glu<br>     120                 125               130 | 439 |
| acc gag atc tcc aaa gaa tcg cag gaa atg gat agt cgt ccc aag ttg<br>Thr Glu Ile Ser Lys Glu Ser Gln Glu Met Asp Ser Arg Pro Lys Leu<br>        135               140               145 | 487 |
| gat tta ggc ttc aag gaa ggg caa acc atc aag ctg agt att ggg aac<br>Asp Leu Gly Phe Lys Glu Gly Gln Thr Ile Lys Leu Ser Ile Gly Asn<br>150                  155               160               165 | 535 |
| att aca gcc aag aaa ggg ggt act tct aag ccc cgg gcc tca gga acg<br>Ile Thr Ala Lys Lys Gly Gly Thr Ser Lys Pro Arg Ala Ser Gly Thr<br>             170               175               180 | 583 |
| ggg ggc ctg agc tta ctc cca cct cct cct gga ggc aaa gtc act atc<br>Gly Gly Leu Ser Leu Leu Pro Pro Pro Pro Gly Gly Lys Val Thr Ile<br>        185               190               195 | 631 |
| ccc cca ccg tcc tcc tcc gtt gcc atc agc aac cac gtc acc cca cca<br>Pro Pro Pro Ser Ser Ser Val Ala Ile Ser Asn His Val Thr Pro Pro<br>     200                 205               210 | 679 |
| ccc att cca aaa tct aac cat gga agt aat gat tca gat atc ctg tta<br>Pro Ile Pro Lys Ser Asn His Gly Ser Asn Asp Ser Asp Ile Leu Leu<br>215                  220               225 | 727 |
| gat ttg gat tct cca gct cct gtc ccg act tca gca cca gct cca gct<br>Asp Leu Asp Ser Pro Ala Pro Val Pro Thr Ser Ala Pro Ala Pro Ala<br>230                  235               240               245 | 775 |
| cca gct tct aca agc aat gac ttg tgg gga gac ttt agc act gca tcc<br>Pro Ala Ser Thr Ser Asn Asp Leu Trp Gly Asp Phe Ser Thr Ala Ser<br>          250                 255               260 | 823 |
| agc tct gtt cca aac cag gca cca cag cca tct aac tgg gtc cag ttt<br>Ser Ser Val Pro Asn Gln Ala Pro Gln Pro Ser Asn Trp Val Gln Phe<br>        265               270               275 | 871 |
| tgagtcgcat tggcaagaag ttgaggacac ttgaagaata aaaatgacct caagggcacc | 931 |
| attctatgag ggagttgagg gacggcttaa tttcccagga cccaaatcag tggtcagtct | 991 |
| ttcctgtagc ttctctgtgc attcaggctg gatttttttt ttttttttt ttggttacct | 1051 |
| ctgtgttact tgctgtatat ccaggagaca atctgctgtt tcctgctcag aaccaagcaa | 1111 |
| gggagtagtg ggtattatca cactgactga ctttgcagag ttcagaaggc caacttgatg | 1171 |

```
agtgggagtg acctcgaacg tatgtaaatc cttgaactta tttcagaatc atctcatgat      1231
tccctagtta gcaatttcag gagagacaaa tgccttgaaa ctgtcttctc cactaatccg      1291
agactaaata tggtcaggct ggccccagga ctcatgaagt tagggttttc atgggggtag      1351
atttggagaa agctgtgtcc cggctctctt ctgtaaggcc tccttcaggc ttaccccatg      1411
cagtgaactt cccgtgctgg gtggagcccc atcaccttct tgtgtgttta catgttgttt      1471
cctttgacaa gagggttatg ttggtggcac ctcactgttt tcttgttgaa tagtgcagca      1531
tctttgacca gtgaatattt ctgagatgaa ggggtcaagg ggctgtgctt ccatggtgt       1591 agtctacaga agtgttaat ttcttgcggc cccacgggat tgctgcactg acgcatagaa       1651
ttgatctata ctcaccctgt gtttgacctg aagagtttta acttgatgtg tagagcagag      1711
agctggaagc actaagttcc cattcagtac ccacaatgcc ttgctgcctg gtttgactcc      1771
ttttcataaa catttcattt cagtccatct agcacttctg tggaaagctg ctgttgattg      1831
tgtcagtgtg aaggaggtga agtcacagct ttctttacct atgacagtta ggctttgcac      1891
tagacgttga taccagctag gatatcttaa aggaagttac cgccccatca ctctccagtc      1951
tctggccgcc attccttta cagtgctgtg aagagcgtcc tctgaggtcg gtgggtactg       2011
tctcctgttg gtcgggcagt ttgagggagg agtgggagga ctcacactcc tgcaggtacc      2071
tgtttgggta gcacactggc tgcagagagt cctttcagat atattgtttc tcaatgttct      2131
tcgtagcttt ttctaacttc gggtccattt ttcccatcgc ctcttcccat tcccaggcag      2191
ctctcttgtt gcagagccat gcaggacgt ttaagttcca ataaaacac taagaagaaa        2251 gtatagaatc actagtgact gttgggaaac ctatttctc aatcttcctc cattttgtgt       2311
tctttgtatt cttaagatga taatatatta tgtatttgaa ttgctgaaaa ttgaaaatga      2371
agttgaagat atatgtatat aagcgtatgc tgtattggtg caataatggt aattaaagat      2431
attaaaaaag aaaaaaaaaa aaaaaaaaaa aaaaaaaaaa aaaaaaaaaa aaaaaaaaaa      2491
aaaaaaaaaa aaaaaaaaaa aaaaaaaaaa aaaaaa                                2527

<210> SEQ ID NO 30
<211> LENGTH: 277
<212> TYPE: PRT
<213> ORGANISM: Eukaryote

<400> SEQUENCE: 30

Met Ala Ala Glu Leu Glu Tyr Glu Ser Val Leu Cys Val Lys Pro Asp
 1               5                  10                  15

Val Ser Val Tyr Arg Ile Pro Pro Arg Ala Ser Asn Arg Gly Tyr Arg
                20                  25                  30

Ala Ser Asp Trp Lys Leu Asp Gln Pro Asp Trp Thr Gly Arg Leu Arg
            35                  40                  45

Ile Thr Ser Lys Gly Lys Ile Ala Tyr Ile Lys Leu Glu Asp Lys Val
        50                  55                  60

Ser Gly Glu Leu Phe Ala Gln Ala Pro Val Glu Gln Tyr Pro Gly Ile
65                  70                  75                  80

Ala Val Glu Thr Val Ala Asp Ser Ser Arg Tyr Phe Val Ile Arg Ile
                85                  90                  95

Gln Asp Gly Thr Gly Arg Ser Ala Phe Ile Gly Ile Gly Phe Thr Asp
            100                 105                 110

Arg Gly Asp Ala Phe Asp Phe Asn Val Ser Leu Gln Asp His Phe Lys
        115                 120                 125

Trp Val Lys Gln Glu Thr Glu Ile Ser Lys Glu Ser Gln Glu Met Asp
```

```
                130                 135                 140
Ser Arg Pro Lys Leu Asp Leu Gly Phe Lys Glu Gly Gln Thr Ile Lys
145                 150                 155                 160

Leu Ser Ile Gly Asn Ile Thr Ala Lys Lys Gly Gly Thr Ser Lys Pro
                165                 170                 175

Arg Ala Ser Gly Thr Gly Leu Ser Leu Leu Pro Pro Pro Gly
            180                 185                 190

Gly Lys Val Thr Ile Pro Pro Ser Ser Val Ala Ile Ser Asn
        195                 200                 205

His Val Thr Pro Pro Ile Pro Lys Ser Asn His Gly Ser Asn Asp
        210                 215                 220

Ser Asp Ile Leu Leu Asp Leu Asp Ser Pro Ala Pro Val Pro Thr Ser
225                 230                 235                 240

Ala Pro Ala Pro Ala Pro Ala Ser Thr Ser Asn Asp Leu Trp Gly Asp
                245                 250                 255

Phe Ser Thr Ala Ser Ser Ser Val Pro Asn Gln Ala Pro Gln Pro Ser
                260                 265                 270

Asn Trp Val Gln Phe
            275

<210> SEQ ID NO 31
<211> LENGTH: 2922
<212> TYPE: DNA
<213> ORGANISM: Eukaryote
<220> FEATURE:
<221> NAME/KEY: CDS
<222> LOCATION: (28)...(768)

<400> SEQUENCE: 31
attcggcacg agccagagtg aagggggc atg gag aag tgg acg gcc tgg gag ccg       54
                                Met Glu Lys Trp Thr Ala Trp Glu Pro
                                  1               5 cag ggc gcc gat gcg ctg cgg cgc ttt caa ggg ttg ctg ctg gac cgc         102
Gln Gly Ala Asp Ala Leu Arg Arg Phe Gln Gly Leu Leu Leu Asp Arg
 10              15                  20                  25 cgc ggc cgg ctg cac tgc caa gtg ttg cgc ctg cgc gaa gtg gcc cgg         150
Arg Gly Arg Leu His Cys Gln Val Leu Arg Leu Arg Glu Val Ala Arg
                 30                  35                  40 agg ctc gag cgt cta cgg agg cgc tcc ttg gca gcc aac gta gct ggc         198
Arg Leu Glu Arg Leu Arg Arg Arg Ser Leu Ala Ala Asn Val Ala Gly
             45                  50                  55 agc tct ctg agc gct gct ggc gcc cta gca gcc atc gtg ggg tta tca         246
Ser Ser Leu Ser Ala Ala Gly Ala Leu Ala Ala Ile Val Gly Leu Ser
         60                  65                  70 ctc agc ccg gtc acc ctg gga gcc tcg ctc gtg gcg tcc gcc gtg ggc         294
Leu Ser Pro Val Thr Leu Gly Ala Ser Leu Val Ala Ser Ala Val Gly
     75                  80                  85 tta ggg gtg gcc acc gcc gga ggg gca gtc acc atc acg tcc gac ctc         342
Leu Gly Val Ala Thr Ala Gly Gly Ala Val Thr Ile Thr Ser Asp Leu
 90                  95                 100                 105 tct ctg atc ttc tgc aat tcc cgg gag gta cgg agg gtg caa gag atc         390
Ser Leu Ile Phe Cys Asn Ser Arg Glu Val Arg Arg Val Gln Glu Ile
                 110                 115                 120 gcc gcc acc tgc cag gac cag atg cgc gaa ctc ctg agc tgc ctt gag         438
Ala Ala Thr Cys Gln Asp Gln Met Arg Glu Leu Leu Ser Cys Leu Glu
             125                 130                 135 ttc ttc tgt cag tgg cag ggg cgc ggg gac cgc cag ctg ctg cag agc         486
Phe Phe Cys Gln Trp Gln Gly Arg Gly Asp Arg Gln Leu Leu Gln Ser
         140                 145                 150
```

-continued

| | |
|---|---|
| ggg agg gac gcc tcc atg gct ctt tac aac tct gtc tac ttc atc gtc<br>Gly Arg Asp Ala Ser Met Ala Leu Tyr Asn Ser Val Tyr Phe Ile Val<br>155                       160                     165 | 534 |
| ttc ttc ggc tcg cgt ggc ttc ctc atc ccc agg cgt gcg gag ggg gcc<br>Phe Phe Gly Ser Arg Gly Phe Leu Ile Pro Arg Arg Ala Glu Gly Ala<br>170                     175                     180                     185 | 582 |
| acc aaa gtc agc cag gcc gtg ctg aag gcc aag att cag aaa ctg tct<br>Thr Lys Val Ser Gln Ala Val Leu Lys Ala Lys Ile Gln Lys Leu Ser<br>190                     195                     200 | 630 |
| gag agc ctg gag tcc tgc act ggt gcc ctg gat gaa ctt agt gag cag<br>Glu Ser Leu Glu Ser Cys Thr Gly Ala Leu Asp Glu Leu Ser Glu Gln<br>205                     210                     215 | 678 |
| ctg gaa tcc cgg gtc cag ctc tgt acc aag gcc ggc cgt ggt cac aac<br>Leu Glu Ser Arg Val Gln Leu Cys Thr Lys Ala Gly Arg Gly His Asn<br>220                     225                     230 | 726 |
| ctc agg aac tcc cct gat ctg gat gca gcg ttg ttt ttc taa<br>Leu Arg Asn Ser Pro Asp Leu Asp Ala Ala Leu Phe Phe<br>235                     240                     245 | 768 |
| gagcatcctc tagctgtgtg aatgttcta gattcgcagc atccacaagg aagtgctaca | 828 |
| tgggcggagt gcaaaggatt tcagaagctc ttcttgcagg gcatcagtcc gtagctcctt | 888 |
| gtgtgtgcga aagacttttc acttgtgtaa tcccaactga gtatgtgacc ctaaacagtc | 948 |
| actttgggga ctccccaaat cctttttagc tgcacacagc ttgtcagact gtccttcaat | 1008 |
| tagagttatt ggggtggggg ggcttgatgg cttgagtaat agaggtctgg cgaggtgtct | 1068 |
| ccctcttgga cctcttatgt gttgttacta gaatcctgag attctcaaat gttggtgaga | 1128 |
| ggagactttt acttttcaac tttgcttcgg cagtttccga tacacaggac tccagaatcc | 1188 |
| agaacaagaa agaagaacct tgtgtttgta gggtgtgcag acccagacgg ggccgaggag | 1248 |
| ctgacttgct cagctctcac acgcagccag tttatccact cacagaccaa acctggctac | 1308 |
| tgcatagact gttccagtgt ggcttcaaat ccacacctct aggtaccctg agaaggaaag | 1368 |
| ccacctgaag agtcactcta atcccaacac gctcacccccc ttcacgtcca taaggagct | 1428 |
| gggcaagggg tgagatgaag accctgacaa ttttaaatga ctgtagcata gagagccatg | 1488 |
| gcctttgagt ttaagagtct tgatcccagg ttctgtcccc cactgtcctg tgacttagcc | 1548 |
| accttgtctt gctacagatg gtggtaggag gccaccctgt tgcgaagtcc tgagataatg | 1608 |
| acaaacacag aggctagctc acaaaaatgt acttcctggc ctggcttctg aagggttaac | 1668 |
| tgttgggctc catcccagat ttctgagatc aggaactcca aatatgaggc ccgcctctgg | 1728 |
| ctgattctga tgccccataa atgtttgaaa atgacacagc aaaggttcat ctccagccag | 1788 |
| gtgtggtggg acacacctgt aaggccagcg cttggagatg gagacagggg gaccagtagt | 1848 |
| tcagggtcat tcttggctac atagcaaact caaggccacc ctggtctcaa aaaccaaaac | 1908 |
| aaaaagccat cttctgactc ccttcaattg ttcaaagcct ttccagggcc ttcagaatca | 1968 |
| cgctcagagt gttctgggaa gattagccca gaagccagag aaagagtacg ctgtgtgctt | 2028 |
| gtaaagccag ttactctgtc ccctgtgaac taggagacag agcacttccg acccctataga | 2088 |
| gggcagtagt ggccattcct tgtaggggac tggtatagaa gtaatgtgaa ctatttaaaa | 2148 |
| atagttattt aattgctgcc ttcacatttg attttattta accttcacat tatttagaaa | 2208 |
| ataataagag tagtaagtgt ctgaatagga agggagtctc ttaaggctct ttccaagagc | 2268 |
| tcaggtttgg atttctagag tccccccgac cccagagagg actctttagt gtttgacacg | 2328 |
| gtctttgtaa gtaagatggg gagtcctgga gagagagacc aagctgattt ttaaactagg | 2388 |

| | |
|---|---|
| aaatggagtc ttgaactgtg aagatttga aaagttaagc ctatgtgtct tgaaggtact | 2448 |
| tggccagaaa agcacttggc ttgaaaaaga aaacctgttt aattcagggg tggaggaata | 2508 |
| gagacagatg aagaaagcat ttagacctcg gaaacctgat gtcctatgaa attctgtttt | 2568 |
| tataaaattg tgttatggtg gagatctgtt gcatttcgac tttgtggctg taagaaacct | 2628 |
| gttatctatg tttaagaaag tacttctaat ttattcaatg tcttcctaaa ttatcctttta | 2688 |
| aaaaaaaaag ttggaaagtc tatgagaccg tacctaagaa accttgactg tgtatttaag | 2748 |
| ttatttaatg ccatgcattt gtgaagcccc ttcccagtga tggctgtggt gtgtctgagg | 2808 |
| aaatgtaagt ttggcatgag ggggagggc tgctgtttct atatttgttt ttgttttcta | 2868 |
| taaacagtaa tcaggatgta tcctggtttc atttgacatt gaaaaaaaaa aaaa | 2922 |

<210> SEQ ID NO 32
<211> LENGTH: 246
<212> TYPE: PRT
<213> ORGANISM: Eukaryote

<400> SEQUENCE: 32

Met Glu Lys Trp Thr Ala Trp Glu Pro Gln Gly Ala Asp Ala Leu Arg
1               5                   10                  15

Arg Phe Gln Gly Leu Leu Leu Asp Arg Arg Gly Arg Leu His Cys Gln
            20                  25                  30

Val Leu Arg Leu Arg Glu Val Ala Arg Arg Leu Glu Arg Leu Arg Arg
        35                  40                  45

Arg Ser Leu Ala Ala Asn Val Ala Gly Ser Ser Leu Ser Ala Ala Gly
    50                  55                  60

Ala Leu Ala Ala Ile Val Gly Leu Ser Leu Ser Pro Val Thr Leu Gly
65                  70                  75                  80

Ala Ser Leu Val Ala Ser Ala Val Gly Leu Gly Val Ala Thr Ala Gly
                85                  90                  95

Gly Ala Val Thr Ile Thr Ser Asp Leu Ser Leu Ile Phe Cys Asn Ser
            100                 105                 110

Arg Glu Val Arg Arg Val Gln Glu Ile Ala Ala Thr Cys Gln Asp Gln
        115                 120                 125

Met Arg Glu Leu Leu Ser Cys Leu Glu Phe Phe Cys Gln Trp Gln Gly
    130                 135                 140

Arg Gly Asp Arg Gln Leu Leu Gln Ser Gly Arg Asp Ala Ser Met Ala
145                 150                 155                 160

Leu Tyr Asn Ser Val Tyr Phe Ile Val Phe Phe Gly Ser Arg Gly Phe
                165                 170                 175

Leu Ile Pro Arg Arg Ala Glu Gly Ala Thr Lys Val Ser Gln Ala Val
            180                 185                 190

Leu Lys Ala Lys Ile Gln Lys Leu Ser Glu Ser Leu Glu Ser Cys Thr
        195                 200                 205

Gly Ala Leu Asp Glu Leu Ser Glu Gln Leu Glu Ser Arg Val Gln Leu
    210                 215                 220

Cys Thr Lys Ala Gly Arg Gly His Asn Leu Arg Asn Ser Pro Asp Leu
225                 230                 235                 240

Asp Ala Ala Leu Phe Phe
                245

<210> SEQ ID NO 33
<211> LENGTH: 1446
<212> TYPE: DNA
<213> ORGANISM: Eukaryote

```
<220> FEATURE:
<221> NAME/KEY: misc_feature
<222> LOCATION: (1)...(1446)
<223> OTHER INFORMATION: n = A,T,C or G

<400> SEQUENCE: 33
gctttggaaa ccggactgca ggctaaactg gcttcttttg aatccttgga agcataaagg      60
acaagtagca gggctcgcag tcttccattt gtcactggag aagaacttat aattcagaag     120
atctgggtct ggacccaggc tgaccacttt ggagctttga gactctggga ttgtgatcca     180
gttctgagct ggtgataaac actccttgtg acttttggtc aattcagcta ccagattcca     240
gccaacatga ccctcgcagc ctataaggag aagatgaagg aactcccact agtgtctctg     300
ttctgctcct gttttctgtc tgatcccctg aataaatcat cctacaaata tgaaggctgg     360
tgtgggagac agtgtaggag gaaaggtcaa agccagcgga aaggcagtgc tgactggaga     420
gaaagaaaag aacaggcaga tacggtagac ctgaactggt gtgtcatctc tgatatggaa     480
gtcatcgagc tgaataagtg tacctcgggc cagtcctttg aagtcatcct gaagccacct     540
tcctttgacg gggtgcctga gtttaatgcc tccctcccaa gacgtcgaga cccatcgcta     600
gaagagatac agaagaagct agaagcagca gaggagcgaa ggaagtacca ggaagctgag     660
ctcctaaaac accttgcaga gaaacgagag catgagcgtg aggtaatcca gaaagctatc     720
gaggaaaaca caaacttcat caagatggcg aaagagaagc tggcccagaa gatggagtcc     780
aataaggaaa accgggaggc ccatctggct gccatgttgg agcggctgca agagaaggac     840
aagcacgcag aggaggtgcg gaaaaacaag gagctgaagg aagaggcctc caggtaaagc     900
ccanaggcca aggaagtttc caggacagcc ggacagctcc cgcagcaacc tggttccagc     960
agcatcggcc gctggctgct ctcccagcac tggggttcgg ggggaggggg gtggccaaag    1020
gggcgtttcc tctgcttttg gtgtttgtac atgtaaaaga ttgaccagtg aagccatcct    1080
atttgtttct ggggaacaat gatggggtgg gagagggac agagagtgtt tggaaaagga    1140
ggtgaagatg agcccgagga ctttgtgaca ctgtccactg actgcagact tgggccaagg    1200
cccccgcttt tcacggctct gcctggacat tcggcctcca ggttcctagt ggagagaaga    1260
tgtgacagaa gttcagagtg aagggccgag tcctggtggg gtggtgtgca gggccagcag    1320
gacgagcccg tctggatgga gtgaaaccta ccctgagcgg gtgggataag gtctgtgtgc    1380
gtctgttcat tgtcatcttt tgatcatcat gaccaacgaa acatttaaaa aaaaaaaaa    1440
aaaaaa                                                              1446

<210> SEQ ID NO 34
<211> LENGTH: 5305
<212> TYPE: DNA
<213> ORGANISM: Eukaryote
<220> FEATURE:
<221> NAME/KEY: misc_feature
<222> LOCATION: (1)...(5305)
<223> OTHER INFORMATION: r = G or A
      y = C or T
      m = A or C
      k = G or T
      s = G or C
      w = A or T
      n = A, T, G, or C

<400> SEQUENCE: 34
gataaacact ccttgtgact tttggtcaat tcagctacca gattccagcc aacatgaccc      60
tcgcaggtag gtacatgcac cagtcagtga tgaacaccat aacacaagcc attttctat     120
```

-continued

```
ctctgtgtgt gtccatgtgt attaaggtgc atccgtgtgt gtgatacaca cgtaggtgca      180
tggcatgcat gtgtgtgcaa atgcatatac aagtccaagg acaggggttg gggatttagc      240
tcantggtag agcacttgcc tangaagcgc aaggccctgg gttcggtccc cagctccgaa      300
aaaagaacc aaaaaaaaaa aaaaaaaaa aaaaaaatt tccanggaca accccaaatt         360
tcctttcncn aaanccancc ancttccatt naaaaaaaan gggtcncncn tgggttaaac      420
catttnnaaa nggcnaacct nacnggccak tgaktgccag gaatcttctt atycctgccc      480
wacctccaat gtctttcaca tgtgaatgct gagggtcaga acttgtgctt acaaggcaga      540
cattttgcca gctctccggc catctttctc tatgtatgta cactcacaga tgcacaggaa      600
gagagggtag agaagccaag aggcaaagtc atttctgggt ggtgggtggg atcacagctg      660
aattcttctt cctcatttgc tctgtgtgta ttatttaatt ttaaaataat acctttataa      720
tagtatcgaa actatgcttt caagtttgta agagaaagtg atcactgggc tgtgtagtga      780
ggggtctttt atattatgca tataacatgg tgcaatggga aggactggca gaggcctcca     840
tgatgaccta tgacttctag ggagactcag tcgtgtcaag ggtacattcc tactctgcag      900
acagcttctc cctggtttga ttcctgtgct gggaagattt gaggagtctt ccagcctgac      960
ctcttctaca gtgggcctgg actttaagga gagtagcaag gaagtctttt tattaatctc     1020
ttacccttta ggcagcagtg tcaagtactt ttagcagaat taaatataga tttcctacaa     1080
actacaaact tcaaagccct ggtttatcct tgggtgggag taggagatgg agggccaggg     1140
tcagggcact gcacttggga tctttacttg agggtactca acgcttggta gtaacaaaaa     1200
gtggggtgag tgacaatgtt aattttcaac tgggaggtag cccaggcttg ggtactttgg     1260
agccagaaag cctgggctga ctcacagaag tggtgctctc tctygyagcc tataaggagw     1320
wgatgaagga actcccacta gtgtctctgt tctgctcctg ttttctgtct gatccccygr     1380
ataaatcatc ctacaaatat gaaggtgagt aggggctagg ctgggataga aaagggtgga     1440
ggcttctgtg tcctgtgttt gtsggtgccc cacattgact cctatcttgt aaaactgtcc     1500
tggtcgcagt gtgtcttatt tcccagaggc tgaggagtct gagcccaggg ggatgtagcc     1560
tgggtgccaa gcagcctcca gggatctgga ttgggccctc ctggagcact gctcctaga      1620
gtccctttr cacattcctt gacaccacag aggacaccag gataagccag acacaagttt     1680
tgagattcca ttcatggagg cccagaacag aaaaagaaaa cttagtgtgt tcaccagggc     1740
ttctagggac aggtagagat gctcctagac aggtccaggg tgggaatagc acttctaacc     1800
tggatggtga cagttcgagc ccctagaccc tatcagagag tactggattg tcatgctgtc     1860
aggaggagtg gtcaggggac agataggtca tctcttcatt tctgtttgcc aggaagggat     1920
gggtttggtc tgtcaataag agagatgggt gtttggatga cctgagtctg ttttttccat     1980
ttaggctggt gtgggagaca gtgtaggagg aaaggtcaaa gccagcggaa aggcagtgct     2040
gactggagag aaagaagaga acagggtagg ccggagccag gggagaggtc cacaagccat     2100
cagagggaca gggcaaggag gggctggcgg tggggatggg tgaaatgaac tggtgtctgt     2160
caccagcgag gaacaacagc agctggtgct atcacaaatc acagctccct gcttaccctg     2220
taaaagccat tgaccttagg gtccaacgtt caggatcgac cagaccccta gtcattggtg     2280
tgccttggga ccctcagctt tcctgtgtct gtgtgcatgt acacatgctc attggggccc     2340
cagctgctcc tcagaaggtg agcagcccca actctgccct ccatagcaga tacggtagac     2400
ctgaactggt gtgtcatctc tgatatggaa gtcatcgagc tgagtaagtg tacctcgggc     2460
cagtcctttg aagtcatcct gaagccacct tcctttgacg gggtgcctga gtttaaagcc     2520
```

```
tccctcccaa gacgtcgaga cccatcgcta gaagagatac agaagaagct agaagcagca    2580
gaggagcgaa ggaaggttag tgtagcccca tgtcacttcc tcccatccca gcgggagcag    2640
gaagtgcagc tccatatctc ttcctcccat cccagtggga gtgggaagga tatttagaca    2700
gcacctcctg agtgctgggc atagaccggt agttctcaac cttcttagtg ctgtaaccct    2760
taatatatat atatatatat atatatatat atatatatat agttcctcat gttgtgatta    2820
cccccatac cataaactta tcccgttgct ctttatgtct tcataattat aattttgcta     2880
ctgttatgaa ttgtgataca actatcagac ctgcacccc taatggcagc agcccacgtg     2940
ttgagaacca ctggcataga tgtagactaa gataccacct gaaggggaca agactatgac    3000
tatgcactgg gtgagcttac agtgtggcta atggctaaaa tgtcacagtc ctcacaaagc    3060
tgcctttgta tgcagcttcc ttgttcccca ttgattctmg tccstcagct cagatgccca    3120
ttttaatgtg agtgtttctt nacctttcag aaanacaaaa caaaacaacc cagctttctc    3180
cactnaattg tgtggtccct ccctttaaat atccaaagca tttatcacac ccaggtctgg    3240
ngtccantat ntattgatat gcgtgtttat ttnnactagg gcaattntct ccnttccctg    3300
gtgtctggag ttgtgagggc cttgaggttt atagaagatc acttagtact tgtgaatgaa    3360
cgcgaggaaa aggagaaaag agactcagaa gctacttngg aaagggctac naaagccaaa    3420
tatgacggaa aggtttgcag tccatgncgt tgttctctgc ttctgggaca gaggaccagg    3480
ttcatctcat ctgggcatgg cactgttcag ctgtggtggt agaaatccac tctaaagggt    3540
cnttctcttt cttttgntgc cctagtacca ggaagctgag ctcctaaaac accttgcaga    3600
gaaacgagag catgagcgtg aggtaatcca gaaagctatc gaggaaaaca acaacttcat    3660
caagatggcg aaagagaagc tggcccagaa gatggagtcc aataaggaaa accgggaggc    3720
ccatctggct gccatgttgg agcggctgca agagaaggta agaggtcctg gattggcagg    3780
aggctccttc catggcaaga acgtgcaacc tacacatcac tctggaggaa gcggcctatg    3840
caggaattga aatgttttcta ccaggcaggg tcctcattgt tctaagggga agatttggga    3900
agtcataggc aagaagctca caccaaaccc tgggtggcct ccggggatct tctanggttt    3960
tgaaccggaa attctgcact gtctcangag cttgctcaca cccttctttt ctaaagaaag    4020
cccgcccagt gcaagtatct aaggagaggc acatgtctac acatttctgg cttcatcatt    4080
gaatgggcag atttgggtta gtgaaagata cagtcagctt ggctttgagc canggataca    4140
gcaagctcgg ttgccaatac agcaggatac aggattctcc ccagagctcc tcgtaagggc    4200
cagagagtan taggttttcc tcaatagtct gcctttgtca ataactcaaa tgtcacctgc    4260
atctgagcgg tgtgcgagac tggggttggt cctccatgtt attctttgga agacgtgctg    4320
acctcatttc ctgagtccca ggctgcctac gtttctcctg cagctcctgg gaagctttag    4380
ctctgtgttt tatttccaag gagccgcctg ctgcgcggtg actcccggga csgatcggtg    4440
gcctcgtccc atggtgagca gcgtggtcct tattccttcc tgcctaccca cctaaaacct    4500
caggcccttg acaattacca cagaaagatc tggcttcatc cagggatgtg agcagcacag    4560
gctggccagt aggtggcagc cctgtgctca tgttcaatta caggagggac agcaaggctt    4620
cttctccac tgagtgcctt ggggagggga cacaatctga gtgtgacttt gggctcctcc     4680
agttaatgag agatactgta agaaaactta agattgcctt tactttttat accaggtctc    4740
atgcattcca ggctggcctc aaattggcta aattgctgag gctagccttg gaattcttat    4800
cattttgtct tcacctccaa gtgcagggat tacaggcatg tgctgccaag cctattcaat    4860
```

```
gcaggtttgg ggcttgaacc cagggctctg tgcatgcaag ctaggcactc tgccaacagt    4920
gccatagccc caactcaagg caaattcttg aggaaaccac agatagaatg ggagagttat    4980
gggattgcag actcagctta aaatacatca caaagttagg ttgtgttgaa gcacttgaat    5040
gtttgtttat ataacgattc tattttatca taactcggtc atcacaagtt tacaaggcaa    5100
acattcttag tccagataag gaaccattc tagaggtcaa atgattccag agattnacag     5160
ggtatacgac aatanattgg ccctggccnc taatcaatgg ctgcttcttg ccgggtaaag    5220
aaaacatcca atataaccca cnnctttcan agcaanaatt tcaaagacaa caagcagggc    5280
aaaaccaggg tccaaagcaa ccact                                          5305
```

<210> SEQ ID NO 35
<211> LENGTH: 796
<212> TYPE: DNA
<213> ORGANISM: Eukaryote
<220> FEATURE:
<221> NAME/KEY: misc_feature
<222> LOCATION: (1)...(796)
<223> OTHER INFORMATION: n = A, T, G, or C

<400> SEQUENCE: 35

```
tgggcgggaa agcagtttgt cttgttgntg aattatgtta nnaagcaaat gaagttatct      60
tccaacacat gtgagggagt ccattgtctg gagtcaagca ntatttccca acagttctct     120
gtcagtacat aacgcaaggt cctccttcag tcagagattt aagacaacac taaagagatg    180
gagagaaata acacatctgt ggtgtgtcag ggacgctggc aatgggctga tcttttccca    240
ttcnttntaa actggctgtc ccaaagggcc cnttgtattt agtcaagtga ccattccaag    300
cgccagaatg accagtggag gtgcagagag ctagggtgt cttggggtcg ctgtgaggtg     360
ggtcccctgc aggatgtcta tgcacttgca ggcttataca cctgtgtccc gcgtnttact    420
tgcctccttc caccoctctt aggatacctt cgccgacagc tctgctctgc ccgtggtgac    480
catcttttgc gctccattct cttgcccttt gtcttcccct ggcagccttg tgtgacccgc    540 cttttgtccct cccttcctct ccaggacaag cacgcagagg aggtgcggaa aaacaaggag    600
ctgaaggaag aggcctccag gtaaagccca gaggccaagg aagtttccag acagccgga    660 cagctcccgc agcaacctgg ttccagcagc atcggctgct ggctgctctc ccagcactgg    720
ggttcggggg gaggggggtg gccaaagggg cgtttcctct gcttttggtg tttgtacatg    780
taaaagattg acctgt                                                    796
```

<210> SEQ ID NO 36
<211> LENGTH: 214
<212> TYPE: PRT
<213> ORGANISM: Eukaryote

<400> SEQUENCE: 36

```
Met Thr Leu Ala Ala Tyr Lys Glu Lys Met Lys Glu Leu Pro Leu Val
 1               5                  10                  15

Ser Leu Phe Cys Ser Cys Phe Leu Ser Asp Pro Leu Asn Lys Ser Ser
            20                  25                  30

Tyr Lys Tyr Glu Gly Trp Cys Gly Arg Gln Cys Arg Arg Lys Gly Gln
        35                  40                  45

Ser Gln Arg Lys Gly Ser Ala Asp Trp Arg Glu Arg Glu Gln Ala
    50                  55                  60

Asp Thr Val Asp Leu Asn Trp Cys Val Ile Ser Asp Met Glu Val Ile
 65                  70                  75                  80
```

```
Glu Leu Asn Lys Cys Thr Ser Gly Gln Ser Phe Glu Val Ile Leu Lys
                85                  90                  95

Pro Pro Ser Phe Asp Gly Val Pro Glu Phe Asn Ala Ser Leu Pro Arg
            100                 105                 110

Arg Arg Asp Pro Ser Leu Glu Glu Ile Gln Lys Lys Leu Glu Ala Ala
        115                 120                 125

Glu Glu Arg Arg Lys Tyr Gln Glu Ala Glu Leu Leu Lys His Leu Ala
    130                 135                 140

Glu Lys Arg Glu His Glu Arg Glu Val Ile Gln Lys Ala Ile Glu Glu
145                 150                 155                 160

Asn Asn Asn Phe Ile Lys Met Ala Lys Glu Lys Leu Ala Gln Lys Met
                165                 170                 175

Glu Ser Asn Lys Glu Asn Arg Glu Ala His Leu Ala Ala Met Leu Glu
            180                 185                 190

Arg Leu Gln Glu Lys Asp Lys His Ala Glu Gly Val Arg Lys Asn Lys
        195                 200                 205

Glu Leu Lys Glu Glu Ala
    210

<210> SEQ ID NO 37
<211> LENGTH: 3976
<212> TYPE: DNA
<213> ORGANISM: Eukaryote
<220> FEATURE:
<221> NAME/KEY: CDS
<222> LOCATION: (51)...(1790)

<400> SEQUENCE: 37
```

| | | |
|---|---|---|
| cggcgatggc ggcggctgct gtggtggcag cgacggtccc cgcgcagtcg atg ggc | | 56 |
|                                                                   Met Gly | | |
|                                                                       1 | | |

```
gcg gac ggc gcg tcc tcc gtg cac tgg ttc cgc aaa gga cta cgg ctc      104
Ala Asp Gly Ala Ser Ser Val His Trp Phe Arg Lys Gly Leu Arg Leu
        5                  10                  15 cac gac aac ccc gcg ctg tta gct gcc gtg cgc ggg gcg cgc tgt gtg      152
His Asp Asn Pro Ala Leu Leu Ala Ala Val Arg Gly Ala Arg Cys Val
     20                  25                  30 cgc tgc gtc tac atc ctc gac ccg tgg ttc gcg gcc tcc tcg tca gtg      200
Arg Cys Val Tyr Ile Leu Asp Pro Trp Phe Ala Ala Ser Ser Ser Val
 35                  40                  45                  50 ggc atc aac cga tgg agg ttc cta ctg cag tct cta gaa gat ctg gac      248
Gly Ile Asn Arg Trp Arg Phe Leu Leu Gln Ser Leu Glu Asp Leu Asp
                 55                  60                  65 aca agc tta aga aag ctg aat tcc cgt ctg ttt gta gtc cgg ggt cag      296
Thr Ser Leu Arg Lys Leu Asn Ser Arg Leu Phe Val Val Arg Gly Gln
             70                  75                  80 cca gct gat gtg ttc cca agg ctt ttc aag gaa tgg ggg gtg acc cgc      344
Pro Ala Asp Val Phe Pro Arg Leu Phe Lys Glu Trp Gly Val Thr Arg
         85                  90                  95 ttg acc ttt gaa tat gac tcc gaa ccc ttt ggg aaa gaa cgg gat gca      392
Leu Thr Phe Glu Tyr Asp Ser Glu Pro Phe Gly Lys Glu Arg Asp Ala
     100                 105                 110 gcc att atg aag atg gcc aag gag gcg ggt gtg gag gtg gtg act gag      440
Ala Ile Met Lys Met Ala Lys Glu Ala Gly Val Glu Val Val Thr Glu
115                 120                 125                 130 aac tct cac acc ctt tat gac tta gac aga atc atc gaa ctg aat ggg      488
Asn Ser His Thr Leu Tyr Asp Leu Asp Arg Ile Ile Glu Leu Asn Gly
                 135                 140                 145 cag aaa cca ccc ctt acc tac aag cgc ttt cag gct ctc atc agc cgt      536
```

```
                                                                    -continued Gln Lys Pro Pro Leu Thr Tyr Lys Arg Phe Gln Ala Leu Ile Ser Arg
            150                 155                 160 atg gag ctg ccc aag aag cca gtg ggg gct gtg agc agc cag cat atg        584
Met Glu Leu Pro Lys Lys Pro Val Gly Ala Val Ser Ser Gln His Met
        165                 170                 175 gag aac tgc aga gct gag atc cag gag aac cat gat gac acc tat ggc        632
Glu Asn Cys Arg Ala Glu Ile Gln Glu Asn His Asp Asp Thr Tyr Gly
    180                 185                 190 gtg cct tcc tta gag gaa ctg gga ttc ccc aca gaa gga ctt ggc cca        680
Val Pro Ser Leu Glu Glu Leu Gly Phe Pro Thr Glu Gly Leu Gly Pro
195                 200                 205                 210 gct gtt tgg caa gga gga gag aca gaa gct ctg gcc cgc ctg gat aag        728
Ala Val Trp Gln Gly Gly Glu Thr Glu Ala Leu Ala Arg Leu Asp Lys
                215                 220                 225 cac ttg gaa cgg aag gcc tgg gtt gcc aac tat gag aga cct cgg atg        776
His Leu Glu Arg Lys Ala Trp Val Ala Asn Tyr Glu Arg Pro Arg Met
            230                 235                 240 aat gcc aat tcc ttg ctg gcc agc ccc aca ggc ctc agc ccc tac ctg        824
Asn Ala Asn Ser Leu Leu Ala Ser Pro Thr Gly Leu Ser Pro Tyr Leu
        245                 250                 255 cgc ttt ggc tgc ctc tcc tgc cgc ctc ttc tac tac cgc ctg tgg gac        872
Arg Phe Gly Cys Leu Ser Cys Arg Leu Phe Tyr Tyr Arg Leu Trp Asp
    260                 265                 270 ttg tac aga aag gtg aag agg aac agc aca ccc ccc ctc tcc tta ttt        920
Leu Tyr Arg Lys Val Lys Arg Asn Ser Thr Pro Pro Leu Ser Leu Phe
275                 280                 285                 290 gga caa ctc cta tgg cga gaa ttc ttc tat aca gcg gcc acc aac aac        968
Gly Gln Leu Leu Trp Arg Glu Phe Phe Tyr Thr Ala Ala Thr Asn Asn
                295                 300                 305 ccc agg ttt gac cga atg gag ggg aac ccc atc tgc atc cag atc ccc       1016
Pro Arg Phe Asp Arg Met Glu Gly Asn Pro Ile Cys Ile Gln Ile Pro
            310                 315                 320 tgg gac cgc aac ccc gaa gcc ctg gcc aag tgg gcc gag ggc aag aca       1064
Trp Asp Arg Asn Pro Glu Ala Leu Ala Lys Trp Ala Glu Gly Lys Thr
        325                 330                 335 ggc ttc cct tgg att gac gcc atc atg acc caa ctg agg cag gag ggc       1112
Gly Phe Pro Trp Ile Asp Ala Ile Met Thr Gln Leu Arg Gln Glu Gly
    340                 345                 350 tgg atc cac cac ctg gcc cgg cac gct gtg gcc tgc ttc ctc acc cga       1160
Trp Ile His His Leu Ala Arg His Ala Val Ala Cys Phe Leu Thr Arg
355                 360                 365                 370 ggg gac ctc tgg gtc agc tgg gag agc ggg gtc cgg gta ttt gat gag       1208
Gly Asp Leu Trp Val Ser Trp Glu Ser Gly Val Arg Val Phe Asp Glu
                375                 380                 385 ttg ctc ctg gat gca gat ttc agc gtg aat gca ggc agc tgg atg tgg       1256
Leu Leu Leu Asp Ala Asp Phe Ser Val Asn Ala Gly Ser Trp Met Trp
            390                 395                 400 ctg tcc tgc agt gct ttc ttc caa cag ttc ttc cac tgc tac tgc cct       1304
Leu Ser Cys Ser Ala Phe Phe Gln Gln Phe Phe His Cys Tyr Cys Pro
        405                 410                 415 gtg ggc ttt ggc cga cgc acg gac ccc agt ggg gac tac atc cgg cga       1352
Val Gly Phe Gly Arg Arg Thr Asp Pro Ser Gly Asp Tyr Ile Arg Arg
    420                 425                 430 tac ctg ccc aaa ctg aaa ggc ttc ccc tct cga tat atc tat gag ccc       1400
Tyr Leu Pro Lys Leu Lys Gly Phe Pro Ser Arg Tyr Ile Tyr Glu Pro
435                 440                 445                 450 tgg aat gct ccc gag tcg gtt cag aag gcc gct aag tgc atc att ggc       1448
Trp Asn Ala Pro Glu Ser Val Gln Lys Ala Ala Lys Cys Ile Ile Gly
                455                 460                 465
```

-continued

| | |
|---|---|
| gtg gac tac cca cgg ccc atc gtc aac cac gca gag act agt cgg ctc<br>Val Asp Tyr Pro Arg Pro Ile Val Asn His Ala Glu Thr Ser Arg Leu<br>                    470                              475                          480 | 1496 |
| aac att gag cgg atg aag cag atc tac caa cag ctg tca cga tac cgg<br>Asn Ile Glu Arg Met Lys Gln Ile Tyr Gln Gln Leu Ser Arg Tyr Arg<br>                485                              490                        495 | 1544 |
| ggg ctc tgt ctg ttg gca tct gtc cct tcc tgt gta gaa gac ctc agt<br>Gly Leu Cys Leu Leu Ala Ser Val Pro Ser Cys Val Glu Asp Leu Ser<br>   500                             505                              510 | 1592 |
| cac cct gtg gca gag cct ggt tct agc cag gct ggg agc atc agc aac<br>His Pro Val Ala Glu Pro Gly Ser Ser Gln Ala Gly Ser Ile Ser Asn<br>515                      520                              525                        530 | 1640 |
| aca ggc ccc aga cca ctg tcc agt ggc cca gcc tcc ccc aaa cgc aag<br>Thr Gly Pro Arg Pro Leu Ser Ser Gly Pro Ala Ser Pro Lys Arg Lys<br>                535                              540                        545 | 1688 |
| ctg gaa gca gct gag gaa cct cca ggt gaa gaa ctg agc aag cgg gct<br>Leu Glu Ala Ala Glu Glu Pro Pro Gly Glu Glu Leu Ser Lys Arg Ala<br>              550                              555                            560 | 1736 |
| aga gtg aca gtg act cag atg cct gcc cag gag cca cca agc aag gac<br>Arg Val Thr Val Thr Gln Met Pro Ala Gln Glu Pro Pro Ser Lys Asp<br>   565                             570                              575 | 1784 |
| tcc tga gactggagag ccattgctcc gtgagcaaag cccaggtgcc tgagctgcca<br>Ser | 1840 |
| tggccacaga gaagacatgg aacctacaga gaagacagtc accaacagac agagcgagcg | 1900 |
| actgtgtgtg tgcagaggga ggtgtggtgt gccgtttgcg tgtgcatgca tctgtttaca | 1960 |
| ctctcatgat cctgaatgtt gcctgtgctg gaggagcccc tagatcatgc cttcttacca | 2020 |
| gggctgtttc ttgacttcca gacataagac tagaacccgc agcagtaacc gtcagcccaa | 2080 |
| atctgcccct gggagcccca tagggtggt aagaccctag cttgaattct ggtctctgcc | 2140 |
| tccccagact cttcttcctc cctccttta acaaggagct ggagggccac attttgact | 2200 |
| ctcatctaaa gcatggagtt tcagaggcag tcagagtcct gctgacttag ttcccacttt | 2260 |
| tctgacacta gaacctgagc aggctggaat agatgtgtcc tgttgatctt aaacagcctg | 2320 |
| gccagtcttc ttataaaatc ctgtgccatt aacaggcttc cctgatgtct aaggctacag | 2380 |
| actagtgtgt tgtgtgccca gtactgctta tgtcagcctc agacataata tcagtctttg | 2440 |
| tagaaccttc taaaaaaaac cacatgggga atagactccc agtcttctgt cccttcccta | 2500 |
| gcagctaagg tccagtctcg accttctaga agctgtggac aggctagggt ctgaactggt | 2560 |
| gaaagaaacc caggtcccac agctgcaggg cccctggttc ctctggctgt actcctgaca | 2620 |
| ccacatgctc cagccagtac tgctgatatc cagccaggca agctggacag cctggctggt | 2680 |
| cagcacctgc cctgcagtgt cagctgccca ggactgagct tccggagact cagacagact | 2740 |
| tagggtgga gcactgcctc tggcagttgg cgagaggtca gagaccatgc ctggcacatc | 2800 |
| aacatcttcg cagagcagca gtgaaggatt gacatagaga agtcaagcct tgctttccag | 2860 |
| gggagccaac tctccctccc actgttgggt catatggaga aagaagttat gaaaggatct | 2920 |
| gggggtacct gagcaagtct tccttccacc ccgtggcctg catttgagcc acagtgtgtg | 2980 |
| tgtgtgtgtg tgtgtgtgtg tgtgtgtgtg tgtgtgtgtg tgtgtgtgtg tgtgtgtaga | 3040 |
| gagagagaga gagagagaga gagagagaga gagagagaga gagagagaga gagagtttgt | 3100 |
| ttctgtttgg atttttgttc tcacatgtaa cattaagctg gcctctgggc cttttcctct | 3160 |
| ctacctcccc tgtgaccttt cctagcctca gagttgttaa tgcccttggc cctggccttt | 3220 |
| tttttgtgtc agaccagaac cctggggtca ggctcccccc tccagctgtc tagcacatct | 3280 |

-continued

```
gacaggcttc tttttgagat ggcctcaggt tttctcagca gagagctgcc tttagtccaa   3340
ctgtttatgt tcatcatcct gactagaagc atcctacgat tgtgtgaaga acggcatct    3400 gtgatgccat gttcagagtc atggggtgtg gcctccctgt ccctagcccc aggccaagag   3460
gaaagggcca aggctcttg ctggagggac agtagaatgc gtctggagaa ctggtcccag    3520
aggagcaaag gcttattctg gggccagtat ttatttttgca acatcttcag ctatggggac  3580
aatggccttc tctgcttttt tgatgatggc tctctcctca aggtacaagt tggcaaggtc   3640
atctgtcctt ccacctcctt gacatgttgg cccatttcca ggacagcctt ccagtgaatg   3700
gagcagacta ttccacagct gtgggataga gtgtcttgga gccctggaat gacttcatgc   3760
ctccttttgc ctagcctgag tggccctgag gactgtcaca gaacagtgcc ccatgtcctg   3820
ctcctgggcc cgagcatggg gaagagatgg ttgcaggcaa gagcacttta cagcattccc   3880
cattgctggg aaggttgttt ctcctacagt gtgtgaatac ttacctgttt tataaatgtc   3940
tgatcctgtc tgagtaaaaa aaaaaaaaaa aaaaaa                             3976
```

<210> SEQ ID NO 38
<211> LENGTH: 579
<212> TYPE: PRT
<213> ORGANISM: Eukaryote

<400> SEQUENCE: 38

```
Met Gly Ala Asp Gly Ala Ser Ser Val His Trp Phe Arg Lys Gly Leu
 1               5                  10                  15

Arg Leu His Asp Asn Pro Ala Leu Leu Ala Ala Val Arg Gly Ala Arg
            20                  25                  30

Cys Val Arg Cys Val Tyr Ile Leu Asp Pro Trp Phe Ala Ala Ser Ser
        35                  40                  45

Ser Val Gly Ile Asn Arg Trp Arg Phe Leu Leu Gln Ser Leu Glu Asp
    50                  55                  60

Leu Asp Thr Ser Leu Arg Lys Leu Asn Ser Arg Leu Phe Val Val Arg
65                  70                  75                  80

Gly Gln Pro Ala Asp Val Phe Pro Arg Leu Phe Lys Glu Trp Gly Val
                85                  90                  95

Thr Arg Leu Thr Phe Glu Tyr Asp Ser Glu Pro Phe Gly Lys Glu Arg
            100                 105                 110

Asp Ala Ala Ile Met Lys Met Ala Lys Glu Ala Gly Val Glu Val Val
        115                 120                 125

Thr Glu Asn Ser His Thr Leu Tyr Asp Leu Asp Arg Ile Ile Glu Leu
    130                 135                 140

Asn Gly Gln Lys Pro Pro Leu Thr Tyr Lys Arg Phe Gln Ala Leu Ile
145                 150                 155                 160

Ser Arg Met Glu Leu Pro Lys Lys Pro Val Gly Ala Val Ser Ser Gln
                165                 170                 175

His Met Glu Asn Cys Arg Ala Glu Ile Gln Glu Asn His Asp Asp Thr
            180                 185                 190

Tyr Gly Val Pro Ser Leu Glu Glu Leu Gly Phe Pro Thr Glu Gly Leu
        195                 200                 205

Gly Pro Ala Val Trp Gln Gly Gly Glu Thr Glu Ala Leu Ala Arg Leu
    210                 215                 220

Asp Lys His Leu Glu Arg Lys Ala Trp Val Ala Asn Tyr Glu Arg Pro
225                 230                 235                 240

Arg Met Asn Ala Asn Ser Leu Leu Ala Ser Pro Thr Gly Leu Ser Pro
                245                 250                 255
```

```
Tyr Leu Arg Phe Gly Cys Leu Ser Cys Arg Leu Phe Tyr Tyr Arg Leu
            260                 265                 270

Trp Asp Leu Tyr Arg Lys Val Lys Arg Asn Ser Thr Pro Pro Leu Ser
            275                 280                 285

Leu Phe Gly Gln Leu Leu Trp Arg Glu Phe Phe Tyr Thr Ala Ala Thr
            290                 295                 300

Asn Asn Pro Arg Phe Asp Arg Met Glu Gly Asn Pro Ile Cys Ile Gln
305                 310                 315                 320

Ile Pro Trp Asp Arg Asn Pro Glu Ala Leu Ala Lys Trp Ala Glu Gly
                325                 330                 335

Lys Thr Gly Phe Pro Trp Ile Asp Ala Ile Met Thr Gln Leu Arg Gln
            340                 345                 350

Glu Gly Trp Ile His His Leu Ala Arg His Ala Val Ala Cys Phe Leu
            355                 360                 365

Thr Arg Gly Asp Leu Trp Val Ser Trp Glu Ser Gly Val Arg Val Phe
            370                 375                 380

Asp Glu Leu Leu Leu Asp Ala Asp Phe Ser Val Asn Ala Gly Ser Trp
385                 390                 395                 400

Met Trp Leu Ser Cys Ser Ala Phe Phe Gln Gln Phe His Cys Tyr
            405                 410                 415

Cys Pro Val Gly Phe Gly Arg Arg Thr Asp Pro Ser Gly Asp Tyr Ile
            420                 425                 430

Arg Arg Tyr Leu Pro Lys Leu Lys Gly Phe Pro Ser Arg Tyr Ile Tyr
            435                 440                 445

Glu Pro Trp Asn Ala Pro Glu Ser Val Gln Lys Ala Ala Lys Cys Ile
            450                 455                 460

Ile Gly Val Asp Tyr Pro Arg Pro Ile Val Asn His Ala Glu Thr Ser
465                 470                 475                 480

Arg Leu Asn Ile Glu Arg Met Lys Gln Ile Tyr Gln Gln Leu Ser Arg
                485                 490                 495

Tyr Arg Gly Leu Cys Leu Leu Ala Ser Val Pro Ser Cys Val Glu Asp
            500                 505                 510

Leu Ser His Pro Val Ala Glu Pro Gly Ser Ser Gln Ala Gly Ser Ile
            515                 520                 525

Ser Asn Thr Gly Pro Arg Pro Leu Ser Ser Gly Pro Ala Ser Pro Lys
530                 535                 540

Arg Lys Leu Glu Ala Ala Glu Glu Pro Gly Glu Glu Leu Ser Lys
545                 550                 555                 560

Arg Ala Arg Val Thr Val Thr Gln Met Pro Ala Gln Glu Pro Pro Ser
            565                 570                 575

Lys Asp Ser

<210> SEQ ID NO 39
<211> LENGTH: 629
<212> TYPE: DNA
<213> ORGANISM: Eukaryote
<220> FEATURE:
<221> NAME/KEY: misc_feature
<222> LOCATION: (1)...(629)
<223> OTHER INFORMATION: r = G or A
      y = C or T
      n = A,T,C or G

<400> SEQUENCE: 39
ttggcacaca agtctgtctt caggacagct gatccatttt acttacraat tcagaaagta     60
```

-continued

```
aacattggca gtatggatct ggttacttca tggtaactgc tctagaattt acgccaaggc    120
catctctttt gcctcactgt ttagtgaccg gagtaaagca tggggccact gaaactccac    180
tttacaattg ggcttctaaa tttaaggaaa attttttga tttaaccaca actggattcc      240
aaagttcatc ttattcyaaa ttaggcccac tgagcctgtg atgttttgga atatatgatt    300
agtccacttg gttcactgga tgttacctat catgttatgt agagaaacag ccataactat    360
tggtcacgat gtcgtcctcc gaattgggaa tggctctgtt gttggaaaca agtatttgt     420 aaacacgttg atcaaagcgg tgtgctttgg cctttccggg aatcactgat tatgtttgaa    480
aacttccttt aattgtattt gcaataagct attntcccct ntnatgncnc tgccatgctt    540
ccttgctttg cactgtggtc gcatgccatc ngctggttaa cccangatgg cttgctgcnc    600
tgatatncac catgcnaaat accacttct                                     629
```

<210> SEQ ID NO 40
<211> LENGTH: 2461
<212> TYPE: DNA
<213> ORGANISM: Eukaryote

<400> SEQUENCE: 40

```
tgaattgcag taactagcct tgcctttcta ttctgtagaa atgacaggt cttcacaatc      60 cttcaccagt ggctactaag ctataattag ctgaatagaa agaatgtgga agtggtctga    120
ggcatataga gcatatgcca agaacactac catatatggc atcagctttg gttaccagag    180
aaattttctt agtcattaga ccatataaca gtaatatatc atatgtaaat ctttagattt    240
caatttgaga atcctccaaa aaaaaggagc aaagaatgca taagctatgt gttggcaaaa    300
gtaatttata ttaaaatttt gacctgcctt tgtaagatta gtggtaaat gtcatagtgg      360 tgggtttta cgtcttaacc aatctctgag gtttatttct cctgcagggg atggttcatg    420
gcctctcttc ccgctgtagg aagatagcag aaggatgagg attaattgta gcatttcact    480
gatcctcgtc ccagggacta gggacaatag aaatctgcaa acatggagag tctgtcataa    540
atatttgctt tttgaaggtg ttggtctttg ttgattctg tcagaaaatg gcattataca    600
aattatgggg agcaaccaac ttttctgttc tgttttgaa gtgctactat gaaccattca    660
gagtcgtatt tttttttttt aaattttggg ccagatatcc ccagctaatg aaaaatagtc    720
accattcctt gaaaagttg gaagctagaa ccccaattc caaattatg ttgaagatgt      780 ttctcaggct actgtatata gaaataatgt ttttaagaaa aatcaaagag aggagaaaaa    840
aaaaacctat gcagagaccc tactactttg tggtttctat tgtccctata catcatttca    900
gcaaatctac tggcagttct tgtcagcaag tccttcagtg catatgctgc acaaaacaaa    960
acaaaaatct gcatggcacc aaaaaccaaa caagcaaacc aaaaacccag acaccctatg   1020
tatctgttgg aggcatgtag gtggtacaaa tgactagcca tgagcacaca tggcttcttg   1080
tcatgtcact tttcataatt atttactgca aaatgattga gaggctttg gtgcaggcag    1140 ccattagcct gcttcctttg ttacctctgg atcactttgc agtaaattgc aggtctttta    1200
aaagattcaa gcttcggttt tctcaaaaca aaacaattat cctgtcttac ctgaaaatgc    1260
agggttgtgg gcaaaagagg ctggttataa taatgccctc atattgagtg gtctgtaaat    1320
ggctgcacac ttcaggcact agagttgccg aggatgcgtt gttaatgtga ccttgactgg    1380
ctttacaggg gtgtagaaca gtctacacgg gcgactattt gcatccatct tgctctcgag    1440
gtggatggaa ataagaaaag gctggagtgt gtaagtcatg cacataagta ttcactgtaa    1500
attttatttt catttttaac ccaattatgg tactttgtcc aatgcacaac tgatctctca    1560
```

```
gtagatattc atttgaaaat agtgtggcct tgaccagcga gaaggggaag aagtgactta    1620
gcttgtgtta agatgacctg tttgctgaga gtggtcattc tgcagcaccc taatgtcatg    1680
gttttgatta gggagagtta atgtttttga ccctgaattg agttttcttc tatttttagg    1740
aagtatcaga attgctctga tgagtaacaa agttgactgt tttgatgtcc aatctcaggt    1800
tttaaaatag agtggtataa aagtccactg ttactaattc ttaagacaat tttgatttag    1860
tgtgccctaa aagtcacgtg cataataagg cctgctcaga gggcagggcc tccatctgtt    1920
tgctcctttc catgttgtac gcacttcact tgaaaaggtg tcaagtgact ttgcattgta    1980
gatttccatt ttaaccccaa catagttctc aaagataaag cacttttga acatgaaata     2040
catgggtaat gtgtgatgtg gatcatggtt tctcaggccc ctagataatc cacttctgag    2100
tattgttcta tgtaaggaga atagaggtct tcgctaatgt tcgagtttgt attcctgaat    2160
ggaatgcact tgctagtttc caatggatgg gagagtaaac actgctgcat tcacaattga    2220
tacgttgctt tcccttgagc cttaaggtaa cttttctttt ctgtcaacaa cagcactgaa    2280
gttctagtaa gtgaatgaga ttatctgttt tcagggttgg ttttagagta ctgtaaatta    2340
attagctgtc ttcctaaaga ggaactccct ttaactccct tcgatagact gaaagtgggt    2400
gtggggaggg ggagggaaga gagggaggta gtttgtagaa aaaaaaaaa aaaaaaaaa     2460
a                                                                    2461
```

<210> SEQ ID NO 41
<211> LENGTH: 1131
<212> TYPE: DNA
<213> ORGANISM: Eukaryote
<220> FEATURE:
<221> NAME/KEY: misc_feature
<222> LOCATION: (1)...(1131)
<223> OTHER INFORMATION: r = G or A
      n = A,T,C or G

<400> SEQUENCE: 41

```
ggcccccct anaaggtcga ggntatcgat aagcttnaat atcgaattcg gcacgaggcc      60
accaggtctt tgcattgtct ctttaaaagt ggtgtataag ggggaaattg gcaagacaga    120
catttctaaa cagaggggaa cacagacaga cagacagaca gacagacaca caaacacaca    180
aacacacaca cacacacaca cacacacaca cacacacaca cacacacaca cacacacaca    240
cacacccag actgcgtatg tggcataaca tacagcttgc atgggaagca gcccctgcr     300
cattgcttat acatcctcga gtcctttcat ctttttttcct aaaacgtgtg cacccgctat    360
aaagtgggtg atgggctcgt cagagctggg ctgattctgt ggccggtgac caccatgcct    420
caggtccctc aacctccatc acccatggcc caatccataa ctgccaccct tgaaaccca     480
aagcagtctg agggtgctct ctgcctgtca ctcagaggcc tgggacgttg aacccaaaaa    540
agctaaactt atgaaagccg ggctgaaatg gggcccgggg cctgggatag ctcaggcagg    600
ggttttccac tctgatgttt ccactgggcc agttttgttt ctttgtctct atttctctg     660
ttcatcccgc tgagtgtttg tatccatgat gattccagca tgaagtacgt agcacactcc    720
agttaggaga aatttttaa agatacaaga ctagcgtggt ggtgagatga gatagtcttc     780
tcgtgctcgc agcaacctga aggggcaata aggacaaaga aggccatgtg gcagggttag    840
ccccctccag accaggggta caacggacag ttgtggtgag cctcggaaag gcagggtaa     900
ccttccctct ccgttcttca cccatggcca gagcaaggca ggtagtgaaa gggatatgct    960
tgatgcagaa aagccagctc aggcatggca ggtgggattt atagctggtt ttgtttaaag   1020
```

```
cgaaggcctg atatttgata aatgcagtaa ccagcggttg agagtgacaa gcccttaaat   1080
gcgaacatta atcaaaggag aacttaaacg gccccttta cagaaggact t             1131
```

<210> SEQ ID NO 42
<211> LENGTH: 1473
<212> TYPE: DNA
<213> ORGANISM: Eukaryote

<400> SEQUENCE: 42

```
cgagttttt tttttatgt actttgaaaa tatatttaaa acattaaaa attctatatt     60 taaaacatat attatatgtt aattggtaca cttaaataga acctgtattt acaataggct   120
tctgatgtgg ttaagtttta atgccaattt tttttcaat aacataatta tataaatata   180
ctaaaataca ataaatattt ttcttgtttt acatggtgaa taatatcttt accatagaga   240
gaacaaggcc acagacattt acttacagtt tcaatgggaa tcactataaa aagcatcagg   300
cctgctgcca tgcatgaaac acttctgcca aaagagacc acagcaagac tttcagaaca   360
gaacagaaca gaacaggacg gaaacagaac gaacagaaac agaggagaga ttttaacaaa   420
tcaatctcag gtcaacataa accaccgaca tggagctatg atgtatctta gtgggtatga   480
gagccagcca ctgaccacac agttgcggag ggtctcctat gaagccacct aatcgacctg   540
gcccttcgaa taccgtgaga ttgtgatggg gctccttta tttgtttgac taacgtctct   600
cagaatgaag ctgcaaaaag ttagcatata gcagatattc aaagcattcc ttaataggtt   660
aaaaatgatg acagagatta atgttgtcaa acggcacaaa acaatctagg ctacgtgaag   720
tcttccaaaa acaggggatt cagtgggact ccagaagaca gactagttct aaaggaacag   780
ttgaacaaaa agaaactatt tgctgatggt atcttcactc cctgagtcac agtggacagc   840
cactttgttt cacccttttcc actcctaaga tgaagcaatt gtttgcctct ttttctgatg   900
cccaggagcc cagtcaggta accactaaca cattcgcgct ggcggaaaac ctcactaggg   960
aaatgggctt aacactagtt ctcattgggg ccattcattc aggcttccag cttgacttct  1020
cctaacccca agaggtaaag tgtagaaggg acccttgtgc tgaatggaca gaactatcag  1080
gagctttctg tgctcttcac ttaagcagta tttcctcctg tgttcttgtc tctttcacag  1140
tgaaagcacc ttcctatgcc ttgtcattct agcccttaca gacagacatt gctcattctg  1200
cctaagtttt ggtgcttttt ctggttttgt ttgtttgttt tcttcttcct ttttcctttt  1260
caccaaaatg tctcaaaaaa ataaataaat aaaacctagg cttcctgaag tctaagcgca  1320
aagaaagtta agtctcttca cagcaaacat ttcccatcat gctgcactga tagcatcact  1380
gctatgccat atttggatcc aaagctgctc caggttaatc caactttatc cataattatt  1440
taaaatggga tggaggccat aaatggattt gag                                1473
```

<210> SEQ ID NO 43
<211> LENGTH: 326
<212> TYPE: DNA
<213> ORGANISM: Eukaryote

<400> SEQUENCE: 43

```
agtctgggac taaacgtca cagcagaaaa aaaataaaaa aaataatttt gcttttctt     60 tctttcattt agcagcataa ataagtttgg ccactgggag tacagtacag gggtgggaca   120
acgatcccgt atttgaagac ctacttctag caccagcatc aagaactaaa tccacctcag   180
gactcacaga acccaggaca acttgccatc tttgagcaac atatgcattg aagagtgtat   240
```
atagaagcaa cagtaaatag attaacagag gctaatactg tgattgattg acattggcaa       300
tggttggcaa aaaaaaaaaa aaaaaa                                             326

<210> SEQ ID NO 44
<211> LENGTH: 429
<212> TYPE: DNA
<213> ORGANISM: Eukaryote
<220> FEATURE:
<221> NAME/KEY: misc_feature
<222> LOCATION: (1)...(429)
<223> OTHER INFORMATION: n = A,T,C or G

<400> SEQUENCE: 44
acttgataaa attgtatttt tttttctaca gtcatttgta caatttgtta caaaaccata        60
gaagactaca acttgtttta aatcattttt ggtctgcaaa tatgtaaaat ctgtggtgca       120
attatcatgt atttacaggg ccttgttagt cattttcaat gattatttca acaatgtcac       180
actctcaaca taagacatgg cttaagacaa atatattagt acatanatat tctgagaaca       240
tatttccatn aatggaaagt ngctgctaat acanatacag aatatacata agntgttttc       300
tagcttttta aaacagtttt taaaatggna angtgaaaaa agagcccta ggancatttt        360 atcccaaaaa aatccttacn aaatattnaa ggggccaggg ggggaattaa aaatctaaaa       420 anggtggtc                                                                429

<210> SEQ ID NO 45
<211> LENGTH: 1210
<212> TYPE: DNA
<213> ORGANISM: Eukaryote
<220> FEATURE:
<221> NAME/KEY: misc_feature
<222> LOCATION: (1)...(1210)
<223> OTHER INFORMATION: r = G or A
      m = A or C
      s = G or C
      w = A or T

<400> SEQUENCE: 45
aargggrcca ccccaccgsg ctaaaggccc aggggccccc cccttggagm cccaggggtt        60
ttggcccmcc ccctcaccca aatggtctgc caatgaccca ggtactcaca acatgttcca      120
ggaggagmct ggggccagga ttttgaccag agggtatggg aagggaaagg ggagaagaaa      180
tcgacatttt tttttattat ttatttttaaa tgtttacawt ttctttgtgt tgttccaagc     240
cctgaataga aacagatagc attaaaggac tctgttccca cccttctct gtctctctct        300 cccccacttg tgctaactta ggataacact ctctatttcg ttttgttttct aaagtgatttt    360 gtggacttgt gccgtgtgaa ctgcattaaa aaggttctgt tttcaaagat cgattgtcgt      420
tcctgtgggg acagtggctc ctaagaaatc tgcattgtag gagaagacaa tgaaagaccc     480
tggccctgtc tctcaaaact taactctctg tatgatttaa aaaaaaattc catttacttt      540
actttgtggt tacttgattt tgaggaagaa aatattcaac tttgtataaa gactaggtat     600 cagggttttct tttgcagtgg gagttgtata tatatcgtat tttggtatat cgtagaaact    660
caagctttat gcatccgtat ttgggatatg tcaatgacgt gcagtgaaat ttgctattag     720
accctggagg caaacgagtt gtacaaggtt ttatggctcc atggggaatt ctaatttcct    780
ttctggggac cttttgtccc gttttttacag taatggtgaa atggtcctag gagggtctct    840
ctagtcgaat tctccaggca ggaccacgtg ctcaaaaaat ctttgtatag ttttaaatttt    900 ttgaggagta tctctgctca gaagcatctg tggtggtgtg tgttgcgttg ttctgtgtac    960

-continued

| | |
|---|---|
| tgtgtgtgac acaagcctac agtatttgca ctaaggaaag ctgtttagag cttgctgcta | 1020 |
| tggagggaag aacatattaa aacttatttt ccctcggggw ttrtwcwmgt tttatgtwct | 1080 |
| tgttgtcttg ttggctttcc tactttccac tgagtagcat tttgtagaat aaaatgaatt | 1140 |
| aagatcagmw rwrwrmaaaa aaaaaaaaaa aaaaaaaaaa aaaaaaaaaa aaaaaaaaaa | 1200 |
| aaaaaaaaaa | 1210 |

<210> SEQ ID NO 46
<211> LENGTH: 700
<212> TYPE: DNA
<213> ORGANISM: Eukaryote
<220> FEATURE:
<221> NAME/KEY: misc_feature
<222> LOCATION: (1)...(700)
<223> OTHER INFORMATION: n = A,T,C or G

<400> SEQUENCE: 46

| | |
|---|---|
| aattccccat ggagccataa aaccttgtac aactcgtttg cctccagggt ctaatagcaa | 60 |
| atttcactgc acgtcattga catatcccaa atacggatgc ataaagcttg agtttctacg | 120 |
| ataaccaaa atacgatata tatacaactc ccactgcaaa agaaaccctg atacctagtc | 180 |
| tttatacaaa gttgaatatt ttcttcctca aaatcaagta accacaaagt aaagtaaatg | 240 |
| gaattttttt taaatcatac agagagttaa gttttgagag acagggccag ggtctttcat | 300 |
| tgtcttctcc tacaatgcag atttcttagg agccactgtc cccacaggaa cgacaatcga | 360 |
| tctttgaaaa cagaaccttt ttaatgcagt tcacacggca caagtccaca aatcactttn | 420 |
| gaaacaaaac gaaatagaga gtgttatcct aagtnagcac aagtgggggn gagngagaca | 480 |
| gagaaggggt gggaacagag tcctttaatg cnatctgttt ctattcaggc ttggaacaac | 540 |
| acaaagaaat gtaaacattt agnataaata atagaataaa tgtcgggttc ttctcccctg | 600 |
| tcccttccca tacccnctgg caaaatctgn cccaggtcct cccggaacat ggtgngagta | 660 |
| cctgggtcca ttgnagncca tttggngagg gcgtggccaa | 700 |

<210> SEQ ID NO 47
<211> LENGTH: 3316
<212> TYPE: DNA
<213> ORGANISM: Eukaryote
<220> FEATURE:
<221> NAME/KEY: CDS
<222> LOCATION: (94)...(993)

<400> SEQUENCE: 47

| | |
|---|---|
| ggcacgagcc gaggctcagc acagcacgga taggggcgcg gagcgcactg agaaccctac | 60 |
| tttcccgtga gcccgagccc ggcaaatggg cga atg aag aag gag agc agg gac<br>                                                Met Lys Lys Glu Ser Arg Asp<br>                                                 1                 5 | 114 |
| atg gac tgc tat ctg cgt cgc ctc aaa cag gag ctg atg tcc atg aag<br>Met Asp Cys Tyr Leu Arg Arg Leu Lys Gln Glu Leu Met Ser Met Lys<br>         10                   15                   20 | 162 |
| gag gtg ggg gat ggc tta cag gat cag atg aac tgc atg atg ggt gca<br>Glu Val Gly Asp Gly Leu Gln Asp Gln Met Asn Cys Met Met Gly Ala<br>  25                   30                   35 | 210 |
| ctt caa gaa ctg aag ctc tta cag gtg cag aca gca ttg gaa cag ctg<br>Leu Gln Glu Leu Lys Leu Leu Gln Val Gln Thr Ala Leu Glu Gln Leu<br> 40                 45                  50                   55 | 258 |
| gag atc tct gga ggc gcg ccc acc ttc agc tgc cct aag agc tca cag<br>Glu Ile Ser Gly Gly Ala Pro Thr Phe Ser Cys Pro Lys Ser Ser Gln<br>                 60                   65                   70 | 306 |

-continued

| | |
|---|---|
| gaa cag acc gag tgc cct cgc tgg cag ggt agt gga ggg cct gct ggg<br>Glu Gln Thr Glu Cys Pro Arg Trp Gln Gly Ser Gly Gly Pro Ala Gly<br>           75                 80                 85 | 354 |
| ctt gct gcc tgt ccc tcc tcc agt caa cca tct ttt gac ggc agc ccc<br>Leu Ala Ala Cys Pro Ser Ser Ser Gln Pro Ser Phe Asp Gly Ser Pro<br>           90                 95                100 | 402 |
| aag ttt cca tgc cgt agg agt atc tgt ggg aag gag ctg gct gtc ctt<br>Lys Phe Pro Cys Arg Arg Ser Ile Cys Gly Lys Glu Leu Ala Val Leu<br>105                       110               115 | 450 |
| ccc aag acc cag atg cca gag gac cag agc tgt acc caa caa ggg ata<br>Pro Lys Thr Gln Met Pro Glu Asp Gln Ser Cys Thr Gln Gln Gly Ile<br>120                       125               130               135 | 498 |
| gag tgg gtg gag cca gat gac tgg acc tcc acg ttg atg tca cgg ggc<br>Glu Trp Val Glu Pro Asp Asp Trp Thr Ser Thr Leu Met Ser Arg Gly<br>                   140               145               150 | 546 |
| aga aat cgg cag cct ctg gtg ttg gga gac aat gtt ttc gca gac ctg<br>Arg Asn Arg Gln Pro Leu Val Leu Gly Asp Asn Val Phe Ala Asp Leu<br>               155               160               165 | 594 |
| gtg ggc aac tgg cta gac tta cca gaa ctg gaa aag ggc ggg gag agg<br>Val Gly Asn Trp Leu Asp Leu Pro Glu Leu Glu Lys Gly Gly Glu Arg<br>          170               175               180 | 642 |
| ggt gag act ggg gga tcc ggt gaa ccc aaa gga gaa aaa ggt cag tcc<br>Gly Glu Thr Gly Gly Ser Gly Glu Pro Lys Gly Glu Lys Gly Gln Ser<br>185                       190               195 | 690 |
| aga gag ctg ggt cgt aag ttt gcc cta act gca aac att ttt agg aag<br>Arg Glu Leu Gly Arg Lys Phe Ala Leu Thr Ala Asn Ile Phe Arg Lys<br>200                       205               210               215 | 738 |
| ttc ttg cgt agt gtg cgg cct gac cga gac cgg ctg ctc aag gag aag<br>Phe Leu Arg Ser Val Arg Pro Asp Arg Asp Arg Leu Leu Lys Glu Lys<br>               220               225               230 | 786 |
| cct ggt tgg atg act cct atg gtt tct gag tca cga gca gga cgc tcg<br>Pro Gly Trp Met Thr Pro Met Val Ser Glu Ser Arg Ala Gly Arg Ser<br>          235               240               245 | 834 |
| aag aaa gtc aag aag agg agc ctt tct aag ggc tcg gga cgg ttc cct<br>Lys Lys Val Lys Lys Arg Ser Leu Ser Lys Gly Ser Gly Arg Phe Pro<br>250                       255               260 | 882 |
| ttt tcc agc aca gga gag ccc aga cat att gaa acc ccg gcc aca agc<br>Phe Ser Ser Thr Gly Glu Pro Arg His Ile Glu Thr Pro Ala Thr Ser<br>          265               270               275 | 930 |
| agt ccc aag gct tta gaa ccc tcc tgt agg ggc ttt gac att aac aca<br>Ser Pro Lys Ala Leu Glu Pro Ser Cys Arg Gly Phe Asp Ile Asn Thr<br>280                       285               290               295 | 978 |
| gct gtt tgg gtc tga attcgagaga tgctcactga cctaaaatgc agacttgtga<br>Ala Val Trp Val | 1033 |
| gggccctggg ggagggtggg cagatggcat ggtcttcagg ccagatgcaa gttcccatcc | 1093 |
| tcagaaagaa agcagagttc ttagtcaggc ctcagtagaa cagtggagag aggctgtcac | 1153 |
| aggccaggct gagctgagtc cctggagaga atgtgtgtat ttgtgtgtgt gtgtgtgtgt | 1213 |
| gtgtgtgtgt gtgtgtgtgt gtgtgtgtat gtgtgtgtgt atgcgtgtgc atgcactgtt | 1273 |
| gttgttagag gctggatgtg acaataattg ggagaggcag gaaaggagtc caggacaagc | 1333 |
| ctatgatatt cctccattac cttacccaag acctcatttg aacattctat atgcaaaggg | 1393 |
| gcatttagcc ctcaggtttc ccagaggaac tcccaataaa gacctgtctc agggaccccc | 1453 |
| aaccattttt taatggtctg cttccctgac aaggcactga tgcaggcaag gggtttgttt | 1513 |
| ttgttttaag ggttggtatc ccagaatgga gcaccggaaa taggaaaatc cctatttata | 1573 |
| gcccttccta ggaccaagat ttcacccatg gctgggtgct ggggacgcag aacaagcaga | 1633 |

```
gggtgtgcg  tgcgtgcgtg  cgtgcgtgcg  tgcatgtggt  gttgaggaag  cctgagatgc   1693
tcccagatct  ctaaagtgca  gaggagaagc  aatgtgcgtt  caccccggtg  attccataag   1753
cagccatctc  tgagagcaca  ctcggctgcc  aggaggaaaa  acaggtcagg  ccaatctcat   1813
ggttatcaat  ggaccctaga  gtcatacgct  gcctggtcca  gcagtgagag  cccatcctga   1873
ctccctgttg  cctatcttaa  tgctcctgca  gggcagcaga  tggttggggt  gaacccagag   1933
ataataccca  tacattgaga  acatttctta  gtctacatct  catagtcatt  cagcgaactg   1993
gacacatcta  cccgcatcac  cctggaggtc  aacaggggac  cctgagggtg  gggctgatgc   2053
caggcacttt  atatagtgag  caggcgtgca  agtctgggac  ccagggaatc  catctcagcc   2113
cccacccctt  agccaggaga  gaacaaagta  ggcccctgtt  caagcccagc  tcggaggctg   2173
ccttagctcc  tccttcgccc  cctcctgcag  acccagctca  gcttgatgag  gtgtgacaac   2233
tgcaattaga  ggcaagccgc  ctgctgcccc  cagagcatta  agagcaaatt  agagaagaaa   2293
aatcacaaga  gaagctcttc  tgcctgcagt  ctagactccc  aggggactgg  gtggaggaag   2353
gaagagctta  gggcataggg  atgaggaggt  aaaagtaaca  gcaggaaggg  tcacctgcaa   2413
gttcccacgc  agttaaatga  taggtggcct  tttttttttt  ttttttaatct  gtagcttttt   2473
gtcaggcaat  gtgcctatct  ctttcagaac  aattaatcag  tggggtcaaa  gggccctgcc   2533
atgctggctg  cccccatcag  gctactcaaa  aaggaaagca  gttccaagct  ccagcctgtg   2593
ggcatcaggc  ctatctgctc  tggcctggtg  tttatcagct  aggctcgctc  tttctggtca   2653
aatgggtcct  catccattct  gtccccactg  aacttctgtc  tctggtgaag  gaaggtaact   2713
gtagctgcct  ctgatggctg  ctgcaatgtg  tgtggagaat  gaacatgtga  aaaccccaca   2773
ccctgaaggg  tggcacatat  gacacattta  ctcaagagga  cacaggactg  ggacggtgta   2833
ggaagccaac  tcatttgttt  tgtggactag  tcactgttca  cattatttaa  atcgactgac   2893
gtgacagact  ccttctttga  ctgggcactg  tgacagaagg  agagaactca  gcaatgggaa   2953
agctggcctc  cacagctacc  aaggcacaca  agaaatcca  gttaaccacc  acctggccag   3013
aaaagggtca  agggaccaaa  acaaaatgat  tagcaagtaa  ttttggcttc  taagagaacc   3073
cacaggtgtc  tgtcaccttg  atctttatt   ttctgctaca  cccaggaaat  ggttgctcat   3133
tttacccagt  agactcggag  aagttaatgc  tttcaaggtc  acacagtaca  aagctgggat   3193
tgaaacagtt  tgtaactgac  ttccaatctt  gtgttcatgc  tacctggcaa  actgtccata   3253
tttgctccac  agccagatcc  agaataacat  ttgtctcctc  tcgtgcaaaa  aaaaaaaaa    3313
aaa                                                                      3316
```

<210> SEQ ID NO 48
<211> LENGTH: 299
<212> TYPE: PRT
<213> ORGANISM: Eukaryote

<400> SEQUENCE: 48

Met Lys Lys Glu Ser Arg Asp Met Asp Cys Tyr Leu Arg Arg Leu Lys
 1               5                  10                  15

Gln Glu Leu Met Ser Met Lys Glu Val Gly Asp Gly Leu Gln Asp Gln
            20                  25                  30

Met Asn Cys Met Met Gly Ala Leu Gln Glu Leu Lys Leu Leu Gln Val
        35                  40                  45

Gln Thr Ala Leu Glu Gln Leu Glu Ile Ser Gly Gly Ala Pro Thr Phe
    50                  55                  60

Ser Cys Pro Lys Ser Ser Gln Glu Gln Thr Glu Cys Pro Arg Trp Gln

```
65                  70                  75                  80
Gly Ser Gly Gly Pro Ala Gly Leu Ala Ala Cys Pro Ser Ser Ser Gln
                85                  90                  95
Pro Ser Phe Asp Gly Ser Pro Lys Phe Pro Cys Arg Arg Ser Ile Cys
                100                 105                 110
Gly Lys Glu Leu Ala Val Leu Pro Lys Thr Gln Met Pro Glu Asp Gln
                115                 120                 125
Ser Cys Thr Gln Gln Gly Ile Glu Trp Val Glu Pro Asp Asp Trp Thr
        130                 135                 140
Ser Thr Leu Met Ser Arg Gly Arg Asn Arg Gln Pro Leu Val Leu Gly
145                 150                 155                 160
Asp Asn Val Phe Ala Asp Leu Val Gly Asn Trp Leu Asp Leu Pro Glu
                165                 170                 175
Leu Glu Lys Gly Gly Glu Arg Gly Glu Thr Gly Gly Ser Gly Glu Pro
                180                 185                 190
Lys Gly Glu Lys Gly Gln Ser Arg Glu Leu Gly Arg Lys Phe Ala Leu
            195                 200                 205
Thr Ala Asn Ile Phe Arg Lys Phe Leu Arg Ser Val Arg Pro Asp Arg
    210                 215                 220
Asp Arg Leu Leu Lys Glu Lys Pro Gly Trp Met Thr Pro Met Val Ser
225                 230                 235                 240
Glu Ser Arg Ala Gly Arg Ser Lys Lys Val Lys Lys Arg Ser Leu Ser
                245                 250                 255
Lys Gly Ser Gly Arg Phe Pro Phe Ser Ser Thr Gly Glu Pro Arg His
                260                 265                 270
Ile Glu Thr Pro Ala Thr Ser Ser Pro Lys Ala Leu Glu Pro Ser Cys
            275                 280                 285
Arg Gly Phe Asp Ile Asn Thr Ala Val Trp Val
    290                 295

<210> SEQ ID NO 49
<211> LENGTH: 949
<212> TYPE: DNA
<213> ORGANISM: Eukaryote
<220> FEATURE:
<221> NAME/KEY: misc_feature
<222> LOCATION: (1)...(949)
<223> OTHER INFORMATION: r = A or G
      y = T or C
      m = A or C
      k = G or T
      s = G or C
      w = A or T
      b = G, C, or T; not A
      d = A, G, or T; not C
      h = A, C, or T; not G
      v = A, G, or C; not T
      n = A, T, G, or C

<400> SEQUENCE: 49
tttktttkta atttttttt  tttnatttgg gttgattcct tgtntttan  ttgccaaatn      60 ttaccgatca ntgancaaag caagcacagc caaaatcgga cctcacctta attccgtctt     120
cacacaaaaa taaaaaaacg gcaaactcac ccccattttt aatttgttt  ttaattttac    180 ttacttattt tatttattta ttttttggca aaaaaatctc aggaatggcc ctgggccacc     240
tactatatta atcattttga taacatgaaa aatgatgggc tcctcctaat gaaaaascaa     300
ggaaaggaaa aggccagggg aatgagctca aaattgatgc ccacktgggg agcatctggt     360
gaataatcgc tcacktcttt cttccacagt accttgtttt gatcatttcc acagcacatt     420
```

| | |
|---|---|
| tctcctccar aaacscgaaa acacaascg tktgggttct gcattttaa ggataarara | 480 |
| raraaagagg ttgggtatag taggacaggt tgtcagaaga gatgctgcta tggtcacgag | 540 |
| gggccggttt cacctgctat tgttgtcgcc tccttcagtt ccactgcctt tatgtcccct | 600 |
| cctctctctt gttttagctg ttacacatac agtaatacct gaatatccaa cggtatagtt | 660 |
| cacaaggggg taatcaatgt taaatctaaa atagaattta aaaaaaaag attttgacat | 720 |
| aaaagagcct tgatttttaaa aaaaaagag agagatgtaa tttaaaaagt ttattataaa | 780 |
| ttaaattcag caaaaatttg ctacaaagta tagaagta taaaataaaa gttatyhgtt | 840 |
| tcaaamtavc dtrtcgamct cvtcvabccc grggaakccm ctaskkcbar hscggccccc | 900 |
| accscssysk akmtycatkc ttttgawwcc ctttagtgag ggttaanaa | 949 |

<210> SEQ ID NO 50
<211> LENGTH: 785
<212> TYPE: DNA
<213> ORGANISM: Eukaryote
<220> FEATURE:
<221> NAME/KEY: misc_feature
<222> LOCATION: (1)...(785)
<223> OTHER INFORMATION: n = A,T,C or G

<400> SEQUENCE: 50

| | |
|---|---|
| cagcctctca ctctctngct ctctttctgt ctcttcctcg ctccctctct ttctctcctc | 60 |
| cctctgcctt cccagtgcat aaagtctctg tcgctcccgg aacttgttgg caatgcctat | 120 |
| ttttcagctt tcccccgcgt tctctaaact aactatttaa aggtctgcgg tcgcaaatgg | 180 |
| tttgactaaa cgtaggatgg gacttaagtt gaacggcaga tatatttcac tgatcctcgc | 240 |
| ggtgcaaata gcttacctgg tgcaggccgt gagagcagca ggcaagtgcg atgcagtctt | 300 |
| taagggcttt tcagactgtt tgctcaagct gggtgacagc atggccaact acccgcaggg | 360 |
| cctggacgac aagacgaaca tcaagaccgt gtgcacatac tgggaggatt ccacagctg | 420 |
| cacggtcaca gctcttacgg attgccagga aggggcgaaa gatatgtggg ataaactgag | 480 |
| aaaagaatcg aaaaacctca atatccaagg cagcttattc gaactctgcg gcagcggcaa | 540 |
| cggggcggcg gggtccctgc tcccggcgct ttccgtgctc ctggtgtctc tctcggcagc | 600 |
| tttagcgacc tggctttcct tctgagcacg gggccgggtc ccccctccgc tcacccaccc | 660 |
| acactcactc catgctcccg gaaaatcgag aggaaagagc cattcgttct ctaaggacgt | 720 |
| tgttgattct ctgttgatat tgaaaacact catatgggga ttgttgggna aatcctgttt | 780 |
| ctctc | 785 |

<210> SEQ ID NO 51
<211> LENGTH: 782
<212> TYPE: DNA
<213> ORGANISM: Eukaryote
<220> FEATURE:
<221> NAME/KEY: misc_feature
<222> LOCATION: (1)...(782)
<223> OTHER INFORMATION: y = C or T
    m = A or C
    k = G or T
    w = A or T
    n = A,T,C or G

<400> SEQUENCE: 51

| | |
|---|---|
| aaaccnagaa ccccccttg nagaaccntt gtttcctttc aagcccaagg aaggcggggc | 60 |
| ccaacctttg gtgttntttg aacaggcctt gaacaggagg ntwaggagaa atttccggtt | 120 |

```
gtggaacccc aacaggaacc ccttggcacc cctggcccca aggttgtgma actttggttt     180
gcttaatttg gaccgttttt gccttgagga ttcatgactt ttttttgkgc ccttgtgagc     240
caagatgttg ggttttccca tcaacawtaa taaccccttg cttttggggg tgattcccct     300
ggggagtttc ctgatgaatt cccccacagc tcctggggtt ttcatcttgt tcttactgtt     360
gtctggatta ggagggcgga gagggtggac tccctgagac aagataagca ggtggagaca     420
tagaagaggg agggacattt aacatagtaa cattttcaga ggtgacagag atgatacacg     480
ggcagctgga mttttgtgaa ggacagagga gctggcagac ccacagggcc atacctttga     540
gggacaggtg aatggctggt taccagagac aggactggta gacagtcaag tacctcacta     600
cgatgtgcca agagatytgg gatcctggga aatgtgtgga aagaggatt tgacactccc      660 cacccccaag gcccttcccc tttgctgaca gcattgctgt ggtcgtggcc tgttgccttg     720
tcctctgtcc ctgggtgggg cacaccctcc tgtgctgtgc ttgccttgtg catcaataaa     780
cc                                                                    782

<210> SEQ ID NO 52
<211> LENGTH: 1613
<212> TYPE: DNA
<213> ORGANISM: Eukaryote
<220> FEATURE:
<221> NAME/KEY: misc_feature
<222> LOCATION: (1)...(1613)
<223> OTHER INFORMATION: r = G or A
      n = A,T,C or G

<400> SEQUENCE: 52
gcantttgga gttattgctt aaaaccaggn taaggcactt tgtcccacag gacccaggaa      60
tcntaaangg gttgaaattg ggncggggaa ccccaggata taatgcnact tttgttaggg     120
ggagagttca gctctaactg gtagtagtgt gaaagtaagc accttgactt caattttgga     180
aagcacttgg taaatggaga aactttgga gtttccctat catctatatc agtctttgaa      240
cacaccctca gtcccagcc tcaaggctca ataaaggacc acatagcagg tctgaggctc      300
actgctctca gcccttaaca cagggcagtg gagagcaggg tgatcttccc tctctggagc     360
ttctccttgg ccttcttctc cacttgggct tctgctcagc agcagatata ttctgggttc     420
cataaggaat ccagctgtcc cagtggcttg accctgtcaa ggcaagatat caactctgag     480
gatgacccag tcatggagga agagagtgtg acaagatccg cagtttgaag caaaactgtg     540
tttggtcttt tcaagaaaca aatgggcaca ttgagttctg ttcagtgtca gaggatatct     600
ttccctttgc tcccagattt ccagaaatgg ataatgttttt catttctgtg ggaagggtca    660
agaaacataa aattgctcaa caatgcttgc ttcccttgag ggttgttgag caaaggccga     720
tatgcctccc tgcattctct tctacctcaa gattttggaa ttcaattctg aacagaaat     780 ttatttacac aagaacactt gttgtcagcc ttggttactg tgggagttac ataagggtga    840
cagtctgtat cttctaartt aaacaggaac tgggctttgg cggcctattg acccagttta    900
tatctaaata taactgtggc tccaaatgat tggccaataa cattccctt acccttcaaag    960 ttttctccat cagtcatttc tgtggcagca cagttccaat gtcatatgcc cctgcaaatt    1020
gtgaaagtaa ttagtgacaa ataaccctc cccccttttca gtggccaaac tgtcagctgt    1080
agcagcgctg cgaaagcgag tactacacta tgtacggaaa gcctgttcct tatcacggac    1140
tagactcaag aaatgccatc tccgaacggt ggcattcaag gtggtagtcg tttgaatgga    1200
acagtcatct atgtggacat tgttaaagtg ttttaaagag tattttgaaa attaagttta    1260
```

-continued

| | |
|---|---|
| cattttacaa ctgctttatt tttattgaaa caattgtata taaatattac cctctttcac | 1320 |
| tgttaattaa agtaaaccta gaccttgtag acaagtgggt caactgatat gtatagaagc | 1380 |
| tgtgatgtag acaatacctt tctcttgtgt aaatggtcat aaatatagct gttcctgtgt | 1440 |
| ttttataagt tgagggtatt ttgttgtttt ataacaacaa aatttattgc atttgaaatg | 1500 |
| gtttttatgt aatagaatca tgcaaacagt gaaggattat aacatggtat atgtaaatgt | 1560 |
| ataaacttta gaaagaaata aatacaacaa atttcaaaaa aaaaaaaaaa aaa | 1613 |

<210> SEQ ID NO 53
<211> LENGTH: 1669
<212> TYPE: DNA
<213> ORGANISM: Eukaryote

<400> SEQUENCE: 53

| | |
|---|---|
| ggcacgagga cagattctga gatggaaact taaattacat cccagaggca gggaaactat | 60 |
| gaagtcaccg ttcctagacc accccttact gaggttccac ggtcacactg acggcaggac | 120 |
| ccacaagggc agggtattgg tctgccctcc tttctcctgt ctgtctgact tacctaactt | 180 |
| tggtctcggc tgctgacact tggaaaggac caaattactt gatagtattt ccccctgttt | 240 |
| gtgtaatagc ctgaaacctt ggagaggttc cagaatactt ctgtatatag ggcacaggtg | 300 |
| aagacattgt ccaaagctta tttatttatc tatttattta ccctggctga gtaaccacac | 360 |
| cagtaggggg aaaactaaaa tgtgttgagt gtaaacaaag tcaccagcct ggctagaaat | 420 |
| tctccctgga aaacatccat tttgatacaa tgtaaacgtt agtgttcacc cttagataca | 480 |
| tgttgaaaga gagctttggt acgcggaagt ggcatctttg gtcacacacc atgccaaagt | 540 |
| gaagaggtgg ccagtggagg tcttccggtc ctgtcgggat catttgtgaa tacattcttt | 600 |
| gcccctctta agtacttgtt tactaaacat gtgcagtggt aggtattagt gttagatcac | 660 |
| agtgggcact tccctgggga tctggggaag accagagctt gcaactctgc ctgttttgat | 720 |
| ccctatttct cacagtgctg tattaaaaaa aataggattt aagacagata accacctta | 780 |
| cattgtgagt gtgtttgcct tgtctaacga cagataattc cttaacattt ctcttcacct | 840 |
| tagtacttta ggctaattat acacgtctgt ctatgccatg agtaagtgga ctgtagtcgg | 900 |
| accaaaagaa aacaaatgag ccgttggacc atttgtgcag tcagtttctg gtccttagat | 960 |
| gtatcctaag cagtaagtgt ctgattgtac cctggtggta tgatcagttg tctcgtagct | 1020 |
| gtctcagctc cacagtttac aatgcaaatc tgtctcaaga tcttcacgtc actgctgctg | 1080 |
| agagcaggga gaattctctg cagctgtttc aaagttgtgg cccggccttg aatcctctgt | 1140 |
| taattactgt gtgagccaga gggagctgcc cagcaagggt gggcccccag ccggcagggg | 1200 |
| aactttctag actccccgct cattcaattg atctaggcat tcgggcctgc acttgacca | 1260 |
| ttctcgccct gtgaaatgtc ccacactttg aagcaaatac aattcacagc acagtacaca | 1320 |
| caaaaccct ggcataagac aggggaggtt cttcttattt tgtgagccgg ttgccctgga | 1380 |
| aacggataac aaagggcagc cttccacttc tggcataatg gtggagcctc ttttctcagg | 1440 |
| cttgacacct gtctgaataa gagtgattag agccgcataa tatccctctc ttggctattg | 1500 |
| aatatgtggt tcacatacca aaccctgtag aagttagaag acgtcgtgt tcgtatgttg | 1560 |
| tttgcttcca ctacattttt gaggttttgt aaaactgtta ttttttttca cgatgtgaaa | 1620 |
| ctgaaggtca ataaattatt agagattttc aaaaaaaaaa aaaaaaaa | 1669 |

<210> SEQ ID NO 54
<211> LENGTH: 1586

<210> SEQ ID NO 54
<211> LENGTH: 1586
<212> TYPE: DNA
<213> ORGANISM: Eukaryote
<220> FEATURE:
<221> NAME/KEY: misc_feature
<222> LOCATION: (1)...(1586)
<223> OTHER INFORMATION: n = A,T,C or G

<400> SEQUENCE: 54

```
cttaaaaccc ctagatttcc tgttacatac taacacaggt cttcccttc actccaaccc      60
caggtttcag gcctcagagc catgctgggg ttggagaaaa ctgcattcct atgagggtaa    120
aaagtagctg ccctctctga cccttcttg ctaggcttca tgcgggatgg gagagggtat    180
ccccaggatg gggacagagg aagcctggct agggccttct agcccaataa gccaaacagg    240
aactataagc agatcaaaat cctacactag cttattaggg ccctgttagt tgaaaacctt    300
gttgctgtcc caagttcttc agttacaacc gagtacactt actcttccaa ctgtcctaag    360
ggtcactacc cagccagctt tggatcttca gcacttttaa aagctgaaac tccctcttgc    420
ccttcttgtc tattcctcac tgccagttgg ggcctaggct cagtcctggg caaatgccca    480
tgatcctgct gctgtgggaa gtttgatagg gcatttggct caaatttcaa aaggcctcgc    540
tcctgacctg atttctcgaa gctccagtag ttctagaccc ctccaatctc tcatctgact    600
ggttgcaagg cttatttttc ttttgtactt tcctatagag catttctgta gcatttgagt    660
gtggcgatat ttttgttgtg tgtagatttc taagaaccaa cactactcag tctcctgcta    720
gtctgactcc tgaagcatca gacctcgtca tacggtattg actgtgtatg tgcctttcac    780
cttgagcatg cttcaggatt ttttttctta aaccacagaa cttaataca caagggaacc    840
agaattcaca aagtcctatg caaccctaga caggaggagg ttagagagtc tgtcttgatt    900
ggtgatttca gagacccnag agaaatttgt accagtttgt attaatgtca gtactaccag    960
cactttgcca aaactaagga tgtcagaggg acctgtttct agagtgagtc ccaattacat   1020
caaagggcaa cttacagctt tctccagtaa gtctgagtgg ttctcttgag ctggtgtcac   1080
tttctaacct ttgccagtct agcccagcag ggccctgtgt gtgtgagtgc agtttggtgc   1140
tgttttggag tatgcctgct ccccagcctg gaaccctctc agcaacttgc tgggacctat   1200
aatgtcttag gtgcaacaag gaccctacca gagctcctgg gtggctttca agatccacgt   1260
agctttgtgt gagggactg aatgcagaca aaccacagcc tgcttcaaat accttctttc   1320
cctaccacct agttccaaat ggaaccaaca agttgagtgc atctctgttg ggtgttttgt   1380
gttgagactg gctgaagtga aaactctttg actgaccatg ttgtgatgtg tcgacagact   1440
caaggacaca accacctcga gctggtcatg tggcatgcct gtgtatgtgt gtaacaggat   1500
tctgaatgtt aggttgtaat gctattcctg tatgggagaa aaaataata taacaaata    1560
aaaatctatt taaagcacaa aaaaaa                                       1586
```

<210> SEQ ID NO 55
<211> LENGTH: 770
<212> TYPE: DNA
<213> ORGANISM: Eukaryote
<220> FEATURE:
<221> NAME/KEY: misc_feature
<222> LOCATION: (1)...(770)
<223> OTHER INFORMATION: n = A,T,C or G

<400> SEQUENCE: 55

```
ccatggggac tggtttgtca ccnattgccc atggnttggt tggtaggtgt tttttggtgg      60
acattttgt ttcncgtttt gaactccaga ttattgggtt tttgttttaa tttatttttg    120
```

```
tcagaggaaa aataatttaa catccatctc acaggcttgc ttgactgttc agttccaagg      180
tcctgctcac ttttcttgt cttgcctctg ctctggcttt cttcatgata gtgctggacg      240
tggagctgag agtctcgttt actctaggca acccctctac ctgaagccag agcccagcac      300
tccgtaccac cacagacttc tgaagctggc aaagttttag aagctgggag ttttctgatt      360
ctctcattat taagtttctc ctcagtcttt agatagaggt aaatgtgggc ttgtaagaaa      420
agaaacgaaa gcacgtaatg tacacctatt ctgaattatg caaattagct cttactcagg      480
gtcaactaaa ttacttcaac tcgcccttta gtttactctt aatttgcaaa agagaaaaa      540 agaaggaaaa ctaaatagga ctatgatttg gggagccaaa ttgataatct gatgtaaaag      600
ttgctgtgtt aaacataaat tattaagtgt agacttttt cctaggatat tgtattcatt       660
ttgtgatatc gcctagaatg atgtattaga taaaaatcaa ttttgtaagt atgtaaatat      720
gtcataaata aatactttga cttatttctc aaaaaaaaaa aaaaaaaaa                  770
```

<210> SEQ ID NO 56
<211> LENGTH: 983
<212> TYPE: DNA
<213> ORGANISM: Eukaryote

<400> SEQUENCE: 56

```
gattttatat tcaatgttgt ttatttaatc cattgcagtt ggtgaatgcc ttttcctcct       60
agacaccctg tattatacca tttggggatt aagtcaaagt taagtatatt tttttcttac      120
ttgagctcta tatatgcaat tcagatatct tcctgatgac agttttatat gtaaatgtaa      180
tttaactttc tttccgtgtt gacgaagttc tgtaggtgtt agggttagaa gtctcagcac      240
tcacttctct cactggatgt gcagtgtgcc tgccatggcg cacggcttct cagtaatgat      300
gccatctctg ctacttttac agaaggagaa gtttactttt gaggtgggta tgtgttgata      360
tctaaacact gtgtgttgct tgcttagata ggcaagacac actgctgtgc gtggctcctg      420
tggtgcacct agcccagggg aacgtagcct cagtacttcc gctggcttct tcatgcctaa      480
gaagcagggg cctttcttgt ttgctgggct ctggctttaa aagttgtcct ttgggtctgg      540
agatgtagct ctgtgacaga acaccagcta atgtcaggtc ctgcggtcag tctctggtac      600
acacaagcgc acactcacat gatgggggga tgaaaggctg tccttgtgta acagtattcg      660 atgggcgtt gcctggatga cgatgtttat gtactctgaa ggcagatcct gaaggcaccc       720
tgttcttccc ttccttgtgt aactgagtct gcactagctt agccactgtt ttagaggcca     780
tcctagtggg cgaacaggag gcatcgcact gggtgatggt ttgccttcag tcctcaagta     840
acagcggccg acttatgccg atggcttgtt tgaaatcaaa tattaccaag ttggcctagt     900
ctgccttctg tgaagaaggg gagaaaggaa gggtggaaag gtggatggaa agcctttggg     960
gaactagtct gatctctcaa ggg                                             983
```

<210> SEQ ID NO 57
<211> LENGTH: 1763
<212> TYPE: DNA
<213> ORGANISM: Eukaryote
<220> FEATURE:
<221> NAME/KEY: misc_feature
<222> LOCATION: (1)...(1763)
<223> OTHER INFORMATION: y = C or T
      n = A,T,C or G

<400> SEQUENCE: 57

```
cttcagttcc tttgaggggn ctttccttcg aaggggatac gcctaccttt cacgagttgc       60
```

-continued

```
gcagtttgtc tgcaagactc tatgagaagc agataagcga taagtttgct caacatcttc      120
tcgggcataa gtcggacacc atggcatcac agtatcgtga tgacagaggc agggagtggg      180
acaaaattga aatcaaataa tgattttatt ttgactgata gtgacctgtt cgttgcaaca      240
aattgataag caatgctttt ttataatgcc aacttagtat aaaaaagctg aacgagaaac      300
gtaaaatgat ataaatatca atatattaaa ttagattttg cataaaaaac agactacata      360
atactgtaaa acacaacata tgcagtcact atgaatcaac tacttagatg gtattagtga      420
cctgtaacag agcattagcg caaggtgatt tttgtcttct tgcgctaatt ttttgtcatc      480
aaacctgtcg cactccagag aagcacaaag cctcgcaatc cagtgcaaag cttgcatgcc      540
tgcaggtcga ctcatatgcg gtgtgaaata ccgcacagat gcgtaaggag aaaataccgc      600
atcaggcggc catcgccctg atagacggtt tttcgccctt gacgttgga gtccacgttc      660 tttaatagtg gactcttgtt ccaaactgga acaacactca accctatctc ggtctattct      720
tttgatttat aagggatttt gccgatttcg gcctattggt taaaaatga gctgatttaa      780 caaaaattta acgcgaattt taacaaaata ttaacgctta caatttgcca ttcgccattc      840
aggctgcgca actgttggga agggcgatcg gtgcgggcct cttcgctatt acgccagctg      900
gcgaaagggg gatgtgctgc aaggcgatta agttgggtaa cgccagggtt ttcccagtca      960
cgacgttgta aaacgacggc cagtgaattg taatacgact cactataggg cgaattgggt     1020
accgggcccc ccctcgaggt cgacggtatc gataagcttg atatcgaatt cggcacgagc     1080
cgcagccgat atgcagtccc cggcggtgct cgtcacctcc aggcaagttc agaatgcgca     1140
cacgggyctc gacctgactg taccacagca ccaggaggtg cggggtaaga tgatgtcagg     1200
ccatgtggag taccagatcc tggtggtgac ccggttggct gtgttcaagt cagccaagca     1260
ccggcccgag gatgtcgtcc agttcttggt ctccaaaaaa tacagcgaga tcgaggagtt     1320
ttaccagaaa ctgtacagtc gttacccaga agccagcctg cccccactgc ctaggaaggt     1380
cctgtttgtc ggggagtctg acatccggga aggagagcc atgtttgatg agattctacg     1440
ctgtgtctcc aaggatgccc agttggcggg cagcccagag ctgctagaat cttaggcac     1500 caggtccccg ggggctacag gctttgccac ccgagatccc tctgtcttgg gatgacgaca     1560
gccagccggc caggggacag tgatgaggct tttgacttct ttgagcaaca gggatgaagt     1620
gcaagccacc cacattgggc ctgagcaaca angaaatgtt gagaaggtcc ntggaaggaa     1680
ngaggaggga agggaggaag gangataact tgggatcccc cttggggcaa tcaatgcggc     1740
ctcccaaagg aaagncccta aag                                             1763
```

<210> SEQ ID NO 58
<211> LENGTH: 4634
<212> TYPE: DNA
<213> ORGANISM: Rattus norvegicus
<220> FEATURE:
<221> NAME/KEY: misc_feature
<222> LOCATION: (1)...(4634)
<223> OTHER INFORMATION: r = G or A
     y = C or T
     m = A or C
     k = G or T
     s = G or C
     w = A or T
     n = A,T,C or G

<400> SEQUENCE: 58

```
ctgccagccg aggctcctgc cgctgtgacc cgcgctccgc ccgccgccgg gccgggaccc       60
tgatagctaa tgtcagaaga aagtgactct gtgagaacca gccctctgt ggcctcactc      120
```

```
tccgaaaatg agctgccacc gcctcccccg aacctcccr gctacgtgtg ctcgctgaca     180
gaagacttgg tcaccaaggc cagggaagag cttcaggaga agcccgagtg gagactccgg    240
gatgtgcagg cccttcgaga catggtacgg aaggagtacc ataccctgag tacatcgctg    300
gatgatgcct tcctgttgcg ctttctgagg gcccgaaagt ttgattatga ccggccctg     360 cagctgctgg tcaactacca tggctgcagg cggagctggc cagaggtctt cagcaacctg    420
aggccatcag ccctgaaaga cgttcttaac tctggattcc tcacagtgct gccccacaca    480
gaccccaggg gctgccatgt cctctgcatc cgaccagaca gatggatacc gagcaactac    540
ccgatcaccg agaacatccg cgccatctac ttgacgttag aaaaactcat tcagtccgag    600
gagacccagg tgaacgggt tgtaatcctc gccgactaca agggagtgag cttatcaaag    660
gcgtctcact ttggcccctt tatcgccaga aaggtgattg catccttca ggatggcttc     720 cccattcgga taaaagcagt tcacatagta acgaacctc ggatatttaa gggcatttttc    780 gccatcataa aaccatttct gaaggagaaa attgcaaaca ggttcttcct ccatgggtct    840
gacctgagct ctctgcacac gagccttcca aggaatatcc tccccaaaga gtatgggggc    900
accgctgggg agctggacac tgccagctgg aacgcggtgc tgctggcctc ggaggatgat    960
tttgtgaaag agttctgcca gcctgagtct ggctgcgatg gtctcttggg ccagcccctg   1020
ctgcctgagg ggctgatctc agacgcgcag tgtgacgact ccatgcgagc catgaagtcc   1080
cagctctact cctgctatta gccctcttcc gggagaatca ccatgtgtaa ttccttcctt   1140
cttcgaatgc acaggctgaa gatgccagga cctcggtctt gctccatcac agtgcagcac   1200
ggagctgcct gcagagattt aaggagagcc atcacaggc agacctctga ccagctaggt    1260
tattccaaga agacatggaa attgccctgg tgattcccag atgtctgtac tctaagtctg   1320
caactgttac tctggaagct gcatctgttt cttatgcatc ttggaaagaa ctagggtcaa   1380
agtcactctg aagtgaccag gagtagacaa cttgattgat catgagtctg aaacaattgc   1440
caatcctgaa aggtggccat gcgtgagact ttgagtctct ttcccataaa ctgtaggtgt   1500
tgactactgc tgcttatctg caaaggtcag ggttcaggcc ccagttggca ttgctgggtc   1560
tgggaagcac tgctaactga gtggtagaaa cgccaggccc aggcagcact taaaggttaa   1620
aggtcaaatt tggaagctaa ggctataaat catcctgggt tccaggctta aatcttgcaa   1680
tggacactct ccccaaacca taaagcctta gctctggttc tccatggaat catgcaggtc   1740
aacataaaat actggattct tggactgcgt ggctaaaagc acttagacta rgagtccagt   1800
gtgtgactgg atggataggg gcctcagctt gtcaactcta agttagmgmt ccatggaatg   1860
aaggccttgr gggctgctca agttctgtta ggtttctgct tggaaagatg accacctgga   1920
ggtggccggg ccttttttggt ttggcttggt tttgtgttat agacacaagc cttatggaaa   1980
ggaaccgtct ggcctttaaa gaaattacta tgttcctggg agttggtggt aaccagctgc   2040
ttttgcagat gatgggtgaa ctggaaaggg atggcttttg tgaggctgac caagtcttgt   2100
acgcggatgt tgtacagatt cctcccacac cggagacatt cgtactatat agaaacagc    2160 cacggacttg tgctctttca gtttgtgtcc ctggaaacat acgggggca ggctgttgct    2220 ggttcacctg ggggccctgc cctcccagac acggagtgc ttgtctagcg tgggagggcc    2280
agttggccag attgttagct ctgcgttggg gtgtcgtaga caactgacag gatttttagcc   2340 ttaacccaag cactgagtga ggtgattttt cccttggctt ttggcgtgtc tttggtattc   2400
accatgtatt gtggtgtcag gtagtgtcag gtactgttgg ctgtgtgtct cctagactaa   2460
```

```
gcgggcgttg satacagctt acatacagtg cttggagacc aaaggtcagt tggttgtaat        2520
aagctggtcc acccttaaca gacttcccaa acatyacaga agctyttatg gmccttacct        2580
aataatgcca attctggagg acactctttt accatagawk csaatccttg atctcctggc        2640
tcctggttga gcttccgcac tgatacaccc tcttgrctgc ccatcagggc catttgctgc        2700
tgagttctgc attgcttaak ctsckgsygy tttctgccta aagggatggc cacccagaca        2760
cctaaaaaga cccgggatgg ctctctagcc ttggtggaga gtcttattag aagttttctt        2820
tgggggattg gggatttggc tcagtggtag agcgcttgcc tggcaagcac aaggccctgg        2880
gttcggtccc cagctcttaa aaaaaaaaa agttttcttt ggtagttggg gaaaaggcag        2940
aaggaaaaaa acaaagggaa agatgaatct ctcagtccta cctggttccc taaatttaaa        3000
tcgtgtcatg tgactagtta agtctctttg acttaacaaa gggacaccag gttcttgggg        3060
agaaatctca gagcaaaatg ttgcctgttg staaccttct ggtaaccara ggarccttga        3120
taarcttarg agykgactgt atgtccatgc tcttgtgact ctagagactc tggcacctca        3180
ggttnaagca ggctgtgagc cagatgtcct ggtgccaagc aaccccactg ttgagcagca        3240
ggggcaccat aggcctcagc taggggagcg cactggtaga gccagcaagt gagcaggaat        3300
ctgactttag ggtaaaaatc tagacagttc tgacagctgg aagtcaactt ttcctccatt        3360
caaagtcatg tggcattggg aagggctag ggaaatagaa gtgggttcca gctttatctt        3420
cctacacagt ctcgagtata gcattaacac cgagtgctgg acagaggttg tctgctgaac        3480
actcaatcct gctcctgact gactctggaa ataaggacat tccactctgc ttggcgcgga        3540
gatgccctag tgtgcggccg cggggcttc tctttctcaa gtcctctaca gnacttccag        3600
gcagttcatc ttcctaggaa aaggtatgga ggttctgcct tcatggtaga aacacaggat        3660
aaaatctaca gtaaacaacc ggtaagtgct ggcttcttac gccttggctt tctccaggca        3720
caggtgggtt cgactactcc catttcatct ttgtaagcac ctcaggttat agggcagttt        3780
cttcagagtt gggggactg gagccattcc ccctgtaatg cctgaggtgg ccttaccacc        3840
tagcagccag tttggccagc aacagccaca ctgctgttat ggtatcataa tacctcatcc        3900
tcgggtttcc ttcagaaagg raaawgctaa ctcagttgat gtaagtgttg ctgtgctggg        3960
atcctgtcat gtgggaggga acaccaaata cacaggctct caggagacat cttgctaagg        4020
cttctcttta ctgcagtctg ctcacgttgt aaatctgccc tctgttctcc tgactcaraa        4080
agactcagcc mcaaatcaag aagcgccatc aaacgttcct tctcakkggg aacgtgctcc        4140
acaggaaggt ccagwgggat ttgcarctag agtcacgttt tactggkttg tgamcaaatt        4200
tactggtttt carttacctg gggkcctatg kgkkttttma accttttccc atmaggcagt        4260
tagtagtagc cactttgggt tcctgtggac gtgcctcagc ttctcggcat aggaacccaa        4320
caggtagaat acttgaaact tctcagtggc caagacctcg ataccctctc tgatgggtgg        4380
gaactgggct atttttcctga ccaatctagg ccaccatttt agtccctggt cacattcctt        4440
actccaaact gaaattcagt ttggctttga gtatgtgcac acgtggtggg ttcacctact        4500
tcagtgttga ccaaaagttt attttttctag tgcattttc taaatggtaa aaatatgtaa        4560
ttttagtatg catgactggg tctccaaaat aaaaactgag tgtattgtga aaaaaaaaa        4620 aaaaaaaaa aaaa                                                          4634
```

<210> SEQ ID NO 59
<211> LENGTH: 1030
<212> TYPE: DNA
<213> ORGANISM: Rattus norvegicus

<220> FEATURE:
<221> NAME/KEY: CDS
<222> LOCATION: (1)...(1030)

<400> SEQUENCE: 59

| atg tca gaa gaa agt gac tct gtg aga acc agc ccc tct gtg gcc tca | 48 |
|---|---|
| Met Ser Glu Glu Ser Asp Ser Val Arg Thr Ser Pro Ser Val Ala Ser | |
| 1               5                   10                  15 | |

| ctc tcc gaa aat gag ctg cca ccg cct ccc ccg gaa cct ccc ggc tac | 96 |
|---|---|
| Leu Ser Glu Asn Glu Leu Pro Pro Pro Pro Pro Glu Pro Pro Gly Tyr | |
|         20                  25                  30 | |

| gtg tgc tcg ctg aca gaa gac ttg gtc acc aag gcc agg gaa gag ctt | 144 |
|---|---|
| Val Cys Ser Leu Thr Glu Asp Leu Val Thr Lys Ala Arg Glu Glu Leu | |
|             35                  40                  45 | |

| cag gag aag ccc gag tgg aga ctc cgg gat gtg cag gcc ctt cga gac | 192 |
|---|---|
| Gln Glu Lys Pro Glu Trp Arg Leu Arg Asp Val Gln Ala Leu Arg Asp | |
| 50                  55                  60 | |

| atg gta cgg aag gag tac cca tac ctg agt aca tcg ctg gat gat gcc | 240 |
|---|---|
| Met Val Arg Lys Glu Tyr Pro Tyr Leu Ser Thr Ser Leu Asp Asp Ala | |
| 65                  70                  75                  80 | |

| ttc ctg ttg cgc ttt ctg agg gcc cga aag ttt gat tat gac cgg gcc | 288 |
|---|---|
| Phe Leu Leu Arg Phe Leu Arg Ala Arg Lys Phe Asp Tyr Asp Arg Ala | |
|                 85                  90                  95 | |

| ctg cag ctg ctg gtc aac tac cat ggc tgc agg cgg agc tgg cca gag | 336 |
|---|---|
| Leu Gln Leu Leu Val Asn Tyr His Gly Cys Arg Arg Ser Trp Pro Glu | |
|             100                 105                 110 | |

| gtc ttc agc aac ctg agg cca tca gcc ctg aaa gac gtt ctt aac tct | 384 |
|---|---|
| Val Phe Ser Asn Leu Arg Pro Ser Ala Leu Lys Asp Val Leu Asn Ser | |
|         115                 120                 125 | |

| gga ttc ctc aca gtg ctg ccc cac aca gac ccc agg ggc tgc cat gtc | 432 |
|---|---|
| Gly Phe Leu Thr Val Leu Pro His Thr Asp Pro Arg Gly Cys His Val | |
| 130                 135                 140 | |

| ctc tgc atc cga cca gac aga tgg ata ccg agc aac tac ccg atc acc | 480 |
|---|---|
| Leu Cys Ile Arg Pro Asp Arg Trp Ile Pro Ser Asn Tyr Pro Ile Thr | |
| 145                 150                 155                 160 | |

| gag aac atc cgc gcc atc tac ttg acg tta gaa aaa ctc att cag tcc | 528 |
|---|---|
| Glu Asn Ile Arg Ala Ile Tyr Leu Thr Leu Glu Lys Leu Ile Gln Ser | |
|                 165                 170                 175 | |

| gag gag acc cag gtg aac ggg gtt gta atc ctc gcc gac tac aag gga | 576 |
|---|---|
| Glu Glu Thr Gln Val Asn Gly Val Val Ile Leu Ala Asp Tyr Lys Gly | |
|             180                 185                 190 | |

| gtg agc tta tca aag gcg tct cac ttt ggc ccc ttt atc gcc aga aag | 624 |
|---|---|
| Val Ser Leu Ser Lys Ala Ser His Phe Gly Pro Phe Ile Ala Arg Lys | |
|         195                 200                 205 | |

| gtg att ggc atc ctt cag gat ggc ttc ccc att cgg ata aaa gca gtt | 672 |
|---|---|
| Val Ile Gly Ile Leu Gln Asp Gly Phe Pro Ile Arg Ile Lys Ala Val | |
| 210                 215                 220 | |

| cac ata gta aac gaa cct cgg ata ttt aag ggc att ttc gcc atc ata | 720 |
|---|---|
| His Ile Val Asn Glu Pro Arg Ile Phe Lys Gly Ile Phe Ala Ile Ile | |
| 225                 230                 235                 240 | |

| aaa cca ttt ctg aag gag aaa att gca aac agg ttc ttc ctc cat ggg | 768 |
|---|---|
| Lys Pro Phe Leu Lys Glu Lys Ile Ala Asn Arg Phe Phe Leu His Gly | |
|                 245                 250                 255 | |

| tct gac ctg agc tct ctg cac acg agc ctt cca agg aat atc ctc ccc | 816 |
|---|---|
| Ser Asp Leu Ser Ser Leu His Thr Ser Leu Pro Arg Asn Ile Leu Pro | |
|             260                 265                 270 | |

| aaa gag tat ggg ggc acc gct ggg gag ctg gac act gcc agc tgg aac | 864 |
|---|---|
| Lys Glu Tyr Gly Gly Thr Ala Gly Glu Leu Asp Thr Ala Ser Trp Asn | |
|         275                 280                 285 | |

| gcg gtg ctg ctg gcc tcg gag gat gat ttt gtg aaa gag ttc tgc cag | 912 |
|---|---|

```
Ala Val Leu Leu Ala Ser Glu Asp Asp Phe Val Lys Glu Phe Cys Gln
        290                 295                 300 cct gag tct ggc tgc gat ggt ctc ttg ggc cag ccc ctg ctg cct gag      960
Pro Glu Ser Gly Cys Asp Gly Leu Leu Gly Gln Pro Leu Leu Pro Glu
305                 310                 315                 320 ggg ctg atc tca gac gcg cag tgt gac gac tcc atg cga gcc atg aag     1008
Gly Leu Ile Ser Asp Ala Gln Cys Asp Asp Ser Met Arg Ala Met Lys
                325                 330                 335 tcc cag ctc tac tcc tgc tat t                                        1030
Ser Gln Leu Tyr Ser Cys Tyr
            340

<210> SEQ ID NO 60
<211> LENGTH: 1029
<212> TYPE: DNA
<213> ORGANISM: Homo sapiens
<220> FEATURE:
<221> NAME/KEY: CDS
<222> LOCATION: (1)...(1029)

<400> SEQUENCE: 60 atg tcc gaa gaa agg gac tct ctg aga acc agc cct tct gtg gcc tca       48
Met Ser Glu Glu Arg Asp Ser Leu Arg Thr Ser Pro Ser Val Ala Ser
1               5                   10                  15 ctc tct gaa aat gag ctg cca cca cca cct gag cct ccg ggc tat gtg       96
Leu Ser Glu Asn Glu Leu Pro Pro Pro Pro Glu Pro Pro Gly Tyr Val
                20                  25                  30 tgc tca ctg aca gaa gac ctg gtc acc aaa gcc cgg gaa gag ctg cag      144
Cys Ser Leu Thr Glu Asp Leu Val Thr Lys Ala Arg Glu Glu Leu Gln
            35                  40                  45 gaa aag ccg gaa tgg aga ctt cga gat gtg cag gcc ctt cgt gac atg      192
Glu Lys Pro Glu Trp Arg Leu Arg Asp Val Gln Ala Leu Arg Asp Met
        50                  55                  60 gtg cgg aag gag tac ccc aac ctg agc aca tcc ctc gac gat gcc ttc      240
Val Arg Lys Glu Tyr Pro Asn Leu Ser Thr Ser Leu Asp Asp Ala Phe
65                  70                  75                  80 ctg ctg cgc ttc ctc cga gcc cgc aag ttt gat tac gac cgg gcc ctg      288
Leu Leu Arg Phe Leu Arg Ala Arg Lys Phe Asp Tyr Asp Arg Ala Leu
                85                  90                  95 cag ctc ctc gtc aac tac cac agc tgt aga aga agc tgg ccc gaa gtc      336
Gln Leu Leu Val Asn Tyr His Ser Cys Arg Arg Ser Trp Pro Glu Val
            100                 105                 110 ttc aat aac ttg aag cca tca gcc tta aaa gat gtc ctt gct tcc ggg      384
Phe Asn Asn Leu Lys Pro Ser Ala Leu Lys Asp Val Leu Ala Ser Gly
        115                 120                 125 ttc ctc acc gtg ctg ccc cac act gac ccc agg ggc tgc cat gtc gtc      432
Phe Leu Thr Val Leu Pro His Thr Asp Pro Arg Gly Cys His Val Val
130                 135                 140 tgc atc cgc cca gac aga tgg ata cca agc aac tat cca att act gaa      480
Cys Ile Arg Pro Asp Arg Trp Ile Pro Ser Asn Tyr Pro Ile Thr Glu
145                 150                 155                 160 aac atc cga gcc ata tac ttg acc tta gaa aaa ctc att cag tct gaa      528
Asn Ile Arg Ala Ile Tyr Leu Thr Leu Glu Lys Leu Ile Gln Ser Glu
                165                 170                 175 gaa acc cag gtg aat gga att gta att ctt gca gac tac aaa gga gtg      576
Glu Thr Gln Val Asn Gly Ile Val Ile Leu Ala Asp Tyr Lys Gly Val
            180                 185                 190 agt tta tca aaa gca tct cac ttt ggc cct ttt ata gcc aaa aag gtg      624
Ser Leu Ser Lys Ala Ser His Phe Gly Pro Phe Ile Ala Lys Lys Val
        195                 200                 205 att ggc atc ctc cag gat ggt ttc ccc att cgg ata aaa gca gtc cat      672
```

```
Ile Gly Ile Leu Gln Asp Gly Phe Pro Ile Arg Ile Lys Ala Val His
        210                 215                 220 gtg gtg aat gaa cct cga ata ttt aaa ggc att ttt gcc atc ata aaa        720
Val Val Asn Glu Pro Arg Ile Phe Lys Gly Ile Phe Ala Ile Ile Lys
225                 230                 235                 240 cca ttt cta aag gag aaa ata gca aac aga ttc ttc ctc cat ggg tct        768
Pro Phe Leu Lys Glu Lys Ile Ala Asn Arg Phe Phe Leu His Gly Ser
                245                 250                 255 gac ttg aac tct ctc cac aca aac ctt cca aga agc atc ctc ccc aag        816
Asp Leu Asn Ser Leu His Thr Asn Leu Pro Arg Ser Ile Leu Pro Lys
        260                 265                 270 gag tat ggg ggc acg gct ggg gag ctg gac act gcc acc tgg aac gca        864
Glu Tyr Gly Gly Thr Ala Gly Glu Leu Asp Thr Ala Thr Trp Asn Ala
    275                 280                 285 gta ctg ctg gct tca gaa gac gat ttt gtg aaa gag ttc tgc caa cct        912
Val Leu Leu Ala Ser Glu Asp Asp Phe Val Lys Glu Phe Cys Gln Pro
290                 295                 300 gtt cct gcc tgt gac agc atc ctg ggc cag acg ctg ctg ccc gag ggc        960
Val Pro Ala Cys Asp Ser Ile Leu Gly Gln Thr Leu Leu Pro Glu Gly
305                 310                 315                 320 ctg acc tca gat gca cag tgt gac gac tcc ttg cga gct gtg aag tca       1008
Leu Thr Ser Asp Ala Gln Cys Asp Asp Ser Leu Arg Ala Val Lys Ser
                325                 330                 335 cag ctg tac tcc tgc tac tag                                           1029
Gln Leu Tyr Ser Cys Tyr
            340
```

<210> SEQ ID NO 61
<211> LENGTH: 341
<212> TYPE: PRT
<213> ORGANISM: Rattus norvegicus
<220> FEATURE:
<221> NAME/KEY: VARIANT
<222> LOCATION: (1)...(341)
<223> OTHER INFORMATION: Xaa = Any Amino Acid

<400> SEQUENCE: 61

```
Met Ser Glu Glu Ser Asp Ser Val Arg Thr Ser Pro Ser Val Ala Ser
 1               5                  10                  15

Leu Ser Glu Asn Glu Leu Pro Pro Pro Pro Glu Pro Pro Xaa Tyr
                20                  25                  30

Val Cys Ser Leu Thr Glu Asp Leu Val Thr Lys Ala Arg Glu Glu Leu
            35                  40                  45

Gln Glu Lys Pro Glu Trp Arg Leu Arg Asp Val Gln Ala Leu Arg Asp
        50                  55                  60

Met Val Arg Lys Glu Tyr Pro Tyr Leu Ser Thr Ser Leu Asp Asp Ala
65                  70                  75                  80

Phe Leu Leu Arg Phe Leu Arg Ala Arg Lys Phe Asp Tyr Asp Arg Ala
                85                  90                  95

Leu Gln Leu Leu Val Asn Tyr His Gly Cys Arg Arg Ser Trp Pro Glu
            100                 105                 110

Val Phe Ser Asn Leu Arg Pro Ser Ala Leu Lys Asp Val Leu Asn Ser
        115                 120                 125

Gly Phe Leu Thr Val Leu Pro His Thr Asp Pro Arg Gly Cys His Val
    130                 135                 140

Leu Cys Ile Arg Pro Asp Arg Trp Ile Pro Ser Asn Tyr Pro Ile Thr
145                 150                 155                 160

Glu Asn Ile Arg Ala Ile Tyr Leu Thr Leu Glu Lys Leu Ile Gln Ser
                165                 170                 175
```

-continued

```
Glu Glu Thr Gln Val Asn Gly Val Val Ile Leu Ala Asp Tyr Lys Gly
            180                 185                 190

Val Ser Leu Ser Lys Ala Ser His Phe Gly Pro Phe Ile Ala Arg Lys
        195                 200                 205

Val Ile Gly Ile Leu Gln Asp Gly Phe Pro Ile Arg Ile Lys Ala Val
    210                 215                 220

His Ile Val Asn Glu Pro Arg Ile Phe Lys Gly Ile Phe Ala Ile Ile
225                 230                 235                 240

Lys Pro Phe Leu Lys Glu Lys Ile Ala Asn Arg Phe Phe Leu His Gly
                245                 250                 255

Ser Asp Leu Ser Ser Leu His Thr Ser Leu Pro Arg Asn Ile Leu Pro
            260                 265                 270

Lys Glu Tyr Gly Gly Thr Ala Gly Glu Leu Asp Thr Ala Ser Trp Asn
        275                 280                 285

Ala Val Leu Leu Ala Ser Glu Asp Phe Val Lys Glu Phe Cys Gln
    290                 295                 300

Pro Glu Ser Gly Cys Asp Gly Leu Leu Gly Gln Pro Leu Leu Pro Glu
305                 310                 315                 320

Gly Leu Ile Ser Asp Ala Gln Cys Asp Ser Met Arg Ala Met Lys
                325                 330                 335

Ser Gln Leu Tyr Ser
            340
```

<210> SEQ ID NO 62
<211> LENGTH: 342
<212> TYPE: PRT
<213> ORGANISM: Homo sapiens

<400> SEQUENCE: 62

```
Met Ser Glu Glu Arg Asp Ser Leu Arg Thr Ser Pro Ser Val Ala Ser
1               5                   10                  15

Leu Ser Glu Asn Glu Leu Pro Pro Pro Glu Pro Pro Gly Tyr Val
            20                  25                  30

Cys Ser Leu Thr Glu Asp Leu Val Thr Lys Ala Arg Glu Glu Leu Gln
        35                  40                  45

Glu Lys Pro Glu Trp Arg Leu Arg Asp Val Gln Ala Leu Arg Asp Met
    50                  55                  60

Val Arg Lys Glu Tyr Pro Asn Leu Ser Thr Ser Leu Asp Asp Ala Phe
65                  70                  75                  80

Leu Leu Arg Phe Leu Arg Ala Arg Lys Phe Asp Tyr Asp Arg Ala Leu
                85                  90                  95

Gln Leu Leu Val Asn Tyr His Ser Cys Arg Arg Ser Trp Pro Glu Val
            100                 105                 110

Phe Asn Asn Leu Lys Pro Ser Ala Leu Lys Asp Val Leu Ala Ser Gly
        115                 120                 125

Phe Leu Thr Val Leu Pro His Thr Asp Pro Arg Gly Cys His Val Val
    130                 135                 140

Cys Ile Arg Pro Asp Arg Trp Ile Pro Ser Asn Tyr Pro Ile Thr Glu
145                 150                 155                 160

Asn Ile Arg Ala Ile Tyr Leu Thr Leu Glu Lys Leu Ile Gln Ser Glu
                165                 170                 175

Glu Thr Gln Val Asn Gly Ile Val Ile Leu Ala Asp Tyr Lys Gly Val
            180                 185                 190

Ser Leu Ser Lys Ala Ser His Phe Gly Pro Phe Ile Ala Lys Lys Val
```

-continued

```
            195                 200                 205
Ile Gly Ile Leu Gln Asp Gly Phe Pro Ile Arg Ile Lys Ala Val His
        210                 215                 220

Val Val Asn Glu Pro Arg Ile Phe Lys Gly Ile Phe Ala Ile Ile Lys
225                 230                 235                 240

Pro Phe Leu Lys Glu Lys Ile Ala Asn Arg Phe Phe Leu His Gly Ser
                245                 250                 255

Asp Leu Asn Ser Leu His Thr Asn Leu Pro Arg Ser Ile Leu Pro Lys
                260                 265                 270

Glu Tyr Gly Gly Thr Ala Gly Glu Leu Asp Thr Ala Thr Trp Asn Ala
        275                 280                 285

Val Leu Leu Ala Ser Glu Asp Asp Phe Val Lys Glu Phe Cys Gln Pro
        290                 295                 300

Val Pro Ala Cys Asp Ser Ile Leu Gly Gln Thr Leu Leu Pro Glu Gly
305                 310                 315                 320

Leu Thr Ser Asp Ala Gln Cys Asp Asp Ser Leu Arg Ala Val Lys Ser
                325                 330                 335

Gln Leu Tyr Ser Cys Tyr
                340
```